(12) United States Patent
Macdonald et al.

(10) Patent No.: US 9,364,432 B2
(45) Date of Patent: *Jun. 14, 2016

(54) INTRAVENTRICULAR DRUG DELIVERY SYSTEM FOR IMPROVING OUTCOME AFTER A BRAIN INJURY AFFECTING CEREBRAL BLOOD FLOW

(75) Inventors: R. Loch Macdonald, Toronto (CA); Brian A. Leuthner, Summit, NJ (US)

(73) Assignee: Edge Therapeutics, Inc., Berkely Heights, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/440,276

(22) Filed: Apr. 5, 2012

(65) Prior Publication Data

US 2012/0245561 A1 Sep. 27, 2012

Related U.S. Application Data

(63) Continuation-in-part of application No. 12/137,320, filed on Jun. 11, 2008, now Pat. No. 8,303,974.

(60) Provisional application No. 61/471,779, filed on Apr. 5, 2011, provisional application No. 60/976,902, filed on Oct. 29, 2007, provisional application No. 60/943,124, filed on Jun. 11, 2007.

(51) Int. Cl.

| A61K 9/00 | (2006.01) |
|---|---|
| A61K 47/34 | (2006.01) |
| A61K 9/10 | (2006.01) |
| A61K 9/16 | (2006.01) |
| A61K 31/4422 | (2006.01) |
| A61K 31/4439 | (2006.01) |
| A61K 31/4545 | (2006.01) |
| A61K 31/496 | (2006.01) |

(52) U.S. Cl.
CPC .............. *A61K 9/0085* (2013.01); *A61K 9/0019* (2013.01); *A61K 9/10* (2013.01); *A61K 9/1647* (2013.01); *A61K 31/4422* (2013.01); *A61K 31/4439* (2013.01); *A61K 31/4545* (2013.01); *A61K 31/496* (2013.01); *A61K 47/34* (2013.01)

(58) Field of Classification Search
None
See application file for complete search history.

(56) References Cited

U.S. PATENT DOCUMENTS

| 4,757,128 A | 7/1988 | Domb et al. |
|---|---|---|
| 5,399,665 A | 3/1995 | Barrera et al. |
| 5,407,609 A | 4/1995 | Tice et al. |
| 5,650,489 A | 7/1997 | Lam et al. |
| 5,712,171 A | 1/1998 | Zambias et al. |
| 5,747,058 A | 5/1998 | Tipton et al. |
| 5,804,159 A | 9/1998 | Eibl et al. |
| 5,968,542 A | 10/1999 | Tipton et al. |
| 5,977,163 A | 11/1999 | Li et al. |
| 5,993,855 A | 11/1999 | Yoshimoto et al. |
| 6,123,956 A * | 9/2000 | Baker et al. ................... 424/426 |
| 6,358,536 B1 | 3/2002 | Thomas et al. |
| 6,730,313 B2 | 5/2004 | Helmus et al. |
| 7,608,750 B2 | 10/2009 | Akira et al. |
| 7,713,551 B2 | 5/2010 | McGurk et al. |
| 7,790,140 B2 | 9/2010 | Bolotin et al. |
| 7,923,032 B2 * | 4/2011 | Pratt et al. ...................... 424/489 |
| 8,252,302 B2 | 8/2012 | MacDonald et al. |
| 8,288,336 B2 * | 10/2012 | Vitek et al. ...................... 514/1.1 |
| 8,303,974 B2 | 11/2012 | MacDonald et al. |
| 8,703,843 B2 | 4/2014 | Alkinson et al. |
| 8,728,528 B2 | 5/2014 | Biggs et al. |
| 2003/0135196 A1 * | 7/2003 | Hesson et al. ................. 604/500 |
| 2004/0105888 A1 | 6/2004 | Pratt et al. |
| 2004/0235801 A1 | 11/2004 | Julien et al. |
| 2006/0094643 A1 | 5/2006 | Svirkin et al. |
| 2006/0111282 A1 | 5/2006 | Haaning et al. |
| 2006/0205733 A1 | 9/2006 | Dixon et al. |
| 2006/0217340 A1 | 9/2006 | Braydon et al. |
| 2006/0229269 A1 | 10/2006 | Wellman et al. |
| 2007/0092574 A1 | 4/2007 | Cook et al. |
| 2007/0190154 A1 | 8/2007 | Zeigerson et al. |
| 2007/0190160 A1 * | 8/2007 | Turos et al. ................... 424/490 |
| 2007/0207211 A1 | 9/2007 | Zeigerson et al. |
| 2008/0188400 A1 | 8/2008 | Ropke et al. |
| 2008/0280811 A1 | 11/2008 | Feener et al. |
| 2008/0287879 A1 | 11/2008 | Harkins, Jr. et al. |
| 2008/0305147 A1 | 12/2008 | Macdonald et al. |

(Continued)

FOREIGN PATENT DOCUMENTS

| EP | 0486959 | 5/1992 |
|---|---|---|
| JP | 2000070366 A | 3/2000 |

(Continued)

OTHER PUBLICATIONS

Wartenberg "Update on the Management of Subarachnoid Hemorrhage" (2013).*
http://www.brain-aneurysm.com/cv.html.
MacDonald, R. L, et al. Site-Specific, Sustained-Release Nimodipine to Prevent Vasospasm. Drug Discovery and Development, Oct. 4, 2010.
Beierlein, W. et al., "Forty Years of Clinical Aprotinin Use: A Review of 124 Hypersensitivity Reactions," Ann. Thorac. Surg., (Feb. 2005), vol. 79, pp. 741-748.
Aikawa, H. et al., "Experimental chronic subdural hematoma in mice. Gross morphology and light microscopic observations," J. Neurosurg., (Nov. 1987), vol. 67, No. 5, pp. 710-716.
Diringer, M.N. et al., "Risk of Thromboembolic Events in Controlled Trials of rFVIIa in Spontaneous Intracerebral Hemorrhage," Stroke, (Mar. 2008), vol. 39, pp. 850-856.

(Continued)

*Primary Examiner* — Robert A Wax
*Assistant Examiner* — Danah Al-Awadi
(74) *Attorney, Agent, or Firm* — Chiesa Shahinian & Giantomasi PC

(57) ABSTRACT

The described invention provides a flowable sustained release microparticulate composition, a kit for treating at least one cerebral artery in a subarachnoid space at risk of interruption due to a brain injury, a method of preparing the composition, and a method for treating an interruption of a cerebral artery in a subarachnoid space at risk of interruption caused by brain injury in a mammal, which reduces signs or symptoms of at least one delayed complication associated with brain injury.

19 Claims, 20 Drawing Sheets

(56) References Cited

U.S. PATENT DOCUMENTS

| | | | |
|---|---|---|---|
| 2009/0156481 A1 | 6/2009 | Brun et al. |
| 2010/0008968 A1 | 1/2010 | Lampe et al. |
| 2010/0069602 A1 | 3/2010 | Raiche et al. |
| 2010/0189763 A1 | 7/2010 | Nettles et al. |
| 2010/0216948 A1 | 8/2010 | Tipton et al. |
| 2010/0291027 A1 | 11/2010 | Campbell et al. |
| 2011/0033463 A1 | 2/2011 | Thakker et al. |
| 2011/0142937 A1 | 6/2011 | MacDonald et al. |
| 2011/0204533 A1 | 8/2011 | Winchester et al. |
| 2011/0236497 A1 | 9/2011 | Tice et al. |
| 2013/0059008 A1 | 3/2013 | Alkinson et al. |

FOREIGN PATENT DOCUMENTS

| | | |
|---|---|---|
| JP | 2004105234 A | 4/2004 |
| WO | 95/18972 | 7/1995 |
| WO | 96/22529 | 7/1996 |
| WO | 0147571 A2 | 7/2001 |
| WO | 2004/047768 | 6/2004 |
| WO | 2006/084005 | 8/2006 |
| WO | 2008/154585 | 12/2008 |
| WO | 2014/164904 | 10/2014 |

OTHER PUBLICATIONS

Frati, A. et al., "Inflammation Markers and Risk Factors for Recurrence in 35 Patients with a Postraumatic Chronic Subdural Hematoma: a Prospective Study," J. Neurosurg., (Jan. 2004), vol. 100, No. 1, pp. 24-32.
Goodman & Gillman's The Pharmacological Basis of Therapeutics, Joel G. Hardman and Lee E. Limbird, Eds., McGraw Hill, 2001, pp. 1519-1520, pp. 1531-1532.
Elger, B. et al., "Ancrod reduces intracerebral hemorrhage quantified in vivo by magnetic resonance imaging in rats," J. Stroke Cerebrovasc. Dis., Jan.-Feb. 1998, vol. 7, No. 1, pp. 10-16.
Watanabe, S. et al. "Production of clinical form of chronic subdural hematoma in experimental animals," J. Neurosurg., (Nov. 1972), vol. 37, pp. 552-561.
Kou, J.H. et al. "Bioerosion and biocompatability of poly(d,l-lactic-co-glycolic acid) implants in brain," J. Controlled Release, (1997), vol. 43, pp. 123-130.
Mayer, S.A. et al., "Efficacy and Safety of Recombinant Activated Factor VII for Acute Intracerebral Hemorrhage," The New England Journal of Medicine, (May 15, 2008), vol. 358, No. 20, pp. 2127-2137.
Meltzer, M.E. et al., "The Impact of the Fibrinolytic System on the Risk of Venous and Arterial Thrombosis," Seminars Thrombosis Hemostasis, (2005), vol. 35, No. 5, pp. 468-477.
Monroe, D.M. et al., "Platelets and Thrombin Generation," Arterioscler. Thromb. Vasc. Biol., (Sep. 2002), vol. 22, pp. 1381-1389.
Nakaguchi, H. et al., "Factors in the Natural History of Chronic Subdural Hematomas that Influence their Postoperative Recurrence," J. Neurosurg., (Aug. 2001), vol. 95, No. 2, pp. 256-262.
Nomura, S. et al., "Characterization of Local Hyperfibrinolysis in Chronic Hematomas by SDS-PAGE and Immunoblot", J. Neurosurg., (Dec. 1994), vol. 81, No. 6, pp. 910-913.
Pradilla et al. "Pharmacokinetics of controlled-release polymers in the subarachnoid space after subarachnoid hemorrhage in rabbits" J. Neurosurg. Jul. 2004; 101(1) (Abstract).
Mayer, S.A., "Intracerebral hemorrhage: natural history and rationale of ultra-early hemostatic therapy," Intensive Care Med., (2002), vol. 28, pp. S235-S240.
Weiss, A. et al., "Signal Transduction by Lymphocyte Antigen Receptors," Cell, (Jan. 28, 1994), vol. 76, No. 2, pp. 263-274.
Veziers, J. et al. "Analysis of brain biocompatability of drug-releasing biodegradable microspheres by scanning and transmission electron microscopy," J. Neurosurg., (Sep. 2001), vol. 95, pp. 489-494.
Apfelbaum, R. et al. "Experimental production of subdural hematomas," J. Neurosurg., (Mar. 1974), vol. 40, pp. 336-346.
Han, N.J. et al. "One vs. Two Burr Hole Craniostomy in Surgical Treatment of Chronic Subdural Hematoma," J. Korean Neurosurg. Soc., (2009), vol. 46, pp. 87-92.
Tallon, J. et al. "The epidemiology of surgically treated acute subdural and epidural hematomas in patients with head injuries: a population-based study," Can. J. Surg., (Oct. 2008), vol. 51, No. 5, pp. 339-345.
Shim, Y.S. et al. "What are the Causative Factors for a Slow, Progressive Enlargement of a Chronic Subdural Hematoma?" Yonsei Med. J., (2007), vol. 48, No. 2, pp. 210-217.
Labadie, E. et al. "Physiopathogenesis of subdural hematomas; Part 1: Histological and biochemical comparisons of subcutaneous hematoma in rats with subdural hematomas in man." J. Neurosurg., (Oct. 1976), vol. 45, pp. 382-392.
Starke, R. et al. "Impact of a Protocol for Acute Antifibrinolytic Therapy on Aneurysm Rebleeding After Subarachnoid Hemorrhage," Stroke, (2008), vol. 39, pp. 2617-2621.
Sugiu, K. et al. "Rebleeding From a Vertebral Artery Dissecting Aneurysm After Endovascular Internal Trapping: Adverse Effect of Intrathecal Urokinase Injection or Incomplete Occlusion?" Neurol. Med. Chir. (Tokyo), (Dec. 2009), vol. 49, pp. 597-600.
Glover, D. et al. "Physiopathogenesis of subdural hematomas; Part 2: Inhibition of growth of experimental hematomas with dexamethasone." J. Neurosurg., (Oct. 1976), vol. 45, pp. 393-397.
Vandenabeele, F. et al. "Ultrastructure of the human spinal arachnoid mater and dura mater," J. Anat., (1996), vol. 189, pp. 417-430.
Datta, S. et al. "Neuroradiological aspects of subdural haemorrhages," Arch. Dis. Child, (2005), vol. 90, pp. 947-951.
Roos, Y. et al. "Antifibrinolytic therapy for aneurysmal subarachnoid haemorrhage." Cochrane Database of Systematic Reviews, 2003; Issue 2, Art No. CD001245 (Abstract).
MacLellan, C. et al. "Intracerebral hemorrhage models in rat: comparing collagenase to blood infusion." J. Cereb. Blood Flow Metab., 2008; 28:516-525.
Weigel, R. et al. "Outcome of contemporary surgery for chronic subdural haematoma: evidence based review." J. Neurol. Neurosurg. Psychiatry, 2003; 74:937-943.
Tokmak, M. et al. "The role of exudation in chronic subdural hematomas." J. Neurosurg., Aug. 2007; 107:290-295.
Haines, D.E. "On the Question of a Subdural Space." The Anatomical Record, 1991; 230:3-21.
Rosenberg, GA. et al. "Collagenase-induced intracerebral hemorrhage in rats." Stroke, 1990; 21:801-807.
Qureshi, A. et al. "Spontaneous Intracerebral Hemorrhage." N. Engl. J. Med., May 2001; 344(19):1450-1460.
Carmichael, S.T. et al. "Genomic profiles of damage and protection in human intracerebral hemorrhage." J. Cereb. Blood Flow Metab., Nov. 2008; 28(11):1860-1875.
Murakami, H. et al. "Why do chronic subdural hematomas continue to grow slowly and not coagulate? Role of thrombomodulin in the mechanism." J. Neurosurg., 2002; 96:877-884.
Broderick, J.P. et al. "Volume of intracerebral hemorrhage. A powerful and easy-to-use predictor of 30-day mortality." Stroke, 1993; 24:987-993.
Broderick, J.P. et al. "Guidelines for the Management of Spontaneous Intracerebral Hemorrhage: A Statement for Healthcare Professionals From a Special Writing Group of the Stroke Council, American Heart Association." Stroke, 1999; 30:905-915.
Mayberg, M. R. et al., "The significance of morphological changes in cerebral arteries after subarachnoid hemorrhage," J. Neurosurg., (1990), vol. 72, pp. 626-633.
Mayberg, M. R. et al., "The role of hemoglobin in arterial narrowing after subarachnoid hemorrage," J. Neurosurg., (1990), vol. 72, pp. 634-640.
Sands, Z et al. "Voltage-gated ion channels". Current Biology, vol. 15; No. 2. pp. R44-R47, 2005.
Petegem F. V. et al. "The structural biology of voltage-gated calcium channel function and regulation". Biochemical Society Transactions; vol. 34 (5) pp. 887-893; 2006.
Catterall, A. W. et al. International Union of Pharmacology. XLVIII. Nomenclature and Structure-Function Relationships of Voltage-Gated Calcium Channels. The American Society for Pharmacology and Experimental Therapeutics; Pharmacol Rev 57: 411-425 (2005).

(56) References Cited

OTHER PUBLICATIONS

Yamakage, M. and Namiki, A. "Calcium channels—basic aspects of their structure, function and gene encoding; anesthetic action on the channels—a review." Canadian Journal of Anesthesia; Feb. 2002;49 (2):151-64.
Dolphin, A. "A short history of voltage-gated calcium channels." British Journal of Pharmacology. Jan. 2006; 147 (Suppl 1): S56-S62.
Dreier, J. P. et al., Brain 132: 1866-81 (2009).
Reagan-Shaw, S. et al. "Dose translation from animal to human studies revisited." FASEB J. Mar. 2008, 22 (3):659-61. Epub Oct. 17, 2007.
Principles of Neural Science, 2nd ed. (E.R. Kandel ed, Elsevier Science Publishing Co., Inc. NY pp. 854-856.) and 4th ed. p. 8.
Llinas, R. et al., "Electrophysiological properties of in vitro Purkinje cell somata in mammalian cerebellar slices", J. Physiol., Aug. 1980, vol. 305, pp. 171-195.
Yan, L. et al., "The spider toxin omega-Aga IIIA defines a high affinity site on neuronal high voltage-activated calcium channels", J. Biol. Chem., Jul. 14, 2000, vol. 275, No. 28, pp. 21309-21316.
Newcomb, R. et al., "Selective peptide antagonist of the class E calcium channel from the venom of the tarantula *Hysterocrates gigas*", Biochemistry, Nov. 3, 1998, vol. 37, No. 44, pp. 15353-15362.
Tottene, A. et al., "alpha(1 E) subunits form the pore of three cerebellar R-type calcium channels with different pharmacological and permeation properties", J. Neurosci., Jan. 1, 2000, vol. 20, No. 1, pp. 171-178.
Wang, G. et al., "An R-type Ca(2+) current in neurohypophysial terminals preferentially regulates oxytocin secretion", J. Neuroscience, Nov. 1, 1999, vol. 19, No. 21, pp. 9235-9241.
Coplin, W. M. et al., "Cerebrospinal fluid creatine kinase-BB isoenzyme activity and outcome after subarachnoid hemorrhage", Arch. Neurol., Nov. 1999, vol. 56, No. 11, pp. 1348-1352.
Langer, R., "New methods of drug delivery", Science, Sep. 28, 1990, vol. 248, No. 4976, pp. 1527-1533.
Sawhney, A.S. et al., "Bioerodible hydrogels based on photopolymerized poly(ethylene glycol)-co-poly(alpha.-hydroxyacid) diacrylate macromers", Macromolecules, 1993, vol. 26, No. 4, pp. 581-587.
Lilinas, R. et al., Blocking and isolation of a calcium channel from neurons in mammals and cephalopods utilizing a toxin fraction (FTX) from funnel-web spider poison, Proc. Natl. Acad. Sci. U.S.A., Mar. 1989, vol. 86, No. 5, pp. 1689-1693.
Kasuya et al. Efficacy and Safety of Nicardipine Prolonged-Release Implants for Preventing Vasospasm in Humans. Stroke 2002; 33: 1011-1015.
Barth et al. Effect of Nicardipine Prolonged Release Implant on Cerebral Vasospasm and Clinical Outcome After Severe Aneurysmal Subarachnoid Hemorrahge. Stroke 2007, 38 pp. 330-336; published online Dec. 2006.
European CGRP in Subarachnoid Haemorrhage Study Group, "Effect of calcitonin-gene-related peptide in patients with delayed postoperative cerebral ischaemia after aneurysmal subarachnoid haemorrhage," Lancet, (1992), vol. 339, pp. 831-834.
Dorhout Mees, S. et al., "Calcium antagonists for aneurysmal subarachnoid haemorrhage," Cochrane Database of Systemic Reviews, (2007), Issue 3, pp. 1-50.
Haley, E.G. Jr. et al., "A randomized trial of two doses of nicardipine in aneurysmal subarachnoid hemorrhage," J. Neurosurg., (1994), vol. 80, pp. 788-796.
Jang, Y.G., et al., "Metaanalysis of Tirilazad Mesylate in Patients with Aneurysmal Subarachnoid Hemorrhage," Neurocrit Care, (2009), vol. 10, 141-147.
Nieuwkamp, D.J. et al., "Changes in case fatality of aneurysmal subarachnoid haemorrhage over time, according to age, sex, and region: a meta-analysis," Lancet Neurol, (2009), vol. 8, pp. 635-642.
Van Gijn, J. and Rinkel G.J.E., "Subarachnoid haemorrhage: diagnosis, causes and management," Brain, (2001), vol. 124, pp. 249-278.
Vergouwen, M.D.I. et al., "Effect of Statin Treatment on Vasospasm, Delayed Cerebral Ischemia, and Functional Outcome in Patients With Aneurysmal Subarachnoid Hemorrhage: A Systemic Review and Meta-Analysis Update," Stroke, (2010), vol. 41, pp. e47-e52.
Wong, G.K.C. et al., "Intravenous Magnesium Sulfate for Aneurysmal Subarachnoid Hemorrhage (IMASH): A Randomized, Double-Blinded, Placebo-Controlled, Multicenter Phase III Trial," Stroke, (2010), vol. 41, pp. 921-926.
Wang, G, et.al. An R-Type Ca2+ Current in Neurohypophysial Terminals Preferentially Regulates Oxytocin Secretion. The Journal of Neuroscience, Nov. 1, 1999, 19(21): 9235-9241.
Fundamental Immunology, 4th Ed., William E. P. ed. Lippincott-Raven Pub, Philadelphia (1999) pp. 1051-1053.
Clozel, M. et al. BQ-123, "A Peptidic Endothelin Eta Receptor Antagonist, Prevents the Early Cerebral Vasospasm, Following Subarachnoid Hemorrhage After Intracisternal But Not Intravenous Injection." Life Sciences. 1993;52(9): 825-834.
Sato, S. et al. "Effects of an Endothelin Eta Receptor Antagonist, S-0139 on Cerebral Vasospasm and Behavioral Change in Dogs Intracisternally Administered Endothelin-1." Life Sciences, vol. 62 (13) PL191-PL197 (1998).
Office Action issued on Sep. 30, 2015 by the Japanese Patent Office for corresponding Japanese Patent Application No. 2013-553640.
Marbacher S., et al., "Prevention of delayed cerebral vasospasm by continuous intrathecal infusion of glycerol-trinate and nimodipine in the rabbit model in vivo", Intensive Care Medicine, 2008, pp. 932-938, vol. 34, Springer-Vertag.
Hanggi D., et al., "The effect of an intracisternal nimdipine slow-release system on cerebral vasospasm after experimental subarachnoid haemorrhage in the rat", Acta Neurochirugica Supplementum, 2008, pp. 103-107, vol. 104, Springer-Vertag.
Baumann M.D, et al, "Intrathecal delivery of a polymeric nanocomposite hydrogel after spinal cord injury", Biomaterials, 2010, pp. 7631-7639, Elsevier.
Mehta A.K., et al., "Nimodipine loaded PLGA nanoparticles: Formulation optimization using factoria design, characterization and in vitro evaluation", Current Drug Delivery, 2007, pp. 185-193, Bentham Science Publishers Ltd.
Rosenwasser R.H., et al., "Safety of intraventricular sodium nitroprusside and thiosulfate for the treatment of cerebral vasospasm in the intensive care unit", Stroke. 2002, pp. 165-166.
Yamaguchi M., et al., "Ras protein contributes to cerebral vasospasm in a canine double-hemorrhage model", Stroke, 2004, pp. 1750-1755, www.strokeha.org.
Kudo T., "Postoperative oculomotor palsy due to vasospasm in a patient with a ruptured internal carotid artery aneurysm: A case report", Neurosurgery, 1986, pp. 274-277, vol. 19, Congress of Neurological Surgeons.

\* cited by examiner

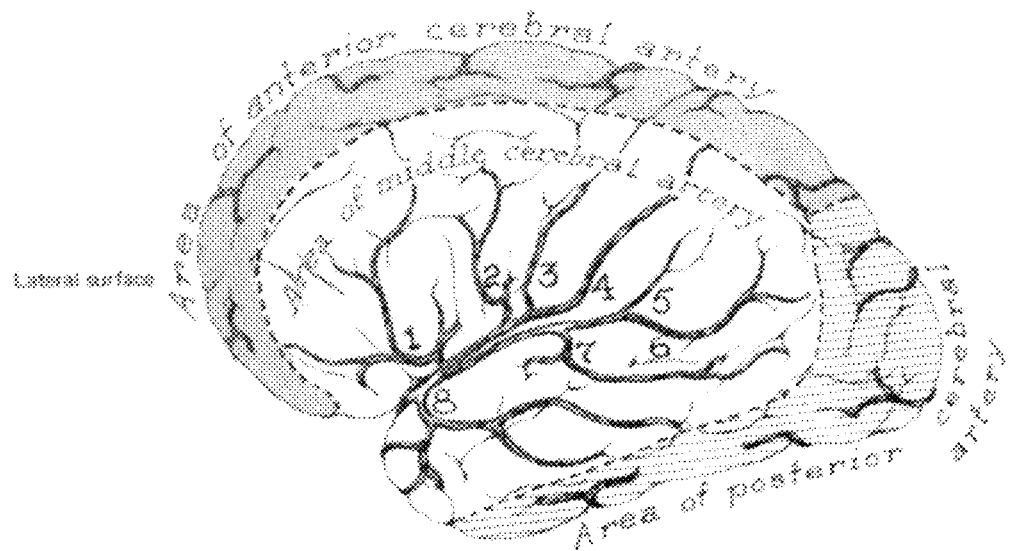
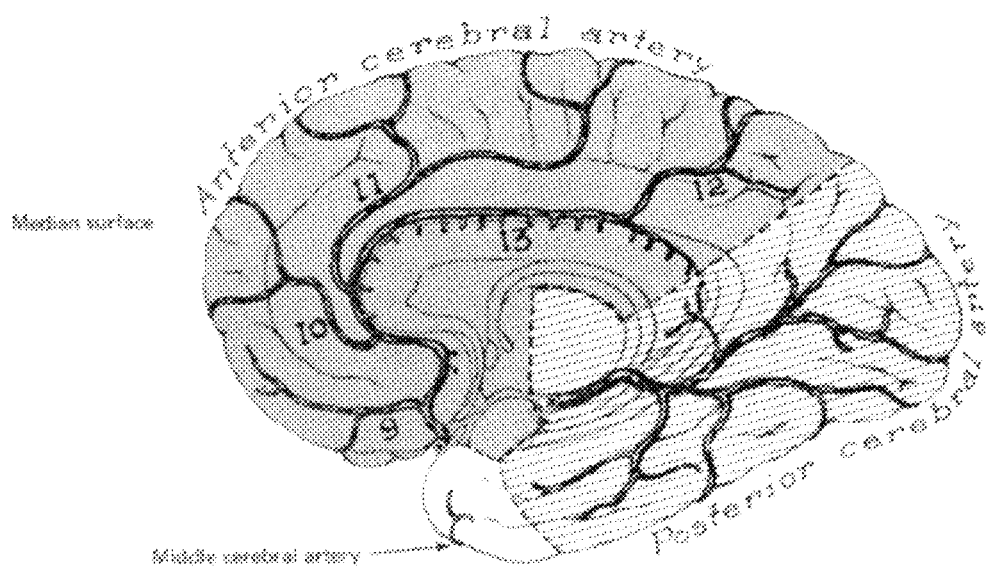
FIGURE 5

INTRAVENTRICULAR DRUG DELIVERY SYSTEM FOR IMPROVING OUTCOME AFTER A BRAIN INJURY AFFECTING CEREBRAL BLOOD FLOW

CROSS REFERENCE TO RELATED APPLICATIONS

This application claims the benefit of priority to U.S. Provisional Application No. 61/471,779 filed Apr. 5, 2011, and is a continuation in part of U.S. application Ser. No. 12/137,320, entitled "A Drug Delivery System for the Prevention of Cerebral Vasospasm," filed Jun. 11, 2008, which claims the benefit to priority of U.S. Provisional Application No. 60/976,902 (filed Oct. 29, 2007) and No. 60/943,124 (filed Jun. 11, 2007). The content of each of these applications is incorporated by reference herein in its entirety.

FIELD OF INVENTION

The present invention relates to a delivery system for therapeutic agents delivered locally to the cerebral arteries to prevent or reduce the incidence or severity of adverse consequences of subarachnoid hemorrhage resulting from a disease, disorder or condition, or injury.

BACKGROUND OF THE INVENTION

Central Nervous System

The central nervous system is a bilateral and essentially symmetrical structure with seven main parts: the spinal cord, medulla oblongata, pons, cerebellum, midbrain, diencephalon, and the cerebral hemispheres. FIG. 1 shows a lateral view of the human brain from Stedman's Medical Dictionary, $27^{th}$ Edition, plate 7 at A7 (2000).

The spinal cord, the most caudal part of the central nervous system, receives and processes sensory information from the skin, joints, and muscles of the limbs and trunk and controls movement of the limbs and the trunk. It is subdivided into cervical, thoracic, lumbar and sacral regions. The spinal cord continues rostrally as the brainstem, which consists of the medulla, pons, and midbrain. The brainstem receives sensory information from the skin and muscles of the head and provides the motor control for the muscles of the head. It also conveys information from the spinal cord to the brain and from the brain to the spinal cord, and regulates levels of arousal and awareness through the reticular formation. The brainstem contains several collections of cell bodies, the cranial nerve nuclei. Some of these receive information from the skin and muscles of the head; others control motor output to muscles of the face, neck and eyes. Still others are specialized for information from the special senses: hearing, balance and taste. (Kandel, E. et al., Principles of Neural Science, $4^{th}$ Ed., p. 8, 2000).

The medulla oblongata, which lies directly rostral to the spinal cord, includes several centers responsible for vital autonomic functions, such as digestion, breathing and the control of heart rate (Kandel, E. et al., Principles of Neural Science, $4^{th}$ Ed., p. 8, 2000).

The pons, which lies rostral to the medulla, conveys information about movement from the cerebral hemispheres to the cerebellum (Kandel, E. et al., Principles of Neural Science, $4^{th}$ Ed., p. 8, 2000).

The cerebellum lies behind the pons and is connected to the brain stem by several major fiber tracts called peduncles. The cerebellum modulates the force and range of movement, and is involved in the learning of motor skills. It also contributes to learning and cognition (Kandel, E. et al., Principles of Neural Science, $4^{th}$ Ed., p. 8, 2000).

The midbrain, which lies rostral to the pons, controls many sensory and motor functions, including eye movements and the coordination of visual and auditory reflexes (Kandel, E. et al., Principles of Neural Science, $4^{th}$ Ed., p. 8, 2000).

The diencephalon lies rostral to the midbrain and contains two structures. One, the thalamus, processes most of the information reaching the cerebral cortex from the rest of the central nervous system and is involved in other functions including motor control, autonomic function and cognition. The other, the hypothalamus, regulates autonomic, endocrine, and visceral function (Kandel, E. et al., Principles of Neural Science, $4^{th}$ Ed., p. 8, 2000).

The cerebral hemispheres consist of a heavily wrinkled outer layer, the cerebral cortex, and deep-lying gray-matter structures—the basal ganglia, which participate in regulating motor performance; the hippocampus, which is involved with aspects of learning and memory storage; and the amygdaloid nuclei, which coordinate the autonomic and endocrine responses of emotional states (Kandel, E. et al., Principles of Neural Science, $4^{th}$ Ed., p. 8, 2000).

The cerebral cortex is divided into four lobes: the frontal lobe, parietal lobe, temporal lobe and occipital lobe. The surfaces of the cerebral hemispheres contain many grooves or furrows, known as fissures and sulci. The portions of brain lying between these grooves are called convolutions or gyri. The lateral cerebral fissure (fissure of Sylvius) separates the temporal from the frontal lobe. The central sulcus (Rolandic sulcus) separates the frontal from the parietal lobe (Kandel, E. et al., Principles of Neural Science, $4^{th}$ Ed., p. 8, 2000).

1. Meninges of the Brain

The meninges, three distinct connective tissue membranes that enclose and protect the brain and spinal cord, are named (from outer to inner layer) the dura mater, the arachnoid, and the pia mater. FIG. 2 shows an illustrative sagittal view of the human brain (J. G. Chusid, Correlative Neuroanatomy & Functional Neurology, $18^{th}$ Ed., p. 46, 1982). FIG. 3 is a drawing of a cross section of the three meningeal layers that cover the brain (Haines, D. E., Anatomical Record 230: 3-21, 1991). The dura mater sends inward four processes that divide the cavity of the skull into a series of freely communicating compartments and further provides for the protection of the different parts of the brain.

1.1. Dura Mater

The dura mater is a dense fibrous structure that covers the brain and spinal cord. It has an inner meningeal and an outer periosteal or endosteal layer. The dural layers over the brain generally are fused, except where they separate to provide space for the venous sinuses and where the inner layer forms septa between brain portions. The outer layer attaches firmly to the inner surface of the cranial bones and sends vascular and fibrous extensions into the bone itself. Around the margin of the foramen magnum (the large opening in the base of the skull forming the passage from the cranial cavity to the spinal cavity) it is closely adherent to the bone, and is continuous with the spinal dura mater.

The cranial dura mater consists of fibroblasts, abundant extracellular collagen and a few elastic fibers arranged in flattened laminae which are imperfectly separated by lacunar spaces and blood vessels into two layers: an inner (meningeal) layer and an outer (endosteal) layer, closely connected together, except in certain situations, where they separate to form sinuses for the passages of venous blood or form septae between portions of the brain. The outer surface of the dura mater is rough and fibrillated (composed of fibers), and adheres closely to the inner surfaces of the bones, the adhesions being most marked opposite the cranial sutures (the immovable joints between the bones of the skull or cranium). The endosteal layer is the internal periosteum for the cranial bones, and contains the blood vessels for their supply. The meningeal layer is lined on its inner surface by a layer of unique elongated, flattened fibroblasts that have been called dural border cells. There is no collagen in this layer and the cells are not connected by cell junctions. They are frequently separated by extracellular spaces filled with amorphous non-filamentous material. The meningeal layer further comprises two lamellas: the compact lamella and the loose lamella; the former generally contains tight fibrous tissue and few blood vessels, but the latter contains some blood vessels.

The processes of the cranial dura mater, which project into the cavity of the skull, are formed by reduplications of the inner (or meningeal) layer of the membrane. These processes include: (1) the falx cerebri, (2) the tentorium cerebelli, (3) the falx cerebelli, and (4) the diaphragma sellae.

The falx cerebri is a strong, arched process with a sickle-like form which descends vertically in the longitudinal fissure between the cerebral hemispheres. It is narrow in front, where it is attached to the ethmoid bone (the bone at the base of the cranium and the root of the nose) at the crista galli (the triangular midline process of the ethmoid bone); and broad behind, where it is connected with the upper surface of the tentorium cerebelli (an arched fold of dura mater that covers the upper surface of the cerebellum). Its upper margin is convex, and attached to the inner surface of the skull in the middle line, as far back as the internal occipital protuberance; it contains the superior sagittal sinus. Its lower margin is free and concave, and contains the inferior sagittal sinus.

The tentorium cerebelli is an arched lamina, elevated in the middle, and inclining downward toward the circumference. It covers the superior surface of the cerebellum, and supports the occipital lobes of the brain. Its anterior border is free and concave, and bounds a large oval opening (the incisura tentorii) for the transmission of the cerebral peduncles (the massive bundle of corticofugal nerve fibers passing longitudinally over the ventral surface of the midbrain on each side of the midline) as well as ascending sensory and autonomic fibers and other fiber tracts. The tentorium cerebelli is attached behind, by its convex border, to the transverse ridges upon the inner surface of the occipital bone, and there encloses the transverse sinuses; and, in front, to the superior angle of the petrous part of the temporal bone on either side, enclosing the superior petrosal sinuses. At the apex of the petrous part of the temporal bone, the free and attached borders meet, and, crossing one another, are continued forward to be fixed to the anterior and posterior clinoid processes respectively. The posterior border of the falx cerebri is attached to the middle line of its upper surface. The straight sinus is placed at the junction of the falx cerebri and the tentorium cerebelli.

The falx cerebelli is a small triangular process of dura mater that separates the two cerebellar hemispheres. Its base is attached, above, to the under and back part of the tentorium; and its posterior margin is attached to the lower division of the vertical crest on the inner surface of the occipital bone. As it descends, it sometimes divides into two smaller folds, which are lost on the sides of the foramen magnum.

The diaphragma sellae is a small circular horizontal fold, which roofs in the sella turcica (a saddlelike prominence on the upper surface of the sphenoid bone of the skull, situated in the middle cranial fossa and dividing it into two halves) and almost completely covers the pituitary gland (hypophysis); a central opening of variable size transmits the infundibulum (a funnel-shaped extension of the hypothalamus connecting the pituitary gland to the base of the brain).

The arteries of the dura mater are numerous. The meningeal branches of the anterior and posterior ethmoidal arteries and of the internal carotid artery, and a branch from the middle meningeal artery supply the dura of the anterior cranial fossa. The middle and accessory meningeal arteries of the internal maxillary artery; a branch from the ascending pharyngeal artery, which enters the skull through the foramen lacerum; branches from the internal carotid artery, and a recurrent branch from the lacrimal artery supply the dura of the middle cranial fossa. Meningeal branches from the occipital artery, one entering the skull through the jugular foramen, and another through the mastoid foramen; the posterior meningeal artery from the vertebral artery; occasional meningeal branches from the ascending pharyngeal artery, entering the skull through the jugular foramen and hypoglossal canal; and a branch from the middle meningeal artery supply the dura of the posterior cranial fossa.

The veins returning the blood from the cranial dura mater anastomose with the diploic veins or end in the various sinuses. Many of the meningeal veins do not open directly into the sinuses, but open indirectly through a series of ampullae, termed venous lacunae. These are found on either side of the superior sagittal sinus, especially near its middle portion, and are often invaginated by arachnoid granulations; they also exist near the transverse and straight sinuses. They communicate with the underlying cerebral veins, and also with the diploic and emissary veins.

The nerves of the cranial dura mater are filaments derived from the trigeminal, glossopharyngeal, vagal, second and third spinal, sphenopalatine, otic, and superior cervical ganglia and supply unmyelinated and myelinated sensory and autonomic fibers.

1.2. Arachnoid

The middle meningeal layer, the arachnoid, is a delicate avascular membrane lying between the pia mater and the dura mater. It is separated from the overlying dura mater by the subdural space and from the underlying pia mater by the subarachnoid space, which contains cerebrospinal fluid.

The arachnoid consists of an outer cell layer of low cuboidal mesothelium. There is a space of variable thickness filled with cerebrospinal fluid and traversed by trabeculae and membranes consisting of collagen fibrils and cells resembling fibroblasts. The inner layer and the trabecula are covered by a somewhat low type of cuboidal mesothelium, which in places are flattened to a pavement type and blends on the inner deep layer with the cells of the pia mater. The arachnoid further contains a plexus of nerves derived from the motor root of the trigeminal, the facial, and the accessory cranial nerves.

The cranial part (arachnoidea encephali) of the arachnoid invests the brain loosely, and does not dip into the sulci (depressions or fissures in the surface of the brain) between the gyri (upraised folds or elevations in the surface of the brain), nor into the fissures, with the exception of the longitudinal fissure and several other larger sulci and fissures. On the upper surface of the brain, the arachnoid is thin and transparent; at the base it is thicker. It is slightly opaque toward the central part of the brain, where it extends across between the two temporal lobes in front of the pons so as to leave a considerable space between the pons and the brain.

The arachnoid surrounds the cranial and spinal nerves, and encloses them in loose sheaths as far as their points of exit from the skull.

Subarachnoid Cavity

The subarachnoid cavity or subarachnoid space, which is the space between the outer cellular layer of the arachnoid and the pia mater, is occupied by tissue consisting of trabeculae of delicate connective tissue and intercommunicating channels in which the cerebrospinal fluid is contained. This cavity is small on the surface of the hemispheres of the brain; on the summit of each gyms, the pia mater and the arachnoid are in close contact, but triangular spaces are left in the sulci between the gyri, in which the subarachnoid trabecular tissue is found, because the pia mater dips into the sulci, whereas the arachnoid bridges across them from gyms to gyms. At certain parts of the base of the brain, the arachnoid is separated from the pia mater by wide intervals, which communicate freely with each other and are named subarachnoid cisternae; the subarachnoid tissue in these cisternae is less abundant.

Subarachnoid Cisternae (Cisternae Subarachnoidales)

The cisterna cerebellomedullaris (cisterna magna) is triangular on sagittal section, and results from the arachnoid bridging over the space between the medulla oblongata and the under surfaces of the hemispheres of the cerebellum; it is continuous with the subarachnoid cavity of the spinal cord at the level of the foramen magnum.

The cisterna pontis is a considerable space on the ventral aspect of the pons. It contains the basilar artery, and is continuous caudal to the pons with the subarachnoid cavity of the spinal cord, and with the cisterna cerebellomedullaris; in front of the pons, it is continuous with the cisterna interpeduncularis.

The cisterna interpeduncularis (cisterna basalis) is a wide cavity where the arachnoid extends across between the two temporal lobes. It encloses the cerebral peduncles and the structures contained in the interpeduncular fossa, and contains the arterial circle of Willis. In front, the cisterna interpeduncularis extends forward across the optic chiasma, forming the cisterna chiasmatis, and on to the upper surface of the corpus callosum. The arachnoid stretches across from one cerebral hemisphere to the other immediately beneath the free border of the falx cerebri, and thus leaves a space in which the anterior cerebral arteries are contained. The cisterna fossae cerebri lateralis is formed in front of either temporal lobe by the arachnoid bridging across the lateral fissure. This cavity contains the middle cerebral artery. The cisterna venae magnae cerebri occupies the interval between the splenium of the corpus callosum and the superior surface of the cerebellum; it extends between the layers of the tela chorioidea of the third ventricle and contains the great cerebral vein.

The subarachnoid cavity communicates with the general ventricular cavity of the brain by three openings; one, the foramen of Majendie, is in the middle line at the inferior part of the roof of the fourth ventricle; the other two (the foramina of Luschka) are at the extremities of the lateral recesses of that ventricle, behind the upper roots of the glossopharyngeal nerves.

The arachnoid villi are tufted prolongations of pia-arachnoid that protrude through the meningeal layer of the dura mater and have a thin limiting membrane. Tufted prolongations of pia-arachnoid composed of numerous arachnoid villi that penetrate dural venous sinuses and effect transfer of cerebrospinal fluid to the venous system are called arachnoid granulations.

An arachnoidal villus represents an invasion of the dura by the arachnoid membrane, whereby arachnoid mesothelial cells come to lie directly beneath the vascular endothelium of the great dural sinuses. Each villus consists of the following parts: (1) in the interior is a core of subarachnoid tissue, continuous with the meshwork of the general subarachnoid tissue through a narrow pedicle, by which the villus is attached to the arachnoid; (2) around this tissue is a layer of arachnoid membrane, limiting and enclosing the subarachnoid tissue; (3) outside this is the thinned wall of the lacuna, which is separated from the arachnoid by a potential space, which corresponds to and is continuous with the potential subdural space; and (4) if the villus projects into the sagittal sinus, it will be covered by the greatly thinned wall of the sinus, which may consist merely of endothelium. Fluid injected into the subarachnoid cavity will find its way into these villi. Such fluid passes from the villi into the venous sinuses into which they project.

1.3. Pia Mater

The pia mater is a thin connective tissue membrane that is applied to the surface of the brain and spinal cord. Blood vessels supplying the brain travel through the pia into the brain. The pia mater is absent at the foramen of Majendie and the two foramina of Luschka and is perforated by all the blood vessels as they enter or leave the nervous system, and therefore is considered to be an incomplete membrane. In perivascular spaces, the pia apparently enters as a mesothelial lining of the outer surface of the space; a variable distance from the exterior, these cells become unrecognizable and are apparently lacking, replaced by neuroglia elements. The inner walls of the perivascular spaces likewise seem to be covered for a certain distance by the mesothelial cells, reflected with the vessels from the arachnoid covering of these vascular channels as they traverse the subarachnoid spaces.

The cranial pia mater (pia mater encephali; pia of the brain) invests the entire surface of the brain, dips between the cerebral gyri and cerebellar laminae, and is invaginated to form the tela chorioidea of the third ventricle, and the choroid plexuses of the lateral and third ventricles. As it passes over the roof of the fourth ventricle, it forms the tela chorioidea and the choroid plexuses of the fourth ventricle. On the cerebellum the membrane is more delicate; the vessels from its deep surface are shorter, and its relations to the cortex are not so intimate.

The pia mater forms sheaths for the cranial nerves

2. Circulation of the Brain

FIGS. 4, 5, 6 and 7 show schematic illustrations of the brain's blood vessels. Each cerebral hemisphere is supplied by an internal carotid artery, which arises from a common carotid artery beneath the angle of the jaw, enters the cranium through the carotid foramen, traverses the cavernosus sinus (giving off the ophthalmic artery), penetrates the dura and divides into the anterior and middle cerebral arteries. The large surface branches of the anterior cerebral artery supply the cortex and white matter of the inferior frontal lobe, the medial surface of the frontal and parietal lobes and the anterior corpus callosum. Smaller penetrating branches supply the deeper cerebrum and diencephalon, including limbic structures, the head of the caudate, and the anterior limb of the internal capsule. The large surface branches of the middle cerebral artery supply most of the cortex and white matter of the hemisphere's convexity, including the frontal, parietal, temporal and occipital lobes, and the insula. Smaller penetrating branches supply the deep white matter and diencephalic structures such as the posterior limb of the internal capsule, the putamen, the outer globus pallidus, and the body of the caudate. After the internal carotid artery emerges from the cavernous sinus, it also gives off the anterior choroidal artery, which supplies the anterior hippocampus and, at a caudal level, the posterior limb of the internal capsule. Each vertebral artery arises from a subclavian artery, enters the cranium through the foramen magnum, and gives off an anterior spinal artery and a posterior inferior cerebellar artery. The vertebral arteries join at the junction of the pons and the medulla to form the basilar artery, which at the level of the pons gives off the anterior inferior cerebellar artery and the internal auditory artery, and, at the midbrain, the superior cerebellar artery. The basilar artery then divides into the two posterior cerebral arteries. The large surface branches of the posterior cerebral arteries supply the inferior temporal and medial occipital lobes and the posterior corpus callosum; the smaller penetrating branches of these arteries supply diencephalic structures, including the thalamus and the subthalamic nuclei, as well as part of the midbrain (see Principles of Neural Sciences, 2d Ed., Eric R. Kandel and James H. Schwartz, Elsevier Science Publishing Co., Inc., New York, pp. 854-56 (1985)).

Interconnections between blood vessels (anastomoses) protect the brain when part of its vascular supply is compromised. Anastomoses are interconnections between blood vessels that protect the brain when part of its vascular supply is compromised. At the circle of Willis, the two anterior cerebral arteries are connected by the anterior communicating artery and the posterior cerebral arteries are connected to the internal carotid arteries by the posterior communicating arteries. Other important anastomoses include connections between the ophthalmic artery and branches of the external carotid artery through the orbit, and connections at the brain surface between branches of the middle, anterior, and posterior cerebral arteries (Principles of Neural Sciences, 2d Ed., Eric R. Kandel and James H. Schwartz, Elsevier Science Publishing Co., Inc., New York, pp. 85456 (1985)).

The circle of Willis at the base of the brain is the principal arterial anastomotic trunk of the brain. Blood reaches it mainly via the vertebral and internal carotid arteries (See FIG. 4); anastomoses occur between arterial branches of the circle of Willis over the cerebral hemispheres and via extracranial arteries that penetrate the skull through various foramina.

The circle of Willis is formed by anastamoses between the internal carotid, basilar, anterior cerebral, anterior communicating, posterior cerebral, and posterior communicating arteries. The internal carotid artery terminates in the anterior cerebral and middle cerebral arteries. Near its termination, the internal carotid artery gives rise to the posterior communicating artery, which joins caudally with the posterior cerebral artery. The anterior cerebral arteries connect via the anterior communicating artery.

2.1. Cerebral Arteries

The blood supply to the cerebral cortex mainly is via cortical branches of the anterior cerebral, middle cerebral, and posterior cerebral arteries, which reach the cortex in the pia mater. FIG. 5 shows an illustrative view of the arterial supply of the cerebral cortex where 1 is the orbitofrontal artery; 2 is the prerolandic artery; 3 is the rolandic artery; 4 is the anterior parietal artery; 5 is the posterior parietal artery; 6 is the angular artery; 7 is the posterior temporal artery; 8 is the anterior temporal artery; 9 is the orbital artery; 10 is the frontopolar artery; 11 is the callosomarginal artery; 12 is the posterior internal frontal artery; and 13 is the pericallosal artery (Correlative Neuroanatomy & Functional Neurology, 18$^{th}$ Ed., p. 50, 1982).

The lateral surface of each cerebral hemisphere is supplied mainly by the middle cerebral artery. The medial and inferior surfaces of the cerebral hemispheres are supplied by the anterior cerebral and posterior cerebral arteries.

The middle cerebral artery, a terminal branch of the internal carotid artery, enters the lateral cerebral fissure and divides into cortical branches that supply the adjacent frontal, temporal, parietal and occipital lobes. Small penetrating arteries, the lenticulostriate arteries, arise from the basal portion of the middle cerebral artery to supply the internal capsule and adjacent structures.

The anterior cerebral artery extends medially from its origin from the internal carotid artery into the longitudinal cerebral fissure to the genu of the corupus callosum, where it turns posteriorly close to the corpus callosum. It gives branches to the medial frontal and parietal lobes and to the adjacent cortex along the medial surface of these lobes.

The posterior cerebral artery arises from the basilar artery at its rostral end usually at the level of the midbrain, curves dorsally around the cerebral peduncle, and sends branches to the medial and inferior surfaces of the temporal lobe and to the medial occipital lobe. Branches include the calcarine artery and perforating branches to the posterior thalamus and subthalamus.

The basilar artery is formed by the junction of the vertebral arteries. It supplies the upper brain stem via short paramedian, short cicumferential, and long circumferential branches.

The midbrain is supplied by the basilar, posterior cerebral, and superior cerebellar arteries. The pons is supplied by the basilar, anterior cerebellar, inferior cerebellar, and superior cerebellar arteries. The medulla oblongata is supplied by the vertebral, anterior spinal, posterior spinal, posterior inferior cerebellar, and basilar arteries. The cerebellum is supplied by the cerebellar arteries (superior cerebellar, anterior inferior cerebellar, and posterior inferior cerebellar arteries).

The choroid plexuses of the third and lateral ventricles are supplied by brances of the internal carotid and posterior cerebral arteries. The choroid plexus of the fourth ventricle is supplied by the posterior inferior cerebellar arteries.

Venous drainage from the brain chiefly is into the dural sinuses, vascular channels lying within the tough structure of the dura. The dural sinuses contain no valves and, for the most part, are triangular in shape. The superior longitudinal sinus is in the falx cerebri.

The human brain constitutes only about 2% of the total weight of the body, but it receives about 15% of cardiac output, and its oxygen consumption is approximately 20% of that for the total body. These values indicate the high metabolic rate and oxygen requirement of the brain that are compensated by a correspondingly high rate of blood flow per unit brain weight. Cerebral circulation is supplied by the internal carotid arteries and the vertebral arteries. The total blood flow to the brain is about 750-1000 ml/min; of this amount about 350 ml flows through each internal carotid artery and about 100-200 ml flows through the vertebral basilar system. The venous outflow is drained by the internal jugular veins and the vertebral veins.

The term "stroke" or "cerebrovascular accident" as used herein refers to the neurological symptoms and signs, usually focal and acute, that result from diseases involving blood vessels. Strokes are either occlusive (due to closure of a blood vessel) or hemorrhagic (due to bleeding from a vessel). The term "ischemia" as used herein refers to a lack of blood supply and oxygen that occurs when reduced perfusion pressure distal to an abnormal narrowing (stenosis) of a blood vessel is not compensated by autoregulatory dilation of the resistance vessels. When ischemia is sufficiently severe and prolonged, neurons and other cellular elements die; this condition is referred to as "infarction."

Hemorrhage may occur at the brain surface (extraparenchymal), for example from the rupture of congenital aneurysms at the circle of Willis, causing subarachnoid hemorrhage (SAH). Hemorrhage also may be intraparenchymal, for example from rupture of vessels damaged by long-standing hypertension, and may cause a blood clot (intracerebral hematoma) within the cerebral hemispheres, in the brain stem, or in the cerebellum. Hemorrhage may be accompanied by ischemia or infarction. The mass effect of an intracerebral hematoma may compromise the blood supply of adjacent brain tissue; or subarachnoid hemorrhage may cause reactive vasospasm of cerebral surface vessels, leading to further ischemic brain damage. Infarcted tissue may also become secondarily hemorrhagic. Aneurysms occasionally can rupture into the brain, causing an intracerebral hematoma, and into the cerebral ventricles, causing intraventricular hemorrhage.

Although most occlusive strokes are due to atherosclerosis and thrombosis and most hemorrhagic strokes are associated with hypertension or aneurysms, strokes of either type may occur at any age from many causes, including, without limitation: cardiac disease, trauma, infection, neoplasm, blood dyscrasia, vascular malformation, immunological disorder, and exogenous toxins.

2.2. Vasoconstriction and Vasodilation

The term "vasoconstriction" as used herein refers to the narrowing of the blood vessels resulting from contracting of the muscular wall of the vessels. When blood vessels constrict, the flow of blood is restricted or slowed. The term "vasodilation", which is the opposite of vasoconstriction as used herein, refers to the widening of blood vessels. The terms "vasoconstrictors," "vasopressors," or "pressors" as used herein refer to factors causing vasoconstriction. Vasoconstriction usually results in an increase of blood pressure and may be slight or severe. Vasoconstriction may result from disease, medication, or psychological conditions. Medications that cause vasoconstriction include, but are not limited to, catecholamines, antihistamines, decongestants, methylphenidate, cough and cold combinations, pseudoephedrine, and caffeine.

A vasodilator is a drug or chemical that relaxes the smooth muscle in blood vessels causing them to dilate. Dilation of arterial blood vessels (mainly arterioles) leads to a decrease in blood pressure. The relaxation of smooth muscle relies on removing the stimulus for contraction, which depends predominately on intracellular calcium ion concentrations and phosphorylation of myosin light chain (MLC). Thus, vasodilation predominantly works either 1) by lowering intracellular calcium concentration, or 2) by dephosphorylation of MLC, which includes the stimulation of myosin light chain phosphatase and the induction of calcium symporters and antiporters (which pump calcium ions out of the intracellular compartment). The re-uptake of ions into the sarcoplasmic reticulum of smooth muscle via exchangers and expulsion of ions across the plasma membrane also helps to accomplish vasodilation. The specific mechanisms to accomplish these effects vary from vasodilator to vasodilator and may be grouped as endogenous and exogenous. The term "endogenous" as used herein refers to proceeding from within or derived internally; or resulting from conditions within the organism rather than externally caused. The term "exogenous" as used herein refers to originating from outside; derived externally; or externally caused rather than resulting from conditions within the organism.

Vasodilation directly affects the relationship between mean arterial pressure and cardiac output and total peripheral resistance (TPR). Cardiac output may be computed by multiplying the heart rate (in beats/minute) and the stroke volume (the volume of blood ejected during systole). TPR depends on several factors, including, but not limited to, the length of the vessel, the viscosity of blood (determined by hematocrit), and the diameter of the blood vessel. Blood vessel diameter is the most important variable in determining resistance. An increase in either cardiac output or TPR cause a rise in the mean arterial pressure. Vasodilators work to decrease TPR and blood pressure through relaxation of smooth muscle cells in the tunica media layer of large arteries and smaller arterioles.

Vasodilation occurs in superficial blood vessels of warm-blooded animals when their ambient environment is hot; this process diverts the flow of heated blood to the skin of the animal, where heat may be more easily released into the atmosphere. Vasoconstriction is the opposite physiological process. Vasodilation and vasoconstriction are modulated naturally by local paracrine agents produced by endothelial cells (e.g., bradykinin, adenosine, nitric oxide, endothelins), as well as by an organism's autonomic nervous system and adrenal glands, both of which secrete catecholamines, such as norepinephrine and epinephrine, respectively.

Vasodilators are used to treat conditions such as hypertension, where the patient has an abnormally high blood pressure, as well as angina and congestive heart failure, where maintaining a lower blood pressure reduces the patient's risk of developing other cardiac problems.

2.3. Cerebral Ventricles

Cerebral ventricles, which are chambers in the brain that contain cerebrospinal fluid, include two lateral ventricles, one third ventricle, and one fourth ventricle. The lateral ventricles are in the cerebral hemispheres. They drain via the foramen of Monroe into the third ventricle, which is located between the two diencephalic structures of the brain. The third ventricle lead, by way of the aqueduct of Sylvius, to the fourth ventricle. The fourth ventricle is in the posterior fossa between the brainstem and the cerebellum. The cerebrospinal fluid drains out of the fourth ventricle through the foramenae of Luschka and Magendie to the basal cisterns. The cerebrospinal fluid then percolates through subarachnoid cisterns and drains out via arachnoid villi into the venous system.

FIG. 8 is a diagram of the ventricular system of the brain. The system is a series of cavities (ventricles) within the brain and is continuous with both the subarachnoid space and central canal of the spinal cord. There are four cerebral ventricles: the right and left lateral ventricles, and the midline third and fourth ventricles. The two lateral ventricles are located within the cerebrum and each connects to the third ventricle through an interventricular foramen of Monroe. The third ventricle is located in the diencephalon and is connected to the fourth ventricle by the cerebral aqueduct of Sylvius. The fourth ventricle is located in the hind brain and it is continuous with the central canal of the spinal cord, at least embryologically. Three foramina connect the fourth ventricle to the subarachnoid space: the median aperture or foramen of Magendie, and left and right lateral apertures (foramena) of Luschka.

2.4. CSF Flow in the Brain

FIG. 9 shows an illustrative view of the CSF flow from the ventricles to the subarachnoid space. The cerebrospinal fluid (CSF) is a clear bodily fluid that occupies the ventricular system, subarachnoid space of the brain, and central canal of the spinal cord. CSF is produced by modified ependymal cells of the choroid plexus found throughout the ventricular system. In addition, it is also formed around blood vessels and ventricular walls, presumably from the extracellular space of the brain. CSF flows from the lateral ventricles via interventricular foramina into the third ventricle. CSF then flows into the fourth ventricle through the cerebral aqueduct. CSF flows out in the subarachnoid space via the median aperture and left and right lateral apertures. Finally, the CSF is reabsorbed into the dural venous sinuses through arachnoid granulations and arachnoid villi. Arachnoid granulations consist of collections of villi. The villi are visible herniations of the arachnoid membrane through the dura and into the lumen of the superior sagittal sinus and other venous structures. The granulations appear to function as valves that allow one-way flow of CSF from the subarachnoid spaces into venous blood. All constituents of CSF leave with the fluid, including small molecules, proteins, microorganisms, and red blood cells.

CSF is produced at a rate of approximately 0.3-0.37 ml/minute or 20 ml/hour or 500 ml/day. The volume of the CSF space is about 150 mls and the CSF turns over 3.7 times a day.

The choroid plexus uses capillary filtration and epithelial secretory mechanisms to maintain the chemical stability of the CSF. While the capillaries that traverse the choroid plexus are freely permeable to plasma solutes, a barrier exists at the level of the epithelial cells that make up the choroid plexus, which is responsible for carrier-mediated active transport. CSF and extracellular fluids of the brain are in a steady state and blood plasma and CSF are in osmotic equilibrium under normal physiological conditions.

2.5. Blood Brain Barrier

The blood brain barrier prevents entry of blood-borne substances into the brain and maintains a stable environment for neurons to function effectively. It results from specialized properties of brain microvessel endothelial cells, the principal anatomic site of the blood brain barrier, their intercellular junctions, and a relative lack of vesicular transport, which makes such cells different from those of general capillaries. Endothelial cells of blood-brain barrier vessels also are not fenestrated; instead they are interconnected by complex arrays of tight junctions, which block diffusion across the vessel wall.

3. Subarachnoid Hemorrhage

The term "subarachnoid hemorrhage" (also referred to as "SAH") refers to bleeding into the subarachnoid space. SAH may occur spontaneously, usually from a cerebral aneurysm, or may result from trauma. Symptoms include an intense headache with a rapid onset (sometimes referred to as a "thunderclap headache"), vomiting, and an altered level of consciousness. Diagnosis generally is made with computed tomography (CT scanning), or occasionally by lumbar puncture. Treatment is by close observation, medication and early neurosurgical investigations and treatments to prevent recurrence and complications. FIG. 10A shows a flow diagram for prognosis following subarachnoid hemorrhage and FIG. 10B shows a flow diagram of pathways proposed to be involved in delayed complications after subarachnoid hemorrhage.

SAH is a medical emergency and may lead to death or severe disability even if recognized and treated at an early stage. Half of all SAH cases are fatal, with 10-15% of patients dying before arriving at a hospital. SAH is considered a form of stroke, and causes between 1% and 7% of all strokes. Where caused by a rupture of an intracranial aneurysm, bleeding is seen in the subarachnoid space, and less commonly in the intraventricular and intracerebral spaces. Bleeding due to SAH may result in brain damage, brain shift, decreased cerebral perfusion and hydrocephalus. It is estimated that the incidence of SAH from a ruptured intracranial aneurysm in the U.S. is 1 case per 10,000 persons, yielding approximately 34,000 new cases of SAH each year. These ruptured aneurysms have a 30-day mortality rate of 45%. Further, an estimated 30% of survivors will have moderate-to-severe disability. FIG. 11 shows time trends in outcome of subarachnoid hemorrhage in seven population-based studies of subarachnoid hemorrhage (SAH), which shows 50% decrease in mortality over 20 years.

Some studies indicate the incidence of SAH is on average 9.1 per 100,000 annually. Studies from Japan and Finland show higher rates in those countries (22.7 per 100,000 and 19.7 per 100,000, respectively), for reasons that are not entirely understood. South and Central America, in contrast, have a rate of 4.2 per 100,000 on average. The group of people at risk for SAH is younger than the population usually affected by stroke, but the risk still increases with age. Young people are much less likely than middle-aged people (risk ratio 0.1, or 10%) to suffer a SAH. The risk continues to rise with age and is 60% higher in the very elderly (over 85) than in those between 45 and 55. Risk of SAH is about 25% higher in women above 55, possibly reflecting the hormonal changes that result from the menopause.

Patients who survive SAH also are at risk of secondary complications. Among these complications are, most notably, aneurysmal re-bleeding, angiographic cerebral vasospasm and delayed cerebral ischemia (DCI).

DCI is the occurrence of focal neurological impairment (such as hemiparesis, aphasia, apraxia, hemianopia, or neglect), and/or a decrease in the Glasgow coma scale (either the total score or one of its individual components [eye, motor on either side, verbal]). This may or may not last for at least one hour, is not apparent immediately after aneurysm occlusion and cannot be attributed to other causes by means of clinical assessment, CT or magnetic resonance imaging (MRI) scanning of the brain, and appropriate laboratory studies. Cerebral infarction may be a consequence of DCI, and infarction due to DCI is defined as the presence of an area of brain cell death resulting from a sudden insufficiency of arterial or venous blood supply on CT or MRI scan of the brain within 6 weeks after SAH, or on the latest CT or MRI scan made before death within 6 weeks, or proven at autopsy, not present on the CT or MRI scan between 24 and 48 hours after early aneurysm occlusion, and not attributable to other causes such as surgical clipping or endovascular treatment. Hypodensities on CT imaging resulting from ventricular catheter or intraparenchymal hematoma generally are not regarded as evidence of cerebral infarction from DCI. Angiographic cerebral vasospasm is a description of a radiological test (either CT angiography [CTA], MR angiography [MRA] MRA or catheter angiography [CA]), and may be a cause of DCI. The term "angiographic cerebral vasospasm" refers to the narrowing of the large capacitance arteries at the base of the brain (i.e., cerebral arteries) following hemorrhage into the subarachnoid space, and leads to reduced perfusion of distal brain regions. Angiographic vasospasm is a consequence of SAH, but also can occur after any condition that deposits blood in the subarachnoid space.

Symptoms

The classic symptom of SAH is thunderclap headache (a headache described as the "worst ever" or an "explosion in the head," developing over seconds to minutes) although it is a symptom in only about a third of all SAH patients. Approximately 10% of patients who seek medical care with this symptom have an underlying SAH. Patients also may present with vomiting, and 1 in 14 have seizures. Neck stiffness and other signs of meningism may be present, as may confusion, decreased level of consciousness, or coma. Intraocular hemorrhage may occur in response to the raised pressure around the brain. Subhyaloid (the hyaloid membrane envelopes the vitreous body of the eye) and vitreous hemorrhage may be visible on fundoscopy. This is known as Terson syndrome (occurring in 3-13% of cases), and is more common in more severe SAH. In a patient with thunderclap headache, none of the aforementioned signs are helpful in confirming or ruling out hemorrhage, although seizures are more common if the bleeding is the result of a ruptured aneurysm as opposed to other causes. Oculomotor nerve abnormalities (affected eye movement downward and outward, inability to lift the eyelid on the same side but normal pupillary reflexes) may indicate bleeding from an aneurysm arising near the posterior communicating artery. Isolated dilation of a pupil may also reflect brain herniation as a result of increased intracranial pressure.

The body releases large amounts of adrenaline and similar hormones as a result of the bleeding, which leads to a sharp increase in the blood pressure. The heart comes under substantial strain, and neurogenic pulmonary edema, stunned myocardium, cardiac arrhythmias, electrocardiographic changes (with occasional giant inverted "cerebral" T waves) and cardiac arrest (3%) may rapidly occur after the onset of hemorrhage.

SAH also may occur in people who have suffered a head injury. Symptoms may include headache, decreased level of consciousness or hemiparesis. SAH is regarded as a severe complication of head injury, especially if it is associated with lower Glasgow Coma Scale levels.

Diagnosis

The initial steps for evaluating a person with a suspected SAH are the steps of obtaining a medical history and performing a physical examination. Since only 10-25% of patients admitted to a hospital with a thunderclap headache are suffering from a SAH, other possible causes usually are considered simultaneously, such as meningitis, migraine, and cerebral venous sinus thrombosis. Intracerebral hemorrhage, which is twice as common as SAH, occasionally is misdiagnosed as SAH.

A diagnosis of SAH cannot be made on clinical grounds alone. Generally, medical imaging [usually computed tomography (CT scan) which has a high sensitivity (>95% correct identification especially on the first day after the onset of bleeding)] of the brain is required to confirm or exclude bleeding. Magnetic resonance imaging (MRI scan) may be more sensitive after several days when compared to CT scan. In people with normal CT or MRI scans, lumbar puncture, in which cerebrospinal fluid (CSF) is removed with a needle from the lumbar sac, shows evidence of hemorrhage in 3% of the group in whom the CT was found to be normal; lumbar puncture is therefore regarded as mandatory if imaging is negative. The CSF sample is examined for xanthochromia, the yellow appearance of centrifugated fluid, or by using spectrophotometry for bilirubin, a breakdown product of hemoglobin in the CSF.

After an SAH is confirmed, its origin needs to be determined. CT angiography (visualizing blood vessels with radiocontrast on a CT scan) to identify aneurysms is generally the first step, although the more invasive catheter angiography (injecting radiocontrast through a catheter advanced to the brain arteries) is the gold standard test but has a higher risk of complications. The latter is useful if there are plans to obliterate the source of bleeding, such as an aneurysm, at the same time.

Causes

Spontaneous SAH most often is due to rupture of cerebral aneurysms (85%). Cerebral aneurysms are weaknesses in the walls of arteries of the brain that become enlarged. They tend to be located in the circle of Willis and its branches. While most cases of SAH are due to bleeding from small aneurysms, larger aneurysms (which are rarer) are more likely to rupture. No aneurysm is detected from the first angiogram in 15-20% of cases of spontaneous SAH. Non-aneurysmal perimesencephalic hemorrhage, in which the blood is limited to the area of the prepontine, interpeduncular and adjacent subarachnoid cisterns, causes another 10% of SAH cases. In these, no aneurysms are generally found. The remaining 5% of cases are due to vasculitic damage to arteries, other disorders affecting the vessels, disorders of the spinal cord blood vessels, and bleeding into various tumors. Most traumatic SAHs occur near a skull fracture or intracerebral contusion.

Classification

Several grading scales are available for SAH. These have been derived by retrospectively matching characteristics of patients with their outcomes. In addition to the ubiquitously used Glasgow Coma Scale (GCS), three other specialized scores are in use. In all scores, a higher number is associated with a worse outcome. A scale of severity was described by Hunt and Hess in 1968 ("Hunt and Hess scale") and categorizes the clinical condition of the patient. The Fisher Grade classifies the appearance of SAH on CT scan. The Fisher scale has been modified by Claassen and coworkers ("Claassen scale"), reflecting the additive risk from SAH size and accompanying intraventricular hemorrhage. The World Federation of Neurological Surgeons classification uses GCS and focal neurological deficit to gauge severity of symptoms. A comprehensive classification scheme has been suggested by Ogilvy and Carter to predict outcome and gauge therapy. The Ogilvy system has five grades, assigning one point for the presence or absence of each of five factors: age greater than 50; Hunt and Hess grade 4 or 5; Fischer scale 3 or 4; aneurysm size greater than 10 mm; and posterior circulation aneurysm 25 mm or more.

Treatment

The management of SAH consists of general measures to stabilize the patient, specific measures to prevent rebleeding by obliterating the bleeding source, prevention of vasospasm, and prevention and treatment of complications.

General Measures

The first priority is to stabilize the patient. Those with a depressed level of consciousness may need to be intubated and mechanically ventilated. Blood pressure, pulse, respiratory rate and Glasgow Coma Scale are monitored frequently. Once the diagnosis is confirmed, admission to an intensive care unit may be preferable, especially given that 15% of such patients have a further episode (rebleeding) in the first hours after admission. Nutrition is an early priority, with oral or nasogastric tube feeding being preferable over parenteral routes. Analgesia (pain control) generally is restricted to non-sedating agents such as codeine, as sedation may impact mental status and thus interfere with the ability to monitor the level of consciousness. Deep vein thrombosis is prevented with compression stockings, intermittent pneumatic compression of the calves, or both.

Prevention of Rebleeding

Patients with a large hematoma associated with depressed level of consciousness or focal neurological symptoms may be candidates for urgent surgical removal of the blood and occlusion of the bleeding aneurysm. A catheter or tube may be inserted into the ventricles to treat hydrocephalus. The remainder are stabilized more extensively, and undergo a transfemoral catheter angiogram or CT angiogram later. After the first 24 hours, rebleeding risk remains about 40% over the subsequent four weeks, suggesting that interventions should be aimed at reducing this risk.

Rebleeding is hard to predict but may happen at any time and carries a dismal prognosis. Interventions to prevent rebleeding, therefore are performed as early as possible. If a cerebral aneurysm is identified on angiography, two measures are available to reduce the risk of further bleeding from the same aneurysm: neurosurgical clipping and endovascular coiling. Clipping requires a craniotomy (opening of the skull) to locate the aneurysm, followed by the placement of a clip or clips across the neck of the aneurysm. Coiling is performed through the large blood vessels: a catheter is inserted into the femoral artery in the groin, and advanced through the aorta to the arteries (both carotid arteries and both vertebral arteries) that supply the brain. When the aneurysm has been located, metallic coils are deployed that lead to formation of a blood clot in the aneurysm and obliteration. The decision as to which treatment is undertaken typically is made by a multidisciplinary team, often including a neurosurgeon and a neuroradiologist.

Aneurysms of the middle cerebral artery and its related vessels are hard to reach and of less optimal configuration for endovascular coiling and tend to be amenable to clipping, while those of the basilar artery and posterior cerebral artery are hard to reach surgically and tend to be more accessible for endovascular management. The main drawback of coiling is the possibility that the aneurysm may recur; this risk is lower in the surgical approach. Patients who have undergone coiling are typically followed up for many years with angiography or other measures to ensure recurrence of aneurysms is identified early.

Prognosis

Early Morbidity and Mortality

The mortality rate for SAH is between 40% and 50%. Of those who survive initial hospitalization, treatment and complications, at least 25% have significant restrictions in their lifestyle, and less than 20% have no residual symptoms whatsoever. Delay in diagnosis of minor SAH without coma (or mistaking the sudden headache for migraine) contributes to poor outcome. Risk factors for poor outcome include higher age, poorer neurological grade, more blood and larger aneurysm on the initial CT scan, location of an aneurysm in the posterior circulation, systolic hypertension, and a previous diagnosis of heart attack, hypertension, liver disease or a previous SAH. During the hospital stay, occurrence of delayed ischemia resulting from vasospasm, development of intracerebral hematoma or intraventricular hemorrhage (bleeding into the ventricles of the brain), and presence of fever on the eighth day of admission also worsen the prognosis.

SAH that does not show an aneurysm by complete catheter angiography may be referred to as "angiogram-negative SAH." This carries a better prognosis than SAH from an aneurysm; however, it still is associated with a risk of ischemia, rebleeding and hydrocephalus. Perimesencephalic SAH (bleeding around the mesencephalon part of the brain), however, has a very low rate of rebleeding or delayed ischemia, and the prognosis of this subtype is better.

Long-Term Outcomes

Symptoms, such as fatigue, mood disturbances, depression, executive dysfunction and related neurocognitive symptoms, are common in people who have suffered SAH. Even in those who have made a good neurological recovery, anxiety, depression, posttraumatic stress disorder and cognitive impairment are common. Over 60% report frequent headaches. Aneurysmal SAH may lead to damage of the hypothalamus and the pituitary gland, two areas of the brain that play a central role in hormonal regulation and production. Studies indicate that at least 25% of people with a previous SAH may develop deficiencies in one or more of the hypothalamic-pituitary hormones, such as growth hormone, prolactin or thyroid-stimulating hormone.

4. Vasospasm

Angiographic cerebral vasospasm is the most common cause of focal ischemia after SAH. It adversely affects outcome in patients with SAH as it accounts for up to 23% of SAH-related disability and death. Of all types of ischemic stroke, vasospasm is unique in that it is to some degree predictable, preventable, and treatable (see Macdonald, R. L. and Weir, B. In Cerebral Vasospasm. Academic Press, Burlington, Mass., USA (2001)).

Vasospasm results in decreased cerebral blood flow and increased cerebral vascular resistance. Without being limited by theory, it generally is believed that vasospasm is caused by local injury to vessels, such as that which results from atherosclerosis and other structural injury including traumatic head injury, aneurysmal subarachnoid hemorrhage and other causes of subarachnoid hemorrhage. Cerebral vasospasm is a naturally occurring vasoconstriction that also may be triggered by the presence of blood in the CSF, a common occurrence after rupture of an aneurysm or following traumatic head injury. Cerebral vasospasm ultimately can lead to brain cell damage, in the form of cerebral ischemia and infarction, due to interrupted blood supply.

DCI is a multifactorial process due to at least three processes, as well as to early brain injury. Angiographic vasospasm is one process that contributes to DCI. Other processes that may contribute to DCI are cortical spreading ischemia and formation of microthromboemboli. Cortical spreading ischemia was described in animal models of SAH as a novel mechanism that may cause DCI. It has been detected in humans with SAH and angiographic vasospasm.

Each year, about 1 in 10,000 people have an aneurysm rupture. Mortality and morbidity increase with the volume of hemorrhage and reflect the age and health status of the patient, with the chance of developing an aneurysm increasing steadily with age. Rebleeding is exceptionally adverse due to the increase in volume of SAH as well as the increased likelihood of extension into the brain and ventricles. Most deaths resulting from aneurysmal rupture occur outside of hospitals or shortly after admission due to the effects of the initial bleed or early rebleeding. Potential manifestation of symptoms from vasospasm occurs only in those patients who survive past the first few days.

The incidence of vasospasm is less than the incidence of SAH (since only some patients with SAH develop vasospasm). The incidence of vasospasm will depend on the type of patient a given hospital receives and the methods by which vasospasm is diagnosed.

The unqualified term "vasospasm" is usually used with reference to angiographically determined arterial narrowing as defined above. Clinical vasospasm most often is used synonymously with delayed cerebral ischemia (DCI). When used in another fashion, for instance, vasospasm based on increased middle cerebral artery transcranial Doppler velocities, this should be specified.

Some degree of angiographic narrowing will occur in at least two-thirds of patients having angiography between 4 and 12 days after SAH. The numbers of patients developing neurological deterioration from this DCI varies with the diligence with which the patient is monitored and the efficacy of prophylaxis, but it has been estimated at about one-third. Of hospitalized SAH patients, about 5% die from vasospasm. When compared to post-SAH patients of intermediate grade, post-SAH patients in very good condition are less likely to develop vasospasm as they have small volume SAH, while post-SAH patients in very poor condition are more likely to die earlier from the initial episode. The presence of thick, widespread subarachnoid clot which can be visualized on the computerized tomographic (CT) scan done in close proximity to the bleeding episode is a key prognostic factor. The chance of vasospasm and consequently DCI is decreased by factors decreasing the duration of exposure to clot. Conversely, the incidence of vasospasm and DCI is increased by the utilization of antifibrinolytic drugs which prolong the exposure of arteries to clot and possibly cause ischemia by other mechanisms. Poor admission clinical grade is associated with DCI, presumably because they both indicate larger volumes of SAH. A definite relationship between age, hypertension, or sex and DCI has not been established. It is possible that smokers are more prone to vasospasm and DCI. Factors unrelated to the development of vasospasm include season, geography, contrast material, and diabetes.

Patients who develop vasospasm do worse than those who do not. If surgery or aneurysm coiling is performed earlier (within the first day or so) the outcome tends to be better than if treatment is delayed. When operations were preferentially performed during the peak period for vasospasm, outcomes were generally worse. Vasospasm does not result from early surgery or coiling; early surgery or coiling permits more vigorous treatment should vasospasm develop. If a thick clot is present, an attempt at careful removal should be made. The amount of residual clot postoperatively is a prognostic factor for DCI. Open operation exposes the patient to retractor pressure, venous sacrifice, temporary clipping ischemia, brain removal, and arterial injury. Studies have shown post operative decrease in cerebral blood flow, regional cerebral metabolic rate of oxygen, and oxygen extraction ratio. Vasospasm and DCI may be more common in patients who undergo neurosurgical clipping of a ruptured aneurysm as compared to endovascular coiling.

Independent variables, such as admission neurologic grade, increasing age, and massive intracranial or intraventricular hemorrhage, are more closely linked to outcome than vasospasm. Since vasospasm is a graded process, it is expected that only the extreme cases will result in infarction in the absence of systemic hypotension, cardiac dysfunction, anoxia, and intracranial hypertension. Preexisting hypertension and advanced age also strongly influence the vulnerability of the brain to ischemia. The etiological relationship between vasospasm and infarction in fatal cases is not in dispute.

There is evidence that vasospasm may be reduced by clot removal either surgically or pharmacologically. There also are data suggesting that DCI may be lessened by hypertension and hypervolemia as well as by calcium antagonists. Vasospasm also may be abolished by mechanical or transiently by pharmacologic angioplasty.

Incidence of Vasospasm

The incidence of angiographic vasospasm depends on the time interval after the SAH. The peak incidence occurs 6-8 days after SAH (range, 3-12 days). In addition to the time after the SAH, other principal factors that affect the prevalence of vasospasm are the volume and distribution of subarachnoid blood.

Prognostic Factors for Vasospasm

Prognostic factors for angiographic vasospasm include: blood on CT scan; hypertension; anatomical and systemic factors; clinical grade; whether the patient is receiving antifibrinolytics; age; smoking; physiological parameters; and hydrocephalus.

Diagnosis

The diagnosis of amhiographic vasospasm rests on comparison of blood vessel imaging studies. The diagnosis of delayed cerebral ischemia (DCI) is primarily clinical. Angiographic vasospasm can be asymptomatic; however, when the cerebral blood flow is below ischemic threshold, symptoms become apparent, and this is called DCI. Symptoms typically develop subacutely and may fluctuate. Symptoms may include excess sleepiness, lethargy, stupor, hemiparesis or hemiplegia, abulia, language disturbances, visual fields deficits, gaze impairment, and cranial nerve palsies. Although some symptoms are localized, they are not diagnostic of any specific pathological process; therefore alternative diagnoses, such as rebleeding, hydrocephalus, and seizures, should be excluded promptly using radiographic, clinical and laboratory assessments. Cerebral angiography is the gold standard for visualizing and studying cerebral arteries; transcranial Doppler ultrasonography is also utilized.

The pathophysiology of angiographic vasospasm may involve structural changes and biochemical alterations within the vascular endothelium and smooth muscle cells. The presence of blood in the subarachnoid space may initiate these changes. In addition, hypovolemia and an impaired cerebral autoregulatory function may concurrently interfere with cerebral perfusion. The cumulative effects of these processes can lead to reduction in cerebral blood flow so severe as to cause cerebral ischemia leading to infarction. Additionally, a period of severe constriction could lead to morphologic changes in the walls of the cerebral arteries, which may cause them to remain narrowed without the continued presence of vasoactive substances. The area of the brain supplied by the affected artery then would experience ischemia (meaning a restriction in blood supply).

Other Complications

Hydrocephalus (a condition marked by an excessive accumulation of CSF resulting in dilation of the cerebral ventricles and raised intracranial pressure) may complicate SAH in both the short- and long-term, and may be detected on CT scanning. If the level of consciousness is decreased, surgical drainage of the excess fluid (for instance with a ventricular drain or shunt) is occasionally necessary.

Fluctuations in blood pressure and electrolyte disturbances, as well as pneumonia and cardiac decompensation, occur in about 50% of hospitalized patients with SAH, and may worsen prognosis. They are managed symptomatically.

Seizures occur in about a third of all cases of SAH.

Treatments

Nimodipine, an oral calcium channel antagonist, has been shown in clinical trials to reduce the chance of a poor outcome, however it may not significantly reduce the amount of angiographic vasospasm detected on angiography. Other calcium channel antagonists and magnesium sulfate have been studied, but are not presently recommended. There is no evidence that shows benefit if nimodipine is given intravenously but the studies conducted have included small numbers of patients. In traumatic SAH, the efficacy of oral nimodipine remains in question.

Hemodynamic manipulation, previously referred to as "triple H" therapy, often is used as a measure to treat vasospasm. This entails the use of intravenous fluids and vasoconstrictor drugs to achieve a state of hypertension (high blood pressure), hypervolemia (excess fluid in the circulation) and hemodilution (mild dilution of the blood). Induced hypertension is believed to be the most important component of this treatment although evidence for the use of this approach is inconclusive, and no sufficiently large randomized controlled trials ever have been undertaken to demonstrate its benefits.

If symptomatic vasospasm, also known as DCI, is resistant to medical treatment, angiography may be attempted to identify the sites of angiographic vasospasm and to administer vasodilator medication (drugs that relax the blood vessel wall) directly into the artery (pharmacological angioplasty), and mechanical angioplasty (opening the constricted area with a balloon) may be performed.

6. Voltage-Gated Ion Channels

Voltage-gated ion channels are a class of integral membrane proteins that allow the passage of selected inorganic ions across the cell membrane by opening and closing in response to changes in transmembrane voltage. (Sands, Z. et al., "Voltage-gated ion channels," Current Biology, 15(2): R44-R47 (2005)). These types of ion channels are especially critical in neurons, but are common in many types of cells. They have an important role in excitable neuronal and muscle tissues as they allow a rapid and coordinated depolarization in response to triggering voltage change. Positioned along the axon and at the synapse, voltage-gated ion channels directionally propagate electrical signals.

Structure

Voltage-gated potassium, sodium and calcium ion channels are thought to have similar overall architectures. (Sands, Z. et al., "Voltage-gated ion channels," Current Biology, 15(2): R44-R47 (2005)). Voltage-gated ion channels generally are composed of several subunits arranged such that there is a central pore through which ions can travel down their electrochemical gradients. The channels tend to be quite ion-specific, although similarly sized and charged ions may also travel through them to some extent.

Mechanism

Crystallographic structural studies of a potassium channel, assuming that this structure remains intact in the corresponding plasma membrane, suggest that when a potential difference is introduced over the membrane, the associated electromagnetic field induces a conformational change in the potassium channel. The conformational change distorts the shape of the channel proteins sufficiently such that the channel, or cavity, opens to admit ion influx or efflux to occur across the membrane, down its electrochemical gradient. This subsequently generates an electrical current sufficient to depolarize the cell membrane.

Voltage-gated sodium channels and calcium channels are made up of a single polypeptide with four homologous domains. Each domain contains 6 membrane spanning alpha helices. The voltage sensing helix, S4, has multiple positive charges such that a high positive charge outside the cell repels the helix and induces a conformational change such that ions may flow through the channel. Potassium channels function in a similar way, with the exception that they are composed of four separate polypeptide chains, each comprising one domain. The voltage-sensitive protein domain of these channels (the "voltage sensor") generally contains a region composed of S3b and S4 helices, known as the "paddle" due to its shape, which appears to be a conserved sequence.

6.1. Voltage-Dependent Calcium Channels

Voltage-dependent calcium channels (VDCC) are a group of voltage-gated ion channels that control calcium entry into cells in response to membrane potential changes. (Van Petegem F. et al., Biochemical Society Transactions, 34(5): 887-893 (2006)). Voltage-dependent calcium channels are found in excitable cells (e.g., muscle, glial cells, neurons, etc.). At physiologic or resting membrane potential, VDCCs are normally closed. They are activated (i.e., opened) at depolarized membrane potentials. Activation of particular VDCCs allows $Ca^{2+}$ entry into the cell; muscular contraction, excitation of neurons, upregulation of gene expression, or release of hormones or neurotransmitters results, depending upon the cell type. (Catterall W. A. et al., "International Union of Pharmacology. XLVIII. Nomenclature and structure-function relationships of voltage-gated calcium channels," Pharmacol. Rev., 57(4): 411-25 (2005); Yamakage M. et al, "Calcium channels—basic aspects of their structure, function and gene encoding; anesthetic action on the channels—a review," Can. J. Anaesth., 49(2): 151-64 (2002)).

Voltage-dependent calcium channels are formed as a complex of several different subunits: $\alpha_1$, $\alpha_2\delta$, $\beta_{1-4}$, and $\gamma$. The alpha subunit forms the ion conducting pore while the associated subunits have several functions including modulation of gating. (Dolphin A. C. "A short history of voltage-gated calcium channels," Br. J. Pharmacol., 147 (Suppl 1): S56-62 (2006))

$\alpha_1$ Subunit

The $\alpha_1$ subunit pore (about 190 kDa in molecular mass) is the primary subunit necessary for channel functioning in the VDCC, and consists of the characteristic four homologous I-IV domains containing six transmembrane α-helices each. The alpha subunit forms the $Ca^{2+}$ selective pore, which contains voltage-sensing machinery and the drug/toxin-binding sites. Ten alpha subunits that have been identified in humans. (Dolphin A. C. "A short history of voltage-gated calcium channels," Br. J. Pharmacol., 147 (Suppl 1): S56-62 (2006))

$\alpha_2\delta$ Subunit

The $\alpha_2\delta$ gene encodes two subunits, $\alpha_2$ and $\delta$. They are linked to each other via a disulfide bond and have a combined molecular weight of 170 kDa. The $\alpha_2$ is the extracellular glycosylated subunit that interacts the most with the al subunit. The $\delta$ subunit has a single transmembrane region with a short intracellular portion, which serves to anchor the protein in the plasma membrane. There are 4$\alpha_2\delta$ genes: CACNA2D1 (CACNA2D1), (CACNA2D2), (CACNA2D3), and (CACNA2D4). Co-expression of the $\alpha_2\delta$ enhances the level of expression of the al subunit and causes an increase in current amplitude, faster activation and inactivation kinetics and a hyperpolarizing shift in the voltage dependence of inactivation. Some of these effects are observed in the absence of the beta subunit, whereas, in other cases, the co-expression of beta is required. The $\alpha_2\delta$-1 and $\alpha2\delta$-2 subunits are binding sites for at least two anticonvulsant drugs, gabapentin and pregabalin, that also find use in treating chronic neuropathic pain. (Dolphin A. C. "A short history of voltage-gated calcium channels," Br. J. Pharmacol., 147 (Suppl 1): S56-62 (2006))

β Subunit

The intracellular β subunit (55 kDa) is an intracellular membrane-associated guanylate kinase (MAGUK)-like protein containing a guanylate kinase (GK) domain and an SH3 (src homology 3) domain. The guanylate kinase domain of the β subunit binds to the alpha subunit I-II cytoplasmic loop and regulates HVGCC activity. There are four known isoforms of the β subunit: CACNB1, CACNB2, CACNB3, and CACNB4. (Dolphin A. C. "A short history of voltage-gated calcium channels," Br. J. Pharmacol., 147 (Suppl 1): S56-62 (2006))

Without being limited by theory, it is postulated the cytosolic β subunit has a major role in stabilizing the final alpha subunit conformation and delivering it to the cell membrane by its ability to mask an endoplasmic reticulum retention signal in the alpha subunit. The endoplasmic retention brake is contained in the I-II loop of the alpha subunit that becomes masked when the β subunit binds. Therefore the β subunit functions initially to regulate the current density by controlling the amount of alpha subunit expressed at the cell membrane.

In addition to this potential trafficking role, the β subunit has the added important functions of regulating activation and inactivation kinetics, and hyperpolarizing the voltage-dependence for activation of the alpha subunit pore, so that more current passes for smaller depolarizations. The β subunit acts as an important modulator of channel electrophysiological properties. The interaction between a highly conserved 18-amino acid region on the α1 subunit intracellular linker between domains I and II (the Alpha Interaction Domain, AIDBP) and a region on the GK domain of the β subunit (Alpha Interaction Domain Binding Pocket) is responsible for the regulatory effects exerted by the β subunit. Additionally, the SH3 domain of the β subunit also gives added regulatory effects on channel function, indicating that the β subunit may have multiple regulatory interactions with the α1 subunit pore. The alpha interaction domain sequence does not appear to contain an endoplasmic reticulum retention signal; this may be located in other regions of the I-II α1 subunit linker.

γ Subunit

The γ1 subunit is known to be associated with skeletal muscle VGCC complexes, but the evidence is inconclusive regarding other subtypes of calcium channel. The γ1 subunit glycoprotein (33 kDa) is composed of four transmembrane spanning helices. The γ1 subunit does not affect trafficking, and, for the most part, is not required to regulate the channel complex. However, γ2, γ3, γ4 and γ8 also are associated with α-amino-3-hydroxy-5-methyl-4-isoxazolepropionic acid (AMPA) glutamate receptors, non-NMDA-type ionotropic transmembrane receptors for glutamate that mediate fast synaptic transmissions in the CNS. An NMDA-type receptor is a receptor to which NMDA (N-methyl-D-aspartate) binds specifically. There are 8 genes for gamma subunits: γ1 (CACNG1), γ2 (CACNG2), γ3 (CACNG3), γ4 (CACNG4), (CACNG5), (CACNG6), (CACNG7), and (CACNG8). (Chu P. J. et al., "Calcium channel gamma subunits provide insights into the evolution of this gene family," Gene, 280 (1-2): 37-48 (2002)).

Voltage dependent calcium channels vary greatly in structure and form. Calcium channels are classified as L-, N-, P/Q, T- and R-type according to their pharmacological and electrophysiological properties. These channel subtypes have distinct physiological functions. Molecular cloning has clarified the α1 subunit sequence of each channel. The α1 subunit has a specific role in eliciting activity in an individual channel. Nonetheless, selective antagonists for these channel subtypes are required for defining specific channels involved in each activity. The neural N-type channels are blocked by w-conotoxin GVIA; the R-type channels are resistant to other antagonists and toxins, are blocked by SNX-482, and may be involved in processes in the brain; the closely related P/Q-type channels are blocked by co-agatoxins. The dihydropyridine-sensitive L-type channels are responsible for excitation-contraction coupling of skeletal, smooth, and cardiac muscle and for hormone secretion in endocrine cells and also are antagonized by phenylalkylamines and benzothiazepines.

6.2. Types of Voltage-Gated Calcium Channels

L-Type Calcium Channels

L-type voltage-gated calcium channels are opened when a smooth muscle cell is depolarized. This depolarization may be brought about by stretching of the cell, by an agonist-binding its G protein-coupled receptor (GPCR), or by autonomic nervous system stimulation. Opening of the L-type calcium channel causes influx of extracellular $Ca^{2+}$, which then binds calmodulin. The activated calmodulin molecule activates myosin light-chain kinase (MLCK), which phosphorylates the myosin in thick filaments. Phosphorylated myosin is able to form crossbridges with actin thin filaments, and the smooth muscle fiber (i.e., cell) contracts via the sliding filament mechanism. (Yamakage M. et al, "Calcium channels—basic aspects of their structure, function and gene encoding; anesthetic action on the channels—a review," Can. J. Anaesth., 49(2): 151-64 (2002))

L-type calcium channels also are enriched in the t-tubules of striated muscle cells, such as, skeletal and cardiac myofibers. As in smooth muscle, L-type calcium channels open when these cells are depolarized. In skeletal muscle, since the L-type calcium channel and the calcium-release channel (ryanodine receptor, or RYR) are mechanically gated to each other with the latter located in the sarcoplasmic reticulum (SR), the opening of the L-type calcium channel causes the opening of the RYR. In cardiac muscle, opening of the L-type calcium channel permits influx of calcium into the cell. The calcium binds to the calcium release channels (RYRs) in the SR, opening them (referred to as "calcium-induced calcium release" or "CICR"). $Ca^{2+}$ is released from the SR and is able to bind to troponin C on the actin filaments regardless of how the RYRs are opened, either through mechanical-gating or CICR. The muscles then contract through the sliding filament mechanism, causing shortening of sarcomeres and muscle contraction.

R-Type Voltage Dependent Calcium Channels

R-type voltage dependent calcium channels (VDCC) are involved in regulating calcium flow. The R-type VDCCs play an important role in decreased cerebral blood flow observed following SAH. Without being limited by theory, R-type voltage-dependent $Ca^{2+}$ channels that may be located within small diameter cerebral arteries may regulate global and local cerebral blood flow, since the concentration of intracellular free calcium ions determines the contractile state of vascular smooth muscle. Yamakage M. et al, "Calcium channels—basic aspects of their structure, function and gene encoding; anesthetic action on the channels—a review," Can. J. Anaesth., 49(2): 151-64 (2002).

R-type voltage dependent calcium channel inhibitors are calcium entry blocking drugs whose main pharmacological effect is to prevent or slow the entry of calcium into cells via R-type voltage-gated calcium channels. The gene $Ca_v2.3$ encodes the principal pore-forming unit of R-type voltage-dependent calcium channels being expressed in neurons.

N-Type Calcium Channels

N-type ('N' for "Neural-Type") calcium channels are found primarily at presynaptic terminals and are involved in neurotransmitter release. Strong depolarization by an action potential causes these channels to open and allow influx of $Ca^{2+}$, initiating vesicle fusion and release of stored neurotransmitter. N-type channels are blocked by ω-conotoxin. Yamakage M. et al, "Calcium channels—basic aspects of their structure, function and gene encoding; anesthetic action on the channels—a review," Can. J. Anaesth., 49(2): 151-64 (2002).

P/Q-Type Calcium Channels

P-type ('P' for cerebellar Purkinje cells) calcium channels play a similar role to the N-type calcium channel in neurotransmitter release at the presynaptic terminal, and in neuronal integration in many neuronal types. They also are found in Purkinje fibers in the electrical conduction system of the heart (Winds, R., et al., J. Physiol. (Lond.) 305: 171-95 (1980); Llinds, R. et al., Proc. Natl. Acad. Sci. U.S.A. 86 (5): 1689-93 (1989)). Q-type calcium channel antagonists appear to be present in cerebellar granule cells. They have a high threshold of activation and relatively slow kinetics. Yamakage M. et al, "Calcium channels—basic aspects of their structure, function and gene encoding; anesthetic action on the channels—a review," Can. J. Anaesth., 49(2): 151-64 (2002).

T-Type Calcium Channels

T-type ('T' for transient) calcium channel antagonists are low voltage-activated. They most often are found in neurons and cells that have pacemaker activity and in osteocytes. Mibefradil shows some selectivity for T-type over other types of VDCC. Yamakage M. et al, "Calcium channels—basic aspects of their structure, function and gene encoding; anesthetic action on the channels—a review," Can. J. Anaesth., 49(2): 151-64 (2002).

6.3. Antagonists and Inhibitors of Calcium Channels

Calcium channel antagonists are a class of drugs and natural substances having effects on many excitable cells of the body, such as the muscle of the heart, smooth muscles of the vessels or neuron cells. The main action of calcium channel antagonists is to decrease blood pressure.

Some calcium channel antagonists decrease the force of contraction of the myocardium. This is known as the "negative inotropic effect" of calcium channel antagonists. Most calcium channel antagonists are not the preferred choice of treatment in individuals with cardiomyopathy due to their negative inotropic effects.

Some calcium channel antagonists slow the conduction of electrical activity within the heart by blocking the calcium channel during the plateau phase of the action potential of the heart. This "negative dromotropic effect" causes a lowering of the heart rate and may cause heart blocks (which is known as the "negative chronotropic effect" of calcium channel antagonists). The negative chronotropic effects of calcium channel antagonists make them a commonly used class of agents for control of the heart rate in individuals with atrial fibrillation or flutter.

Calcium channel antagonists act upon voltage-gated calcium channels (VGCCs) in muscle cells of the heart and blood vessels. By blocking the calcium channel they prevent large increases of the calcium levels in the cells when stimulated, which subsequently leads to less muscle contraction. In the heart, a decrease in calcium available for each beat results in a decrease in cardiac contractility. In blood vessels, a decrease in calcium results in less contraction of the vascular smooth muscle and therefore an increase in blood vessel diameter. The resultant vasodilation decreases total peripheral resistance, while a decrease in cardiac contractility decreases cardiac output. Since blood pressure is in part determined by cardiac output and peripheral resistance, blood pressure drops.

Calcium channel antagonists do not decrease the responsiveness of the heart to input from the sympathetic nervous system. Since blood pressure regulation is carried out by the sympathetic nervous system (via the baroreceptor reflex), calcium channel antagonists allow blood pressure to be maintained more effectively than do β-blockers. However, because calcium channel antagonists result in a decrease in blood pressure, the baroreceptor reflex often initiates a reflexive increase in sympathetic activity leading to increased heart rate and contractility. The decrease in blood pressure also likely reflects a direct effect of antagonism of VDCC in vascular smooth muscle, leading to vasodilation. A β-blocker may be combined with a calcium channel antagonist to minimize these effects.

The antagonists for L, N, and P/Q-types of calcium channels are utilized in distinguishing channel subtypes. For the R-type calcium channel subtype, ω-agatoxin IIIA shows blocking activity, even though its selectivity is rather low. This peptide binds to all of the high voltage-activated channels including L, N, and P/Q subtypes (J. Biol. Chem., 275, 21309 (2000)). A putative R-type (or class α1E) selective blocker, SNX-482, a toxin from the tarantula *Hysterocrates gigas*, is a 41 amino acid residue peptide with 3 disulfide linkages (1-4, 2-5 and 3-6 arrangement) (Biochemistry, 37, 15353 (1998), Peptides 1998, 748 (1999)). This peptide blocks the class E calcium channel (IC50=15 nM to 30 nM) and R-type calcium current in the neurohypophysial nerve endings at 40 nM concentration. R-type (class E) calcium channel blocking activity is highly selective; no effect is observed on $K^+$ and $Na^+$ currents, and L, P/Q and T-type calcium currents. N-type calcium current is blocked only weakly 30-50% at 300 nM to 500 nM. Regionally, different sensitivity of R-type current to SNX-482 is observed; no significant effect on R-type current occurs in preparations of the neuronal cell body, retinal ganglion cells and hippocampal pyramidal cells. Using SNX-482, three alpha E-calcium subunits with distinct pharmacological properties are recognized in cerebellar R-type calcium channels (J. Neurosci., 20, 171 (2000)). Similarly, it has been shown that secretion of oxytocin, but not vasopressin, is regulated by R-type calcium current in neurohypophysial terminals (J. Neurosci., 19, 9235 (1999)).

Dihydropyridine calcium channel antagonists often are used to reduce systemic vascular resistance and arterial pressure, but are not used to treat angina (with the exception of amlodipine, which carries an indication to treat chronic stable angina as well as vasospastic angina) since the vasodilation and hypotension can lead to reflex tachycardia. This calcium channel antagonist class is easily identified by the suffix "-dipine."

Phenylalkylamine calcium channel antagonists are relatively selective for myocardium. They reduce myocardial oxygen demand and reverse coronary vasospasm. They have minimal vasodilatory effects compared with dihydropyridines. Their action is intracellular.

Benzothiazepine calcium channel antagonists are an intermediate class between phenylalkylamine and dihydropyridines in their selectivity for vascular calcium channels. Benzothiazepines are able to reduce arterial pressure without producing the same degree of reflex cardiac stimulation caused by dihydropyridines due to their cardiac depressant and vasodilator actions.

L-type VDCC inhibitors are calcium entry blocking drugs whose main pharmacological effect is to prevent or slow entry of calcium into cells via L-type voltage-gated calcium channels. Examples of such L-type calcium channel inhibitors include, but are not limited to: dihydropyridine L-type antagonists such as nisoldipine, nicardipine and nifedipine, AHF (such as 4aR,9aS)-(+)-4a-Amino-1,2,3,4,4a,9a-hexahydro-4a14-fluorene, HCl), isradipine (such as 4-(4-Benzofurazanyl)-1,-4-dihydro-2,6-dimethyl-3,5-pyridinedicarboxylic acid methyl 1-methhylethyl ester), calciseptine (such as isolated from (*Dendroaspis polylepis* ploylepis), H-Arg-Ile-Cys-Tyr-Ile-His-Lys-Ala-Ser-Leu-Pro-Arg-Ala-Thr-Lys-Thr-Cys-Val-Glu-Asn-Thr-Cys-Tyr-Lys-Met-Phe-Ile-Arg-Thr-Gln-Arg-Glu-Tyr-Ile-Ser-Glu-Arg-Gly-Cys-Gly-Cys-Pro-Thr-Ala- Met-Trp-Pro-Tyr-Gl-n-Thr-Glu-Cys-Cys-Lys-Gly-Asp-Arg-Cys-Asn-Lys-OH, Calcicludine (such as isolated from *Dendroaspis angusticeps* (eastern green mamba)), (H-Trp-Gln-Pro-Pro-Trp-Tyr-Cys-Lys-Glu-Pro-Val-Arg-Ile-Gly-Ser-Cys-Lys-Lys-Gln-Phe-Ser-Ser-Phe-Tyr-Phe-Lys-Trp-Thr-Ala-Lys-Lys-Cys-Leu-Pro-Phe-Leu-Phe-Ser-Gly-Cys-Gly-Gly-Asn-Ala- Asn-Arg-Phe-Gln-Thr-Ile-Gly-Glu-Cys-Arg-Lys-Lys-Cys-Leu-Gly-Lys-OH, Cilnidipine (such as also FRP-8653, a dihydropyridine-type inhibitor), Dilantizem (such as (2S,3S)-(+)-cis-3-Acetoxy-5-(2-dimethylaminoethyl)-2,3-dihydro-2-(4-methoxyphenyl)-1,5-benzothiazepin-4(5H)-one hydrochloride), diltiazem (such as benzothiazepin-4(5H)-one, 3-(acetyloxy)-5-[2-(dimethylamino)ethyl]-2,3-dihydro-2-(4-methoxyphenyl)-,(+)-cis-,monohydrochloride), Felodipine (such as 4-(2,3-Dichlorophenyl)-1,4-dihydro-2,6-dimethyl-3,5-pyridinecarboxylic acid ethyl methyl ester), FS-2 (such as an isolate from *Dendroaspis polylepis* polylepis venom), FTX-3.3 (such as an isolate from *Agelenopsis aperta*), Neomycin sulfate (such as $C_{23}H_{46}N_6O_{13}.3H2SO4$), Nicardipine (such as 1,4-Dihydro-2,6-dimethyl-4-(3-nitrophenyl)methyl-2-[methyl(phenylmethypamino]-3,5-pyridinedicarboxylic acid ethyl ester hydrochloride, also YC-93, Nifedipine (such as 1,4-Dihydro-2,6-dimethyl-4-(2-nitrophenyl)-3,5-pyridinedicarboxylic acid dimethyl ester), Nimodipine (such as 4-Dihydro-2,6-dimethyl-4-(3-nitrophenyl)-3,5-pyridinedicarboxylic acid 2-methoxyethyl 1-methylethyl ester) or (Isopropyl 2-methoxyethyl 1,4-dihydro-2,6-dimethyl-4-(m-nitrophenyl)-3,5-pyridinedicarboxylate), Nitrendipine (such as 1,4-Dihydro-2,6-dimethyl-4-(3-nitrophenyl)-3,5-pyridinedicarboxylic acid ethyl methyl ester), S-Petasin (such as (3S,4aR,5R,6R)-[2,3,4,4a,5,6,7,8-Octahydro-3-(2-propenyl)-4a,5-dimethyl-2-o-xo-6-naphthyl] Z-3'-methylthio-1'-propenoate), Phloretin (such as 2',4',6'-Trihydroxy-3-(4-hydroxyphenyl)propiophenone, also 3-(4-Hydroxyphenyl)-1-(2,4,6-trihydroxyphenyl)-1-propanone, also b-(4-Hydroxyphenyl)-2,4,6-trihydroxypropiophenone), Protopine (such as $C_{20}H_{19}NO_5Cl$), SKF-96365 (such as 1-[b-[3-(4-Methoxyphenyl)propoxy]-4-methoxyphenethyl]-1H-imidazole, HCl), Tetrandine (such as 6,6',7,12-Tetramethoxy-2,2'-dimethylberbaman), (.+−.)-Methoxyverapamil or (+)-Verapamil (such as 54N-(3,4-Dimethoxyphenylethyl)methylamino]-2-(3,4-dimethoxyphenyl)-2-iso-propylvaleronitrile hydrochloride), and (R)-(+)-Bay K8644 (such as R-(+)-1,4-Dihydro-2,6-dimethyl-5-nitro-442-(trifluoromethyl)phenyl]-3-py-ridinecarboxylic acid methyl ester). The foregoing examples may be specific to L-type voltage-gated calcium channels or may inhibit a broader range of voltage-gated calcium channels, e.g. N, P/Q, R, and T-type.

7. Endothelins

Endothelins are vasoconstricting peptides produced primarily in the endothelium that increase blood pressure and vascular tone. This family of peptides includes endothelin-1 (ET-1), endothelin-2 (ET-2) and endothelin-3 (ET-3). These small peptides (21 amino acids) have an important role in vascular homeostasis. ET-1 is secreted mostly by vascular endothelial cells. The predominant ET-1 isoform is expressed in vasculature and is the most potent vasoconstrictor. ET-1 also has inotropic, chemotactic and mitogenic properties. It stimulates the sympathetic nervous system, and influences salt and water homeostasis through its effects on the renin-angiotensin-aldosterone system (RAAS), vasopressin and atrial natriuretic peptide. Endothelins are among the strongest vasoconstrictors known and have been implicated in vascular diseases of several organ systems, including the heart, general circulation and brain.

There are two key endothelin receptor types, ETA and ETB. ETA and ETB have distinct pharmacological characteristics. The ETA-receptor affinity is much higher for ET-1 than for ET-3. ETA-receptors are located in the vascular smooth muscle cells, but not in endothelial cells. The binding of endothelin to ETA increases vasoconstriction and the retention of sodium, leading to increased blood pressure. ETB receptors primarily are located on the endothelial cells that line the interior of the blood vessels. Endothelin binding to ETB receptors lowers blood pressure by increasing natriuresis and diuresis, and releasing nitric oxide. ET-1 and ET-3 activate the ETB-receptor equally, which in turn leads to vasodilation via production of NO and prostaglandins. Endothelin-1 (ET-1) also has been demonstrated to cause vascular smooth muscle constriction via ETA-receptor stimulation and to induce NO production in endothelial cells via ETB-receptors. Some ETB-receptors are located in vascular smooth muscle, where they may mediate vasoconstriction. A number of endothelin receptors are regulated by various factors. Angiotensin II and phorbol esters down-regulate endothelin receptors whereas ischemia and cyclosporin increase the number of endothelin receptors.

A number of peptide and nonpeptide ET antagonists have been studied. ETA-receptor antagonists may include, but are not limited to, A-127722 (non-peptide), ABT-627 (non-peptide), BMS 182874 (non-peptide), BQ-123 (peptide), BQ-153 (peptide), BQ-162 (peptide), BQ-485 (peptide), BQ-518 (peptide), BQ-610 (peptide), EMD-122946 (non-peptide), FR 139317 (peptide), IPI-725 (peptide), L-744453 (non-peptide), LU 127043 (non-peptide), LU 135252 (non-peptide), PABSA (non-peptide), PD 147953 (peptide), PD 151242 (peptide), PD 155080 (non-peptide), PD 156707 (non-peptide), RO 611790 (non-peptide), SB-247083 (non-peptide), clazosentan (non-peptide), atrasentan (non-peptide), sitaxsentan sodium (non-peptide), TA-0201 (non-peptide), TBC 11251 (non-peptide), TTA-386 (peptide), WS-7338B (peptide), ZD-1611 (non-peptide), and aspirin (non-peptide). ETA/B-receptor antagonists may include, but are not limited to, A-182086 (non-peptide), CGS 27830 (non-peptide), CP 170687 (non-peptide), J-104132 (non-peptide), L-751281 (non-peptide), L-754142 (non-peptide), LU 224332 (non-peptide), LU 302872 (non-peptide), PD 142893 (peptide), PD 145065 (peptide), PD 160672 (non-peptide), RO-470203 (bosentan, non-peptide), RO 462005 (non-peptide), RO 470203 (non-peptide), SB 209670 (non-peptide), SB 217242 (non-peptide), and TAK-044 (peptide). ETB-receptor antagonists may include, but are not limited to, A-192621 (non-peptide), A-308165 (non-peptide), BQ-788 (peptide), BQ-017 (peptide), IRL 1038 (peptide), IRL 2500 (peptide), PD-161721 (non-peptide), RES 701-1 (peptide), and RO 468443 (peptide).

ET-1 is translated initially to a 212 amino-acid peptide (pre-proendothelin-1). It is further converted to proendothelin-1 after removal of the secretory sequence. Proendothelin-1 then is cleaved by furin to generate the biologically-inactive precursor big endothelin-1. Mature ET-1 is formed upon cleavage of big endothelin-1 by one of several endothelin-converting enzymes (ECEs). There are two splice variants of ECE-1; these are ECE-1a and ECE-1b. Each has functionally distinct roles and tissue distribution. ECE-1a is expressed in the Golgi network of endothelin-producing cells and cleaves big endothelin-1 to form ET-1. ECE-1b is localized at the plasma membrane and cleaves extracellular big endothelin-1. Both ECE-1a and ECE-1b are inhibited by metalloprotease inhibitor phosphoramidon. ECEs also are located on α-actin filaments in smooth muscle cells. ECE inhibition by phosphoramidon completely blocks vasoconstriction to big endothelin-1. ECE inhibitors may include, but are not limited to, B-90063 (non-peptide), CGS 26393 (non-peptide), CGS 26303 (non-peptide), CGS 35066 (non peptide), phosphoramidon (peptide), PP-36 (peptide), SM-19712 (non-peptide), and TMC-66 (non-peptide).

In a healthy individual, a delicate balance between vasoconstriction and vasodilation is maintained by endothelin and other vasoconstrictors on the one hand and nitric oxide, prostacyclin and other vasodilators on the other. Endothelin antagonists may have a role in the treatment of cardiac, vascular and renal diseases associated with regional or systemic vasoconstriction and cell proliferation, such as essential hypertension, pulmonary hypertension, chronic heart failure and chronic renal failure.

8. Transient Receptor Potential Channels

The transient receptor potential (TRP) channel family is a member of the calcium channel group. These channels include transient receptor potential protein and homologues thereof, the vanilloid receptor subtype I, stretch-inhibitable non-selective cation channel, olfactory, mechanosensitive channel, insulin-like growth factor I-regulated calcium channel, and vitamin D-responsive apical, epithelial calcium channel (ECaC). Each of these molecules is at least 700 amino acids in length, and shares certain conserved structural features. Predominant among these structural features are six transmembrane domains, with an additional hydrophobic loop present between the fifth and sixth transmembrane domains. It is believed that this loop is integral to the activity of the pore of the channel formed upon membrane insertion. TRP channel proteins also include one or more ankyrin domains and frequently display a proline-rich region at the N-terminus.

Transient receptor potential (TRP) cation channels are present in vascular smooth muscle and are involved in the smooth muscle depolarizing response to stimuli such as membrane stretch. Uridine triphosphate (UTP) invokes membrane depolarization and constriction of vascular smooth muscle by activating a cation current that exhibits inward rectification, is not rapidly desensitized, and is blocked by $Gd^{3+}$. Canonical transient receptor potential (TRPC) proteins form $Ca^{2+}$ permeable, non-selective cation channels in a variety of mammalian tissues. Suppression of one member of this family of channels, TRPC6, has been reported to prevent an alpha-adenoreceptor-activated cation current in cultured rabbit portal vein myocytes. However, suppression of TRPC6 channels in cerebral vascular smooth muscle does not attenuate the UTP-induced membrane depolarization and vasoconstriction. In contrast, TRPC3, unlike TRPC6, has been found to mediate the agonist induced depolarization, as observed in rat cerebral artery, following UTP activation of the P2Y receptor. Thus, TRPC3 channels in vascular smooth muscle mediate agonist-induced depolarization which contributes to vasoconstriction in resistance-sized cerebral arteries.

The TRP1 channel family comprises a large group of channels mediating an array of signal and sensory transduction pathways. The proteins of the mammalian TRPC subfamily are the products of at least seven genes coding for cation channels that appear to be activated in response to phospholipase C (PLC)-coupled receptors. The putative ion channel subunits TRPC3, TRPC6, and TRPC7 comprise a structurally related subgroup of the family of mammalian TRPC channels. The ion channels formed by these proteins appear to be activated downstream of phospholipase C (PLC). PLC-dependent activation of TRPC6 and TRPC7 has been shown to involve diacylglycerol and is independent of G proteins or inositol 1,4,5-triphosphate (IP3).

TRPC channels are widely expressed among cell types and may play important roles in receptor-mediated $Ca^{2+}$ signaling. The TRPC3 channel is known to be a $Ca^{2+}$-conducting channel activated in response to PLC-coupled receptors. TRPC3 channels have been shown to interact directly with intracellular inositol 1,4,5-trisphosphate receptors (InsP3Rs), i.e., channel activation is mediated through coupling to InsP3Rs.

Agents useful for increasing arterial blood flow, inhibiting vasoconstriction or inducing vasodilation are agents that inhibit TRP channels. These inhibitors embrace compounds that are TRP channel antagonists. Such inhibitors are referred to as activity inhibitors or TRP channel activity inhibitors. As used herein, the term "activity inhibitor" refers to an agent that interferes with or prevents the activity of a TRP channel. An activity inhibitor may interfere with the ability of the TRP channel to bind an agonist such as UTP. An activity inhibitor may be an agent that competes with a naturally occurring activator of TRP channel for interaction with the activation binding site on the TRP channel Alternatively, an activity inhibitor may bind to the TRP channel at a site distinct from the activation binding site, but in doing so, it may, for example, cause a conformational change in the TRP channel, which is transduced to the activation binding site, thereby precluding binding of the natural activator. Alternatively, an activity inhibitor may interfere with a component upstream or downstream of the TRP channel but which interferes with the activity of the TRP channel. This latter type of activity inhibitor is referred to as a functional antagonist. Non-limiting examples of a TRP channel inhibitor that is an activity inhibitor are gadolinium chloride, lanthanum chloride, SKF 96365 and LOE-908.

Current treatments to prevent or reduce angiographic vasospasm and DCI consist of measures to prevent or minimize secondary brain injury, use calcium channel antagonists, hemodynamic management and endovascular therapies. Therapy often is initiated prophylactically in patients and may include: (in stage 1) hemodynamic stabilization including maintaining normovolemia, managing blood pressure, and orally-administered L-type voltage-gated calcium channel antagonists; and (in stage 2) further hemodynamic manipulation or infusion of vasodilator drugs into vasospastic arteries or dilating them with balloons. However, the aforementioned treatments are expensive, time consuming and only partially effective.

For over 35 years, physicians have been trying to prevent or reduce the incidence of adverse consequences of SAH, including angiographic vasospasm and DCI, and have had limited effect due to side effects of current agents or lack of efficacy. There currently are no FDA approved agents for the prevention of vasospasm or the reduction of delayed ischemic neurologic deficits also known as delayed cerebral ischemia (DCI). Current methods to prevent vasospasm have failed due to lack of efficacy or to safety issues, primarily hypotension and cerebral edema. Currently, the only FDA-approved available agent is nimodipine, which has minimal effect on angiographic vasospasm in clinically-used doses, although it improved outcome in SAH patients.

Voltage-gated calcium channel antagonists may be effective in preventing and reversing vasospasm to a certain extent, however, prior art treatments administer doses too low to exert a maximal pharmacologic effect. Endothelin-receptor antagonists also may be effective at preventing and reversing angiographic vasospasm to a certain extent, but this reversal or prevention of angiographic vasospasm does not translate into as marked an improvement in outcome as would be anticipated by the reduction in angiographic vasospasm. Without being limited by theory, it is postulated that the systemic delivery of the voltage-gated calcium channel antagonists may cause side effects that mitigate the beneficial effects on angiographic vasospasm, such as, for example, systemic hypotension and pulmonary vasodilation with pulmonary edema, which prevent the administration of higher systemic doses. Dilation of blood vessels in the lungs also may cause lung edema and lung injury. Second, and without being limited by theory, it is postulated that systemic delivery of the voltage-gated calcium channel antagonists may limit other effects of SAH that contribute to DCI, including cortical spreading ischemia and microthromboemboli.

While conventional therapies have been focusing on treating cerebral vasospasms following subarachnoid hemorrhage, accumulating evidence suggests that there are additional complications derived from subarachnoid hemorrhage, which need to be targeted for treatment interventions in order to improve prognosis following subarachnoid hemorrhage treatment. The described invention offers such an approach.

SUMMARY

According to one aspect, the described invention provides a method of treating at least one cerebral artery in a subarachnoid space at risk of interruption due to a brain injury in a human subject, comprising: a) providing a flowable sustained release microparticulate composition comprising (i) a microparticulate formulation comprising a therapeutic amount of at least one therapeutic agent, wherein the microparticulate formulation comprises a plurality of microparticles of uniform size distribution, wherein the therapeutic agent is dispersed throughout each microparticle, and wherein the therapeutic amount is effective to treat a delayed complication of the interruption of the cerebral artery, (ii) and a pharmaceutical carrier; and b) administering the composition locally into a cerebral ventricle so that the microparticulate formulation flows from the cerebrospinal fluid (CSF) in the cerebral ventricle into the cerebrospinal fluid (CSF) in the subarachnoid space before releasing the therapeutic agent in the subarachnoid space, wherein the therapeutic agent contacts and flows around the at least one cerebral artery in the subarachnoid space without entering systemic circulation in an amount to cause unwanted side effects. According to one embodiment, each microparticle comprises a matrix. According to another embodiment, the at least one therapeutic agent is a calcium channel antagonist, an endothelin antagonist, a transient receptor potential (TRP) protein antagonist, or a combination thereof. According to another embodiment, the delayed complication is selected from the group consisting of an angiographic vasospasm, formation of a plurality of microthromboemboli, a cortical spreading ischemia, a delayed cerebral ischemia (DCI), or a combination thereof. According to another embodiment, the at least one therapeutic agent is a calcium channel antagonist selected from the group consisting of an L-type voltage dependent calcium channel inhibitor, an R-type voltage dependent calcium channel inhibitor, an N-type voltage dependent calcium channel inhibitor, a P/Q-type voltage dependent calcium channel inhibitor, a T-type voltage dependent calcium channel inhibitor, or a combination thereof. According to one embodiment, the L-type voltage dependent calcium channel inhibitor is a dihydropyridine, selected from the group consisting of amlodipine, aranidipine, azelnidipine, bamidipine, benidipine, cinaldipine, efonidipine, felodipine, isradipine, lacidipine, lemildipine, lercanidipine, nicardipine, nifedipine, nilvadipine, nimodipine, nisoldipine, nitrendipine, manidipine, pranidipine, or a combination thereof. According to one embodiment, the dihydropyridine is nimodipine. According to another embodiment, the microparticulate formulation comprises a powder suspension of microparticles. According to another embodiment, the microparticulate formulation further comprises a slow-release compound. According to one embodiment, the slow release compound is a biodegradable polymer. According to one embodiment, the biodegradable polymer is selected from the group consisting of polylactide-polyglycolide, poly(orthoester), and poly(anhydride). According to another embodiment, administering occurs via a surgical injection apparatus. According to another embodiment, the surgical injection apparatus is a needle, a cannula, a catheter, or a combination thereof. According to another embodiment, the flowable sustained release microparticulate composition is capable of releasing the therapeutic amount of the therapeutic agent prior to onset of the delayed complication. According to another embodiment, the sustained release of the therapeutic amount of the therapeutic agent occurs within a half-life ranging from 1 day to 30 days from delivery of the composition to the cerebral ventricle. According to another embodiment, the cerebral ventricle is at least 0.001 mm from the cerebral artery in the subarachnoid space. According to another embodiment, the cerebral ventricle is a lateral ventricle, a third ventricle, a fourth ventricle, or a combination thereof. According to another embodiment, the flowable sustained release microparticulate composition produces a predominantly localized effect around the cerebral artery in the subarachnoid space. According to another embodiment, the therapeutic amount of the therapeutic agent is effective to increase the internal diameter of the cerebral artery in the subarachnoid space. According to another embodiment, the pharmaceutical carrier is a buffer solution.

According to another aspect, the described invention provides a flowable sustained release microparticulate composition comprising: (i) a microparticulate formulation comprising at least one therapeutic agent, and (ii) a pharmaceutically acceptable carrier, wherein the microparticulate formulation comprises a plurality of microparticles of uniform size distribution, wherein the at least one therapeutic agent is dispersed throughout each microparticle, and wherein the composition is suitable for delivery into a cerebral ventricle and is capable of flow in the cerebrospinal fluid (CSF) from the ventricle into the subarachnoid space. According to one embodiment, the therapeutic agent is a calcium channel antagonist, an endothelin antagonist, a transient receptor potential (TRP) protein antagonist, or a combination thereof. According to another embodiment, the microparticles comprise a matrix. According to another embodiment, the flowable sustained release microparticulate composition, upon delivery into the cerebral ventricle, is capable of flow from the cerebrospinal fluid (CSF) in the cerebral ventricle into the cerebrospinal fluid (CSF) in the subarachnoid space before sustained release of the therapeutic agent in the subarachnoid space. According to another embodiment, the therapeutic agent is a calcium channel antagonist selected from the group consisting of an L-type voltage dependent calcium channel inhibitor, an R-type voltage dependent calcium channel inhibitor, an N-type voltage dependent calcium channel inhibitor, a P/Q-type voltage dependent calcium channel inhibitor, a T-type voltage dependent calcium channel inhibitor, or a combination thereof. According to another embodiment, the L-type voltage dependent calcium channel inhibitor is a dihydropyridine, selected from the group consisting of amlodipine, aranidipine, azelnidipine, bamidipine, benidipine, cinaldipine, efonidipine, felodipine, isradipine, lacidipine, lemildipine, lercanidipine, nicardipine, nifedipine, nilvadipine, nimodipine, nisoldipine, nitrendipine, manidipine, pranidipine, or a combination thereof. According to another embodiment, the dihydropyridine is nimodipine. According to another embodiment, the microparticulate formulation comprises a powder suspension of microparticles. According to another embodiment, the microparticulate formulation further comprises a slow-release compound. According to one embodiment, the slow release compound is a biodegradable polymer. According to one embodiment, the biodegradable polymer is selected from the group consisting of polylactide-polyglycolide, poly (orthoester), and poly(anhydride). According to another embodiment, the sustained release of the therapeutic amount of the therapeutic agent is capable of occurring within a half-life ranging from 1 day to 30 days from delivery of the composition to the cerebral ventricle. According to another embodiment, the cerebral ventricle is at least 0.001 mm from the cerebral artery in the subarachnoid space. According to another embodiment, the cerebral ventricle is a lateral ventricle, a third ventricle, a fourth ventricle, or a combination thereof. According to another embodiment, the flowable sustained release microparticulate composition is capable of producing a predominantly localized effect around the cerebral artery in the subarachnoid space. According to another embodiment, the therapeutic amount of the therapeutic agent is effective to increase the internal diameter of the cerebral artery in the subarachnoid space. According to another embodiment, the pharmaceutical carrier is a buffer solution.

According to another aspect, the described invention provides a sterile kit for treating at least one cerebral artery in a subarachnoid space at risk of interruption due to a brain injury comprising: (i) a sterile surgical injection apparatus; (ii) a sterile first syringe comprising a barrel, and a plunger; (iii) a sterile second syringe comprising a barrel and a plunger; (iv) a sterile female luer cap; (v) a sterile male luer cap; (vi) a sterile female syringe connector; (vii) a sterile microparticulate formulation suitable for administration into a cerebral ventricle comprising a therapeutic amount of at least one therapeutic agent, wherein the therapeutic amount is effective to reduce a delayed complication of an interruption of a cerebral artery in a subarachnoid space, wherein the microparticulate formulation comprises a plurality of microparticles of uniform size distribution, and wherein the at least one therapeutic agent is dispersed throughout each microparticle, and (vii) a sterile pharmaceutically acceptable carrier. According to one embodiment, the surgical injection apparatus is a needle, a cannula, a catheter, or a combination thereof. According to another embodiment, the microparticulate formulation comprises a powder suspension of microparticles. According to another embodiment, the microparticles have a diameter ranging from about 30 µm to about 100 µm. According to another embodiment, the microparticulate formulation further comprises a slow-release compound. According to one embodiment, the slow release compound is a biodegradable polymer. According to another embodiment, the biodegradable polymer is selected from the group consisting of polylactide-polyglycolide, poly(orthoester), and poly(anhydride). According to another embodiment, the at least one therapeutic agent is a calcium channel antagonist, an endothelin antagonist, a transient receptor potential (TRP) protein antagonist, or a combination thereof. According to another embodiment, the calcium channel antagonist is selected from the group consisting of an L-type voltage dependent calcium channel inhibitor, an R-type voltage dependent calcium channel inhibitor, an N-type voltage dependent calcium channel inhibitor, a P/Q-type voltage dependent calcium channel inhibitor, a T-type voltage dependent calcium channel inhibitor, or a combination thereof. According to another embodiment, the L-type voltage dependent calcium channel inhibitor is a dihydropyridine, selected from the group consisting of amlodipine, aranidipine, azelnidipine, bamidipine, benidipine, cinaldipine, efonidipine, felodipine, isradipine, lacidipine, lemildipine, lercanidipine, nicardipine, nifedipine, nilvadipine, nimodipine, nisoldipine, nitrendipine, manidipine, pranidipine, or a combination thereof. According to another embodiment, the dihydropyridine is nimodipine. According to another embodiment, the pharmaceutical carrier is a buffer solution. According to another embodiment, the kit further comprises at least two sterile containers, wherein the sterile first container is suitable to hold the sterile microparticulate formulation and the sterile second container is suitable to hold the sterile pharmaceutical carrier. According to another embodiment, the container is a vial, a bottle, a tube, a bag, a packet, a pillow, an ampoule, or a combination thereof. According to another embodiment, the microparticulate formulation is prepacked in the first syringe. According to another embodiment, the pharmaceutical carrier is prepacked in the second syringe.

According to another aspect, the described invention provides a method of preparing a sterile flowable sustained release microparticulate composition comprising: (a) providing a sterile microparticulate formulation comprising a therapeutic amount of at least one therapeutic agent, wherein the therapeutic amount is effective to reduce a delayed complication of an interruption of a cerebral artery in a subarachnoid space, wherein the microparticulate formulation comprises a plurality of microparticles of uniform size distribution, and wherein the at least one therapeutic agent is dispersed throughout each microparticle; (b) drawing the sterile microparticulate formulation of step (a) into a sterile first syringe comprising a first syringe barrel, a first syringe plunger and a female luer cap, and removing air trapped within the first syringe; (c) providing a sterile pharmaceutically acceptable carrier; (d) drawing the sterile pharmaceutical carrier of step (c) into a sterile second syringe fitted with a male luer cap comprising a second syringe barrel and a second syringe plunger; (e) replacing the male luer cap in step (c) with a sterile female syringe connector; (f) connecting the sterile first syringe containing the sterile microparticulate formulation of step (b) with the sterile second syringe containing the sterile pharmaceutically acceptable carrier of step (c) via the female syringe connector of step (d); (g) pushing the sterile first syringe plunger so that the sterile microparticulate formulation and the sterile pharmaceutical carrier mix in the sterile second syringe barrel; (h) pushing the sterile second syringe plunger so that the sterile microparticulate formulation and the sterile pharmaceutical carrier mix in the sterile first syringe barrel; and (i) repeating steps (g) and (i) at least 5-50 times to yield the sterile flowable sustained release microparticulate composition suitable for delivery into a cerebral ventricle. According to one embodiment, the microparticulate formulation comprises a powder suspension of microparticles. According to another embodiment, each microparticle comprises a matrix. According to another embodiment, the microparticulate formulation further comprises a slow-release compound. According to one embodiment, the slow release compound is a biodegradable polymer. According to one embodiment, the biodegradable polymer is selected from the group consisting of polylactide-polyglycolide, poly(orthoester), and poly(anhydride). According to another embodiment, the therapeutic agent is a calcium channel antagonist, an endothelin antagonist, a transient receptor potential (TRP) protein antagonist, or a combination thereof. According to another embodiment, the therapeutic agent is a calcium channel antagonist selected from the group consisting of an L-type voltage dependent calcium channel inhibitor, an R-type voltage dependent calcium channel inhibitor, an N-type voltage dependent calcium channel inhibitor, a P/Q-type voltage dependent calcium channel inhibitor, a T-type voltage dependent calcium channel inhibitor, or a combination thereof. According to another embodiment, the L-type voltage dependent calcium channel inhibitor is a dihydropyridine, selected from the group consisting of amlodipine, aranidipine, azelnidipine, bamidipine, benidipine, cinaldipine, efonidipine, felodipine, isradipine, lacidipine, lemildipine, lercanidipine, nicardipine, nifedipine, nilvadipine, nimodipine, nisoldipine, nitrendipine, manidipine, pranidipine, or a combination thereof. According to another embodiment, the dihydropyridine is nimodipine. According to another embodiment, the pharmaceutical carrier is a buffer solution. According to another embodiment, the surgical injection apparatus is a needle, a cannula, a catheter, or a combination thereof.

BRIEF DESCRIPTION OF THE DRAWINGS

FIG. 5 shows an illustrative view of the arterial supply of the cerebral cortex. 1: orbitofrontal artery; 2: prerolandic artery; 3: rolandic artery; 4: anterior parietal artery; 5: posterior parietal artery; 6: angular artery; 7: posterior temporal artery; 8: anterior temporal artery; 9: orbital artery; 10: frontopolar artery; 11: callosomarginal artery; 12: posterior internal frontal artery; 13: pericallosal artery. (Correlative Neuroanatomy & Functional Neurology, 18th Ed., p. 50 (1982)).

DETAILED DESCRIPTION OF THE INVENTION

Glossary

Figure 1:
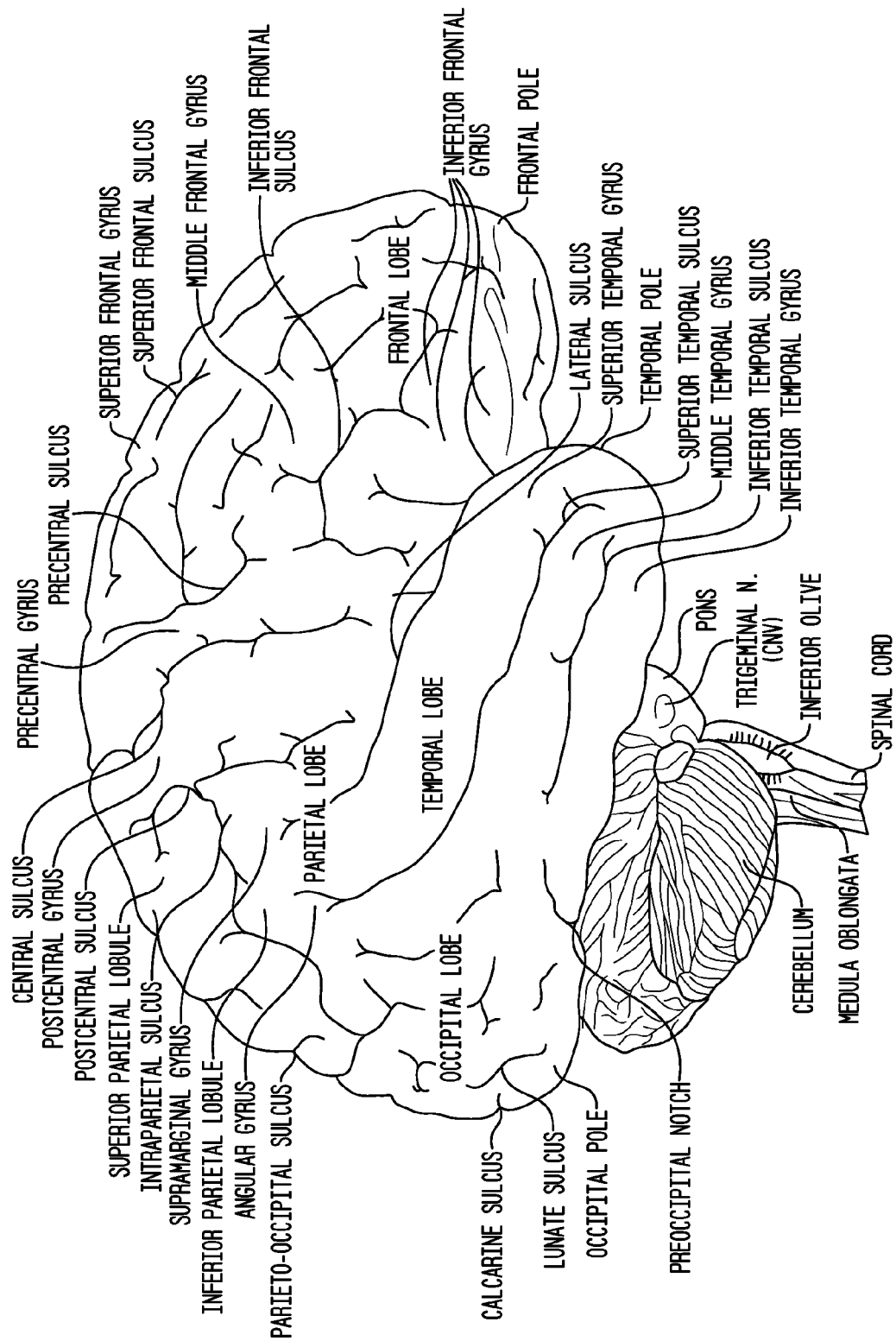
FIG. 1 shows an illustrative lateral view of the human brain (Stedman's Medical Dictionary, 27$^{th}$ Edition, plate 7 at A7 (2000)).
Figure 2:
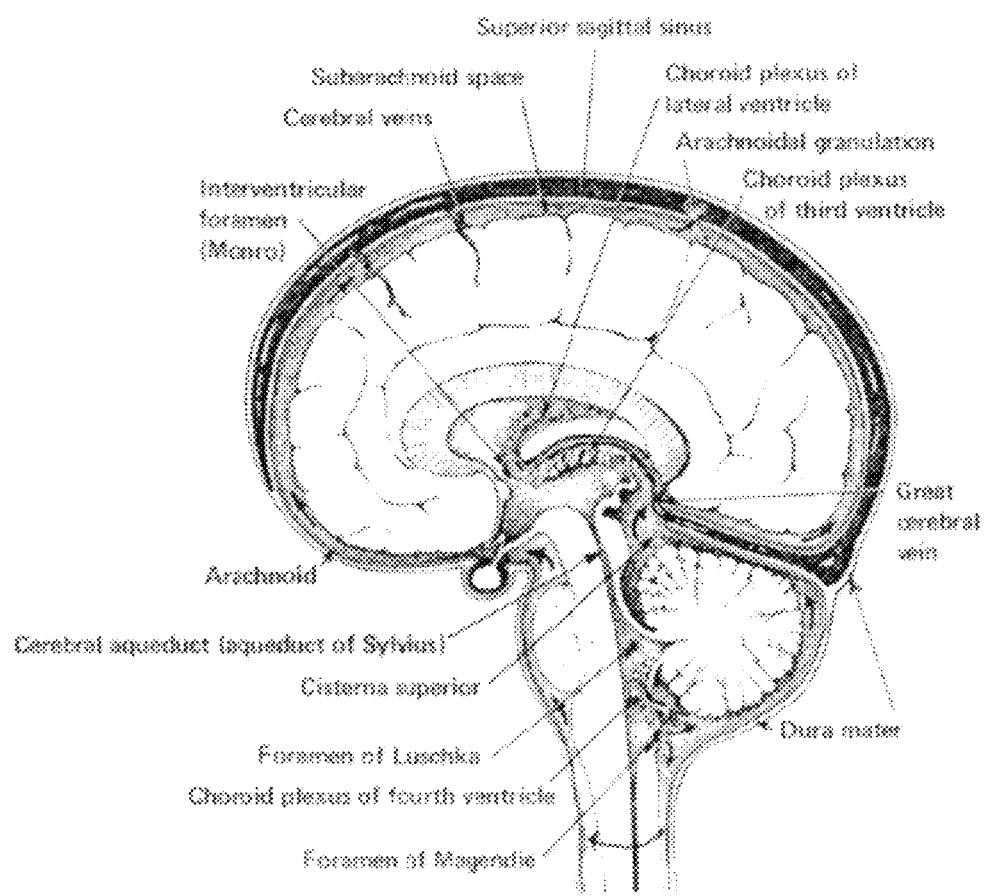
FIG. 2 shows an illustrative sagittal view of the human brain (Correlative Neuroanatomy & Functional Neurology, 18th Ed., p. 46 (1982)).
Figure 3:
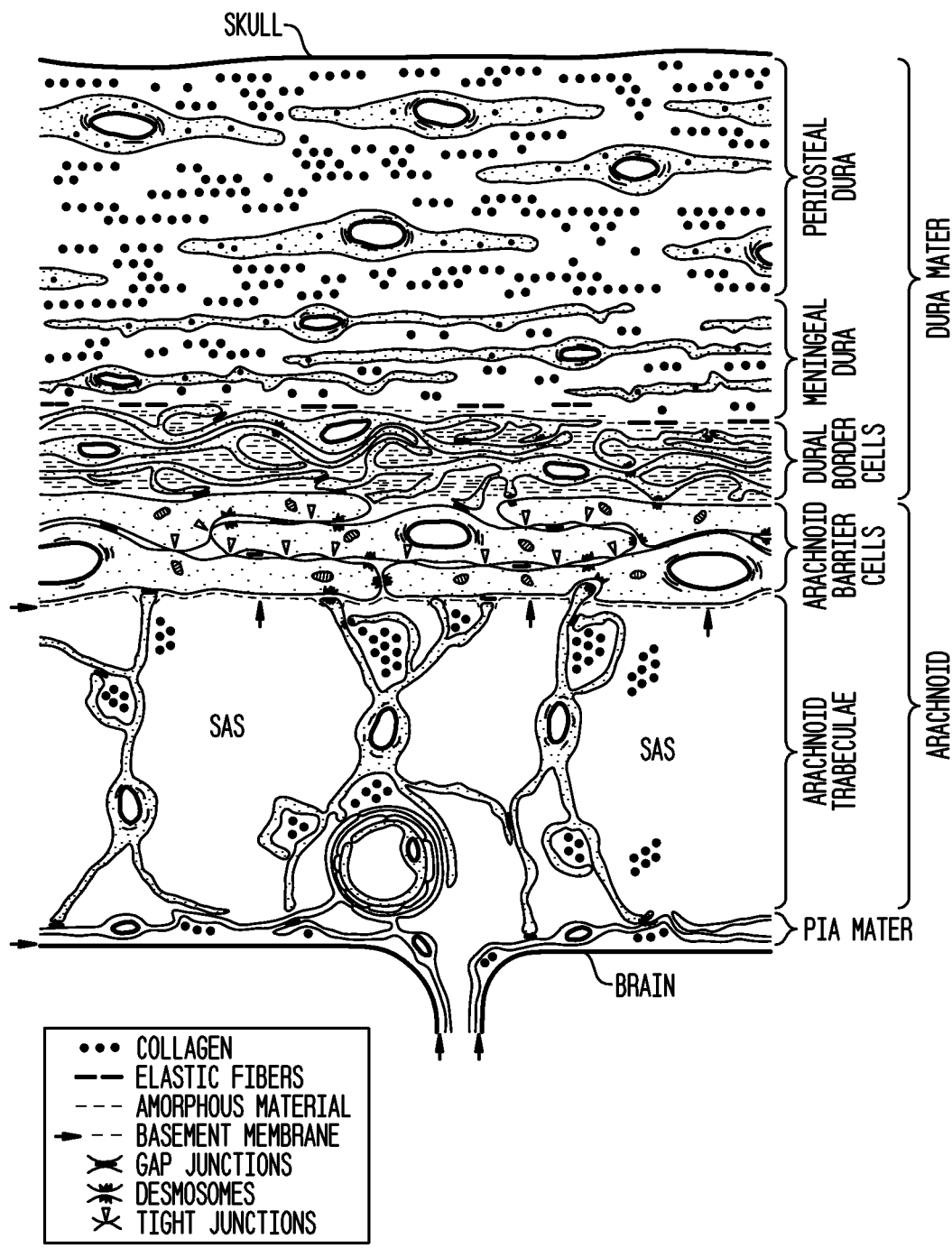
FIG. 3 shows an illustrative view of a cross section of the intact meninges from the inner surface of the skull (upper) to the external surface of the brain (lower). Collagen is present in the periosteal and meningeal dura (large dots, orientation of fibrils not indicated) and in the subarachnoid space (SAS), usually in folds of trabecular cells. The dural border cell layer has no extracellular collagen, few cell junctions, enlarged extracellular spaces (but no basement membrane), and fibroblasts that are distinct from those of the outer portions of the dura. The arachnoid barrier cell layer has essentially no extracellular space, numerous cell junctions, more plump appearing cells, and a comparatively continuous basement membrane on its surface toward the SAS. Note the continuity of cell layers from the arachnoid to the dura (no intervening space), the characteristic appearance of the arachnoid trabeculae, and the relationship of the pia (from Haines D E: On the question of subdural space. Anat Rec 230:3-21, 1991).
Figure 4:
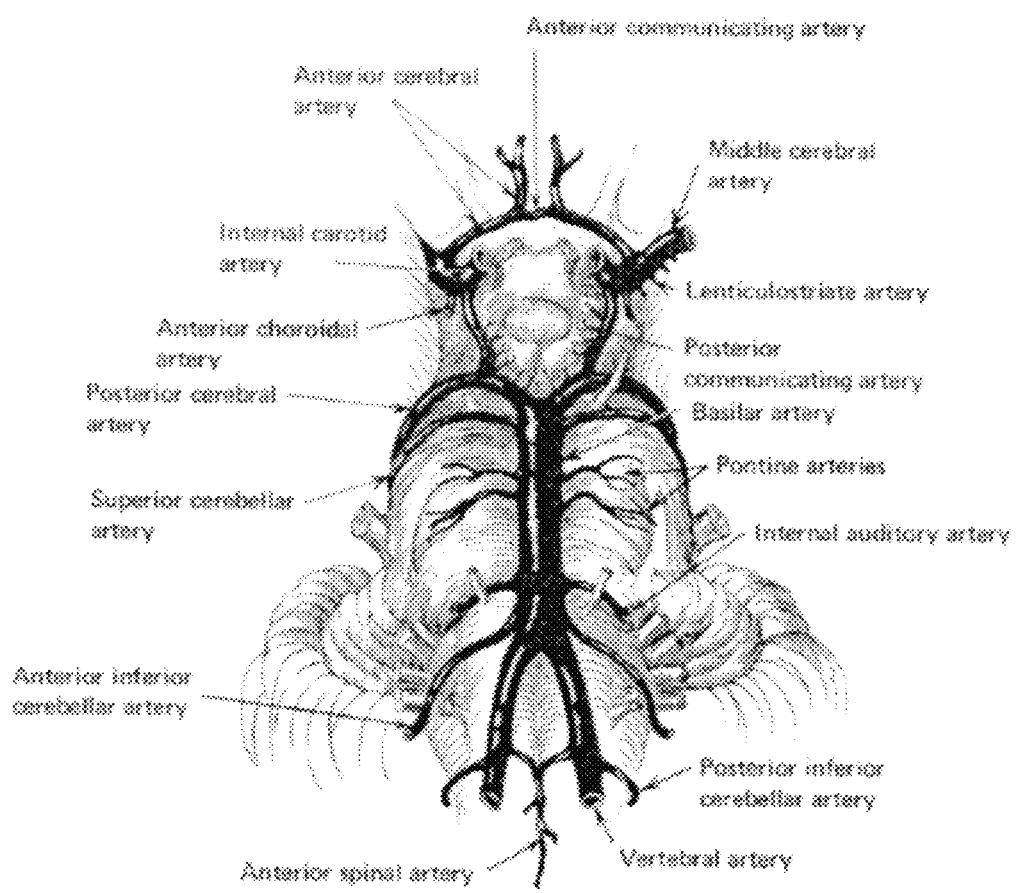
FIG. 4 shows an illustrative view of the circle of Willis and principal arteries of the brain (Correlative Neuroanatomy & Functional Neurology, 18th Ed., p. 48 (1982)).
Figure 6:
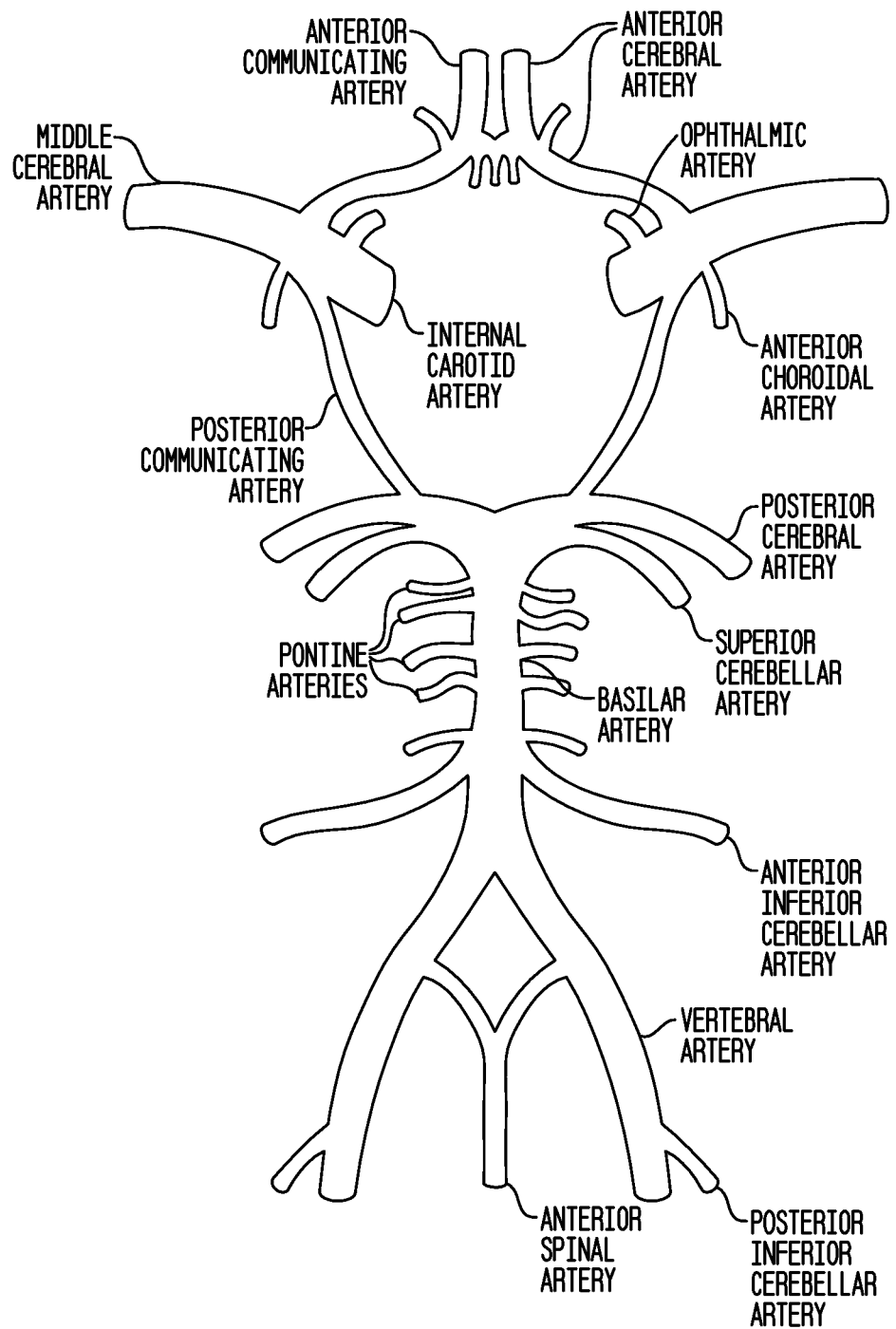
FIG. 6 shows an illustrative view of the cerebral arteries.
Figure 7:
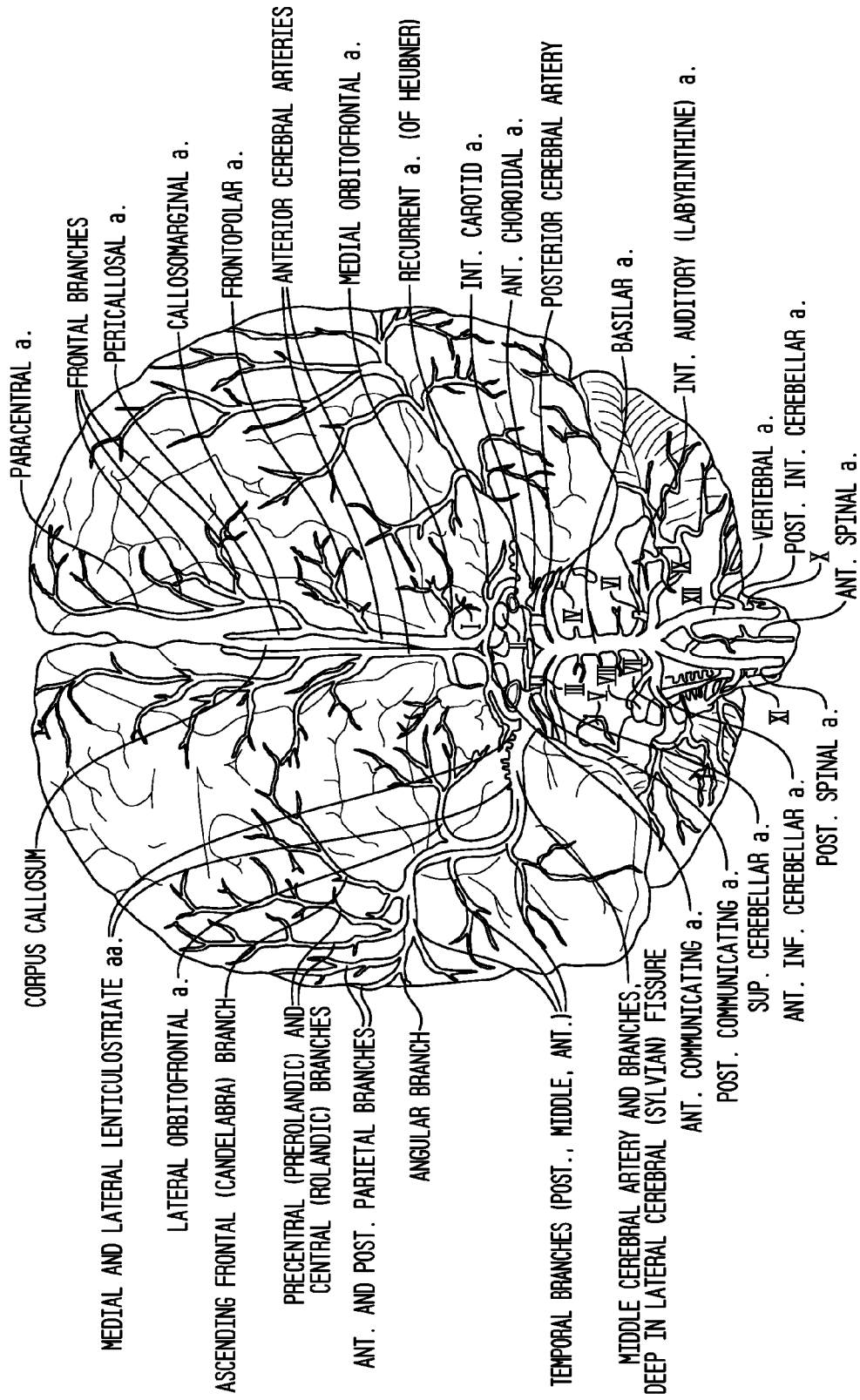
FIG. 7 shows an illustrative view of the cerebral arteries. (from Netter F H. The CIBA Collection of Medical Illustrations: Volumes 1, Nervous System. Vol. 1. Part I. CIBA: USA. 1986. pp. 256).
Figure 8:
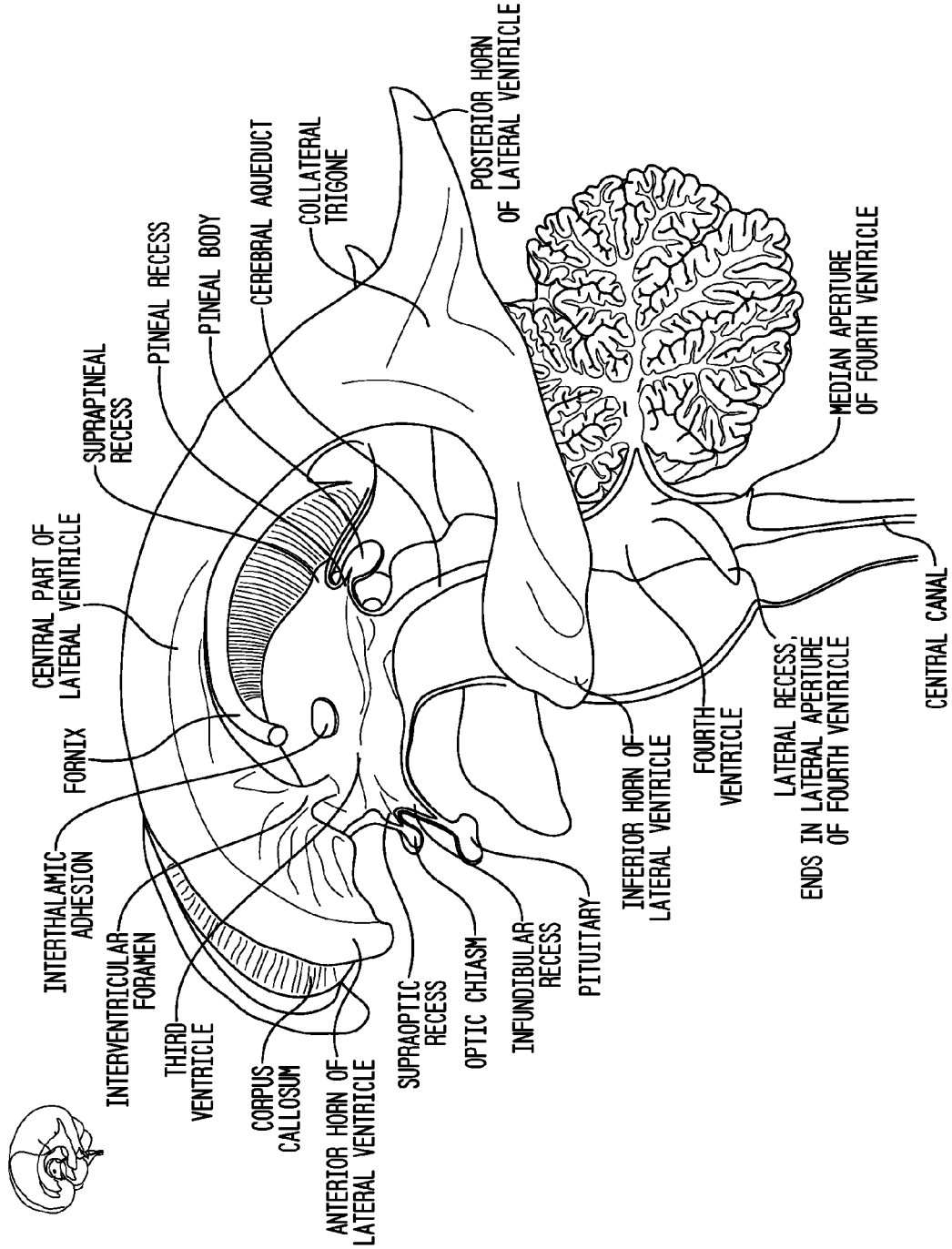
FIG. 8 shows an illustrative view of the cerebral ventricles (page 192, Ross L M, Lamperti E D, Taub E (eds), Schuenke M, Schulte E, Schumacher U. Thieme Atlas of Anatomy. Georg Thieme Verlag: Stuttgart. 2006. pp. 541).
Figure 9:
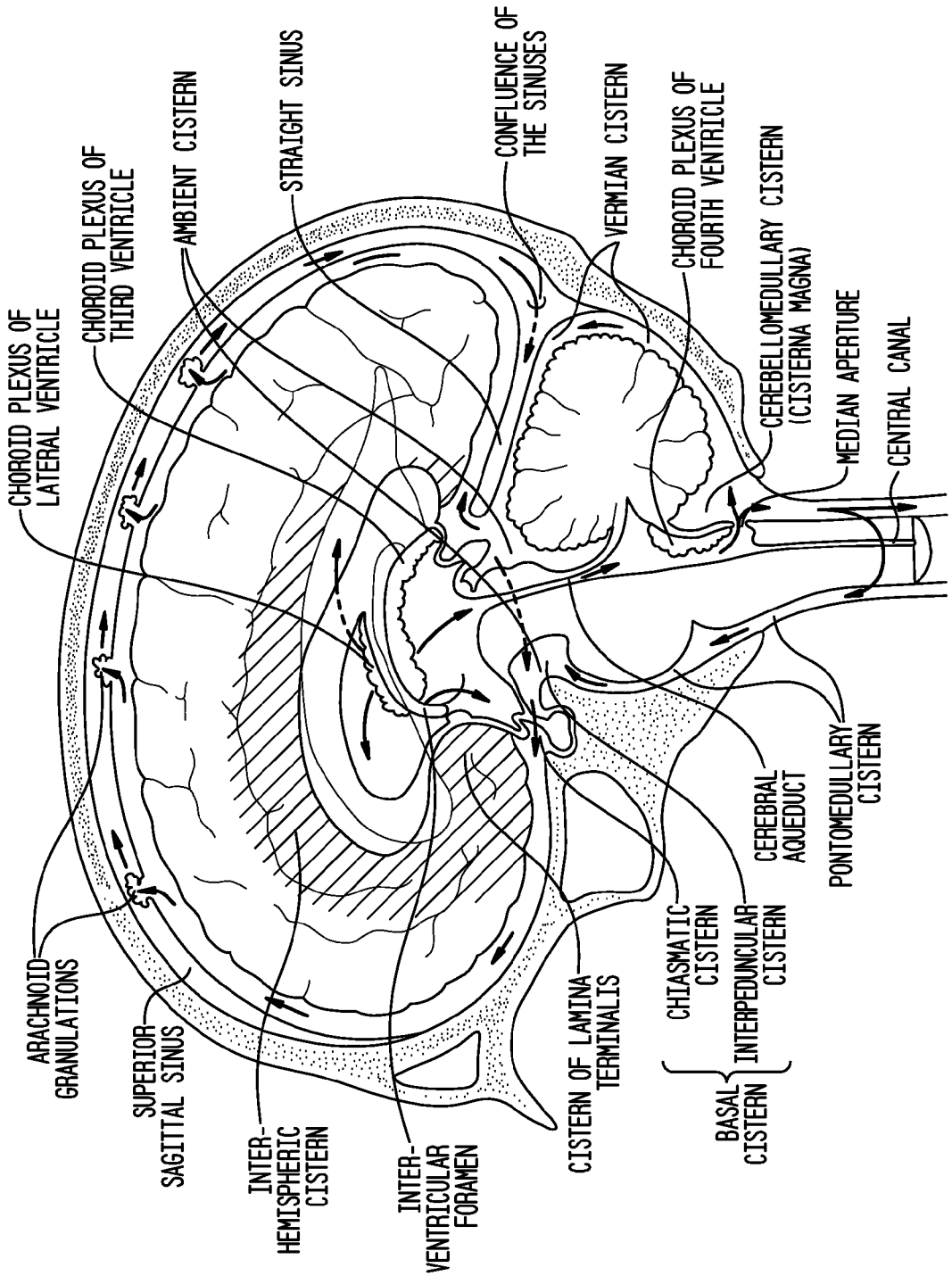
FIG. 9 shows an illustrative view of the CSF flow from the ventricles to the subarachnoid space (page 194, Ross L M, Lamperti E D, Taub E (eds), Schuenke M, Schulte E, Schumacher U. Thieme Atlas of Anatomy. Georg Thieme Verlag: Stuttgart. 2006. pp. 541).
Figure 10A:
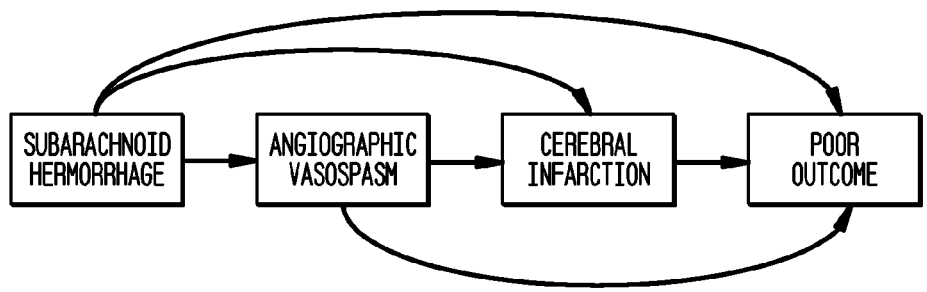
FIG. 10A shows a simple flow diagram for prognosis following subarachnoid hemorrhage.
Figure 10B:
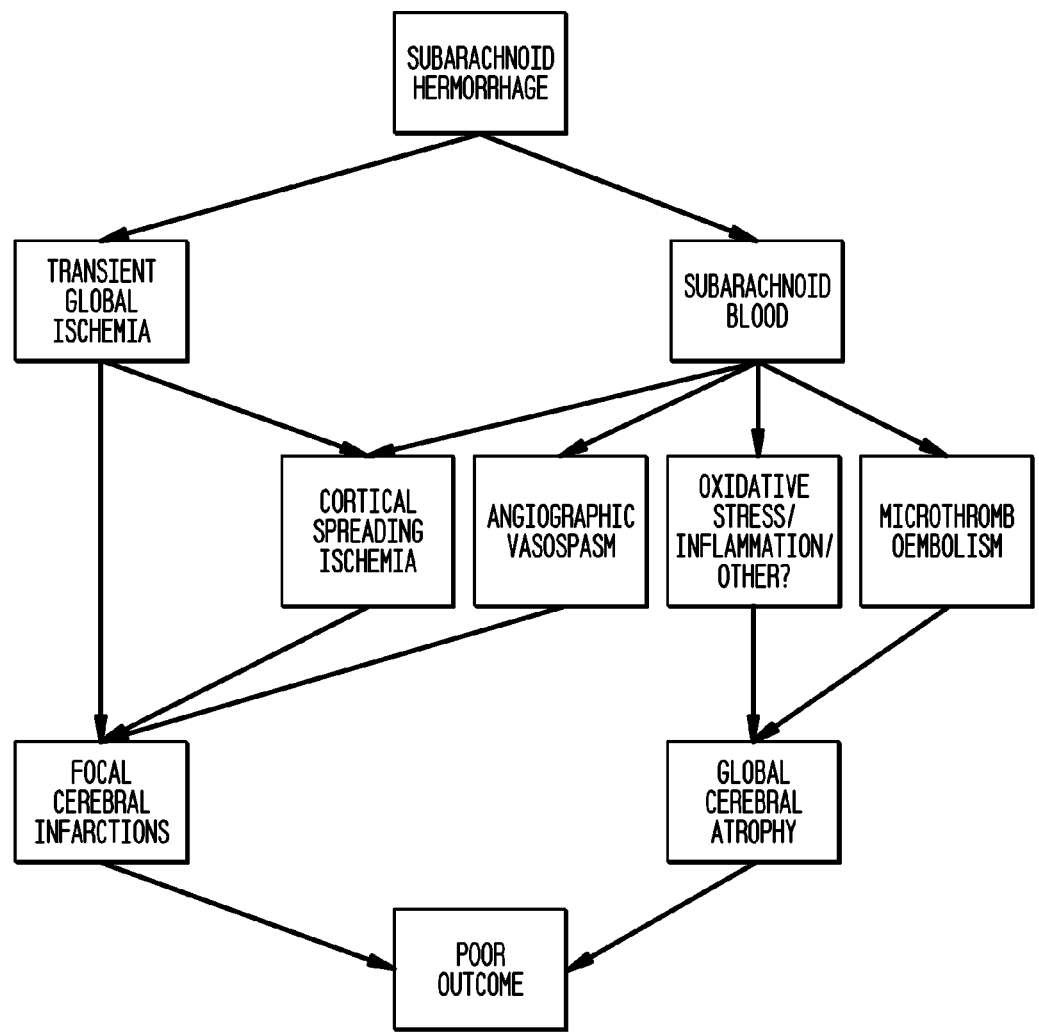
FIG. 10B shows a flow diagram of pathways proposed to be involved in delayed complications after subarachnoid hemorrhage.
Figure 11:
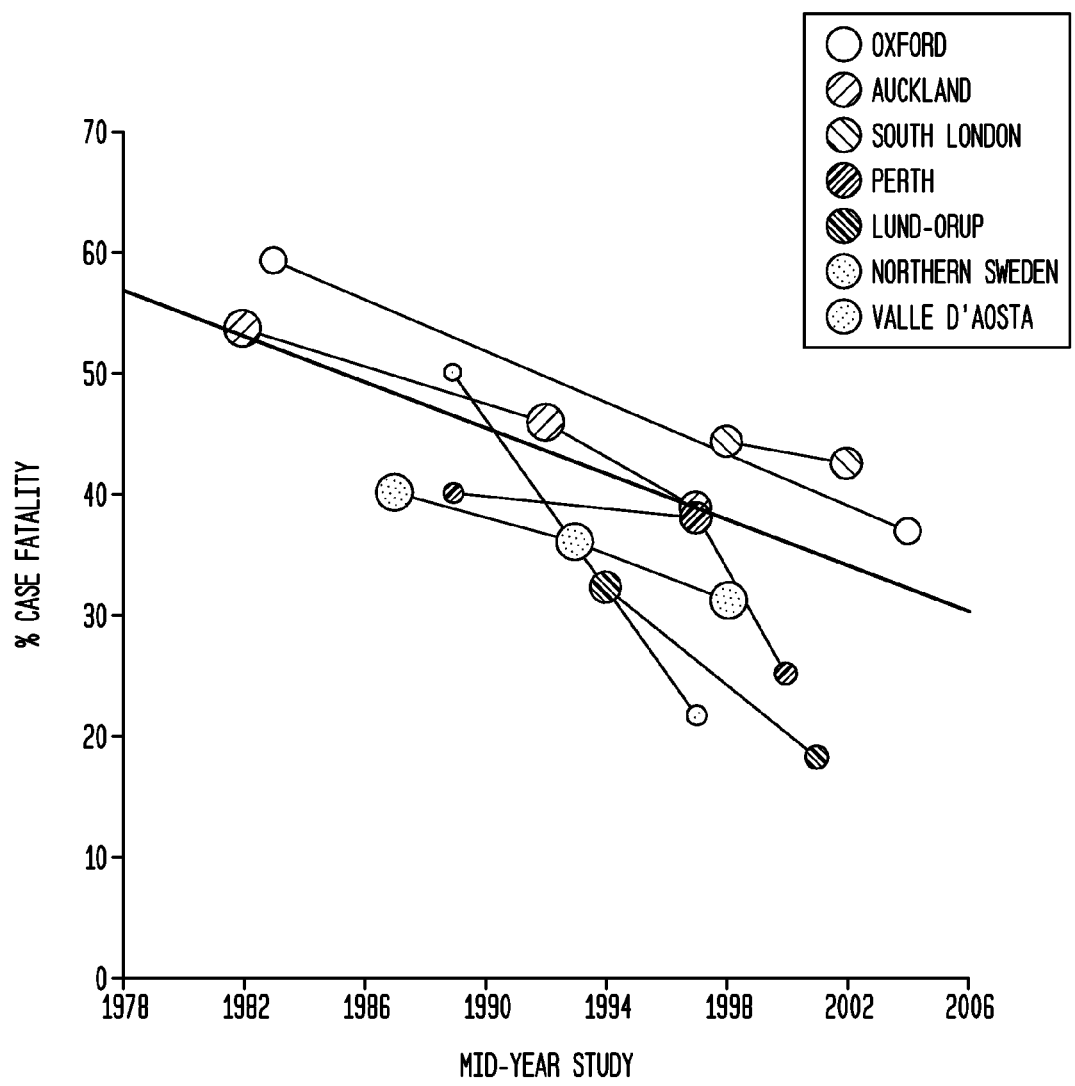
FIG. 11 shows time trends in outcome of subarachnoid hemorrhage in seven population-based studies of subarachnoid hemorrhage (SAH), which shows 50% decrease in mortality over 20 years.

The term "active" as used herein refers to the ingredient, component or constituent of the compositions of the present invention responsible for the intended therapeutic effect.

The term "additive effect", as used herein, refers to a combined effect of two chemicals that is equal to the sum of the effect of each agent given alone.

The term "antagonist" as used herein refers to a substance that interferes with the effects of another substance. Functional or physiological antagonism occurs when two substances produce opposite effects on the same physiological function. Chemical antagonism or inactivation is a reaction between two substances to neutralize their effects. Dispositional antagonism is the alteration of the disposition of a substance (its absorption, biotransformation, distribution, or excretion) so that less of the agent reaches the target or its persistence there is reduced. Antagonism at the receptor for a substance entails the blockade of the effect of an antagonist with an appropriate antagonist that competes for the same site.

The term "administering" as used herein includes in vivo administration, as well as administration directly to tissue ex vivo. Generally, compositions may be administered systemically either orally, buccally, parenterally, topically, by inhalation or insufflation (i.e., through the mouth or through the nose), or rectally in dosage unit formulations containing conventional nontoxic pharmaceutically acceptable carriers, adjuvants, and vehicles as desired, or may be locally administered by means such as, but not limited to, injection, implantation, grafting, topical application, or parenterally.

The term "agonist" as used herein refers to a chemical substance capable of activating a receptor to induce a full or partial pharmacological response. Receptors can be activated or inactivated by either endogenous or exogenous agonists and antagonists, resulting in stimulating or inhibiting a biological response. A physiological agonist is a substance that creates the same bodily responses, but does not bind to the same receptor. An endogenous agonist for a particular receptor is a compound naturally produced by the body which binds to and activates that receptor. A superagonist is a compound that is capable of producing a greater maximal response than the endogenous agonist for the target receptor, and thus an efficiency greater than 100%. This does not necessarily mean that it is more potent than the endogenous agonist, but is rather a comparison of the maximum possible response that can be produced inside a cell following receptor binding. Full agonists bind and activate a receptor, displaying full efficacy at that receptor. Partial agonists also bind and activate a given receptor, but have only partial efficacy at the receptor relative to a full agonist. An inverse agonist is an agent which binds to the same receptor binding-site as an agonist for that receptor and reverses constitutive activity of receptors. Inverse agonists exert the opposite pharmacological effect of a receptor agonist. An irreversible agonist is a type of agonist that binds permanently to a receptor in such a manner that the receptor is permanently activated. It is distinct from a mere agonist in that the association of an agonist to a receptor is reversible, whereas the binding of an irreversible agonist to a receptor is believed to be irreversible. This causes the compound to produce a brief burst of agonist activity, followed by desensitization and internalization of the receptor, which with long-term treatment produces an effect more like an antagonist. A selective agonist is specific for one certain type of receptor.

The terms "anastomosis" and "anastomoses" are used interchangeably to refer to interconnections between blood vessels. These interconnections protect the brain when part of its vascular supply is compromised. At the circle of Willis, the two anterior cerebral arteries are connected by the anterior communicating artery and the posterior cerebral arteries are connected to the internal carotid arteries by the posterior communicating arteries. Other important anastomoses include connections between the ophthalmic artery and branches of the external carotid artery through the orbit, and connections at the brain surface between branches of the middle, anterior, and posterior cerebral arteries (Principles of Neural Sciences, 2d Ed., Eric R. Kandel and James H. Schwartz, Elsevier Science Publishing Co., Inc., New York, pp. 854-56 (1985)).

The term "angiographic vasospasm" as used herein refers to the reduction of vessel size that can be detected on angiographic exams, including, but not limited to, computed tomographic, magnetic resonance or catheter angiography, occurring in approximately 50% of patients following subarachnoid hemorrhage. On the other hand, the term "clinical vasospasm" as used herein refers to the syndrome of confusion and decreased level of consciousness associated with reduced blood flow to the brain parenchyma, occurring in approximatedly 30% of patients, and is now defined as DCI.

The term "antagonist" as used herein refers to a substance that counteracts the effects of another substance.

The term "ataxia" as used herein refers to an inability to coordinate muscle activity during voluntary movement.

The term "biocompatible" as used herein refers to causing no clinically relevant tissue irritation, injury, toxic reaction, or immunological reaction to living tissue.

The term "biodegradable", as used herein, refers to material that will break down actively or passively over time by simple chemical processes, by action of body enzymes or by other similar biological activity mechanisms.

The term "blood vessel", as used herein, refers to a structure, e.g. a tube or a duct conveying or containing blood. Exemplary blood vessels include, but are not limited to, arteries, arterioles, capillaries, veins, and venules.

As shown in FIG. 1, the term "cerebral artery" or its numerous grammatical forms refers to the anterior communication artery, middle cerebral artery, internal carotid artery, anterior cerebral artery, ophthalmic artery, anterior choroidal artery, posterior communicating artery, and basilar artery, and vertebral artery, among others.

The term "cerebral vasospasm" as used herein refers to the delayed occurrence of narrowing of large capacitance arteries at the base of the brain after subarachnoid hemorrhage, often associated with diminished perfusion in the territory distal to the affected vessel. Cerebral vasospasm may occur any time after rupture of an aneurysm but most commonly peaks at seven days following the hemorrhage and often resolves within 14 days when the blood has been absorbed by the body.

The phrase "in proximity" as used herein refers to in the subarachnoid space within less than 10 mm, less than 9.9 mm, less than 9.8 mm, less than 9.7 mm, less than 9.6 mm, less than 9.5 mm, less than 9.4 mm, less than 9.3 mm, less than 9.2 mm, less than 9.1 mm, less than 9.0 mm, less than 8.9 mm, less than 8.8 mm, less than 8.7 mm, less than 8.6 mm, less than 8.5 mm, less than 8.4 mm, less than 8.3 mm, less than 8.2 mm, less than 8.1 mm, less than 8.0 mm, less than 7.9 mm, less than 7.8 mm, less than 7.7 mm, less than 7.6 mm, less than 7.5 mm, less than 7.4 mm, less than 7.3 mm, less than 7.2 mm, less than 7.1 mm, less than 7.0 mm, less than 6.9 mm, less than 6.8 mm, less than 6.7 mm, less than 6.6 mm, less than 6.5 mm, less than 6.4 mm, less than 6.3 mm, less than 6.2 mm, less than 6.1 mm, less than 6.0 mm, less than 5.9 mm, less than 5.8 mm, less than 5.7 mm, less than 5.6 mm, less than 5.5 mm, less than 5.4 mm, less than 5.3 mm, less than 5.2 mm, less than 5.1 mm, less than 5.0 mm, less than 4.9 mm, less than 4.8 mm, less than 4.7 mm, less than 4.6 mm, less than 4.5 mm, less than 4.4 mm, less than 4.3 mm, less than 4.2 mm, less than 4.1 mm, less than 4.0 mm, less than 3.9 mm, less than 3.8 mm, less than 3.7 mm, less than 3.6 mm, less than 3.5 mm, less than 3.4 mm, less than 3.3 mm, less than 3.2 mm, less than 3.1 mm, less than 3.0 mm, less than 2.9 mm, less than 2.8 mm, less than 2.7 mm, less than 2.6 mm, less than 2.5 mm, less than 2.4 mm, less than 2.3 mm, less than 2.2 mm, less than 2.1 mm, less than 2.0 mm, less than 1.9 mm, less than 1.8 mm, less than 1.7 mm, less than 1.6 mm, less than 1.5 mm, less than 1.4 mm, less than 1.3 mm, less than 1.2 mm, less than 1.1 mm, less than 1.0 mm, less than 0.9 mm, less than 0.8 mm, less than 0.7 mm, less than 0.6 mm, less than 0.5 mm, less than 0.4 mm, less than 0.3 mm, less than 0.2 mm, less than 0.1 mm, less than 0.09 mm, less than 0.08 mm, less than 0.07 mm, less than 0.06 mm, less than 0.05 mm, less than 0.04 mm, less than 0.03 mm, less than 0.02 mm, less than 0.01 mm, less than 0.009 mm, less than 0.008 mm, less than 0.007 mm, less than 0.006 mm, less than 0.005 mm, less than 0.004 mm, less than 0.003 mm, less than 0.002 mm, less than 0.001 mm from a blood vessel at risk of interruption, including without limitation, those caused by brain injury.

The term "complication" as used herein refers to a pathological process or event during a disorder that is not an essential part of the disease, although it may result from it or from independent causes. A delayed complication is one that occurs some time after a triggering effect. Complications associated with subarachnoid hemorrhage include, but are not limited to, angiographic vasospasm, microthromboemboli, and cortical spreading ischemia.

The term "condition", as used herein, refers to a variety of health states and is meant to include disorders or diseases caused by any underlying mechanism or disorder, injury, and the promotion of healthy tissues and organs.

The term "contact" and all its grammatical forms as used herein refers to a state or condition of touching or of immediate or local proximity.

The term "controlled release" is intended to refer to any drug-containing formulation in which the manner and profile of drug release from the formulation are regulated. This refers to immediate as well as non-immediate release formulations, with non-immediate release formulations including, but not limited to, sustained release and delayed release formulations.

The term "cortical spreading depolarization" or "CSD" as used herein refers to a wave of near-complete neuronal depolarization and neuronal swelling in the brain that is ignited when passive cation influx across the cellular membrane exceeds ATP-dependent sodium and calcium pump activity. The cation influx is followed by water influx and shrinkage of the extracellular space by about 70%. If normal ion homoeostasis is not restored through additional recruitment of sodium and calcium pump activity, the cell swelling is maintained—a process then termed "cytotoxic edema," since it potentially leads to cell death through a protracted intracellular calcium surge and mitochondrial depolarization. CSD induces dilation of resistance vessels in healthy tissue; hence regional cerebral blood flow increases during the neuronal depolarization phase. (Dreier, J. P. et al., Brain 132: 1866-81 (2009).

The term "cortical spreading ischemia" or "CSI," or "inverse hemodynamic response" refers to a severe microvascular spasm that is coupled to the neuronal depolarization phase. The resulting spreading perfusion deficit prolongs neuronal depolarization [as reflected by a prolonged negative shift of the extracellular direct current (DC) potential] and the intracellular sodium and calcium surge. The hypoperfusion is significant enough to produce a mismatch between neuronal energy demand and supply. (Id.).

The term "delayed cerebral ischemia" or "DCI" as used herein refers to the occurrence of focal neurological impairment (such as hemiparesis, aphasia, apraxia, hemianopia, or neglect), or a decrease in the Glasgow coma scale (either on the total score or on one of its individual components [eye, motor on either side, verbal]). This may or may not last for at least one hour, is not apparent immediately after aneurysm occlusion and cannot be attributed to other causes by means of clinical assessment, CT or magnetic resonance imaging (MRI) scanning of the brain, and appropriate laboratory studies. Angiographic cerebral vasospasm is a description of a radiological test (either CT angiography [CTA], MR angiography [MRA] MRA or catheter angiography [CA]), and may be a cause of DCI.

The term "delayed release" is used herein in its conventional sense to refer to a drug formulation in which there is a time delay between administration of the formulation and the release of the drug there from. "Delayed release" may or may not involve gradual release of drug over an extended period of time, and thus may or may not be "sustained release."

The term "diffuse pharmacologic effect", as used herein, refers to a pharmacologic effect that spreads, disperses or scatters widely over a space or surface.

The term "disease" or "disorder", as used herein, refers to an impairment of health or a condition of abnormal functioning.

The term "dispersion", as used herein, refers to a two-phase system, in which one phase is distributed as particles or droplets in the second, or continuous phase. In these systems, the dispersed phase frequently is referred to as the discontinuous or internal phase, and the continuous phase is called the external phase or dispersion medium. For example, in course dispersions, the particle size is 0.5 µm. In colloidal dispersions, size of the dispersed particle is in the range of approximately 1 nm to 0.5 µm. Molecular dispersion is a dispersion, in which the dispersed phase consists of individual molecules; if the molecules are less than colloidal size, the result is a true solution.

The term "disposed", as used herein, refers to being placed, arranged or distributed in a particular fashion.

The term "drug" as used herein refers to a therapeutic agent or any substance, other than food, used in the prevention, diagnosis, alleviation, treatment, or cure of disease.

The term "effective amount" refers to the amount necessary or sufficient to realize a desired biologic effect.

The term "emulsion" as used herein refers to a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. Usually, separation of the two phases will occur unless a third substance, an emulsifying agent, is incorporated. Thus, a basic emulsion contains at least three components, the two immiscible liquid carriers and the emulsifying agent, as well as the active ingredient. Most emulsions incorporate an aqueous phase into a non-aqueous phase (or vice versa). However, it is possible to prepare emulsions that are basically non-aqueous, for example, anionic and cationic surfactants of the non-aqueous immiscible system glycerin and olive oil.

The term "flowable", as used herein, refers to that which is capable of movement in, or as if in, a stream by continuous change of relative position.

The term "granulomatous inflammation" as used herein refers to an inflammation reaction characterized by a predominance of regular to epithelioid macrophages with or without multinucleated giant cells and connective tissue.

The term "hydrogel" as used herein refers to a substance resulting in a solid, semisolid, pseudoplastic, or plastic structure containing a necessary aqueous component to produce a gelatinous or jelly-like mass.

The term "hypertension" as used herein refers to high systemic blood pressure; transitory or sustained elevation of systemic blood pressure to a level likely to induce cardiovascular damage or other adverse consequences.

The term "hypotension" as used herein refers to subnormal systemic arterial blood pressure; reduced pressure or tension of any kind.

The term "implanting" as used herein refers to grafting, embedding or inserting a substance, composition, or device into a pre-determined location within a tissue.

The term "impregnate", as used herein in its various grammatical forms refers to causing to be infused or permeated throughout; to fill interstices with a substance.

The term "infarction" as used herein refers to a sudden insufficiency of arterial or venous blood supply due to emboli, thrombi, mechanical factors, or pressure that produces a macroscopic area of necrosis. The term "cerebral infarction" as used herein refers to loss of brain tissue subsequent to the transient or permanent loss of circulation and/or oxygen delivery to the cerebrum region of the brain.

The term "inflammation" as used herein refers to the physiologic process by which vascularized tissues respond to injury. See, e.g., FUNDAMENTAL IMMUNOLOGY, 4th Ed., William E. Paul, ed. Lippincott-Raven Publishers, Philadelphia (1999) at 1051-1053, incorporated herein by reference. During the inflammatory process, cells involved in detoxification and repair are mobilized to the compromised site by inflammatory mediators. Inflammation is often characterized by a strong infiltration of leukocytes at the site of inflammation, particularly neutrophils (polymorphonuclear cells). These cells promote tissue damage by releasing toxic substances at the vascular wall or in uninjured tissue. Traditionally, inflammation has been divided into acute and chronic responses.

The term "injury," as used herein, refers to damage or harm to a structure or function of the body caused by an outside agent or force, which may be physical or chemical.

The term "interruption" and its various grammatical forms, as used herein, refers to an alteration in the continuity of blood flow through a blood vessel that is caused by dilation or constriction of the blood vessel induced by chemical, mechanical, and/or physical effects.

The term "ischemia" as used herein refers to a lack of blood supply and oxygen that occurs when reduced perfusion pressure distal to an abnormal narrowing (stenosis) of a blood vessel is not compensated by autoregulatory dilation of the resistance vessels.

The term "isolated molecule" as used herein refers to a molecule that is substantially pure and is free of other substances with which it is ordinarily found in nature or in vivo systems to an extent practical and appropriate for its intended use.

The terms "in the body", "void volume", "resection pocket", "excavation", "injection site", "deposition site" or "implant site" or "site of delivery" as used herein are meant to include all tissues of the body without limit, and may refer to spaces formed therein from injections, surgical incisions, tumor or tissue removal, tissue injuries, abscess formation, or any other similar cavity, space, or pocket formed thus by action of clinical assessment, treatment or physiologic response to disease or pathology as non-limiting examples thereof.

The phrase "localized administration", as used herein, refers to administration of a therapeutic agent in a particular location in the body that may result in a localized pharmacologic effect or a diffuse pharmacologic effect.

The phrase "localized pharmacologic effect", as used herein, refers to a pharmacologic effect limited to a certain location, i.e. in proximity to a certain location, place, area or site. The phrase "predominantly localized pharmacologic effect", as used herein, refers to a pharmacologic effect of a drug limited to a certain location by at least 1 to 3 orders of magnitude achieved with a localized administration as compared to a systemic administration.

The term "long-term" release, as used herein, means that the implant is constructed and arranged to deliver therapeutic levels of the active ingredient for at least 7 days, and potentially up to about 30 to about 60 days.

The term "microparticulate composition", as used herein, refers to a composition comprising a microparticulate formulation and a pharmaceutically acceptable carrier, where the microparticulate formulation comprises a therapeutic agent and a plurality of microparticles.

The term "microthromboembolus" (or plural "microthromboemboli") as used here refers to a small fragment of blood clot that causes obstruction or occlusion of a blood vessel.

The term "modulate" as used herein means to regulate, alter, adapt, or adjust to a certain measure or proportion.

The term "onset of a delayed complication", as used herein, refers to the start or beginning of symptoms associated with the delayed complication.

The term "optionally", as used herein, means that the pharmaceutical composition of the described invention may or may not contain a pharmaceutically acceptable carrier, and includes a pharmaceutical composition containing both a microparticulate formulation of a voltage-gated calcium channel antagonist and a pharmaceutically acceptable carrier.

The term "parenteral" as used herein refers to introduction into the body by way of an injection (i.e., administration by injection) outside the gastrointestinal tract, including, for example, subcutaneously (i.e., an injection beneath the skin), intramuscularly (i.e., an injection into a muscle); intravenously (i.e., an injection into a vein), intrathecally (i.e., an injection into the space around the spinal cord or under the arachnoid membrane of the brain), intrasternal injection, or infusion techniques. A parenterally administered composition is delivered using a needle, e.g., a surgical needle. The term "surgical needle" as used herein, refers to any needle adapted for delivery of fluid (i.e., capable of flow) compositions into a selected anatomical structure. Injectable preparations, such as sterile injectable aqueous or oleaginous suspensions, may be formulated according to the known art using suitable dispersing or wetting agents and suspending agents.

The term "paresis" as used herein refers to partial or incomplete paralysis.

The terms "particles" or "microparticles", as used herein, refer to extremely small constituents, e.g., nanoparticles or microparticles) that may contain in whole or in part at least one therapeutic agent as described herein. The particles may contain therapeutic agent(s) in a core surrounded by a coating. Therapeutic agent(s) also may be dispersed throughout the particles. Therapeutic agent(s) also may be adsorbed into the particles. The particles may be of any order release kinetics, including zero order release, first order release, second order release, delayed release, sustained release, immediate release, etc., and any combination thereof. The particle may include, in addition to therapeutic agent(s), any of those materials routinely used in the art of pharmacy and medicine, including, but not limited to, erodible, nonerodible, biodegradable, or nonbiodegradable material or combinations thereof. The particles may be microcapsules that contain the voltage-gated calcium channel antagonist in a solution or in a semi-solid state. The particles may be of virtually any shape.

The term "pharmaceutically acceptable carrier" as used herein refers to one or more compatible solid or liquid filler, diluents or encapsulating substances which are suitable for administration to a human or other vertebrate animal. The term "carrier" as used herein refers to an organic or inorganic ingredient, natural or synthetic, with which the active ingredient is combined to facilitate the application that does not cause significant irritation to an organism and does not abrogate the biological activity and properties of the active compound of the composition of the described invention. The components of the pharmaceutical compositions also are capable of being commingled in a manner such that there is no interaction which would substantially impair the desired pharmaceutical efficiency. Carriers must be of sufficiently high purity and of sufficiently low toxicity to render them suitable for administration to the mammal being treated. The carrier can be inert, or it can possess pharmaceutical benefits, cosmetic benefits or both. The terms "excipient", "carrier", or "vehicle" are used interchangeably to refer to carrier materials suitable for formulation and administration of pharmaceutically acceptable compositions described herein. Carriers and vehicles useful herein include any such materials know in the art which are nontoxic and do not interact with other components.

The term "pharmaceutical composition" is used herein to refer to a composition that is employed to prevent, reduce in intensity, cure or otherwise treat a target condition or disease.

The term "pharmacologic effect", as used herein, refers to a result or consequence of exposure to an active agent.

The term "prognosis" as used herein refers to an expected future cause and outcome of a disease or disorder, based on medical knowledge.

The term "release" and its various grammatical forms, refers to dissolution of an active drug component and diffusion of the dissolved or solubilized species by a combination of the following processes: (1) hydration of a matrix, (2) diffusion of a solution into the matrix; (3) dissolution of the drug; and (4) diffusion of the dissolved drug out of the matrix.

The term "reduce" or "reducing" as used herein refers to a diminution, a decrease, an attenuation, limitation or abatement of the degree, intensity, extent, size, amount, density, number or occurrence of disorder in individuals at risk of developing the disorder.

The term "subacute inflammation" as used herein refers to a tissue reaction typically seen subsequent to the early inflammatory process characterized by a mixture of neutrophils, lymphocytes, and occasionally macrophages and/or plasma cells.

The term "subarachnoid hemorrhage" or "SAH" is used herein to refer to a condition in which blood collects beneath the arachnoid mater. This area, called the subarachnoid space, normally contains cerebrospinal fluid. The accumulation of blood in the subarachnoid space may lead to stroke, seizures, and other complications. Additionally, SAH may cause permanent brain damage and a number of harmful biochemical events in the brain. Causes of SAH include bleeding from a cerebral aneurysm, vascular anomaly, trauma and extension into the subarachnoid space from a primary intracerebral hemorrhage. Symptoms of SAH include, for example, sudden and severe headache, nausea and/or vomiting, symptoms of meningeal irritation (e.g., neck stiffness, low back pain, bilateral leg pain), photophobia and visual changes, and/or loss of consciousness. SAH is often secondary to a head injury or a blood vessel defect known as an aneurysm. In some instances, SAH can induce angiographic vasospasm that may in turn lead to an ischemic stroke or DCI. A common manifestation of a SAH is the presence of blood in the CSF. Subjects having a SAH may be identified by a number of symptoms. For example, a subject having a subarachnoid hemorrhage will present with blood in the subarachnoid, usually in a large amount. Subjects having a subarachnoid hemorrhage can also be identified by an intracranial pressure that approximates mean arterial pressure, by a fall in cerebral perfusion pressure, or by the sudden transient loss of consciousness (sometimes preceded by a painful headache). In about half of cases, subjects present with a severe headache which may be associated with physical exertion. Other symptoms associated with subarachnoid hemorrhage include nausea, vomiting, memory loss, hemiparesis and aphasia. Subjects having a SAH also may be identified by the presence of creatine kinase-BB isoenzyme activity in their CSF. This enzyme is enriched in the brain but normally is not present in the CSF. Thus, its presence in the CSF is indicative of "leak" from the brain into the subarachnoid space. Assay of creatine-kinase BB isoenzyme activity in the CSF is described by Coplin et al. (Coplin et al 1999 Arch Neurol 56, 1348-1352) Additionally, a spinal tap or lumbar puncture may be used to demonstrate whether blood is present in the CSF, a strong indication of a subarachnoid hemorrhage. A cranial CT scan or an MRI also may be used to identify blood in the subarachnoid region. Angiography also may be used to determine not only whether a hemorrhage has occurred, but also the location of the hemorrhage. Subarachnoid hemorrhage commonly results from rupture of an intracranial saccular aneurysm or from malformation of the arteriovenous system in, and leading to, the brain. Accordingly, a subject at risk of having a subarachnoid hemorrhage includes a subject having a saccular aneurysm as well as a subject having a malformation of the arteriovenous system. Common sites of saccular aneurysms are the top of the basilar artery and the junction of the basilar artery with the superior cerebellar or the anterior inferior cerebellar artery. Subjects having a subarachnoid hemorrhage may be identified by an eye examination, whereby slowed eye movement may indicate brain damage. A subject with a saccular aneurysm may be identified through routine medical imaging techniques, such as CT and MRI. A saccular or cerebral aneurysm forms a mushroom-like or berry-like shape (sometimes referred to as "a dome with a neck" shape).

The terms "subject" or "individual" or "patient" are used interchangeably to refer to a member of an animal species of mammalian origin, including humans.

The phrase "a subject having cerebral vasospasm" as used herein refers to one who has symptoms of or has been diagnosed with cerebral vasospasm and/or presents with diagnostic markers with angiographic vasospasm. A subject at risk of cerebral vasospasm is one who has one or more predisposing factors to the development of cerebral vasospasm. A predisposing factor includes, but is not limited to, existence of a subarachnoid hemorrhage. A subject who has experienced a recent SAH is at significantly higher risk of developing cerebral vasospasm than a subject who has not had a recent SAH. MR angiography, CT angiography and catheter angiography can be used to diagnose cerebral vasospasm Angiography is a technique in which a contrast agent is introduced into the blood stream in order to view blood flow and/or arteries. A contrast agent is required because blood flow and/or arteries sometimes are only weakly apparent in a regular MR scan, CT scan or radiographic film for catheter angiography. Appropriate contrast agents will vary depending upon the imaging technique used. For example, gadolinium is commonly used as a contrast agent used in MR scans. Other MR appropriate contrast agents are known in the art. Diagnostic markers include, but are not limited to, the presence of blood in the CSF, a recent history of a SAH and/or reduction in the lumen diameter of cerebral arteries observed on a catheter, computed tomographic or magnetic resonance angiogram one to 14 days after an SAH or TBI. Presence of blood in the CSF may be detected using CT scans. However, in some instances where the amount of blood is so small as to not be detected by CT, a lumbar puncture is warranted.

The phrase "a subject having delayed cerebral ischemia" or "DCI" as used herein refers to a subject who presents with diagnostic markers associated with DCI. Diagnostic markers include, but are not limited to, the presence of blood in the CSF and/or a recent history of a SAH and/or development of neurological deterioration one to 14 days after SAH when the neurological deterioration is not due to another cause that can be diagnosed, including but not limited to seizures, hydrocephalus, increased intracranial pressure, infection, intracranial hemorrhage or other systemic factors. DCI-associated symptoms include, but are not limited to, paralysis on one side of the body, inability to vocalize the words or to understand spoken or written words, and inability to perform tasks requiring spatial analysis. Such symptoms may develop over a few days, or they may fluctuate in their appearance, or they may present abruptly.

The phrase "a subject having microthromboemboli" as used herein refers to a subject who presents with diagnostic markers associated with microthromboemboli. Diagnostic markers include, but are not limited to, the presence of blood in the CSF and/or a recent history of a SAH and/or development of neurological deterioration one to 14 days after SAH when the neurological deterioration is not due to another cause that can be diagnosed, including but not limited to seizures, hydrocephalus, increased intracranial pressure, infection, intracranial hemorrhage or other systemic factors. Another diagnostic marker may be embolic signals detected on transcranial Doppler ultrasound of large conducting cerebral arteries. Microthromboemboli-associated symptoms include, but are not limited to, paralysis on one side of the body, inability to vocalize the words or to understand spoken or written words, and inability to perform tasks requiring spatial analysis. Such symptoms may develop over a few days, or they may fluctuate in their appearance, or they may present abruptly.

The phrase "a subject having cortical spreading ischemia" as used herein means refers to a subject who presents with diagnostic markers associated with cortical spreading ischemia. Diagnostic markers include, but are not limited to, the presence of blood in the CSF and/or a recent history of a SAH and/or development of neurological deterioration one to 14 days after SAH when the neurological deterioration is not due to another cause that can be diagnosed, including but not limited to seizures, hydrocephalus, increased intracranial pressure, infection, intracranial hemorrhage or other systemic factors. Another diagnostic marker may be detection of propagating waves of depolarization with vasoconstriction detected by electrocorticography. Cortical spreading ischemia-associated symptoms include, but are not limited to, paralysis on one side of the body, inability to vocalize the words or to understand spoken or written words, and inability to perform tasks requiring spatial analysis. Such symptoms may develop over a few days, or they may fluctuate in their appearance, or they may present abruptly.

A subject at risk of DCI, microthromboemboli, cortical spreading ischemia, or angiographic vasospasm is one who has one or more predisposing factors to the development of these conditions. A predisposing factor includes, but is not limited to, existence of a SAH. A subject who has experienced a recent SAH is at significantly higher risk of developing angiographic vasospasm and DCI than a subject who has not had a recent SAH. MR angiography, CT angiography and catheter angiography can be used to diagnose at least one of DCI, microthromboemboli, cortical spreading ischemia or angiographic vasospasm. Angiography is a technique in which a contrast agent is introduced into the blood stream in order to view blood flow and/or arteries. A contrast agent is required because blood flow and/or arteries sometimes are only weakly apparent in a regular MR scan, CT scan or radiographic film for catheter angiography. Appropriate contrast agents will vary depending upon the imaging technique used. For example, gadolinium is commonly used as a contrast agent used in MR scans. Other MR appropriate contrast agents are known in the art.

The term "suitable for delivery", as used herein, refers to being apt, appropriate for, designed for, or proper for release only in a subarachnoid space.

The term "substantially pure", as used herein, refers to a condition of a therapeutic agent such that it has been substantially separated from the substances with which it may be associated in living systems or during synthesis. According to some embodiments, a substantially pure therapeutic agent is at least 70% pure, at least 75% pure, at least 80% pure, at least 85% pure, at least 90% pure, at least 95% pure, at least 96% pure, at least 97% pure, at least 98% pure, or at least 99% pure.

The term "sustained release" (also referred to as "extended release") is used herein in its conventional sense to refer to a drug formulation that provides for gradual release of a drug over an extended period of time, and that preferably, although not necessarily, results in substantially constant blood levels of a drug over an extended time period. Alternatively, delayed absorption of a parenterally administered drug Form Is accomplished by dissolving or suspending the drug in an oil vehicle. Nonlimiting examples of sustained release biodegradable polymers include polyesters, polyester polyethylene glycol copolymers, polyamino-derived biopolymers, polyanhydrides, polyorthoesters, polyphosphazenes, SAIB, photopolymerizable biopolymers, protein polymers, collagen, polysaccharides, chitosans, and alginates.

The term "syndrome," as used herein, refers to a pattern of symptoms indicative of some disease or condition.

The term "synergistic effect", as used herein, refers to a combined effect of two chemicals, which is greater than the sum of the effects of each agent given alone.

The phrase "systemic administration", as used herein, refers to administration of a therapeutic agent with a pharmacologic effect on the entire body. Systemic administration includes enteral administration (e.g. oral) through the gastrointestinal tract and parenteral administration (e.g. intravenous, intramuscular, etc.) outside the gastrointestinal tract.

The terms "therapeutic amount", "therapeutic effective amount" or an "amount effective" of one or more of the therapeutic agents is an amount that is sufficient to provide the intended benefit of treatment. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen may be planned which does not cause substantial toxicity and yet is effective to treat the particular subject. A therapeutic effective amount of the therapeutic agents that can be employed ranges from generally 0.1 mg/kg body weight and about 50 mg/kg body weight. Therapeutic effective amount for any particular application may vary depending on such factors as the disease or condition being treated, the particular therapeutic agent being administered, the size of the subject, or the severity of the disease or condition. One of ordinary skill in the art may determine empirically the effective amount of a particular inhibitor and/or other therapeutic agent without necessitating undue experimentation. It is preferred generally that a maximum dose be used, that is, the highest safe dose according to some medical judgment. However, dosage levels are based on a variety of factors, including the type of injury, the age, weight, sex, medical condition of the patient, the severity of the condition, the route of administration, and the particular therapeutic agent employed. Thus the dosage regimen may vary widely, but can be determined routinely by a surgeon using standard methods. "Dose" and "dosage" are used interchangeably herein.

The term "therapeutic agent" as used herein refers to a drug, molecule, nucleic acid, protein, composition or other substance that provides a therapeutic effect. The terms "therapeutic agent" and "active agent" are used interchangeably. The active agent may be a calcium channel antagonist, an endothelin antagonist, or a transient receptor potential (TRP) protein antagonist.

Therapeutic agent(s), including the calcium channel antagonist, the endothelin antagonist, or the transient receptor potential (TRP) protein antagonist can be provided in particles.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50 which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation.

The term "topical" refers to administration of a composition at, or immediately beneath, the point of application. The phrase "topically applying" describes application onto one or more surfaces(s) including epithelial surfaces. Topical administration, in contrast to transdermal administration, generally provides a local rather than a systemic effect.

The term "transient receptor potential (TRP) protein antagonist" as used herein refers to a protein that is structurally distinct from other calcium channel antagonist and that blocks or antagonizes intracellular calcium increases in cells due to receptor-mediated calcium influx. Transient receptor potential (TRP) protein antagonists include, but are not limited to, SK&F 96365 (1-(beta-[3-(4-methoxy-phenyl)propoxy]-4-methoxyphenethyl)-1H-imidazole hydrochloride) and LOE 908 (RS)-(3,4-dihydro-6,7-dimethoxyisoquinoline-1-gamma 1)-2-phenyl-N,N-dit2-(2,3,4-trimethoxyphenyl)ethyl]acetamide).

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The term "vasoconstriction" as used herein refers to the narrowing of the blood vessels resulting from contracting of the muscular wall of the vessels. When blood vessels constrict, the flow of blood is restricted or slowed.

The term "vasodilation" which is the opposite of vasoconstriction as used herein refers to the widening of blood vessels. The terms "vasoconstrictors," "vasopressors," or "pressors" as used herein refer to factors causing vasoconstriction.

The term "vasospasm" as used herein refers to a decrease in the internal diameter of a cerebral artery that results from contraction of smooth muscle within the wall of the artery which causes a decrease in blood flow, but generally without an increase in systemic vascular resistance. Vasospasm results in decreased cerebral blood flow and increased cerebral vascular resistance. Without being limited by theory, it generally is believed that vasospasm is caused by local injury to vessels, such as that which results from atherosclerosis and other structural injury including traumatic head injury, aneurysmal subarachnoid hemorrhage and other causes of subarachnoid hemorrhage. Cerebral vasospasm is a naturally occurring vasoconstriction that also may be triggered by the presence of blood in the CSF, a common occurrence after rupture of an aneurysm or following traumatic head injury. Cerebral vasospasm ultimately can lead to brain cell damage, in the form of cerebral ischemia and infarction, due to interrupted blood supply. The term "cerebral vasospasm" as used herein further refers to the delayed occurrence of narrowing of large capacitance arteries at the base of the brain after subarachnoid hemorrhage, often associated with diminished perfusion in the territory distal to the affected vessel. Cerebral vasospasm may occur any time after rupture of an aneurysm but most commonly peaks at seven days following the hemorrhage and often resolves within 14 days when the blood has been absorbed by the body. Angiographic vasospasm is a consequence of SAH, but also can occur after any condition that deposits blood in the subarachnoid space. More specifically, the term "angiographic cerebral vasospasm" refers to the narrowing of the large capacitance arteries at the base of the brain (i.e., cerebral arteries) following hemorrhage into the subarachnoid space, and leads to reduced perfusion of distal brain regions.

Anatomical Terms

When referring to animals, that typically have one end with a head and mouth, with the opposite end often having the anus and tail, the head end is referred to as the cranial end, while the tail end is referred to as the caudal end. Within the head itself, rostral refers to the direction toward the end of the nose, and caudal is used to refer to the tail direction. The surface or side of an animal's body that is normally oriented upwards, away from the pull of gravity, is the dorsal side; the opposite side, typically the one closest to the ground when walking on all legs, swimming or flying, is the ventral side. On the limbs or other appendages, a point closer to the main body is "proximal"; a point farther away is "distal". Three basic reference planes are used in zoological anatomy. A "sagittal" plane divides the body into left and right portions. The "midsagittal" plane is in the midline, i.e. it would pass through midline structures such as the spine, and all other sagittal planes are parallel to it. A "coronal" plane divides the body into dorsal and ventral portions. A "transverse" plane divides the body into cranial and caudal portions. When referring to humans, the body and its parts are always described using the assumption that the body is standing upright. Portions of the body which are closer to the head end are "superior" (corresponding to cranial in animals), while those farther away are "inferior" (corresponding to caudal in animals). Objects near the front of the body are referred to as "anterior" (corresponding to ventral in animals); those near the rear of the body are referred to as "posterior" (corresponding to dorsal in animals). A transverse, axial, or horizontal plane is an X-Y plane, parallel to the ground, which separates the superior/head from the inferior/feet. A coronal or frontal plane is an Y-Z plane, perpendicular to the ground, which separates the anterior from the posterior. A sagittal plane is an X-Z plane, perpendicular to the ground and to the coronal plane, which separates left from right. The midsagittal plane is the specific sagittal plane that is exactly in the middle of the body.

Structures near the midline are called medial and those near the sides of animals are called lateral. Therefore, medial structures are closer to the midsagittal plane, lateral structures are further from the midsagittal plane. Structures in the midline of the body are median. For example, the tip of a human subject's nose is in the median line.

Ipsilateral means on the same side, contralateral means on the other side and bilateral means on both sides. Structures that are close to the center of the body are proximal or central, while ones more distant are distal or peripheral. For example, the hands are at the distal end of the arms, while the shoulders are at the proximal ends.

I. Compositions

In one aspect, the described invention provides a flowable sustained release microparticulate composition comprising:
 (i) a microparticulate formulation comprising at least one therapeutic agent, and
 (ii) a pharmaceutically acceptable carrier,
 wherein the microparticulate formulation comprises a plurality of microparticles of uniform size distribution,
wherein the at least one therapeutic agent is dispersed throughout each microparticle, and wherein the composition is suitable for delivery into a cerebral ventricle and is capable of flow in the cerebrospinal fluid (CSF) from the ventricle into the subarachnoid space.

According to one embodiment, the flowable sustained release microparticulate composition, upon delivery into the cerebral ventricle, is capable of dispersion from the cerebral ventricle without release of the at least one therapeutic agent into the cerebral ventricle.

According to another embodiment, the flowable sustained release microparticulate composition, upon delivery into the cerebral ventricle, is capable of sustained release of a therapeutic amount of the at least one therapeutic agent at a site of release in subarachnoid space. According to one embodiment, the site of release is in proximity to at least one blood vessel in the subarachnoid space at risk of interruption caused by a brain injury. According to one embodiment, the at least one blood vessel is at least one cerebral artery in the subarachnoid space.

According to another embodiment, the flowable sustained release microparticulate composition, upon delivery into the cerebral ventricle, is capable of flow from the cerebrospinal fluid (CSF) in the cerebral ventrical into the cerebrospinal fluid (CSF) in the subarachnoid space before sustained release of the therapeutic agent in the subarachnoid space.

According to some embodiments, the cerebral ventricle into which the flowable sustained release microparticulate composition is capable of being delivered is selected from the group consisting of a lateral ventricle, a third ventricle, a fourth ventricle, or a combination thereof. According to some embodiments, the cerebral ventricle is a lateral ventricle. According to one embodiment, the cerebral ventricle is a right lateral ventricle. According to another embodiment, the cerebral ventricle is a left lateral ventricle. According to one embodiment, the cerebral ventricle is a third ventricle. According to another embodiment, the cerebral ventricle is a fourth ventricle.

According to some embodiments, the cerebral ventricle is at least 0.001 mm to at least 10 cm from the at least one cerebral artery in the subarachnoid space at risk of interruption caused by a brain injury. According to one embodiment, the cerebral ventricle is at least 0.001 mm from the at least one cerebral artery in the subarachnoid space at risk of interruption caused by the brain injury. According to another embodiment, the cerebral ventricle is at least 0.005 mm from the at least one cerebral artery in the subarachnoid space at risk of interruption caused by the brain injury. According to another embodiment, the cerebral ventricle is at least 0.01 mm from the at least one cerebral artery in the subarachnoid space at risk of interruption caused by the brain injury. According to another embodiment, the cerebral ventricle is at least 0.05 mm from the at least one cerebral artery in the subarachnoid space at risk of interruption caused by the brain injury. According to another embodiment, the cerebral ventricle is at least 0.1 mm from the at least one cerebral artery in the subarachnoid space at risk of interruption caused by the brain injury. According to another embodiment, the cerebral ventricle is at least 0.5 mm from the at least one cerebral artery in the subarachnoid space at risk of interruption caused by the brain injury. According to another embodiment, the cerebral ventricle is at least 1.0 mm from the at least one cerebral artery in the subarachnoid space at risk of interruption caused by the brain injury. According to another embodiment, the cerebral ventricle is at least 1.5 mm from the at least one cerebral artery in the subarachnoid space at risk of interruption caused by the brain injury. According to another embodiment, the cerebral ventricle is at least 2.0 mm from the at least one cerebral artery in the subarachnoid space at risk of interruption caused by the brain injury. According to another embodiment, the cerebral ventricle is at least 2.5 mm from the at least one cerebral artery in the subarachnoid space at risk of interruption caused by the brain injury. According to another embodiment, the cerebral ventricle is at least 3.0 mm from the at least one cerebral artery in the subarachnoid space at risk of interruption caused by the brain injury. According to another embodiment, the cerebral ventricle is at least 3.5 mm from the at least one cerebral artery in the subarachnoid space at risk of interruption caused by the brain injury. According to another embodiment, the cerebral ventricle is at least 4.0 mm from the at least one cerebral artery in the subarachnoid space at risk of interruption caused by the brain injury. According to another embodiment, the cerebral ventricle is at least 4.5 mm from the at least one cerebral artery in the subarachnoid space at risk of interruption caused by the brain injury. According to another embodiment, the cerebral ventricle is at least 5.0 mm from the at least one cerebral artery in the subarachnoid space at risk of interruption caused by the brain injury. According to another embodiment, the cerebral ventricle is at least 5.5 mm from the at least one cerebral artery in the subarachnoid space at risk of interruption caused by the brain injury. According to another embodiment, the cerebral ventricle is at least 6.0 mm from the at least one cerebral artery in the subarachnoid space at risk of interruption caused by the brain injury. According to another embodiment, the cerebral ventricle is at least 6.5 mm from the at least one cerebral artery in the subarachnoid space at risk of interruption caused by the brain injury. According to another embodiment, the cerebral ventricle is at least 7.0 mm from the at least one cerebral artery in the subarachnoid space at risk of interruption caused by the brain injury. According to another embodiment, the cerebral ventricle is at least 7.5 mm from the at least one cerebral artery in the subarachnoid space at risk of interruption caused by the brain injury. According to another embodiment, the cerebral ventricle is at least 8.0 mm from the at least one cerebral artery in the subarachnoid space at risk of interruption caused by the brain injury. According to another embodiment, the cerebral ventricle is at least 8.5 mm from the at least one cerebral artery in the subarachnoid space at risk of interruption caused by the brain injury. According to another embodiment, the cerebral ventricle is at least 9.0 mm from the at least one cerebral artery in the subarachnoid space at risk of interruption caused by the brain injury. According to another embodiment, the cerebral ventricle is at least 9.5 mm from the at least one cerebral artery in the subarachnoid space at risk of interruption caused by the brain injury. According to another embodiment, the cerebral ventricle is at least 1 cm from the at least one cerebral artery in the subarachnoid space at risk of interruption caused by the brain injury. According to another embodiment, the cerebral ventricle is at least 1.5 cm from the at least one cerebral artery in the subarachnoid space at risk of interruption caused by the brain injury. According to another embodiment, the cerebral ventricle is at least 2.0 cm from the at least one cerebral artery in the subarachnoid space at risk of interruption caused by the brain injury. According to another embodiment, the cerebral ventricle is at least 2.5 cm from the at least one cerebral artery in the subarachnoid space at risk of interruption caused by the brain injury. According to another embodiment, the cerebral ventricle is at least 3.0 cm from the at least one cerebral artery in the subarachnoid space at risk of interruption caused by the brain injury. According to another embodiment, the cerebral ventricle is at least 3.5 cm from the at least one cerebral artery in the subarachnoid space at risk of interruption caused by the brain injury. According to another embodiment, the cerebral ventricle is at least 4.0 cm from the at least one cerebral artery in the subarachnoid space at risk of interruption caused by the brain injury. According to another embodiment, the cerebral ventricle is at least 4.5 cm from the at least one cerebral artery in the subarachnoid space at risk of interruption caused by the brain injury. According to another embodiment, the cerebral ventricle is at least 5.0 cm from the at least one cerebral artery in the subarachnoid space at risk of interruption caused by the brain injury. According to another embodiment, the cerebral ventricle is at least 5.5 cm from the at least one cerebral artery in the subarachnoid space at risk of interruption caused by the brain injury. According to another embodiment, the cerebral ventricle is at least 6.0 cm from the at least one cerebral artery in the subarachnoid space at risk of interruption caused by the brain injury. According to another embodiment, the cerebral ventricle is at least 6.5 cm from the at least one cerebral artery in the subarachnoid space at risk of interruption caused by the brain injury. According to another embodiment, the cerebral ventricle is at least 7.0 cm from the at least one cerebral artery in the subarachnoid space at risk of interruption caused by the brain injury. According to another embodiment, the cerebral ventricle is at least 7.5 cm from the at least one cerebral artery in the subarachnoid space at risk of interruption caused by the brain injury. According to another embodiment, the cerebral ventricle is at least 8.0 cm from the at least one cerebral artery in the subarachnoid space at risk of interruption caused by the brain injury. According to another embodiment, the cerebral ventricle is at least 8.5 cm from the at least one cerebral artery in the subarachnoid space at risk of interruption caused by the brain injury. According to another embodiment, the cerebral ventricle is at least 9.0 cm from the at least one cerebral artery in the subarachnoid space at risk of interruption caused by the brain injury. According to another embodiment, the cerebral ventricle is at least 9.5 cm from the at least one cerebral artery in the subarachnoid space at risk of interruption caused by the brain injury. According to another embodiment, the cerebral ventricle is at least 10 cm from the at least one cerebral artery in the subarachnoid space at risk of interruption caused by the brain injury.

According to some embodiments, the flowable sustained release microparticulate composition is capable of sustained release of a therapeutic amount of the at least one therapeutic agent within a half-life ($t_{1/2}$) ranging from 1 day to 30 days. According to one embodiment, the flowable sustained release microparticulate composition is capable of sustained release of the therapeutic amount of the at least one therapeutic agent within a half-life of 1 day. According to another embodiment, the flowable sustained release microparticulate composition is capable of sustained release of the therapeutic amount of the at least one therapeutic agent within a half-life of 2 days. According to another embodiment, the flowable sustained release microparticulate composition is capable of sustained release of the therapeutic amount of the at least one therapeutic agent within a half-life of 3 days. According to another embodiment, the flowable sustained release microparticulate composition is capable of sustained release of the therapeutic amount of the at least one therapeutic agent within a half-life of 4 days. According to another embodiment, the flowable sustained release microparticulate composition is capable of sustained release of the therapeutic amount of the at least one therapeutic agent within a half-life of 5 days. According to another embodiment, the flowable sustained release microparticulate composition is capable of sustained release of the therapeutic amount of the at least one therapeutic agent within a half-life of 6 days. According to another embodiment, the flowable sustained release microparticulate composition is capable of sustained release of the therapeutic amount of the at least one therapeutic agent within a half-life of 7 days. According to another embodiment, the flowable sustained release microparticulate composition is capable of sustained release of the therapeutic amount of the at least one therapeutic agent within a half-life of 8 days. According to another embodiment, the flowable sustained release microparticulate composition is capable of sustained release of the therapeutic amount of the at least one therapeutic agent within a half-life of 9 days. According to another embodiment, the flowable sustained release microparticulate composition is capable of sustained release of the therapeutic amount of the at least one therapeutic agent within a half-life of 10 days. According to another embodiment, the flowable sustained release microparticulate composition is capable of sustained release of the therapeutic amount of the at least one therapeutic agent within a half-life of 12 days. According to another embodiment, the flowable sustained release microparticulate composition is capable of sustained release of the therapeutic amount of the at least one therapeutic agent within a half-life of 14 days. According to another embodiment, the flowable sustained release microparticulate composition is capable of sustained release of the therapeutic amount of the at least one therapeutic agent within a half-life of 16 days. According to another embodiment, the flowable sustained release microparticulate composition is capable of sustained release of the therapeutic amount of the at least one therapeutic agent within a half-life of 18 days. According to another embodiment, the flowable sustained release microparticulate composition is capable of sustained release of the therapeutic amount of the at least one therapeutic agent within a half-life of 20 days. According to another embodiment, the flowable sustained release microparticulate composition is capable of sustained release of the therapeutic amount of the at least one therapeutic agent within a half-life of 22 days. According to another embodiment, the flowable sustained release microparticulate composition is capable of sustained release of the therapeutic amount of the at least one therapeutic agent within a half-life of 24 days. According to another embodiment, the flowable sustained release microparticulate composition is capable of sustained release of the therapeutic amount of the at least one therapeutic agent within a half-life of 26 days. According to another embodiment, the flowable sustained release microparticulate composition is capable of sustained release of the therapeutic amount of the at least one therapeutic agent within a half-life of 28 days. According to another embodiment, the flowable sustained release microparticulate composition is capable of sustained release of the therapeutic amount of the at least one therapeutic agent within a half-life of 30 days.

According to some embodiments, the flowable sustained release microparticulate composition is capable of sustained release of the therapeutic amount of the at least one therapeutic agent prior to onset of a delayed complication associated with an interruption of a cerebral artery caused by the brain injury. According to some embodiments, the delayed complication is selected from the group consisting of an angiographic vasospasm, a plurality of microthromboemboli, a cortical spreading ischemia, a delayed cerebral ischemia (DCI), or a combination thereof. According to one embodiment, the delayed complication is an angiographic vasospasm. According to another embodiment, the delayed complication is a plurality of microthromboemboli. According to another embodiment, the delayed complication is a cortical spreading ischemia. According to another embodiment, the delayed complication is a delayed cerebral ischemia (DCI).

According to some embodiments, the brain injury is a result of an underlying condition. Exemplary underlying conditions include, but are not limited to, aneurysm, sudden traumatic head injury, subarachnoid hemorrhage (SAH), or a combination thereof. According to one embodiment, the underlying condition is an aneurysm. According to another embodiment, the underlying condition is a traumatic head injury. According to another embodiment, the underlying condition is a subarachnoid hemorrhage (SAH). According to another embodiment, the underlying condition is a combination of an aneurysm, a sudden traumatic head injury, and a subarachnoid hemorrhage (SAH).

According to some embodiments, the flowable sustained release microparticulate composition, upon release in proximity to the at least one cerebral artery in subarachnoid space at risk of interruption caused by brain injury, is effective to reduce vasospasm such that the internal diameter of the at least one cerebral artery in subarachnoid space at risk of interruption is increased as compared to a control. According to some embodiments, the flowable sustained release microparticulate delivery composition, upon release in proximity to at least one cerebral artery in the subarachnoid space at risk of interruption caused by brain injury, is effective in preventing or reducing the incidence or severity of the delayed complication associated with the interruption of the cerebral artery.

According to one embodiment, the predominantly localized pharmacologic effect is a reduction of vasospasm such that the internal diameter of the at least one cerebral artery in the subarachnoid space at risk of interruption is increased as compared to an untreated control. According to one embodiment, the flowable sustained release in microparticulate composition is effective to reduce vasospasm such that the internal diameter of the at least one cerebral artery in the subarachnoid space at risk of interruption is increased as compared to an untreated control.

According to one embodiment, the therapeutic amount of the at least one therapeutic agent in proximity to at least one cerebral artery in subarachnoid space can produce a predominantly localized pharmacologic effect. According to some embodiments, the predominantly localized pharmacologic effect is a reduction of vasospasm such that the internal diameter of the at least one cerebral artery in subarachnoid space at risk of interruption is increased as compared to an untreated control, wherein the at least one cerebral artery is at least 10 mm, at least 9.9 mm, at least 9.8 mm, at least 9.7 mm, at least 9.6 mm, at least 9.5 mm, at least 9.4 mm, at least 9.3 mm, at least 9.2 mm, at least 9.1 mm, at least 9.0 mm, at least 8.9 mm, at least 8.8 mm, at least 8.7 mm, at least 8.6 mm, at least 8.5 mm, at least 8.4 mm, at least 8.3 mm, at least 8.2 mm, at least 8.1 mm, at least 8.0 mm, at least 7.9 mm, at least 7.8 mm, at least 7.7 mm, at least 7.6 mm, at least 7.5 mm, at least 7.4 mm, at least 7.3 mm, at least 7.2 mm, at least 7.1 mm, at least 7.0 mm, at least 6.9 mm, at least 6.8 mm, at least 6.7 mm, at least 6.6 mm, at least 6.5 mm, at least 6.4 mm, at least 6.3 mm, at least 6.2 mm, at least 6.1 mm, at least 6.0 mm, at least 5.9 mm, at least 5.8 mm, at least 5.7 mm, at least 5.6 mm, at least 5.5 mm, at least 5.4 mm, at least 5.3 mm, at least 5.2 mm, at least 5.1 mm, at least 5.0 mm from the site of release in the subarachnoid space. According to one embodiment, the predominantly localized pharmacologic effect is a reduction of vasospasm such that the internal diameter of the at least one cerebral artery that is at least 10 mm from the site of release in the subarachnoid space is increased as compared to an untreated control. According to another embodiment, the predominantly localized pharmacologic effect is a reduction of vasospasm such that the internal diameter of the at least one cerebral artery that is at least 9.9 mm from the site of release in the subarachnoid space is increased as compared to an untreated control. According to another embodiment, the predominantly localized pharmacologic effect is a reduction of vasospasm such that the internal diameter of the at least one cerebral artery that is at least 9.8 mm from the site of release in the subarachnoid space is increased as compared to an untreated control. According to another embodiment, the predominantly localized pharmacologic effect is a reduction of vasospasm such that the internal diameter of the at least one cerebral artery that is at least 9.7 mm from the site of release in the subarachnoid space is increased as compared to an untreated control. According to another embodiment, the predominantly localized pharmacologic effect is a reduction of vasospasm such that the internal diameter of the at least one cerebral artery that is at least 9.6 mm from the site of release in the subarachnoid space is increased as compared to an untreated control. According to another embodiment, the predominantly localized pharmacologic effect is a reduction of vasospasm such that the internal diameter of the at least one cerebral artery that is at least 9.5 mm from the site of release in the subarachnoid space is increased as compared to an untreated control. According to another embodiment, the predominantly localized pharmacologic effect is a reduction of vasospasm such that the internal diameter of the at least one cerebral artery that is at least 9.4 mm from the site of release in the subarachnoid space is increased as compared to an untreated control. According to another embodiment, the predominantly localized pharmacologic effect is a reduction of vasospasm such that the internal diameter of the at least one cerebral artery that is at least 9.3 mm from the site of release in the subarachnoid space is increased as compared to an untreated control. According to another embodiment, the predominantly localized pharmacologic effect is a reduction of vasospasm such that the internal diameter of the at least one cerebral artery that is at least 9.2 mm from the site of release in the subarachnoid space is increased as compared to an untreated control. According to another embodiment, the predominantly localized pharmacologic effect is a reduction of vasospasm such that the internal diameter of the at least one cerebral artery that is at least 9.1 mm from the site of release in the subarachnoid space is increased as compared to an untreated control. According to another embodiment, the predominantly localized pharmacologic effect is a reduction of vasospasm such that the internal diameter of the at least one cerebral artery that is at least 9.0 mm from the site of release in the subarachnoid space is increased as compared to an untreated control. According to another embodiment, the predominantly localized pharmacologic effect is a reduction of vasospasm such that the internal diameter of the at least one cerebral artery that is at least 8.9 mm from the site of release in the subarachnoid space is increased as compared to an untreated control. According to another embodiment, the predominantly localized pharmacologic effect is a reduction of vasospasm such that the internal diameter of the at least one cerebral artery that is at least 8.8 mm from the site of release in the subarachnoid space is increased as compared to an untreated control. According to another embodiment, the predominantly localized pharmacologic effect is a reduction of vasospasm such that the internal diameter of the at least one cerebral artery that is at least 8.7 mm from the site of release in the subarachnoid space is increased as compared to an untreated control. According to another embodiment, the predominantly localized pharmacologic effect is a reduction of vasospasm such that the internal diameter of the at least one cerebral artery that is at least 8.6 mm from the site of release in the subarachnoid space is increased as compared to an untreated control. According to another embodiment, the predominantly localized pharmacologic effect is a reduction of vasospasm such that the internal diameter of the at least one cerebral artery that is at least 8.5 mm from the site of release in the subarachnoid space is increased as compared to an untreated control. According to another embodiment, the predominantly localized pharmacologic effect is a reduction of vasospasm such that the internal diameter of the at least one cerebral artery that is at least 8.4 mm from the site of release in the subarachnoid space is increased as compared to an untreated control. According to another embodiment, the predominantly localized pharmacologic effect is a reduction of vasospasm such that the internal diameter of the at least one cerebral artery that is at least 8.3 mm from the site of release in the subarachnoid space is increased as compared to an untreated control. According to another embodiment, the predominantly localized pharmacologic effect is a reduction of vasospasm such that the internal diameter of the at least one cerebral artery that is at least 8.2 mm from the site of release in the subarachnoid space is increased as compared to an untreated control. According to another embodiment, the predominantly localized pharmacologic effect is a reduction of vasospasm such that the internal diameter of the at least one cerebral artery that is at least 8.1 mm from the site of release in the subarachnoid space is increased as compared to an untreated control. According to another embodiment, the predominantly localized pharmacologic effect is a reduction of vasospasm such that the internal diameter of the at least one cerebral artery that is at least 8.0 mm from the site of release in the subarachnoid space is increased as compared to an untreated control. According to another embodiment, the predominantly localized pharmacologic effect is a reduction of vasospasm such that the internal diameter of the at least one cerebral artery that is at least 7.9 mm from the site of release in the subarachnoid space is increased as compared to an untreated control. According to another embodiment, the predominantly localized pharmacologic effect is a reduction of vasospasm such that the internal diameter of the at least one cerebral artery that is at least 7.8 mm from the site of release in the subarachnoid space is increased as compared to an untreated control. According to another embodiment, the predominantly localized pharmacologic effect is a reduction of vasospasm such that the internal diameter of the at least one cerebral artery that is at least 7.7 mm from the site of release in the subarachnoid space is increased as compared to an untreated control. According to another embodiment, the predominantly localized pharmacologic effect is a reduction of vasospasm such that the internal diameter of the at least one cerebral artery that is at least 7.6 mm from the site of release in the subarachnoid space is increased as compared to an untreated control. According to another embodiment, the predominantly localized pharmacologic effect is a reduction of vasospasm such that the internal diameter of the at least one cerebral artery that is at least 7.5 mm from the site of release in the subarachnoid space is increased as compared to an untreated control. According to another embodiment, the predominantly localized pharmacologic effect is a reduction of vasospasm such that the internal diameter of the at least one cerebral artery that is at least 7.4 mm from the site of release in the subarachnoid space is increased as compared to an untreated control. According to another embodiment, the predominantly localized pharmacologic effect is a reduction of vasospasm such that the internal diameter of the at least one cerebral artery that is at least 7.3 mm from the site of release in the subarachnoid space is increased as compared to an untreated control. According to another embodiment, the predominantly localized pharmacologic effect is a reduction of vasospasm such that the internal diameter of the at least one cerebral artery that is at least 7.2 mm from the site of release in the subarachnoid space is increased as compared to an untreated control. According to another embodiment, the predominantly localized pharmacologic effect is a reduction of vasospasm such that the internal diameter of the at least one cerebral artery that is at least 7.1 mm from the site of release in the subarachnoid space is increased as compared to an untreated control. According to another embodiment, the predominantly localized pharmacologic effect is a reduction of vasospasm such that the internal diameter of the at least one cerebral artery that is at least 7.0 mm from the site of release in the subarachnoid space is increased as compared to an untreated control. According to another embodiment, the predominantly localized pharmacologic effect is a reduction of vasospasm such that the internal diameter of the at least one cerebral artery that is at least 6.9 mm from the site of release in the subarachnoid space is increased as compared to an untreated control. According to another embodiment, the predominantly localized pharmacologic effect is a reduction of vasospasm such that the internal diameter of the at least one cerebral artery that is at least 6.8 mm from the site of release in the subarachnoid space is increased as compared to an untreated control. According to another embodiment, the predominantly localized pharmacologic effect is a reduction of vasospasm such that the internal diameter of the at least one cerebral artery that is at least 6.7 mm from the site of release in the subarachnoid space is increased as compared to an untreated control. According to another embodiment, the predominantly localized pharmacologic effect is a reduction of vasospasm such that the internal diameter of the at least one cerebral artery that is at least 6.6 mm from the site of release in the subarachnoid space is increased as compared to an untreated control. According to another embodiment, the predominantly localized pharmacologic effect is a reduction of vasospasm such that the internal diameter of the at least one cerebral artery that is at least 6.5 mm from the site of release in the subarachnoid space is increased as compared to an untreated control. According to another embodiment, the predominantly localized pharmacologic effect is a reduction of vasospasm such that the internal diameter of the at least one cerebral artery that is at least 6.4 mm from the site of release in the subarachnoid space is increased as compared to an untreated control. According to another embodiment, the predominantly localized pharmacologic effect is a reduction of vasospasm such that the internal diameter of the at least one cerebral artery that is at least 6.3 mm from the site of release in the subarachnoid space is increased as compared to an untreated control. According to another embodiment, the predominantly localized pharmacologic effect is a reduction of vasospasm such that the internal diameter of the at least one cerebral artery that is at least 6.2 mm from the site of release in the subarachnoid space is increased as compared to an untreated control. According to another embodiment, the predominantly localized pharmacologic effect is a reduction of vasospasm such that the internal diameter of the at least one cerebral artery that is at least 6.1 mm from the site of release in the subarachnoid space is increased as compared to an untreated control. According to another embodiment, the predominantly localized pharmacologic effect is a reduction of vasospasm such that the internal diameter of the at least one cerebral artery that is at least 6.0 mm from the site of release in the subarachnoid space is increased as compared to an untreated control. According to another embodiment, the predominantly localized pharmacologic effect is a reduction of vasospasm such that the internal diameter of the at least one cerebral artery that is at least 5.9 mm from the site of release in the subarachnoid space is increased as compared to an untreated control. According to another embodiment, the predominantly localized pharmacologic effect is a reduction of vasospasm such that the internal diameter of the at least one cerebral artery that is at least 5.8 mm from the site of release in the subarachnoid space is increased as compared to an untreated control. According to another embodiment, the predominantly localized pharmacologic effect is a reduction of vasospasm such that the internal diameter of the at least one cerebral artery that is at least 5.7 mm from the site of release in the subarachnoid space is increased as compared to an untreated control. According to another embodiment, the predominantly localized pharmacologic effect is a reduction of vasospasm such that the internal diameter of the at least one cerebral artery that is at least 5.6 mm from the site of release in the subarachnoid space is increased as compared to an untreated control. According to another embodiment, the predominantly localized pharmacologic effect is a reduction of vasospasm such that the internal diameter of the at least one cerebral artery that is at least 5.5 mm from the site of release in the subarachnoid space is increased as compared to an untreated control. According to another embodiment, the predominantly localized pharmacologic effect is a reduction of vasospasm such that the internal diameter of the at least one cerebral artery that is at least 5.4 mm from the site of release in the subarachnoid space is increased as compared to an untreated control. According to another embodiment, the predominantly localized pharmacologic effect is a reduction of vasospasm such that the internal diameter of the at least one cerebral artery that is at least 5.3 mm from the site of release in the subarachnoid space is increased as compared to an untreated control. According to another embodiment, the predominantly localized pharmacologic effect is a reduction of vasospasm such that the internal diameter of the at least one cerebral artery that is at least 5.2 mm from the site of release in the subarachnoid space is increased as compared to an untreated control. According to another embodiment, the predominantly localized pharmacologic effect is a reduction of vasospasm such that the internal diameter of the at least one cerebral artery that is at least 5.1 mm from the site of release in the subarachnoid space is increased as compared to an untreated control. According to another embodiment, the predominantly localized pharmacologic effect is a reduction of vasospasm such that the internal diameter of the at least one cerebral artery that is at least 5.0 mm from the site of release in the subarachnoid space is increased as compared to an untreated control.

According to one embodiment, the sustained release of the therapeutic amount of the at least one therapeutic agent in proximity to at least one cerebral artery in the subarachnoid space can produce a predominantly localized pharmacologic effect over a desired amount of time. According to one embodiment, the release of the therapeutic amount of the at least one therapeutic agent in proximity to at least one cerebral artery in the subarachnoid space produces a predominantly localized pharmacologic effect for 1 day. According to another embodiment, the release of the therapeutic amount of the at least one therapeutic agent in proximity to at least one cerebral artery in the subarachnoid space produces a predominantly localized pharmacologic effect for 2 days. According to another embodiment, the release of the therapeutic amount of the at least one therapeutic agent in proximity to at least one cerebral artery in the subarachnoid space produces a predominantly localized pharmacologic effect for 3 days. According to another embodiment, the release of the therapeutic amount of the at least one therapeutic agent in proximity to at least one cerebral artery in the subarachnoid space produces a predominantly localized pharmacologic effect for 4 days. According to another embodiment, the release of the therapeutic amount of the at least one therapeutic agent in proximity to at least one cerebral artery in the subarachnoid space produces a predominantly localized pharmacologic effect for 5 days. According to another embodiment, the release of the therapeutic amount of the at least one therapeutic agent in proximity to at least one cerebral artery in the subarachnoid space produces a predominantly localized pharmacologic effect for 6 days. According to another embodiment, the release of the therapeutic amount of the at least one therapeutic agent in proximity to at least one cerebral artery in the subarachnoid space produces a predominantly localized pharmacologic effect for 7 days. According to another embodiment, the release of the therapeutic amount of the at least one therapeutic agent in proximity to at least one cerebral artery in the subarachnoid space produces a predominantly localized pharmacologic effect for 8 days. According to another embodiment, the release of the therapeutic amount of the at least one therapeutic agent in proximity to at least one cerebral artery in the subarachnoid space produces a predominantly localized pharmacologic effect for 15 days. According to another embodiment, the release of the therapeutic amount of the at least one therapeutic agent in proximity to at least one cerebral artery in the subarachnoid space produces a predominantly localized pharmacologic effect for 30 days.

Therapeutic Agent

According to some embodiments, the at least one therapeutic agent is a calcium channel antagonist, an endothelin antagonist, a transient receptor potential (TRP) protein antagonist, or a combination thereof.

According to one embodiment, the at least one therapeutic agent is a calcium channel antagonist. According to some embodiments, the calcium channel antagonist is selected from the group consisting of an L-type voltage dependent calcium channel inhibitor, an R-type voltage dependent calcium channel inhibitor, an N-type voltage dependent calcium channel inhibitor, a P/Q-type voltage dependent calcium channel inhibitor, a T-type voltage dependent calcium channel inhibitor, or a combination thereof. According to one embodiment, the calcium channel antagonist is an L-type voltage dependent calcium channel inhibitor. According to another embodiment, the calcium channel antagonist is an R-type voltage dependent calcium channel inhibitor. According to another embodiment, the calcium channel antagonist is an N-type voltage dependent calcium channel inhibitor. According to another embodiment, the calcium channel antagonist is a P/Q-type voltage dependent calcium channel inhibitor. According to another embodiment, the calcium channel antagonist is a T-type voltage dependent calcium channel inhibitor.

For example, L-type voltage dependent calcium channel inhibitor include, but are not limited to: dihydropyridine L-type antagonists such as nisoldipine, nicardipine and nifedipine, AHF (such as 4aR,9aS)-(+)-4a-Amino-1,2,3,4,4a,9a-hexahydro-4aH-fluorene, HCl), isradipine (such as 4-(4-Benzofurazanyl)-1,-4-dihydro-2,6-dimethyl-3,5-pyridinedicarboxylic acid methyl 1-methhylethyl ester), calciseptine (such as isolated from (*Dendroaspis polylepis* ploylepis), H-Arg-Ile-Cys-Tyr-Ile-His-Lys-Ala-Ser-Leu-Pro-Arg-Ala-Thr-Lys-Thr-Cys-Val-Glu-Asn-Thr-Cys-Tyr-Lys-Met-Phe-Ile-Arg-Thr-Gln-Arg-Glu-Tyr-Ile-Ser-Glu-Arg-Gly-Cys-Gly-Cys-Pro-Thr-Ala- Met-Trp-Pro-Tyr-Gln-Thr-Glu-Cys-Cys-Lys-Gly-Asp-Arg-Cys-Asn-Lys-OH, Calcicludine (such as isolated from *Dendroaspis angusticeps* (eastern green mamba)), (H-Trp-Gln-Pro-Pro-Trp-Tyr-Cys-Lys-Glu-Pro-Val-Arg-Ile-Gly-Ser-Cys-Lys-Lys-Gln-Phe-Ser-Ser-Phe-Tyr-Phe-Lys-Trp-Thr-Ala-Lys-Lys-Cys-Leu-Pro-Phe-Leu-Phe-Ser-Gly-Cys-Gly-Gly-Asn-Ala- Asn-Arg-Phe-Gln-Thr-Ile-Gly-Glu-Cys-Arg-Lys-Lys-Cys-Leu-Gly-Lys-OH, Cilnidipine (such as also FRP-8653, a dihydropyridine-type inhibitor), Dilantizem (such as (2S, 3S)-(+)-cis-3-Acetoxy-5-(2-dimethylaminoethyl)-2,3-dihydro-2-(4-methoxyphenyl)-1,5-benzothiazepin-4(5H)-one hydrochloride), diltiazem (such as benzothiazepin-4(5H)-one, 3-(acetyloxy)-5-[2-(dimethylamino)ethyl]-2,3-dihydro-2-(4-methoxyphenyl)-,(+)-cis-, monohydrochloride), Felodipine (such as 4-(2,3-Dichlorophenyl)-1,4-dihydro-2,6-dimethyl-3,5-pyridinecarboxylic acid ethyl methyl ester), FS-2 (such as an isolate from *Dendroaspis polylepis* polylepis venom), FTX-3.3 (such as an isolate from *Agelenopsis aperta*), Neomycin sulfate (such as $C_{23}H_{46}N_6O_{13}.3H_2SO_4$), Nicardipine (such as 1,4-Dihydro-2,6-dimethyl-4-(3-nitrophenyl)methyl-2-[methyl(phenylmethypa-mino]-3,5-pyridinedicarboxylic acid ethyl ester hydrochloride, also YC-93, Nifedipine (such as 1,4-Dihydro-2,6-dimethyl-4-(2-nitrophenyl)-3,5-pyridinedicarboxylic acid dimethyl ester), Nimodipine (such as 4-Dihydro-2,6-dimethyl-4-(3-nitrophenyl)-3,5-pyridinedicarboxylic acid 2-methoxyethyl 1-methylethyl ester) or (Isopropyl 2-methoxyethyl 1,4-dihydro-2,6-dimethyl-4-(m-nitrophenyl)-3,5-pyridinedicarboxylate), Nitrendipine (such as 1,4-Dihydro-2,6-dimethyl-4-(3-nitrophenyl)-3,5-pyridinedicarboxylic acid ethyl methyl ester), S-Petasin (such as (3S,4aR,5R,6R)-[2,3,4,4a,5,6,7,8-Octahydro-3-(2-propenyl)-4a,5-dimethyl-2-O-xo-6-naphthyl] Z-3'-methylthio-1'-propenoate), Phloretin (such as 2',4',6'-Trihydroxy-3-(4-hydroxyphenyl)propiophenone, also 3-(4-Hydroxyphenyl)-1-(2,4,6-trihydroxyphenyl)-1-propanone, also b-(4-Hydroxyphenyl)-2,4,6-trihydroxypropiophenone), Protopine (such as $C_{20}H_{19}NO_5Cl$), SKF-96365 (such as 1-[b-[3-(4-Methoxyphenyl)propoxy]-4-methoxyphenethyl]-1H-imidazole, HCl), Tetrandine (such as 6,6',7,12-Tetramethoxy-2,2'-dimethylberbaman), (.+-.)-Methoxyverapamil or (+)-Verapamil (such as 54N-(3,4-Dimethoxyphenylethyl)methylamino]-2-(3,4-dimethoxyphenyl)-2-iso-propylvaleronitrile hydrochloride), and (R)-(+)-Bay K8644 (such as R-(+)-1,4-Dihydro-2,6-dimethyl-5-nitro-442-(trifluoromethyl)phenyl]-3-pyridinecarboxylic acid methyl ester). The foregoing examples may be specific to L-type voltage-gated calcium channels or may inhibit a broader range of voltage-gated calcium channels, e.g. N, P/Q, R, and T-type.

According to some embodiments, the L-type voltage dependent calcium channel inhibitor is a dihydropyridine. Exemplary dihydropyridines include, but are not limited to, amlodipine, aranidipine, azelnidipine, bamidipine, benidipine, cinaldipine, efonidipine, felodipine, isradipine, lacidipine, lemildipine, lercanidipine, nicardipine, nifedipine, nilvadipine, nimodipine, nisoldipine, nitrendipine, manidipine, pranidipine, etc. According to one embodiment, the dihydropyridine is nimodipine. According to one embodiment, the nimodipine has a half life of 7-10 days when formulated as described herein, and appropriate lipid solubility.

According to some embodiments, the L-type voltage dependent calcium channel inhibitor is a phenylalkylamine. Exemplary phenylalkylamines include, but are not limited to, gallopamil, verapamil, etc. According to some embodiments, the L-type voltage dependent calcium channel inhibitor is a 1-4 benzothiazepine. According to one embodiment, the 1-4 benzothiazepine is diltiazem. According to one embodiment, the L-type voltage dependent calcium channel inhibitor is bepridil.

According to another embodiment, the at least one therapeutic agent is an endothelin antagonist. Exemplary endothelin antagonists include, but are not limited to, A-127722, ABT-627, BMS 182874, BQ-123, BQ-153, BQ-162, BQ-485, BQ-518, BQ-610, EMD-122946, FR 139317, IPI-725, L-744453, LU 127043, LU 135252, PABSA, PD 147953, PD 151242, PD 155080, PD 156707, RO 611790, SB-247083, clazosentan, atrasentan, sitaxsentan sodium, TA-0201, TBC 11251, TTA-386, WS-7338B, ZD-1611, aspirin, A-182086, CGS 27830, CP 170687, J-104132, L-751281, L-754142, LU 224332, LU 302872, PD 142893, PD 145065, PD 160672, RO-470203, bosentan, RO 462005, RO 470203, SB 209670, SB 217242, TAK-044, A-192621, A-308165, BQ-788, BQ-017, IRL 1038, IRL 2500, PD-161721, RES 701-1, RO 468443, etc.

According to another embodiment, the at least one therapeutic agent is a transient receptor potential (TRP) protein antagonist. Exemplary transient receptor potential (TRP) protein antagonists include, but are not limited to, gadolinium chloride, lanthanum chloride, SKF 96365 (1-(beta-[3-(4-methoxy-phenyl)propoxy]-4-methoxyphenethyl)-1H-imidazole hydrochloride), and LOE 908 ((RS)-(3,4-dihydro-6,7-dimethoxyisoquinoline-1-gamma 1)-2-phenyl-N,N-di-[2-(2,3,4-trimethoxyphenyl)ethyl]acetamide).

According to some embodiments, the at least one therapeutic agent is an isolated molecule. According to some embodiments, the at least one therapeutic agent is substantially pure.

Microparticulate Formulation

According to one embodiment, the flowable sustained release microparticulate composition comprises a plurality of microparticles comprising at least one therapeutic agent.

According to some embodiments, the at least one therapeutic agent is provided in the form of a microparticle. According to another embodiment, the least one therapeutic agent is disposed on or in the microparticle. According to one embodiment, the at least one therapeutic agent is dispersed throughout each microparticle. According to some embodiments, the at least one therapeutic agent is impregnated on the surface of each microparticle. According to another embodiment, the at least one therapeutic agent is contained within the core of the microparticle surrounded by a coating. According to another embodiment, the least one therapeutic agent is adsorbed into each microparticle.

According to some such embodiments, the microparticles are of uniform size distribution. According to some embodiments, the uniform distribution of microparticle size is achieved by a homogenization process to form a uniform emulsion comprising microparticles. According to some such embodiments, each microparticle comprises a matrix. According to some embodiments, the matrix comprises the least one therapeutic agent.

According to some embodiments, the microparticle can be of any order release kinetics, including a zero order release, first order release, second order release, delayed release, sustained release, immediate release, and a combination thereof. The microparticle can include, in addition to therapeutic agent(s), any of those materials routinely used in the art of pharmacy and medicine, including, but not limited to, erodible, nonerodible, biodegradable, or nonbiodegradable material or combinations thereof According to some embodiments, the microparticle is a microcapsule that contains the least one therapeutic agent in a solution or in a semi-solid state. According to some embodiments, the microparticle contains the least one therapeutic agent, in whole or in part. According to some embodiments, the microparticle is a nanoparticle that contains the least one therapeutic agent, in whole or in part. According to some embodiments, the microparticles can be of virtually any shape.

According to some embodiments, each microparticle is loaded with at least 40% by weight to at least 80% by weight of the at least one therapeutic agent. According to one embodiment, each microparticle is loaded with at least 40% by weight of the at least one therapeutic agent. According to another embodiment, each microparticle is loaded with at least 45% by weight of the at least one therapeutic agent. According to another embodiment, each microparticle is loaded with at least 50% by weight of the at least one therapeutic agent. According to another embodiment, each microparticle is loaded with at least 55% by weight of the at least one therapeutic agent. According to another embodiment, each microparticle is loaded with at least 60% by weight of the at least one therapeutic agent. According to another embodiment, each microparticle is loaded with at least 63% by weight of the at least one therapeutic agent. According to another embodiment, each microparticle is loaded with at least 65% by weight of the at least one therapeutic agent. According to another embodiment, each microparticle is loaded with at least 70% by weight of the at least one therapeutic agent. According to another embodiment, each microparticle is loaded with at least 75% by weight of the at least one therapeutic agent. According to another embodiment, each microparticle is loaded with at least 80% by weight of the at least one therapeutic agent.

According to some embodiments, the particle size is between about 25 µm to about 100 µm. According to some embodiments, the particle size is between about 30 µm to about 80 µm. According to one embodiment, the particle size is at least about 25 µm. According to another embodiment, the particle size is at least about 30 µm. According to another embodiment, the particle size is at least about 35 µm. According to another embodiment, the particle size is at least about 40 µm. According to another embodiment, the particle size is at least about 45 µm. According to another embodiment, the particle size is at least about 50 µm. According to another embodiment, the particle size is at least about 55 µm. According to another embodiment, the particle size is at least about 60 µm. According to another embodiment, the particle size is at least about 65 µm. According to another embodiment, the particle size is at least about 70 µm. According to another embodiment, the particle size is at least about 75 µm. According to another embodiment, the particle size is at least about 80 µm. According to another embodiment, the particle size is at least about 85 µm. According to another embodiment, the particle size is at least about 90 µm. According to another embodiment, the particle size is at least about 95 µm. According to another embodiment, the particle size is at least about 100 µm.

According to another embodiment, the at least one therapeutic agent can be provided in strings. The strings can contain the at least one therapeutic agent in a core surrounded by a coating, or the at least one therapeutic agent can be dispersed throughout the string, or the at least one therapeutic agent can be absorbed into the string. The string can be of any order release kinetics, including zero order release, first order release, second order release, delayed release, sustained release, immediate release, etc., and any combination thereof. The string can include, in addition to therapeutic agent(s), any of those materials routinely used in the art of pharmacy and medicine, including, but not limited to, erodible, nonerodible, biodegradable, or nonbiodegradable material or combinations thereof.

According to another embodiment, the at least one therapeutic agent can be provided in at least one sheet. The sheet can contain the at least one therapeutic agent and at least one additional therapeutic agent in a core surrounded by a coating, or the at least one therapeutic agent and at least one additional therapeutic agent can be dispersed throughout the sheet, or the at least one therapeutic agent can be absorbed into the sheet. The sheet can be of any order release kinetics, including zero order release, first order release, second order release, delayed release, sustained release, immediate release, etc., and any combination thereof. The sheet can include, in addition to the at least one therapeutic agent and at least one additional therapeutic agent, any of those materials routinely used in the art of pharmacy and medicine, including, but not limited to, erodible, nonerodible, biodegradable, or nonbiodegradable material or combinations thereof.

According to some embodiments, the microparticulate formulation comprises a suspension of microparticles. According to one embodiment, the microparticulate formulation comprises a powder suspension of microparticles. According to some embodiments, the microparticulate formulation further comprises at least one of a suspending agent, a stabilizing agent and a dispersing agent. According to some such embodiments, the microparticulate formulation is presented as a suspension. According to some such embodiments, the microparticulate formulation is presented as a solution. According to some such embodiments, the microparticulate formulation is presented as an emulsion.

According to some embodiments, the microparticulate formulation comprises an aqueous solution of the at least one therapeutic agent in water-soluble form. According to some embodiments, the microparticulate formulation comprises an oily suspension of the at least one therapeutic agent. Oily suspension of the at least one therapeutic agent can be prepared using suitable lipophilic solvents. Exemplary lipophilic solvents or vehicles include, but are not limited to, fatty oils such as sesame oil, or synthetic fatty acid esters, such as ethyl oleate or triglycerides. According to some embodiments, the microparticulate formulation comprises an aqueous suspension of the at least one therapeutic agent. Aqueous injection suspensions can contain substances which increase the viscosity of the suspension, such as sodium carboxymethyl cellulose, sorbitol, hyaluronic acid, or dextran. Optionally, the suspension can also contain suitable stabilizers or agents which increase the solubility of the compounds to allow for the preparation of highly concentrated solutions. Alternatively, the at least one therapeutic agent can be in powder form for constitution with a suitable vehicle, e.g., sterile pyrogen-free water, before use. The microparticulate formulation is dispersed in a vehicle to form a dispersion, with the microparticles as the dispersed phase, and the vehicle as the dispersion medium.

The microparticulate formulation can include, for example, microencapsulated dosage forms, and if appropriate, with one or more excipients, encochleated, coated onto microscopic gold particles, contained in liposomes, pellets for implantation into the tissue, or dried onto an object to be rubbed into the tissue. As used herein, the term "microencapsulation" refers to a process in which very tiny droplets or particles are surrounded or coated with a continuous film of biocompatible, biodegradable, polymeric or non-polymeric material to produce solid structures including, but not limited to, nonpareils, pellets, crystals, agglomerates, microspheres, or nanoparticles. The microparticulate formulation can be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The microparticulate formulations are suitable for use in a variety of drug delivery systems. For a brief review of methods for drug delivery, see Langer (1990) Science 249, 1527-1533, which is incorporated herein by reference.

Microencapsulation Process

Examples of microencapsulation processes and products; methods for the production of emulsion-based microparticles; emulsion-based microparticles and methods for the production thereof; solvent extraction microencapsulation with tunable extraction rates; a microencapsulation process with solvent and salt; a continuous double emulsion process for making microparticles; drying methods for tuning microparticle properties, controlled release systems from polymer blends; polymer mixtures comprising polymers having different non-repeating units and methods for making and using the same; and an emulsion based process for preparing microparticles and workhead assembly for use with same, are disclosed and described in U.S. Pat. No. 5,407,609 (entitled Microencapsulation Process and Products Thereof), U.S. application Ser. No. 10/553,003 (entitled Method for the production of emulsion-based microparticles), U.S. application Ser. No. 11/799,700 (entitled Emulsion-based microparticles and methods for the production thereof), U.S. application Ser. No. 12/557,946 (entitled Solvent Extraction Microencapsulation With Tunable Extraction Rates), U.S. application Ser. No. 12/779,138 (entitled Hyaluronic Acid (HA) Injection Vehicle), U.S. application Ser. No. 12/562,455 entitled Microencapsulation Process With Solvent And Salt), U.S. application Ser. No. 12/338,488 (entitled Process For Preparing Microparticles Having A Low Residual Solvent Volume); U.S. application Ser. No. 12/692,027 (entitled Controlled Release Systems From Polymer Blends); U.S. application Ser. No. 12/692,020 (entitled Polymer Mixtures Comprising Polymers Having Different Non-Repeating Units And Methods For Making And Using Same); U.S. application Ser. No. 10/565,401 (entitled "Controlled release compositions"); U.S. application Ser. No. 12/692,029 (entitled "Drying Methods for Tuning Microparticle Properties); U.S. application Ser. No. 12/968,708 (entitled "Emulsion Based Process for Preparing Microparticles and Workhead for Use with Same); and U.S. application Ser. No. 13/074,542 (entitled Composition and Methods for Improved Retention of a Pharmaceutical Composition at a Local Administration Site") The content of each of these are incorporated herein by reference in its entirety.

According to some embodiments, delivery of the at least one therapeutic agent using microparticle technology involves bioresorbable, polymeric particles that encapsulate the at least one therapeutic agent and at least one additional therapeutic agent.

Microparticle Polymer Matrix

According to one embodiment, the microparticles comprise a matrix. According to some embodiments, the at least one therapeutic agent is impregnated in or on a naturally occurring biopolymer matrix, a synthetic polymer matrix, or a combination thereof. According to one embodiment, the microparticulate composition comprises a polymer matrix, wherein the at least one therapeutic agent is impregnated in the polymer matrix. According to one embodiment, the polymer is a slow release compound. According to one embodiment, the polymer is a biodegradable polymer. According to one embodiment, the polymer is poly (D, L-Lactide-co-glycolide). According to another embodiment, the polymer is poly(orthoester). According to another embodiment, the polymer is poly(anhydride). According to another embodiment, the polymer is polylactide-polyglycolide.

Both non-biodegradable and biodegradable polymeric materials can be used in the manufacture of particles for delivering the therapeutic agents. Such polymers can be natural or synthetic polymers. The polymer is selected based on the period of time over which release is desired. Bioadhesive polymers of particular interest include, but are not limited to, bioerodible hydrogels as described by Sawhney et al in Macromolecules (1993) 26, 581-587, the teachings of which are incorporated herein. Exemplary bioerodible hydrogels include, but are not limited to, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly (lauryl methacrylate), poly(phenyl methacrylate), poly(methyl acrylate), poly(isopropyl acrylate), poly(isobutyl acrylate), and poly(octadecyl acrylate). According to one embodiment, the bioadhesive polymer is hyaluronic acid. In some such embodiments, the bioadhesive polymer include less than about 2.3% of hyaluronic acid.

According to another embodiment, the polymer enhances aqueous solubility of the microparticulate formulation. Examples of suitable polymers include but are not limited to polyethylene glycol, poly-(d-glutamic acid), poly-(l-glutamic acid), poly-(l-glutamic acid), poly-(d-aspartic acid), poly-(l-aspartic acid), poly-(l-aspartic acid) and copolymers thereof. Polyglutamic acids having molecular weights between about 5,000 to about 100,000, with molecular weights between about 20,000 and about 80,000 may be used and with molecular weights between about 30,000 and about 60,000 may also be used. The polymer is conjugated via an ester linkage to one or more hydroxyls of an inventive epothilone using a protocol as essentially described by U.S. Pat. No. 5,977,163 which is incorporated herein by reference. Particular conjugation sites include the hydroxyl off carbon-21 in the case of 21-hydroxy-derivatives of the present invention. Other conjugation sites include, but are not limited, to the hydroxyl off carbon 3 and/or the hydroxyl off carbon 7.

According to some embodiments, the at least one therapeutic agent is impregnated in or on a polyglycolide (PGA) matrix. PGA is a linear aliphatic polyester developed for use in sutures. Studies have reported PGA copolymers formed with trimethylene carbonate, polylactic acid (PLA), and polycaprolactone. Some of these copolymers may be formulated as microparticles for sustained drug release.

According to some embodiments, the at least one therapeutic agent is impregnated in or on a polyester-polyethylene glycol matrix. Polyester-polyethylene glycol compounds can be synthesized; these are soft and may be used for drug delivery.

According to some embodiments, the at least one therapeutic agent is impregnated in or on a poly (amino)-derived biopolymer matrix. Poly (amino)-derived biopolymers can include, but are not limited to, those containing lactic acid and lysine as the aliphatic diamine (see, for example, U.S. Pat. No. 5,399,665), and tyrosine-derived polycarbonates and polyacrylates. Modifications of polycarbonates may alter the length of the alkyl chain of the ester (ethyl to octyl), while modifications of polyarylates may further include altering the length of the alkyl chain of the diacid (for example, succinic to sebasic), which allows for a large permutation of polymers and great flexibility in polymer properties.

According to some embodiments, the at least one therapeutic agent is impregnated in or on a polyanhydride matrix. Polyanhydrides are prepared by the dehydration of two diacid molecules by melt polymerization (see, for example, U.S. Pat. No. 4,757,128). These polymers degrade by surface erosion (as compared to polyesters that degrade by bulk erosion). The release of the drug can be controlled by the hydrophilicity of the monomers chosen.

According to some embodiments, the at least one therapeutic agent is impregnated in or on a photopolymerizable biopolymer matrix. Photopolymerizable biopolymers include, but are not limited to, lactic acid/polyethylene glycol/acrylate copolymers.

According to some embodiments, the at least one therapeutic agent is impregnated in or on a hydrogel matrix. The term "hydrogel" refers to a substance resulting in a solid, semisolid, pseudoplastic or plastic structure containing a necessary aqueous component to produce a gelatinous or jelly-like mass. Hydrogels generally comprise a variety of polymers, including hydrophilic polymers, acrylic acid, acrylamide and 2-hydroxyethylmethacrylate (HEMA).

According to some embodiments, the at least one therapeutic agent is impregnated in or on a naturally-occurring biopolymer matrix. Naturally-occurring biopolymers include, but are not limited to, protein polymers, collagen, polysaccharides, and photopolymerizable compounds.

According to some embodiments, the at least one therapeutic agent is impregnated in or on a protein polymer matrix. Protein polymers have been synthesized from self-assembling protein polymers such as, for example, silk fibroin, elastin, collagen, and combinations thereof.

According to some embodiments, the at least one therapeutic agent is impregnated in or on a naturally-occurring polysaccharide matrix. Naturally-occurring polysaccharides include, but are not limited to, chitin and its derivatives, hyaluronic acid, dextran and cellulosics (which generally are not biodegradable without modification), and sucrose acetate isobutyrate (SAIB).

According to some embodiments, the at least one therapeutic agent is impregnated in or on a chitin matrix. Chitin is composed predominantly of 2-acetamido-2-deoxy-D-glucose groups and is found in yeasts, fungi and marine invertebrates (shrimp, crustaceous) where it is a principal component of the exoskeleton. Chitin is not water soluble and the deacetylated chitin, chitosan, only is soluble in acidic solutions (such as, for example, acetic acid). Studies have reported chitin derivatives that are water soluble, very high molecular weight (greater than 2 million daltons), viscoelastic, non-toxic, biocompatible and capable of crosslinking with peroxides, gluteraldehyde, glyoxal and other aldehydes and carbodiamides, to form gels.

According to some embodiments, the at least one therapeutic agent is impregnated in or on a hyaluronic acid (HA) matrix. Hyaluronic acid (HA), which is composed of alternating glucuronidic and glucosaminidic bonds and is found in mammalian vitreous humor, extracellular matrix of the brain, synovial fluid, umbilical cords and rooster combs from which it is isolated and purified, also can be produced by fermentation processes.

Pharmaceutically Acceptable Carrier

According to some embodiments, the flowable sustained release microparticulate composition comprises (ii) a pharmaceutically acceptable carrier.

According to one embodiment, the pharmaceutically acceptable carrier is a solid carrier or excipient. According to another embodiment, the pharmaceutically acceptable carrier is a gel-phase carrier or excipient. Examples of carriers or excipients include, but are not limited to, calcium carbonate, calcium phosphate, various monomeric and polymeric sugars (including without limitation hyaluronic acid), starches, cellulose derivatives, gelatin, and polymers. An exemplary carrier can also include saline vehicle, e.g. hydroxylpropyl methyl cellulose (HPMC) in phosphate buffered saline (PBS). According to another embodiment, the pharmaceutically acceptable carrier is a buffer solution. Exemplary buffer solutions can include without limitation a phosphate buffered saline (PBS) solution.

According to some embodiments, the pharmaceutically acceptable carrier imparts stickiness to the composition. According to one embodiment, the pharmaceutically acceptable carrier comprises hyaluronic acid. According to some embodiments, the pharmaceutically acceptable carrier comprises 0% to 5% hyaluronic acid. According to one embodiment, the pharmaceutically acceptable carrier comprises less than 0.05% hyaluronic acid. According to another embodiment, the pharmaceutically acceptable carrier comprises less than 0.1% hyaluronic acid. According to another embodiment, the pharmaceutically acceptable carrier comprises less than 0.2% hyaluronic acid. According to another embodiment, the pharmaceutically acceptable carrier comprises less than 0.3% hyaluronic acid. According to another embodiment, the pharmaceutically acceptable carrier comprises less than 0.4% hyaluronic acid. According to another embodiment, the pharmaceutically acceptable carrier comprises less than 0.5% hyaluronic acid. According to another embodiment, the pharmaceutically acceptable carrier comprises less than 0.6% hyaluronic acid. According to another embodiment, the pharmaceutically acceptable carrier comprises less than 0.7% hyaluronic acid. According to another embodiment, the pharmaceutically acceptable carrier comprises less than 0.8% hyaluronic acid. According to another embodiment, the pharmaceutically acceptable carrier comprises less than 0.9% hyaluronic acid. According to another embodiment, the pharmaceutically acceptable carrier comprises less than 1.0% hyaluronic acid. According to another embodiment, the pharmaceutically acceptable carrier comprises less than 1.1% hyaluronic acid. According to another embodiment, the pharmaceutically acceptable carrier comprises less than 1.2% hyaluronic acid. According to another embodiment, the pharmaceutically acceptable carrier comprises less than 1.3% hyaluronic acid. According to another embodiment, the pharmaceutically acceptable carrier comprises less than 1.4% hyaluronic acid. According to another embodiment, the pharmaceutically acceptable carrier comprises less than 1.5% hyaluronic acid. According to another embodiment, the pharmaceutically acceptable carrier comprises less than 1.6% hyaluronic acid. According to another embodiment, the pharmaceutically acceptable carrier comprises less than 1.7% hyaluronic acid. According to another embodiment, the pharmaceutically acceptable carrier comprises less than 1.8% hyaluronic acid. According to another embodiment, the pharmaceutically acceptable carrier comprises less than 1.9% hyaluronic acid. According to another embodiment, the pharmaceutically acceptable carrier comprises less than 2.0% hyaluronic acid. According to another embodiment, the pharmaceutically acceptable carrier comprises less than 2.1% hyaluronic acid. According to another embodiment, the pharmaceutically acceptable carrier comprises less than 2.2% hyaluronic acid. According to another embodiment, the pharmaceutically acceptable carrier comprises less than 2.3% hyaluronic acid. According to another embodiment, the pharmaceutically acceptable carrier comprises less than 2.4% hyaluronic acid. According to another embodiment, the pharmaceutically acceptable carrier comprises less than 2.5% hyaluronic acid. According to another embodiment, the pharmaceutically acceptable carrier comprises less than 2.6% hyaluronic acid. According to another embodiment, the pharmaceutically acceptable carrier comprises less than 2.7% hyaluronic acid. According to another embodiment, the pharmaceutically acceptable carrier comprises less than 2.8% hyaluronic acid. According to another embodiment, the pharmaceutically acceptable carrier comprises less than 2.9% hyaluronic acid. According to another embodiment, the pharmaceutically acceptable carrier comprises less than 3.0% hyaluronic acid. According to another embodiment, the pharmaceutically acceptable carrier comprises less than 3.5% hyaluronic acid. According to another embodiment, the pharmaceutically acceptable carrier comprises less than 4.0% hyaluronic acid. According to another embodiment, the pharmaceutically acceptable carrier comprises less than 4.5% hyaluronic acid. According to another embodiment, the pharmaceutically acceptable carrier comprises less than 5.0% hyaluronic acid.

In some embodiments, the pharmaceutically acceptable carrier includes, but is not limited to, a gel, slow-release solid or semisolid compound, optionally as a sustained release gel. In some such embodiments, the at least one therapeutic agent is embedded into the pharmaceutically acceptable carrier. In some embodiments, the at least one therapeutic agent is coated on the pharmaceutically acceptable carrier. The coating can be of any desired material, preferably a polymer or mixture of different polymers. Optionally, the polymer can be utilized during the granulation stage to form a matrix with the active ingredient so as to obtain a desired release pattern of the active ingredient. The gel, slow-release solid or semisolid compound is capable of releasing the active agent over a desired period of time. The gel, slow-release solid or semisolid compound can be implanted in a tissue within the parenchyma of human brain, including, but not limited to, in proximity to a blood vessel, such as a cerebral artery.

According to another embodiment, the pharmaceutically acceptable carrier comprises a slow-release solid compound. According to one such embodiment, the at least one therapeutic agent is embedded in the slow-release solid compound or coated on the slow-release solid compound. According to yet another embodiment, the pharmaceutically acceptable carrier comprises a slow-release microparticle containing the at least one therapeutic agent.

According to another embodiment, the pharmaceutically acceptable carrier is a gel compound, such as a biodegradable hydrogel.

Additional Components

According to some embodiments, the flowable sustained release microparticulate composition further comprises a preservative agent. According to some such embodiments, the flowable sustained release microparticulate very composition is presented in a unit dosage form. Exemplary unit dosage forms include, but are not limited to, ampoules or multi-dose containers.

The flowable sustained release microparticulate compositions for parenteral (including but not limited to, subcutaneous, intradermal, intramuscular, intravenous, intraarterial, intrathecal, intraventricular and intraarticular) administration include aqueous and non-aqueous sterile injection solutions that can contain anti-oxidants, buffers, bacteriostats and solutes, which render the formulation isotonic with the blood or CSF of the intended recipient; and aqueous and non-aqueous sterile suspensions, which can include suspending agents and thickening agents.

According to some embodiments, the flowable sustained release microparticulate composition is formulated for parenteral injection, surgical implantation, or a combination thereof. According to some such embodiments, the flowable sustained release microparticulate composition is in the form of a pharmaceutically acceptable sterile aqueous or nonaqueous solution, dispersion, suspension or emulsion or a sterile powder for reconstitution into a sterile injectable solution or dispersion. Examples of suitable aqueous and nonaqueous carriers, diluents, solvents or vehicles include, but are not limited to, water, ethanol, dichloromethane, acetonitrile, ethyl acetate, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Suspensions can further contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

According to some embodiments, the flowable sustained release microparticulate composition is formulated in an injectable depot form. Injectable depot forms are made by forming microencapsulated matrices of the therapeutic agent in a biodegradable polymer. Depending upon the ratio of drug to polymer and the nature of the particular polymer employed, the rate of drug release may be controlled. Such long acting formulations can be formulated with suitable polymeric or hydrophobic materials (for example as an emulsion in an acceptable oil) or ion exchange resins, or as sparingly soluble derivatives, for example, as a sparingly soluble salt. Examples of biodegradable polymers include, but are not limited to, polylactide-polyglycolide, poly(orthoesters) and poly(anhydrides). Depot injectable formulations are also prepared by entrapping the drug in liposomes or microemulsions which are compatible with body tissues.

According to some embodiments, the flowable sustained release microparticulate composition further comprises an adjuvant. Exemplary adjuvants include, but are not limited to, preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. Isotonic agents, for example, sugars, sodium chloride and the like, can also be included. Prolonged absorption of the injectable pharmaceutical form can be brought about by the use of agents delaying absorption, for example, aluminum monostearate and gelatin.

The flowable sustained release microparticulate compositions can be sterilized, for example, by terminal gamma irradiation, filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol, dichloromethane, ethyl acetate, acetonitrile, etc. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono- or diglycerides. In addition, fatty acids such as oleic acid are used in the preparation of injectables.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

II. Method of Treating

In another aspect, the present invention provides a method of treating at least one cerebral artery in a subarachnoid space at risk of interruption due to a brain injury in a human subject, comprising:
- a) providing a flowable sustained release microparticulate composition comprising:
  - (i) a microparticulate formulation comprising a therapeutic amount of at least one therapeutic agent, wherein the microparticulate formulation comprises a plurality of microparticles of uniform size distribution, wherein the therapeutic agent is dispersed throughout each microparticle, and wherein the therapeutic amount is effective to treat a delayed complication of the interruption of the cerebral artery,
  - (ii) and a pharmaceutical carrier; and
- b) administering the composition locally into a cerebral ventricle so that the microparticulate formulation flows from the cerebrospinal fluid (CSF) in the cerebral ventricle into the cerebrospinal fluid (CSF) in the subarachnoid space before releasing the therapeutic agent in the subarachnoid space, wherein the therapeutic agent contacts and flows around the at least one cerebral artery in the subarachnoid space without entering systemic circulation in an amount to cause unwanted side effects.

According to one embodiment, the flowable sustained release microparticulate composition, upon delivery to the cerebral ventricle, is capable of sustained release of a therapeutic amount of the at least one therapeutic agent in or at a site of release in subarachnoid space. According to one embodiment, the site of release is in proximity to the at least one cerebral artery in subarachnoid space at risk of interruption.

According to some embodiments, the flowable sustained release microparticulate composition is capable of sustained release of a therapeutic amount of the at least one therapeutic agent within a half-life ($t_{1/2}$) ranging from 1 day to 30 days. According to one embodiment, the flowable sustained release microparticulate composition is capable of sustained release of the therapeutic amount of the at least one therapeutic agent within a half-life of 1 day. According to another embodiment, the flowable sustained release microparticulate composition is capable of sustained release of the therapeutic amount of the at least one therapeutic agent within a half-life of 2 days. According to another embodiment, the flowable sustained release microparticulate composition is capable of sustained release of the therapeutic amount of the at least one therapeutic agent within a half-life of 3 days. According to another embodiment, the flowable sustained release microparticulate composition is capable of sustained release of the therapeutic amount of the at least one therapeutic agent within a half-life of 4 days. According to another embodiment, the flowable sustained release microparticulate composition is capable of sustained release of the therapeutic amount of the at least one therapeutic agent within a half-life of 5 days. According to another embodiment, the flowable sustained release microparticulate composition is capable of sustained release of the therapeutic amount of the at least one therapeutic agent within a half-life of 6 days. According to another embodiment, the flowable sustained release microparticulate composition is capable of sustained release of the therapeutic amount of the at least one therapeutic agent within a half-life of 7 days. According to another embodiment, the flowable sustained release microparticulate composition is capable of sustained release of the therapeutic amount of the at least one therapeutic agent within a half-life of 8 days. According to another embodiment, the flowable sustained release microparticulate composition is capable of sustained release of the therapeutic amount of the at least one therapeutic agent within a half-life of 9 days. According to another embodiment, the flowable sustained release microparticulate composition is capable of sustained release of the therapeutic amount of the at least one therapeutic agent within a half-life of 10 days. According to another embodiment, the flowable sustained release microparticulate composition is capable of sustained release of the therapeutic amount of the at least one therapeutic agent within a half-life of 12 days. According to another embodiment, the flowable sustained release microparticulate composition is capable of sustained release of the therapeutic amount of the at least one therapeutic agent within a half-life of 14 days. According to another embodiment, the flowable sustained release microparticulate composition is capable of sustained release of the therapeutic amount of the at least one therapeutic agent within a half-life of 16 days. According to another embodiment, the flowable sustained release microparticulate composition is capable of sustained release of the therapeutic amount of the at least one therapeutic agent within a half-life of 18 days. According to another embodiment, the flowable sustained release microparticulate composition is capable of sustained release of the therapeutic amount of the at least one therapeutic agent within a half-life of 20 days. According to another embodiment, the flowable sustained release microparticulate composition is capable of sustained release of the therapeutic amount of the at least one therapeutic agent within a half-life of 22 days. According to another embodiment, the flowable sustained release microparticulate composition is capable of sustained release of the therapeutic amount of the at least one therapeutic agent within a half-life of 24 days. According to another embodiment, the flowable sustained release microparticulate composition is capable of sustained release of the therapeutic amount of the at least one therapeutic agent within a half-life of 26 days. According to another embodiment, the flowable sustained release microparticulate composition is capable of sustained release of the therapeutic amount of the at least one therapeutic agent within a half-life of 28 days. According to another embodiment, the flowable sustained release microparticulate composition is capable of sustained release of the therapeutic amount of the at least one therapeutic agent within a half-life of 30 days.

According to some embodiments, the flowable sustained release microparticulate composition is capable of sustained release of the therapeutic amount of the at least one therapeutic agent prior to onset of a delayed complication associated with an interruption of a cerebral artery caused by the brain injury. According to some embodiments, the delayed complication is selected from the group consisting of an angiographic vasospasm, a plurality of microthromboemboli, a cortical spreading ischemia, a delayed cerebral ischemia (DCI), or a combination thereof. According to one embodiment, the delayed complication is an angiographic vasospasm. According to another embodiment, the delayed complication is a plurality of microthromboemboli. According to another embodiment, the delayed complication is a cortical spreading ischemia. According to another embodiment, the delayed complication is a delayed cerebral ischemia (DCI).

According to some embodiments, the brain injury is a result of an underlying condition. Exemplary underlying conditions include, but are not limited to, aneurysm, sudden traumatic head injury, subarachnoid hemorrhage (SAH), or a combination thereof. According to one embodiment, the underlying condition is an aneurysm. According to another embodiment, the underlying condition is a traumatic head injury. According to another embodiment, the underlying condition is a subarachnoid hemorrhage (SAH). According to another embodiment, the underlying condition is a combination of an aneurysm, a sudden traumatic head injury, and a subarachnoid hemorrhage (SAH).

According to some embodiments, the flowable sustained release microparticulate composition, upon release in proximity to the at least one cerebral artery in the subarachnoid space at risk of interruption caused by brain injury, is effective to reduce vasospasm such that the internal diameter of the at least one cerebral artery is increased as compared to an untreated control. According to some embodiments, the flowable sustained release microparticulate composition, upon release in proximity to at least one cerebral artery in the subarachnoid space at risk of interruption, is effective in preventing or reducing the incidence or severity of the delayed complication associated with the interruption of the cerebral artery caused by the brain injury.

According to one embodiment, the predominantly localized pharmacologic effect is a reduction of vasospasm such that the internal diameter of the at least one cerebral artery in the subarachnoid space at risk of interruption is increased as compared to an untreated control. According to one embodiment, the flowable sustained release microparticulate composition is effective to reduce vasospasm such that the internal diameter of the at least one cerebral artery in the subarachnoid space at risk of interruption is increased as compared to an untreated control.

According to one embodiment, the therapeutic amount of the at least one therapeutic agent in proximity to at least one cerebral artery in subarachnoid space can produce a predominantly localized pharmacologic effect. According to some embodiments, the predominantly localized pharmacologic effect is a reduction of vasospasm such that the internal diameter of the at least one cerebral artery in subarachnoid space at risk of interruption is increased as compared to an untreated control, wherein the at least one cerebral artery is at least 10 mm, at least 9.9 mm, at least 9.8 mm, at least 9.7 mm, at least 9.6 mm, at least 9.5 mm, at least 9.4 mm, at least 9.3 mm, at least 9.2 mm, at least 9.1 mm, at least 9.0 mm, at least 8.9 mm, at least 8.8 mm, at least 8.7 mm, at least 8.6 mm, at least 8.5 mm, at least 8.4 mm, at least 8.3 mm, at least 8.2 mm, at least 8.1 mm, at least 8.0 mm, at least 7.9 mm, at least 7.8 mm, at least 7.7 mm, at least 7.6 mm, at least 7.5 mm, at least 7.4 mm, at least 7.3 mm, at least 7.2 mm, at least 7.1 mm, at least 7.0 mm, at least 6.9 mm, at least 6.8 mm, at least 6.7 mm, at least 6.6 mm, at least 6.5 mm, at least 6.4 mm, at least 6.3 mm, at least 6.2 mm, at least 6.1 mm, at least 6.0 mm, at least 5.9 mm, at least 5.8 mm, at least 5.7 mm, at least 5.6 mm, at least 5.5 mm, at least 5.4 mm, at least 5.3 mm, at least 5.2 mm, at least 5.1 mm, at least 5.0 mm from the site of release in the subarachnoid space. According to one embodiment, the predominantly localized pharmacologic effect is a reduction of vasospasm such that the internal diameter of the at least one cerebral artery that is at least 10 mm from the site of release in the subarachnoid space is increased as compared to an untreated control. According to another embodiment, the predominantly localized pharmacologic effect is a reduction of vasospasm such that the internal diameter of the at least one cerebral artery that is at least 9.9 mm from the site of release in the subarachnoid space is increased as compared to an untreated control. According to another embodiment, the predominantly localized pharmacologic effect is a reduction of vasospasm such that the internal diameter of the at least one cerebral artery that is at least 9.8 mm from the site of release in the subarachnoid space is increased as compared to an untreated control. According to another embodiment, the predominantly localized pharmacologic effect is a reduction of vasospasm such that the internal diameter of the at least one cerebral artery that is at least 9.7 mm from the site of release in the subarachnoid space is increased as compared to an untreated control. According to another embodiment, the predominantly localized pharmacologic effect is a reduction of vasospasm such that the internal diameter of the at least one cerebral artery that is at least 9.6 mm from the site of release in the subarachnoid space is increased as compared to an untreated control. According to another embodiment, the predominantly localized pharmacologic effect is a reduction of vasospasm such that the internal diameter of the at least one cerebral artery that is at least 9.5 mm from the site of release in the subarachnoid space is increased as compared to an untreated control. According to another embodiment, the predominantly localized pharmacologic effect is a reduction of vasospasm such that the internal diameter of the at least one cerebral artery that is at least 9.4 mm from the site of release in the subarachnoid space is increased as compared to an untreated control. According to another embodiment, the predominantly localized pharmacologic effect is a reduction of vasospasm such that the internal diameter of the at least one cerebral artery that is at least 9.3 mm from the site of release in the subarachnoid space is increased as compared to an untreated control. According to another embodiment, the predominantly localized pharmacologic effect is a reduction of vasospasm such that the internal diameter of the at least one cerebral artery that is at least 9.2 mm from the site of release in the subarachnoid space is increased as compared to an untreated control. According to another embodiment, the predominantly localized pharmacologic effect is a reduction of vasospasm such that the internal diameter of the at least one cerebral artery that is at least 9.1 mm from the site of release in the subarachnoid space is increased as compared to an untreated control. According to another embodiment, the predominantly localized pharmacologic effect is a reduction of vasospasm such that the internal diameter of the at least one cerebral artery that is at least 9.0 mm from the site of release in the subarachnoid space is increased as compared to an untreated control. According to another embodiment, the predominantly localized pharmacologic effect is a reduction of vasospasm such that the internal diameter of the at least one cerebral artery that is at least 8.9 mm from the site of release in the subarachnoid space is increased as compared to an untreated control. According to another embodiment, the predominantly localized pharmacologic effect is a reduction of vasospasm such that the internal diameter of the at least one cerebral artery that is at least 8.8 mm from the site of release in the subarachnoid space is increased as compared to an untreated control. According to another embodiment, the predominantly localized pharmacologic effect is a reduction of vasospasm such that the internal diameter of the at least one cerebral artery that is at least 8.7 mm from the site of release in the subarachnoid space is increased as compared to an untreated control. According to another embodiment, the predominantly localized pharmacologic effect is a reduction of vasospasm such that the internal diameter of the at least one cerebral artery that is at least 8.6 mm from the site of release in the subarachnoid space is increased as compared to an untreated control. According to another embodiment, the predominantly localized pharmacologic effect is a reduction of vasospasm such that the internal diameter of the at least one cerebral artery that is at least 8.5 mm from the site of release in the subarachnoid space is increased as compared to an untreated control. According to another embodiment, the predominantly localized pharmacologic effect is a reduction of vasospasm such that the internal diameter of the at least one cerebral artery that is at least 8.4 mm from the site of release in the subarachnoid space is increased as compared to an untreated control. According to another embodiment, the predominantly localized pharmacologic effect is a reduction of vasospasm such that the internal diameter of the at least one cerebral artery that is at least 8.3 mm from the site of release in the subarachnoid space is increased as compared to an untreated control. According to another embodiment, the predominantly localized pharmacologic effect is a reduction of vasospasm such that the internal diameter of the at least one cerebral artery that is at least 8.2 mm from the site of release in the subarachnoid space is increased as compared to an untreated control. According to another embodiment, the predominantly localized pharmacologic effect is a reduction of vasospasm such that the internal diameter of the at least one cerebral artery that is at least 8.1 mm from the site of release in the subarachnoid space is increased as compared to an untreated control. According to another embodiment, the predominantly localized pharmacologic effect is a reduction of vasospasm such that the internal diameter of the at least one cerebral artery that is at least 8.0 mm from the site of release in the subarachnoid space is increased as compared to an untreated control. According to another embodiment, the predominantly localized pharmacologic effect is a reduction of vasospasm such that the internal diameter of the at least one cerebral artery that is at least 7.9 mm from the site of release in the subarachnoid space is increased as compared to an untreated control. According to another embodiment, the predominantly localized pharmacologic effect is a reduction of vasospasm such that the internal diameter of the at least one cerebral artery that is at least 7.8 mm from the site of release in the subarachnoid space is increased as compared to an untreated control. According to another embodiment, the predominantly localized pharmacologic effect is a reduction of vasospasm such that the internal diameter of the at least one cerebral artery that is at least 7.7 mm from the site of release in the subarachnoid space is increased as compared to an untreated control. According to another embodiment, the predominantly localized pharmacologic effect is a reduction of vasospasm such that the internal diameter of the at least one cerebral artery that is at least 7.6 mm from the site of release in the subarachnoid space is increased as compared to an untreated control. According to another embodiment, the predominantly localized pharmacologic effect is a reduction of vasospasm such that the internal diameter of the at least one cerebral artery that is at least 7.5 mm from the site of release in the subarachnoid space is increased as compared to an untreated control. According to another embodiment, the predominantly localized pharmacologic effect is a reduction of vasospasm such that the internal diameter of the at least one cerebral artery that is at least 7.4 mm from the site of release in the subarachnoid space is increased as compared to an untreated control. According to another embodiment, the predominantly localized pharmacologic effect is a reduction of vasospasm such that the internal diameter of the at least one cerebral artery that is at least 7.3 mm from the site of release in the subarachnoid space is increased as compared to an untreated control. According to another embodiment, the predominantly localized pharmacologic effect is a reduction of vasospasm such that the internal diameter of the at least one cerebral artery that is at least 7.2 mm from the site of release in the subarachnoid space is increased as compared to an untreated control. According to another embodiment, the predominantly localized pharmacologic effect is a reduction of vasospasm such that the internal diameter of the at least one cerebral artery that is at least 7.1 mm from the site of release in the subarachnoid space is increased as compared to an untreated control. According to another embodiment, the predominantly localized pharmacologic effect is a reduction of vasospasm such that the internal diameter of the at least one cerebral artery that is at least 7.0 mm from the site of release in the subarachnoid space is increased as compared to an untreated control. According to another embodiment, the predominantly localized pharmacologic effect is a reduction of vasospasm such that the internal diameter of the at least one cerebral artery that is at least 6.9 mm from the site of release in the subarachnoid space is increased as compared to an untreated control. According to another embodiment, the predominantly localized pharmacologic effect is a reduction of vasospasm such that the internal diameter of the at least one cerebral artery that is at least 6.8 mm from the site of release in the subarachnoid space is increased as compared to an untreated control. According to another embodiment, the predominantly localized pharmacologic effect is a reduction of vasospasm such that the internal diameter of the at least one cerebral artery that is at least 6.7 mm from the site of release in the subarachnoid space is increased as compared to an untreated control. According to another embodiment, the predominantly localized pharmacologic effect is a reduction of vasospasm such that the internal diameter of the at least one cerebral artery that is at least 6.6 mm from the site of release in the subarachnoid space is increased as compared to an untreated control. According to another embodiment, the predominantly localized pharmacologic effect is a reduction of vasospasm such that the internal diameter of the at least one cerebral artery that is at least 6.5 mm from the site of release in the subarachnoid space is increased as compared to an untreated control. According to another embodiment, the predominantly localized pharmacologic effect is a reduction of vasospasm such that the internal diameter of the at least one cerebral artery that is at least 6.4 mm from the site of release in the subarachnoid space is increased as compared to an untreated control. According to another embodiment, the predominantly localized pharmacologic effect is a reduction of vasospasm such that the internal diameter of the at least one cerebral artery that is at least 6.3 mm from the site of release in the subarachnoid space is increased as compared to an untreated control. According to another embodiment, the predominantly localized pharmacologic effect is a reduction of vasospasm such that the internal diameter of the at least one cerebral artery that is at least 6.2 mm from the site of release in the subarachnoid space is increased as compared to an untreated control. According to another embodiment, the predominantly localized pharmacologic effect is a reduction of vasospasm such that the internal diameter of the at least one cerebral artery that is at least 6.1 mm from the site of release in the subarachnoid space is increased as compared to an untreated control. According to another embodiment, the predominantly localized pharmacologic effect is a reduction of vasospasm such that the internal diameter of the at least one cerebral artery that is at least 6.0 mm from the site of release in the subarachnoid space is increased as compared to an untreated control. According to another embodiment, the predominantly localized pharmacologic effect is a reduction of vasospasm such that the internal diameter of the at least one cerebral artery that is at least 5.9 mm from the site of release in the subarachnoid space is increased as compared to an untreated control. According to another embodiment, the predominantly localized pharmacologic effect is a reduction of vasospasm such that the internal diameter of the at least one cerebral artery that is at least 5.8 mm from the site of release in the subarachnoid space is increased as compared to an untreated control. According to another embodiment, the predominantly localized pharmacologic effect is a reduction of vasospasm such that the internal diameter of the at least one cerebral artery that is at least 5.7 mm from the site of release in the subarachnoid space is increased as compared to an untreated control. According to another embodiment, the predominantly localized pharmacologic effect is a reduction of vasospasm such that the internal diameter of the at least one cerebral artery that is at least 5.6 mm from the site of release in the subarachnoid space is increased as compared to an untreated control. According to another embodiment, the predominantly localized pharmacologic effect is a reduction of vasospasm such that the internal diameter of the at least one cerebral artery that is at least 5.5 mm from the site of release in the subarachnoid space is increased as compared to an untreated control. According to another embodiment, the predominantly localized pharmacologic effect is a reduction of vasospasm such that the internal diameter of the at least one cerebral artery that is at least 5.4 mm from the site of release in the subarachnoid space is increased as compared to an untreated control. According to another embodiment, the predominantly localized pharmacologic effect is a reduction of vasospasm such that the internal diameter of the at least one cerebral artery that is at least 5.3 mm from the site of release in the subarachnoid space is increased as compared to an untreated control. According to another embodiment, the predominantly localized pharmacologic effect is a reduction of vasospasm such that the internal diameter of the at least one cerebral artery that is at least 5.2 mm from the site of release in the subarachnoid space is increased as compared to an untreated control. According to another embodiment, the predominantly localized pharmacologic effect is a reduction of vasospasm such that the internal diameter of the at least one cerebral artery that is at least 5.1 mm from the site of release in the subarachnoid space is increased as compared to an untreated control. According to another embodiment, the predominantly localized pharmacologic effect is a reduction of vasospasm such that the internal diameter of the at least one cerebral artery that is at least 5.0 mm from the site of release in the subarachnoid space is increased as compared to an untreated control.

According to one embodiment, the sustained release of the therapeutic amount of the at least one therapeutic agent in proximity to at least one cerebral artery in the subarachnoid space can produce a predominantly localized pharmacologic effect over a desired amount of time. According to one embodiment, the release of the therapeutic amount of the at least one therapeutic agent in proximity to at least one cerebral artery in the subarachnoid space produces a predominantly localized pharmacologic effect for 1 day. According to another embodiment, the release of the therapeutic amount of the at least one therapeutic agent in proximity to at least one cerebral artery in the subarachnoid space produces a predominantly localized pharmacologic effect for 2 days. According to another embodiment, the release of the therapeutic amount of the at least one therapeutic agent in proximity to at least one cerebral artery in the subarachnoid space produces a predominantly localized pharmacologic effect for 3 days. According to another embodiment, the release of the therapeutic amount of the at least one therapeutic agent in proximity to at least one cerebral artery in the subarachnoid space produces a predominantly localized pharmacologic effect for 4 days. According to another embodiment, the release of the therapeutic amount of the at least one therapeutic agent in proximity to at least one cerebral artery in the subarachnoid space produces a predominantly localized pharmacologic effect for 5 days. According to another embodiment, the release of the therapeutic amount of the at least one therapeutic agent in proximity to at least one cerebral artery in the subarachnoid space produces a predominantly localized pharmacologic effect for 6 days. According to another embodiment, the release of the therapeutic amount of the at least one therapeutic agent in proximity to at least one cerebral artery in the subarachnoid space produces a predominantly localized pharmacologic effect for 7 days. According to another embodiment, the release of the therapeutic amount of the at least one therapeutic agent in proximity to at least one cerebral artery in the subarachnoid space produces a predominantly localized pharmacologic effect for 8 days. According to another embodiment, the release of the therapeutic amount of the at least one therapeutic agent in proximity to at least one cerebral artery in the subarachnoid space produces a predominantly localized pharmacologic effect for 15 days. According to another embodiment, the release of the therapeutic amount of the at least one therapeutic agent in proximity to at least one cerebral artery in the subarachnoid space produces a predominantly localized pharmacologic effect for 30 days.

Administering Step

According to some embodiments, the flowable sustained release microparticulate composition is administered by parenteral injection using a surgical injection apparatus.

According to some embodiments, administering is by passage through a catheter or catheterization. The term "catheterization" refers to a minimally invasive procedure by which the flowable sustained release microparticular composition can access the desired areas of the brain, which can mean less risk of complications and a shorter recovery. According to some embodiments, the catheter is a silicone catheter. According to some embodiments, the catheter is a soft catheter. According to some embodiments, the catheter is a flexible catheter. According to some embodiments, the catheter is a pliable catheter.

More generally, intraventricular delivery of the flowable sustained release microparticulate composition according to the present invention provides a number of advantages over systemic administration. As an example, nimodipine is approved to be administered as a continuous intravenous infusion or orally as pills given every 2 to 4 hours. Intraventricular delivery provides a higher concentration of the therapeutic agent in the cerebrospinal fluid (CSF) locally where the therapeutic agent dispersed through the microparticles can exert its effect. This results in a localized pharmacological effect without entering systemic circulation in an amount to cause systemic effects, such as hypotension. Furthermore, administration directly into a cerebral ventricle, which overcomes the blood brain barrier and allows administration of a therapeutic amount than that lower than that necessary when administered systemically. Without being limited by theory, administration of the flowable sustained release microparticulate formulation of a therapeutic amount of a therapeutic agent into a cerebral ventricle in a sustained release formulation, which allows delivery of the therapeutic amount over days, may prevent DCI.

According to another embodiment, the flowable sustained release microparticulate composition is administered by parenteral injection via a surgical injection apparatus locally into a cerebral ventricle so that the composition is carried by CSF circulation to contact and flow around the cerebral artery in the subarachnoid space at risk of interruption.

According to some such embodiments, the surgical injection apparatus is a needle, a cannula, a catheter, or a combination thereof. According to some embodiments, the surgical injection apparatus is inserted into a cerebral ventricle. According to some embodiments, the cerebral ventricle is selected from the group consisting of a lateral ventricle, a third ventricle, a fourth ventricle, or a combination thereof. According to some embodiments, the cerebral ventricle is a lateral ventricle. According to one embodiment, the cerebral ventricle is a right lateral ventricle. According to another embodiment, the cerebral ventricle is a left lateral ventricle. According to one embodiment, the cerebral ventricle is a third ventricle. According to another embodiment, the cerebral ventricle is a fourth ventricle.

According to some embodiments, the cerebral ventricle is at least 0.001 mm to at least 10 cm from the at least one cerebral artery in the subarachnoid space at risk of interruption caused by a brain injury. According to one embodiment, the cerebral ventricle is at least 0.001 mm from the at least one cerebral artery in the subarachnoid space at risk of interruption caused by the brain injury. According to another embodiment, the cerebral ventricle is at least 0.005 mm from the at least one cerebral artery in the subarachnoid space at risk of interruption caused by the brain injury. According to another embodiment, the cerebral ventricle is at least 0.01 mm from the at least one cerebral artery in the subarachnoid space at risk of interruption caused by the brain injury. According to another embodiment, the cerebral ventricle is at least 0.05 mm from the at least one cerebral artery in the subarachnoid space at risk of interruption caused by the brain injury. According to another embodiment, the cerebral ventricle is at least 0.1 mm from the at least one cerebral artery in the subarachnoid space at risk of interruption caused by the brain injury. According to another embodiment, the cerebral ventricle is at least 0.5 mm from the at least one cerebral artery in the subarachnoid space at risk of interruption caused by the brain injury. According to another embodiment, the cerebral ventricle is at least 1.0 mm from the at least one cerebral artery in the subarachnoid space at risk of interruption caused by the brain injury. According to another embodiment, the cerebral ventricle is at least 1.5 mm from the at least one cerebral artery in the subarachnoid space at risk of interruption caused by the brain injury. According to another embodiment, the cerebral ventricle is at least 2.0 mm from the at least one cerebral artery in the subarachnoid space at risk of interruption caused by the brain injury. According to another embodiment, the cerebral ventricle is at least 2.5 mm from the at least one cerebral artery in the subarachnoid space at risk of interruption caused by the brain injury. According to another embodiment, the cerebral ventricle is at least 3.0 mm from the at least one cerebral artery in the subarachnoid space at risk of interruption caused by the brain injury. According to another embodiment, the cerebral ventricle is at least 3.5 mm from the at least one cerebral artery in the subarachnoid space at risk of interruption caused by the brain injury. According to another embodiment, the cerebral ventricle is at least 4.0 mm from the at least one cerebral artery in the subarachnoid space at risk of interruption caused by the brain injury. According to another embodiment, the cerebral ventricle is at least 4.5 mm from the at least one cerebral artery in the subarachnoid space at risk of interruption caused by the brain injury. According to another embodiment, the cerebral ventricle is at least 5.0 mm from the at least one cerebral artery in the subarachnoid space at risk of interruption caused by the brain injury. According to another embodiment, the cerebral ventricle is at least 5.5 mm from the at least one cerebral artery in the subarachnoid space at risk of interruption caused by the brain injury. According to another embodiment, the cerebral ventricle is at least 6.0 mm from the at least one cerebral artery in the subarachnoid space at risk of interruption caused by the brain injury. According to another embodiment, the cerebral ventricle is at least 6.5 mm from the at least one cerebral artery in the subarachnoid space at risk of interruption caused by the brain injury. According to another embodiment, the cerebral ventricle is at least 7.0 mm from the at least one cerebral artery in the subarachnoid space at risk of interruption caused by the brain injury. According to another embodiment, the cerebral ventricle is at least 7.5 mm from the at least one cerebral artery in the subarachnoid space at risk of interruption caused by the brain injury. According to another embodiment, the cerebral ventricle is at least 8.0 mm from the at least one cerebral artery in the subarachnoid space at risk of interruption caused by the brain injury. According to another embodiment, the cerebral ventricle is at least 8.5 mm from the at least one cerebral artery in the subarachnoid space at risk of interruption caused by the brain injury. According to another embodiment, the cerebral ventricle is at least 9.0 mm from the at least one cerebral artery in the subarachnoid space at risk of interruption caused by the brain injury. According to another embodiment, the cerebral ventricle is at least 9.5 mm from the at least one cerebral artery in the subarachnoid space at risk of interruption caused by the brain injury. According to another embodiment, the cerebral ventricle is at least 1 cm from the at least one cerebral artery in the subarachnoid space at risk of interruption caused by the brain injury. According to another embodiment, the cerebral ventricle is at least 1.5 cm from the at least one cerebral artery in the subarachnoid space at risk of interruption caused by the brain injury. According to another embodiment, the cerebral ventricle is at least 2.0 cm from the at least one cerebral artery in the subarachnoid space at risk of interruption caused by the brain injury. According to another embodiment, the cerebral ventricle is at least 2.5 cm from the at least one cerebral artery in the subarachnoid space at risk of interruption caused by the brain injury. According to another embodiment, the cerebral ventricle is at least 3.0 cm from the at least one cerebral artery in the subarachnoid space at risk of interruption caused by the brain injury. According to another embodiment, the cerebral ventricle is at least 3.5 cm from the at least one cerebral artery in the subarachnoid space at risk of interruption caused by the brain injury. According to another embodiment, the cerebral ventricle is at least 4.0 cm from the at least one cerebral artery in the subarachnoid space at risk of interruption caused by the brain injury. According to another embodiment, the cerebral ventricle is at least 4.5 cm from the at least one cerebral artery in the subarachnoid space at risk of interruption caused by the brain injury. According to another embodiment, the cerebral ventricle is at least 5.0 cm from the at least one cerebral artery in the subarachnoid space at risk of interruption caused by the brain injury. According to another embodiment, the cerebral ventricle is at least 5.5 cm from the at least one cerebral artery in the subarachnoid space at risk of interruption caused by the brain injury. According to another embodiment, the cerebral ventricle is at least 6.0 cm from the at least one cerebral artery in the subarachnoid space at risk of interruption caused by the brain injury. According to another embodiment, the cerebral ventricle is at least 6.5 cm from the at least one cerebral artery in the subarachnoid space at risk of interruption caused by the brain injury. According to another embodiment, the cerebral ventricle is at least 7.0 cm from the at least one cerebral artery in the subarachnoid space at risk of interruption caused by the brain injury. According to another embodiment, the cerebral ventricle is at least 7.5 cm from the at least one cerebral artery in the subarachnoid space at risk of interruption caused by the brain injury. According to another embodiment, the cerebral ventricle is at least 8.0 cm from the at least one cerebral artery in the subarachnoid space at risk of interruption caused by the brain injury. According to another embodiment, the cerebral ventricle is at least 8.5 cm from the at least one cerebral artery in the subarachnoid space at risk of interruption caused by the brain injury. According to another embodiment, the cerebral ventricle is at least 9.0 cm from the at least one cerebral artery in the subarachnoid space at risk of interruption caused by the brain injury. According to another embodiment, the cerebral ventricle is at least 9.5 cm from the at least one cerebral artery in the subarachnoid space at risk of interruption caused by the brain injury. According to another embodiment, the cerebral ventricle is at least 10 cm from the at least one cerebral artery in the subarachnoid space at risk of interruption caused by the brain injury.

Figure 14:
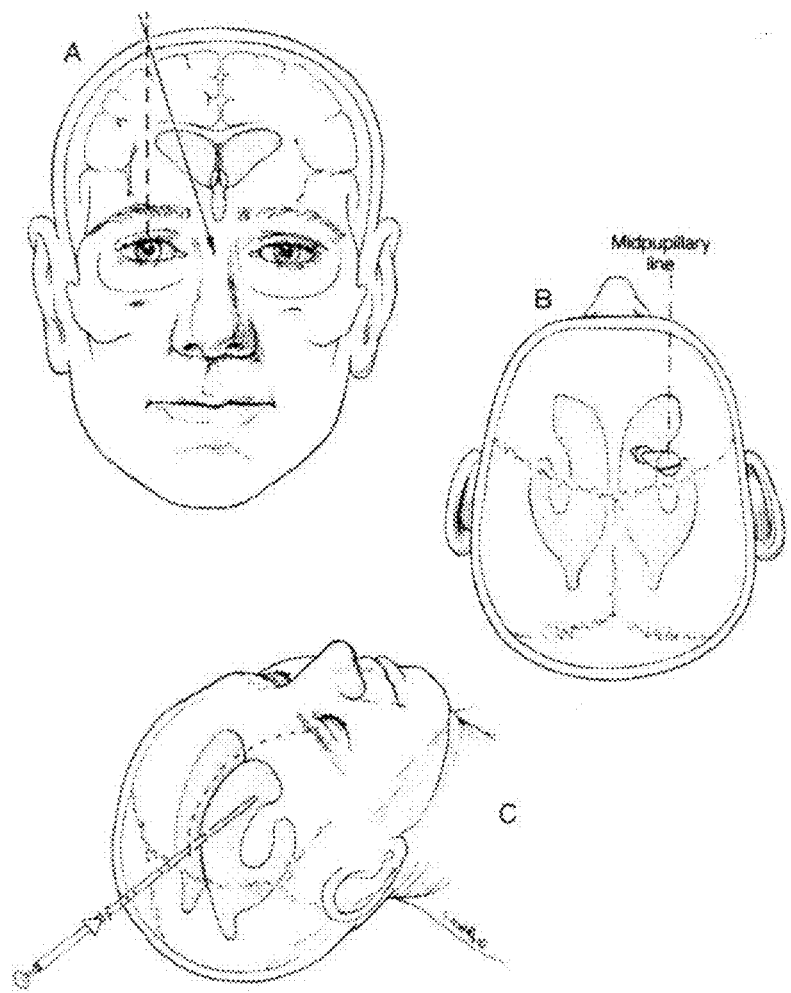
FIG. 14 shows an exemplary view of the application of a microparticulate composition of the described invention containing a calcium channel antagonist, an endothelin receptor antagonist, or a TRP protein antagonist, or a combination thereof, to the cerebral ventricles through an intraventricular catheter (Figure from Mccomb J G: Techniques of CSF diversion. In: Scott R M (ed). Hydrocephalus. Vol. 3. Williams & Wilkins: Baltimore. 1990. page 48, pp. 128).
Figure 15:
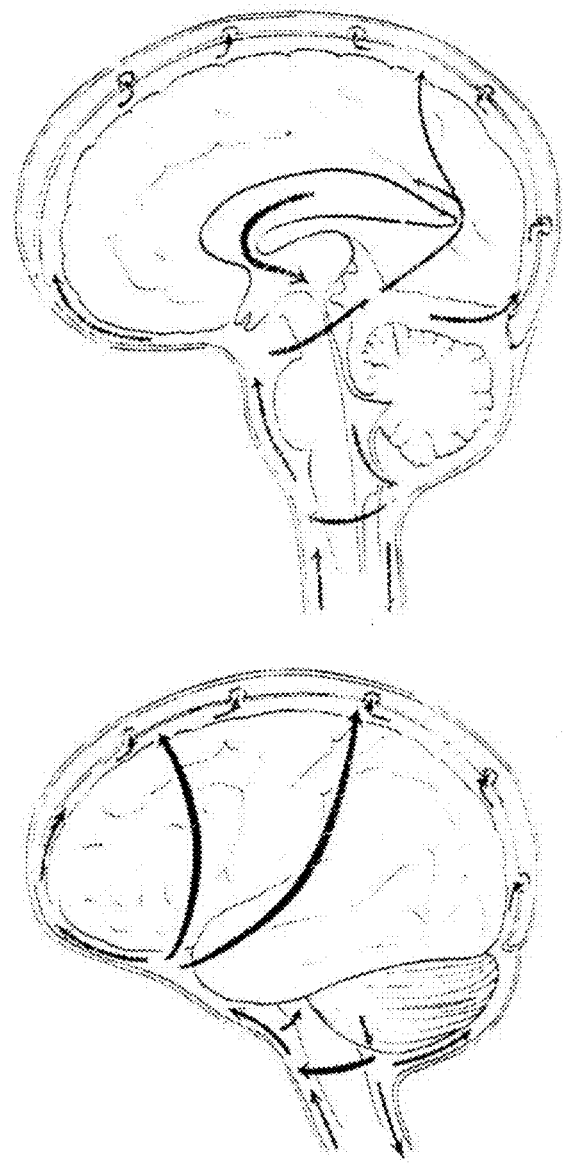
FIG. 15 is a schematic depicting a microparticulate composition of the described invention comprising a calcium channel antagonist, an endothelin receptor antagonist, or a TRP protein antagonist, or a combination thereof, in or on microparticles being carried by CSF flow from the ventricles to the arteries of the subarachnoid space (Pollay M: Cerebrospinal fluid. In: Tindall G T, Cooper P R, Barrow D L (eds). The Practice of Neurosurgery. Vol. 1. Williams & Wilkins: Baltimore. 1996. page 36, pp. 1381).

The cerebral ventricles may be cannulated or catheterized as is well-known in the art and as described in various neurosurgical textbooks. This is called insertion of a ventricular catheter or drain or ventriculostomy. According to some embodiments, a hole of varying size can be drilled in the skull and the outer dura mater covering the brain incised. The pia mater is incised and a catheter (a hollow tube generally made of silicone elastomer or some other biocompatible, nonabsorbable compound) is inserted through the brain into the ventricle of choice. This usually is the lateral ventricle but any ventricle could be catheterized. The catheter can be used to monitor the pressure inside the head, to drain CSF or to administer substances into the CSF. FIG. 14 shows an exemplary view of the application of a microparticulate composition of the described invention containing a calcium channel antagonist, an endothelin receptor antagonist, or a TRP protein antagonist, or a combination thereof, to the cerebral ventricles through an intraventricular catheter (Figure from Mccomb J G: Techniques of CSF diversion. In: Scott R M (ed). Hydrocephalus. Vol. 3. Williams & Wilkins: Baltimore. 1990. page 48, pp. 128). FIG. 15 is a schematic depicting a microparticulate composition of the described invention comprising a calcium channel antagonist, an endothelin receptor antagonist, or a TRP protein antagonist, or a combination thereof, in or on microparticles being carried by CSF flow from the ventricles to the arteries of the subarachnoid space (Pollay M: Cerebrospinal fluid. In: Tindall G T, Cooper P R, Barrow D L (eds). The Practice of Neurosurgery. Vol. 1. Williams & Wilkins: Baltimore. 1996. page 36, pp. 1381).

According to some embodiments, the flowable sustained release microparticulate composition comprising the at least one therapeutic agent can be delivered to the cerebral ventricles and is carried by the flow of cerebrospinal fluid (CSF) into the CSF in the subarachnoid space. The circulation of CSF is often slowed after SAH and the subarachnoid space contains blood clots. Thus, the flowable sustained release microparticulate composition can become trapped in the blood clots and thereby facilitating localized release of the pharmacological agent(s) from the composition where it/they would exert a pharmacological effect to the adjacent arteries and brain. According to one embodiment, release of the therapeutic agent occurs in the CSF of the subarachnoid space.

According to one embodiment, the flowable sustained release microparticulate composition comprising the at least one therapeutic agent can be delivered by inserting a catheter into the ventricle and injecting the flowable sustained release microparticulate composition through the catheter such that the composition emanates from the end of the catheter locally into the ventricle.

According to another embodiment, the flowable sustained release microparticulate composition is administered as a single bolus injection. According to another embodiment, the injection is repeated after a pre-determined time period. According to some such embodiments, the pre-determined time period ranges from 1 minute or more to 10 days or more. For example, a repeat injection can be given if monitoring of the patient shows that the patient still had evidence of an interruption of a cerebral artery.

Therapeutic Agent

According to some embodiments, the at least one therapeutic agent is a calcium channel antagonist, an endothelin antagonist, a transient receptor potential (TRP) protein antagonist, or a combination thereof.

According to one embodiment, the at least one therapeutic agent is a calcium channel antagonist. According to some embodiments, the calcium channel antagonist is selected from the group consisting of an L-type voltage dependent calcium channel inhibitor, an R-type voltage dependent calcium channel inhibitor, an N-type voltage dependent calcium channel inhibitor, a P/Q-type voltage dependent calcium channel inhibitor, a T-type voltage dependent calcium channel inhibitor, or a combination thereof. According to one embodiment, the calcium channel antagonist is an L-type voltage dependent calcium channel inhibitor. According to another embodiment, the calcium channel antagonist is an R-type voltage dependent calcium channel inhibitor. According to another embodiment, the calcium channel antagonist is an N-type voltage dependent calcium channel inhibitor. According to another embodiment, the calcium channel antagonist is a P/Q-type voltage dependent calcium channel inhibitor. According to another embodiment, the calcium channel antagonist is a T-type voltage dependent calcium channel inhibitor.

For example, L-type voltage dependent calcium channel inhibitor include, but are not limited to: dihydropyridine L-type antagonists such as nisoldipine, nicardipine and nifedipine, AHF (such as 4aR,9aS)-(+)-4a-Amino-1,2,3,4,4a,9a-hexahydro-4aH-fluorene, HCl), isradipine (such as 4-(4-Benzofurazanyl)-1,-4-dihydro-2,6-dimethyl-3,5-pyridinedicarboxylic acid methyl 1-methhylethyl ester), calciseptine (such as isolated from (*Dendroaspis polylepis ploylepis*), H-Arg-Ile-Cys-Tyr-Ile-His-Lys-Ala-Ser-Leu-Pro-Arg-Ala-Thr-Lys-Thr-Cys-Val-Glu-Asn-Thr-Cys-Tyr-Lys-Met-Phe-Ile-Arg-Thr-Gln-Arg-Glu-Tyr-Ile-Ser-Glu-Arg-Gly-Cys-Gly-Cys-Pro-Thr-Ala- Met-Trp-Pro-Tyr-Gln-Thr-Glu-Cys-Cys-Lys-Gly-Asp-Arg-Cys-Asn-Lys-OH, Calcicludine (such as isolated from *Dendroaspis angusticeps* (eastern green mamba)), (H-Trp-Gln-Pro-Pro-Trp-Tyr-Cys- Lys-Glu-Pro-Val-Arg-Ile-Gly-Ser-Cys-Lys-Lys-Gln-Phe-Ser-Ser-Phe-Tyr-Phe-Lys-Trp-Thr-Ala-Lys-Lys-Cys-Leu-Pro-Phe-Leu-Phe-Ser-Gly-Cys-Gly-Gly-Asn-Ala- Asn-Arg-Phe-Gln-Thr-Ile-Gly-Glu-Cys-Arg-Lys-Lys-Cys-Leu-Gly-Lys-OH, Cilnidipine (such as also FRP-8653, a dihydropyridine-type inhibitor), Dilantizem (such as (2S, 3S)-(+)-cis-3-Acetoxy-5-(2-dimethylaminoethyl)-2,3-dihydro-2-(4-methoxyphenyl)-1,5-benzothiazepin-4(5H)-one hydrochloride), diltiazem (such as benzothiazepin-4(5H)-one, 3-(acetyloxy)-5-[2-(dimethylamino)ethyl]-2,3-dihydro-2-(4-methoxyphenyl)-,(+)-cis-,monohydrochloride), Felodipine (such as 4-(2,3-Dichlorophenyl)-1,4-dihydro-2,6-dimethyl-3,5-pyridinecarboxylic acid ethyl methyl ester), FS-2 (such as an isolate from *Dendroaspis polylepis* polylepis venom), FTX-3.3 (such as an isolate from *Agelenopsis aperta*), Neomycin sulfate (such as $C_{23}H_{46}N_6O_{13}.3H_2SO_4$), Nicardipine (such as 1,4-Dihydro-2,6-dimethyl-4-(3-nitrophenyl)methyl-2-[methyl(phenylmethypa-mino]-3,5-pyridinedicarboxylic acid ethyl ester hydrochloride, also YC-93, Nifedipine (such as 1,4-Dihydro-2,6-dimethyl-4-(2-nitrophenyl)-3,5-pyridinedicarboxylic acid dimethyl ester), Nimodipine (such as 4-Dihydro-2,6-dimethyl-4-(3-nitrophenyl)-3,5-pyridinedicarboxylic acid 2-methoxyethyl 1-methylethyl ester) or (Isopropyl 2-methoxyethyl 1,4-dihydro-2,6-dimethyl-4-(m-nitrophenyl)-3,5-pyridinedicarboxylate), Nitrendipine (such as 1,4-Dihydro-2,6-dimethyl-4-(3-nitrophenyl)-3,5-pyridinedicarboxylic acid ethyl methyl ester), S-Petasin (such as (3S,4aR,5R,6R)-[2,3,4,4a,5,6,7,8-Octahydro-3-(2-propenyl)-4a,5-dimethyl-2-O-xo-6-naphthyl] Z-3'-methylthio-1'-propenoate), Phloretin (such as 2',4',6'-Trihydroxy-3-(4-hydroxyphenyl)propiophenone, also 3-(4-Hydroxyphenyl)-1-(2,4,6-trihydroxyphenyl)-1-propanone, also b-(4-Hydroxyphenyl)-2,4,6-trihydroxypropiophenone), Protopine (such as $C_{20}H_{19}NO_5Cl$), SKF-96365 (such as 1-[b-[3-(4-Methoxyphenyl)propoxy]-4-methoxyphenethyl]-1H-imidazole, HCl), Tetrandine (such as 6,6',7,12-Tetramethoxy-2,2'-dimethylberbaman), (.+−.)-Methoxyverapamil or (+)-Verapamil (such as 54N-(3,4-Dimethoxyphenylethyl)methylamino]-2-(3,4-dimethoxyphenyl)-2-iso-propylvaleronitrile hydrochloride), and (R)-(+)-Bay K8644 (such as R-(+)-1,4-Dihydro-2,6-dimethyl-5-nitro-442-(trifluoromethyl)phenyl]-3-pyridinecarboxylic acid methyl ester). The foregoing examples may be specific to L-type voltage-gated calcium channels or may inhibit a broader range of voltage-gated calcium channels, e.g. N, P/Q, R, and T-type.

According to some embodiments, the L-type voltage dependent calcium channel inhibitor is a dihydropyridine. Exemplary dihydropyridines include, but are not limited to, amlodipine, aranidipine, azelnidipine, bamidipine, benidipine, cinaldipine, efonidipine, felodipine, isradipine, lacidipine, lemildipine, lercanidipine, nicardipine, nifedipine, nilvadipine, nimodipine, nisoldipine, nitrendipine, manidipine, pranidipine, etc. According to one embodiment, the dihydropyridine is nimodipine. According to one embodiment, the nimodipine has a half life of 7-10 days when formulated as described herein, and appropriate lipid solubility.

According to some embodiments, the L-type voltage dependent calcium channel inhibitor is a phenylalkylamine. Exemplary phenylalkylamines include, but are not limited to, gallopamil, verapamil, etc. According to some embodiments, the L-type voltage dependent calcium channel inhibitor is a 1-4 benzothiazepine. According to one embodiment, the 1-4 benzothiazepine is diltiazem. According to one embodiment, the L-type voltage dependent calcium channel inhibitor is bepridil.

According to another embodiment, the at least one therapeutic agent is an endothelin antagonist. Exemplary endothelin antagonists include, but are not limited to, A-127722, ABT-627, BMS 182874, BQ-123, BQ-153, BQ-162, BQ-485, BQ-518, BQ-610, EMD-122946, FR 139317, IPI-725, L-744453, LU 127043, LU 135252, PABSA, PD 147953, PD 151242, PD 155080, PD 156707, RO 611790, SB-247083, clazosentan, atrasentan, sitaxsentan sodium, TA-0201, TBC 11251, TTA-386, WS-7338B, ZD-1611, aspirin, A-182086, CGS 27830, CP 170687, J-104132, L-751281, L-754142, LU 224332, LU 302872, PD 142893, PD 145065, PD 160672, RO-470203, bosentan, RO 462005, RO 470203, SB 209670, SB 217242, TAK-044, A-192621, A-308165, BQ-788, BQ-017, IRL 1038, IRL 2500, PD-161721, RES 701-1, RO 468443, etc.

According to another embodiment, the at least one therapeutic agent is a transient receptor potential (TRP) protein antagonist. Exemplary transient receptor potential (TRP) protein antagonists include, but are not limited to, gadolinium chloride, lanthanum chloride, SKF 96365 (1-(beta-[3-(4-methoxy-phenyl)propoxy]-4-methoxyphenethyl)-1H-imidazole hydrochloride), and LOE 908 ((RS)-(3,4-dihydro-6,7-dimethoxyisoquinoline-1-gamma 1)-2-phenyl-N,N-di-[2-(2,3,4-trimethoxyphenyl)ethyl]acetamide).

According to some embodiments, the at least one therapeutic agent is an isolated molecule. According to some embodiments, the at least one therapeutic agent is substantially pure.

Microparticulate Formulation

According to one embodiment, the flowable sustained release microparticulate composition comprises a plurality of microparticles comprising at least one therapeutic agent.

According to some embodiments, the at least one therapeutic agent is provided in the form of a microparticle. According to another embodiment, the least one therapeutic agent is disposed on or in the microparticle. According to one embodiment, the at least one therapeutic agent is dispersed throughout each microparticle. According to some embodiments, the at least one therapeutic agent is impregnated on the surface of each microparticle. According to another embodiment, the at least one therapeutic agent is contained within the core of the microparticle surrounded by a coating. According to another embodiment, the least one therapeutic agent is adsorbed into each microparticle.

According to some such embodiments, the microparticles are of uniform size distribution. According to some embodiments, the uniform distribution of microparticle size is achieved by a homogenization process to form a uniform emulsion comprising microparticles. According to some such embodiments, each microparticle comprises a matrix. According to some embodiments, the matrix comprises the least one therapeutic agent.

According to some embodiments, the microparticle can be of any order release kinetics, including a zero order release, first order release, second order release, delayed release, sustained release, immediate release, and a combination thereof. The microparticle can include, in addition to therapeutic agent(s), any of those materials routinely used in the art of pharmacy and medicine, including, but not limited to, erodible, nonerodible, biodegradable, or nonbiodegradable material or combinations thereof According to some embodiments, the microparticle is a microcapsule that contains the least one therapeutic agent in a solution or in a semi-solid state. According to some embodiments, the microparticle contains the least one therapeutic agent, in whole or in part. According to some embodiments, the microparticle is a nanoparticle that contains the least one therapeutic agent, in whole or in part. According to some embodiments, the microparticles can be of virtually any shape.

According to some embodiments, each microparticle is loaded with at least 40% by weight to at least 80% by weight of the at least one therapeutic agent. According to one embodiment, each microparticle is loaded with at least 40% by weight of the at least one therapeutic agent. According to another embodiment, each microparticle is loaded with at least 45% by weight of the at least one therapeutic agent. According to another embodiment, each microparticle is loaded with at least 50% by weight of the at least one therapeutic agent. According to another embodiment, each microparticle is loaded with at least 55% by weight of the at least one therapeutic agent. According to another embodiment, each microparticle is loaded with at least 60% by weight of the at least one therapeutic agent. According to another embodiment, each microparticle is loaded with at least 63% by weight of the at least one therapeutic agent. According to another embodiment, each microparticle is loaded with at least 65% by weight of the at least one therapeutic agent. According to another embodiment, each microparticle is loaded with at least 70% by weight of the at least one therapeutic agent. According to another embodiment, each microparticle is loaded with at least 75% by weight of the at least one therapeutic agent. According to another embodiment, each microparticle is loaded with at least 80% by weight of the at least one therapeutic agent.

According to some embodiments, the particle size is between about 25 μm to about 100 μm. According to some embodiments, the particle size is between about 30 μm to about 80 μm. According to one embodiment, the particle size is at least about 25 μm. According to another embodiment, the particle size is at least about 30 μm. According to another embodiment, the particle size is at least about 35 μm. According to another embodiment, the particle size is at least about 40 μm. According to another embodiment, the particle size is at least about 45 μm. According to another embodiment, the particle size is at least about 50 μm. According to another embodiment, the particle size is at least about 55 μm. According to another embodiment, the particle size is at least about 60 μm. According to another embodiment, the particle size is at least about 65 μm. According to another embodiment, the particle size is at least about 70 μm. According to another embodiment, the particle size is at least about 75 μm. According to another embodiment, the particle size is at least about 80 μm. According to another embodiment, the particle size is at least about 85 μm. According to another embodiment, the particle size is at least about 90 μm. According to another embodiment, the particle size is at least about 95 μm. According to another embodiment, the particle size is at least about 100 μm.

According to another embodiment, the at least one therapeutic agent can be provided in strings. The strings can contain the at least one therapeutic agent in a core surrounded by a coating, or the at least one therapeutic agent can be dispersed throughout the string, or the at least one therapeutic agent can be absorbed into the string. The string can be of any order release kinetics, including zero order release, first order release, second order release, delayed release, sustained release, immediate release, etc., and any combination thereof. The string can include, in addition to therapeutic agent(s), any of those materials routinely used in the art of pharmacy and medicine, including, but not limited to, erodible, nonerodible, biodegradable, or nonbiodegradable material or combinations thereof.

According to another embodiment, the at least one therapeutic agent can be provided in at least one sheet. The sheet can contain the at least one therapeutic agent and at least one additional therapeutic agent in a core surrounded by a coating, or the at least one therapeutic agent and at least one additional therapeutic agent can be dispersed throughout the sheet, or the at least one therapeutic agent can be absorbed into the sheet. The sheet can be of any order release kinetics, including zero order release, first order release, second order release, delayed release, sustained release, immediate release, etc., and any combination thereof. The sheet can include, in addition to the at least one therapeutic agent and at least one additional therapeutic agent, any of those materials routinely used in the art of pharmacy and medicine, including, but not limited to, erodible, nonerodible, biodegradable, or nonbiodegradable material or combinations thereof.

According to some embodiments, the microparticulate formulation comprises a suspension of microparticles. According to one embodiment, the microparticulate formulation comprises a powder suspension of microparticles. According to some embodiments, the microparticulate formulation further comprises at least one of a suspending agent, a stabilizing agent and a dispersing agent. According to some such embodiments, the microparticulate formulation is presented as a suspension. According to some such embodiments, the microparticulate formulation is presented as a solution. According to some such embodiments, the microparticulate formulation is presented as an emulsion.

According to some embodiments, the microparticulate formulation comprises an aqueous solution of the at least one therapeutic agent in water-soluble form. According to some embodiments, the microparticulate formulation comprises an oily suspension of the at least one therapeutic agent. Oily suspension of the at least one therapeutic agent can be prepared using suitable lipophilic solvents. Exemplary lipophilic solvents or vehicles include, but are not limited to, fatty oils such as sesame oil, or synthetic fatty acid esters, such as ethyl oleate or triglycerides. According to some embodiments, the microparticulate formulation comprises an aqueous suspension of the at least one therapeutic agent. Aqueous injection suspensions can contain substances which increase the viscosity of the suspension, such as sodium carboxymethyl cellulose, sorbitol, hyaluronic acid, or dextran. Optionally, the suspension can also contain suitable stabilizers or agents which increase the solubility of the compounds to allow for the preparation of highly concentrated solutions. Alternatively, the at least one therapeutic agent can be in powder form for constitution with a suitable vehicle, e.g., sterile pyrogen-free water, before use. The microparticulate formulation is dispersed in a vehicle to form a dispersion, with the microparticles as the dispersed phase, and the vehicle as the dispersion medium.

The microparticulate formulation can include, for example, microencapsulated dosage forms, and if appropriate, with one or more excipients, encochleated, coated onto microscopic gold particles, contained in liposomes, pellets for implantation into the tissue, or dried onto an object to be rubbed into the tissue. As used herein, the term "microencapsulation" refers to a process in which very tiny droplets or particles are surrounded or coated with a continuous film of biocompatible, biodegradable, polymeric or non-polymeric material to produce solid structures including, but not limited to, nonpareils, pellets, crystals, agglomerates, microspheres, or nanoparticles. The microparticulate formulation can be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The microparticulate formulations are suitable for use in a variety of drug delivery systems. For a brief review of methods for drug delivery, see Langer (1990) Science 249, 1527-1533, which is incorporated herein by reference.

Microencapsulation Process

Examples of microencapsulation processes and products; methods for the production of emulsion-based microparticles; emulsion-based microparticles and methods for the production thereof; solvent extraction microencapsulation with tunable extraction rates; a microencapsulation process with solvent and salt; a continuous double emulsion process for making microparticles; drying methods for tuning microparticle properties, controlled release systems from polymer blends; polymer mixtures comprising polymers having different non-repeating units and methods for making and using the same; and an emulsion based process for preparing microparticles and workhead assembly for use with same, are disclosed and described in U.S. Pat. No. 5,407,609 (entitled Microencapsulation Process and Products Thereof), U.S. application Ser. No. 10/553,003 (entitled Method for the production of emulsion-based microparticles), U.S. application Ser. No. 11/799,700 (entitled Emulsion-based microparticles and methods for the production thereof), U.S. application Ser. No. 12/557,946 (entitled Solvent Extraction Microencapsulation With Tunable Extraction Rates), U.S. application Ser. No. 12/779,138 (entitled Hyaluronic Acid (HA) Injection Vehicle), U.S. application Ser. No. 12/562,455 entitled Microencapsulation Process With Solvent And Salt), U.S. application Ser. No. 12/338,488 (entitled Process For Preparing Microparticles Having A Low Residual Solvent Volume); U.S. application Ser. No. 12/692,027 (entitled Controlled Release Systems From Polymer Blends); U.S. application Ser. No. 12/692,020 (entitled Polymer Mixtures Comprising Polymers Having Different Non-Repeating Units And Methods For Making And Using Same); U.S. application Ser. No. 10/565,401 (entitled "Controlled release compositions"); U.S. application Ser. No. 12/692,029 (entitled "Drying Methods for Tuning Microparticle Properties); U.S. application Ser. No. 12/968,708 (entitled "Emulsion Based Process for Preparing Microparticles and Workhead for Use with Same); and U.S. application Ser. No. 13/074,542 (entitled Composition and Methods for Improved Retention of a Pharmaceutical Composition at a Local Administration Site") The content of each of these are incorporated herein by reference in its entirety.

According to some embodiments, delivery of the at least one therapeutic agent using microparticle technology involves bioresorbable, polymeric particles that encapsulate the at least one therapeutic agent and at least one additional therapeutic agent.

Microparticle Polymer Matrix

According to one embodiment, the microparticles comprise a matrix. According to some embodiments, the at least one therapeutic agent is impregnated in or on a naturally occurring biopolymer matrix, a synthetic polymer matrix, or a combination thereof. According to one embodiment, the microparticulate composition comprises a polymer matrix, wherein the at least one therapeutic agent is impregnated in the polymer matrix. According to one embodiment, the polymer is a slow release compound. According to one embodiment, the polymer is a biodegradable polymer. According to one embodiment, the polymer is poly (D, L-Lactide-co-glycolide). According to another embodiment, the polymer is poly(orthoester). According to another embodiment, the polymer is poly(anhydride). According to another embodiment, the polymer is polylactide-polyglycolide.

Both non-biodegradable and biodegradable polymeric materials can be used in the manufacture of particles for delivering the therapeutic agents. Such polymers can be natural or synthetic polymers. The polymer is selected based on the period of time over which release is desired. Bioadhesive polymers of particular interest include, but are not limited to, bioerodible hydrogels as described by Sawhney et al in Macromolecules (1993) 26, 581-587, the teachings of which are incorporated herein. Exemplary bioerodible hydrogels include, but are not limited to, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly (lauryl methacrylate), poly(phenyl methacrylate), poly(methyl acrylate), poly(isopropyl acrylate), poly(isobutyl acrylate), and poly(octadecyl acrylate). According to one embodiment, the bioadhesive polymer is hyaluronic acid. In some such embodiments, the bioadhesive polymer include less than about 2.3% of hyaluronic acid.

According to another embodiment, the polymer enhances aqueous solubility of the microparticulate formulation. Examples of suitable polymers include but are not limited to polyethylene glycol, poly-(d-glutamic acid), poly-(1-glutamic acid), poly-(1-glutamic acid), poly-(d-aspartic acid), poly-(1-aspartic acid), poly-(1-aspartic acid) and copolymers thereof. Polyglutamic acids having molecular weights between about 5,000 to about 100,000, with molecular weights between about 20,000 and about 80,000 may be used and with molecular weights between about 30,000 and about 60,000 may also be used. The polymer is conjugated via an ester linkage to one or more hydroxyls of an inventive epothilone using a protocol as essentially described by U.S. Pat. No. 5,977,163 which is incorporated herein by reference. Particular conjugation sites include the hydroxyl off carbon-21 in the case of 21-hydroxy-derivatives of the present invention. Other conjugation sites include, but are not limited, to the hydroxyl off carbon 3 and/or the hydroxyl off carbon 7.

According to some embodiments, the at least one therapeutic agent is impregnated in or on a polyglycolide (PGA) matrix. PGA is a linear aliphatic polyester developed for use in sutures. Studies have reported PGA copolymers formed with trimethylene carbonate, polylactic acid (PLA), and polycaprolactone. Some of these copolymers may be formulated as microparticles for sustained drug release.

According to some embodiments, the at least one therapeutic agent is impregnated in or on a polyester-polyethylene glycol matrix. Polyester-polyethylene glycol compounds can be synthesized; these are soft and may be used for drug delivery.

According to some embodiments, the at least one therapeutic agent is impregnated in or on a poly (amino)-derived biopolymer matrix. Poly (amino)-derived biopolymers can include, but are not limited to, those containing lactic acid and lysine as the aliphatic diamine (see, for example, U.S. Pat. No. 5,399,665), and tyrosine-derived polycarbonates and polyacrylates. Modifications of polycarbonates may alter the length of the alkyl chain of the ester (ethyl to octyl), while modifications of polyarylates may further include altering the length of the alkyl chain of the diacid (for example, succinic to sebasic), which allows for a large permutation of polymers and great flexibility in polymer properties.

According to some embodiments, the at least one therapeutic agent is impregnated in or on a polyanhydride matrix.

Polyanhydrides are prepared by the dehydration of two diacid molecules by melt polymerization (see, for example, U.S. Pat. No. 4,757,128). These polymers degrade by surface erosion (as compared to polyesters that degrade by bulk erosion). The release of the drug can be controlled by the hydrophilicity of the monomers chosen.

According to some embodiments, the at least one therapeutic agent is impregnated in or on a photopolymerizable biopolymer matrix. Photopolymerizable biopolymers include, but are not limited to, lactic acid/polyethylene glycol/acrylate copolymers.

According to some embodiments, the at least one therapeutic agent is impregnated in or on a hydrogel matrix. The term "hydrogel" refers to a substance resulting in a solid, semisolid, pseudoplastic or plastic structure containing a necessary aqueous component to produce a gelatinous or jelly-like mass. Hydrogels generally comprise a variety of polymers, including hydrophilic polymers, acrylic acid, acrylamide and 2-hydroxyethylmethacrylate (HEMA).

According to some embodiments, the at least one therapeutic agent is impregnated in or on a naturally-occurring biopolymer matrix. Naturally-occurring biopolymers include, but are not limited to, protein polymers, collagen, polysaccharides, and photopolymerizable compounds.

According to some embodiments, the at least one therapeutic agent is impregnated in or on a protein polymer matrix. Protein polymers have been synthesized from self-assembling protein polymers such as, for example, silk fibroin, elastin, collagen, and combinations thereof.

According to some embodiments, the at least one therapeutic agent is impregnated in or on a naturally-occurring polysaccharide matrix. Naturally-occurring polysaccharides include, but are not limited to, chitin and its derivatives, hyaluronic acid, dextran and cellulosics (which generally are not biodegradable without modification), and sucrose acetate isobutyrate (SAIB).

According to some embodiments, the at least one therapeutic agent is impregnated in or on a chitin matrix. Chitin is composed predominantly of 2-acetamido-2-deoxy-D-glucose groups and is found in yeasts, fungi and marine invertebrates (shrimp, crustaceous) where it is a principal component of the exoskeleton. Chitin is not water soluble and the deacetylated chitin, chitosan, only is soluble in acidic solutions (such as, for example, acetic acid). Studies have reported chitin derivatives that are water soluble, very high molecular weight (greater than 2 million daltons), viscoelastic, non-toxic, biocompatible and capable of crosslinking with peroxides, gluteraldehyde, glyoxal and other aldehydes and carbodiamides, to form gels.

According to some embodiments, the at least one therapeutic agent is impregnated in or on a hyaluronic acid (HA) matrix. Hyaluronic acid (HA), which is composed of alternating glucuronidic and glucosaminidic bonds and is found in mammalian vitreous humor, extracellular matrix of the brain, synovial fluid, umbilical cords and rooster combs from which it is isolated and purified, also can be produced by fermentation processes.

Pharmaceutically Acceptable Carrier

According to some embodiments, the flowable sustained release microparticulate composition comprises (ii) a pharmaceutically acceptable carrier.

According to one embodiment, the pharmaceutically acceptable carrier is a solid carrier or excipient. According to another embodiment, the pharmaceutically acceptable carrier is a gel-phase carrier or excipient. Examples of carriers or excipients include, but are not limited to, calcium carbonate, calcium phosphate, various monomeric and polymeric sugars (including without limitation hyaluronic acid), starches, cellulose derivatives, gelatin, and polymers. An exemplary carrier can also include saline vehicle, e.g. hydroxylpropyl methyl cellulose (HPMC) in phosphate buffered saline (PBS). According to another embodiment, the pharmaceutically acceptable carrier is a buffer solution. Exemplary buffer solutions can include without limitation a phosphate buffered saline (PBS) solution.

According to some embodiments, the pharmaceutically acceptable carrier imparts stickiness to the composition. According to one embodiment, the pharmaceutically acceptable carrier comprises hyaluronic acid. According to some embodiments, the pharmaceutically acceptable carrier comprises 0% to 5% hyaluronic acid. According to one embodiment, the pharmaceutically acceptable carrier comprises less than 0.05% hyaluronic acid. According to another embodiment, the pharmaceutically acceptable carrier comprises less than 0.1% hyaluronic acid. According to another embodiment, the pharmaceutically acceptable carrier comprises less than 0.2% hyaluronic acid. According to another embodiment, the pharmaceutically acceptable carrier comprises less than 0.3% hyaluronic acid. According to another embodiment, the pharmaceutically acceptable carrier comprises less than 0.4% hyaluronic acid. According to another embodiment, the pharmaceutically acceptable carrier comprises less than 0.5% hyaluronic acid. According to another embodiment, the pharmaceutically acceptable carrier comprises less than 0.6% hyaluronic acid. According to another embodiment, the pharmaceutically acceptable carrier comprises less than 0.7% hyaluronic acid. According to another embodiment, the pharmaceutically acceptable carrier comprises less than 0.8% hyaluronic acid. According to another embodiment, the pharmaceutically acceptable carrier comprises less than 0.9% hyaluronic acid. According to another embodiment, the pharmaceutically acceptable carrier comprises less than 1.0% hyaluronic acid. According to another embodiment, the pharmaceutically acceptable carrier comprises less than 1.1% hyaluronic acid. According to another embodiment, the pharmaceutically acceptable carrier comprises less than 1.2% hyaluronic acid. According to another embodiment, the pharmaceutically acceptable carrier comprises less than 1.3% hyaluronic acid. According to another embodiment, the pharmaceutically acceptable carrier comprises less than 1.4% hyaluronic acid. According to another embodiment, the pharmaceutically acceptable carrier comprises less than 1.5% hyaluronic acid. According to another embodiment, the pharmaceutically acceptable carrier comprises less than 1.6% hyaluronic acid. According to another embodiment, the pharmaceutically acceptable carrier comprises less than 1.7% hyaluronic acid. According to another embodiment, the pharmaceutically acceptable carrier comprises less than 1.8% hyaluronic acid. According to another embodiment, the pharmaceutically acceptable carrier comprises less than 1.9% hyaluronic acid. According to another embodiment, the pharmaceutically acceptable carrier comprises less than 2.0% hyaluronic acid. According to another embodiment, the pharmaceutically acceptable carrier comprises less than 2.1% hyaluronic acid. According to another embodiment, the pharmaceutically acceptable carrier comprises less than 2.2% hyaluronic acid. According to another embodiment, the pharmaceutically acceptable carrier comprises less than 2.3% hyaluronic acid. According to another embodiment, the pharmaceutically acceptable carrier comprises less than 2.4% hyaluronic acid. According to another embodiment, the pharmaceutically acceptable carrier comprises less than 2.5% hyaluronic acid. According to another embodiment, the pharmaceutically acceptable carrier comprises less than 2.6% hyaluronic acid. According to another embodiment, the pharmaceutically acceptable carrier comprises less than 2.7% hyaluronic acid. According to another embodiment, the pharmaceutically acceptable carrier comprises less than 2.8% hyaluronic acid. According to another embodiment, the pharmaceutically acceptable carrier comprises less than 2.9% hyaluronic acid. According to another embodiment, the pharmaceutically acceptable carrier comprises less than 3.0% hyaluronic acid. According to another embodiment, the pharmaceutically acceptable carrier comprises less than 3.5% hyaluronic acid. According to another embodiment, the pharmaceutically acceptable carrier comprises less than 4.0% hyaluronic acid. According to another embodiment, the pharmaceutically acceptable carrier comprises less than 4.5% hyaluronic acid. According to another embodiment, the pharmaceutically acceptable carrier comprises less than 5.0% hyaluronic acid.

In some embodiments, the pharmaceutically acceptable carrier includes, but is not limited to, a gel, slow-release solid or semisolid compound, optionally as a sustained release gel. In some such embodiments, the at least one therapeutic agent is embedded into the pharmaceutically acceptable carrier. In some embodiments, the at least one therapeutic agent is coated on the pharmaceutically acceptable carrier. The coating can be of any desired material, preferably a polymer or mixture of different polymers. Optionally, the polymer can be utilized during the granulation stage to form a matrix with the active ingredient so as to obtain a desired release pattern of the active ingredient. The gel, slow-release solid or semisolid compound is capable of releasing the active agent over a desired period of time. The gel, slow-release solid or semisolid compound can be implanted in a tissue within the parenchyma of human brain, including, but not limited to, in proximity to a blood vessel, such as a cerebral artery.

According to another embodiment, the pharmaceutically acceptable carrier comprises a slow-release solid compound. According to one such embodiment, the at least one therapeutic agent is embedded in the slow-release solid compound or coated on the slow-release solid compound. According to yet another embodiment, the pharmaceutically acceptable carrier comprises a slow-release microparticle containing the at least one therapeutic agent.

According to another embodiment, the pharmaceutically acceptable carrier is a gel compound, such as a biodegradable hydrogel.

Additional Components

According to some embodiments, the flowable sustained release microparticulate composition further comprises a preservative agent. According to some such embodiments, the flowable sustained release microparticulate very composition is presented in a unit dosage form. Exemplary unit dosage forms include, but are not limited to, ampoules or multi-dose containers.

The flowable sustained release microparticulate compositions for parenteral (including but not limited to, subcutaneous, intradermal, intramuscular, intravenous, intraarterial, intrathecal, intraventricular and intraarticular) administration include aqueous and non-aqueous sterile injection solutions that can contain anti-oxidants, buffers, bacteriostats and solutes, which render the formulation isotonic with the blood or CSF of the intended recipient; and aqueous and non-aqueous sterile suspensions, which can include suspending agents and thickening agents.

According to some embodiments, the flowable sustained release microparticulate composition is formulated for parenteral injection, surgical implantation, or a combination thereof. According to some such embodiments, the flowable sustained release microparticulate composition is in the form of a pharmaceutically acceptable sterile aqueous or nonaqueous solution, dispersion, suspension or emulsion or a sterile powder for reconstitution into a sterile injectable solution or dispersion. Examples of suitable aqueous and nonaqueous carriers, diluents, solvents or vehicles include, but are not limited to, water, ethanol, dichloromethane, acetonitrile, ethyl acetate, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Suspensions can further contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

According to some embodiments, the flowable sustained release microparticulate composition is formulated in an injectable depot form. Injectable depot forms are made by forming microencapsulated matrices of the therapeutic agent in a biodegradable polymer. Depending upon the ratio of drug to polymer and the nature of the particular polymer employed, the rate of drug release may be controlled. Such long acting formulations can be formulated with suitable polymeric or hydrophobic materials (for example as an emulsion in an acceptable oil) or ion exchange resins, or as sparingly soluble derivatives, for example, as a sparingly soluble salt. Examples of biodegradable polymers include, but are not limited to, polylactide-polyglycolide, poly(orthoesters) and poly(anhydrides). Depot injectable formulations are also prepared by entrapping the drug in liposomes or microemulsions which are compatible with body tissues.

According to some embodiments, the flowable sustained release microparticulate composition further comprises an adjuvant. Exemplary adjuvants include, but are not limited to, preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. Isotonic agents, for example, sugars, sodium chloride and the like, can also be included. Prolonged absorption of the injectable pharmaceutical form can be brought about by the use of agents delaying absorption, for example, aluminum monostearate and gelatin.

The flowable sustained release microparticulate compositions can be sterilized, for example, by terminal gamma irradiation, filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol, dichloromethane, ethyl acetate, acetonitrile, etc. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono- or diglycerides. In addition, fatty acids such as oleic acid are used in the preparation of injectables.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

III. Methods of Preparing a Flowable Sustained Release Microparticulate Composition In another aspect, the described invention provides a method of preparing a sterile flowable sustained release microparticulate composition comprising:
(a) providing a sterile microparticulate formulation comprising a therapeutic amount of at least one therapeutic agent, wherein the therapeutic amount is effective to reduce a delayed complication of an interruption of a cerebral artery in a subarachnoid space, wherein the microparticulate formulation comprises a plurality of microparticles of uniform size distribution, and wherein the at least one therapeutic agent is dispersed throughout each microparticle;
(b) drawing the sterile microparticulate formulation of step (a) into a sterile first syringe comprising a first syringe barrel, a first syringe plunger and a female luer cap, and removing air trapped within the first syringe;
(c) providing a sterile pharmaceutically acceptable carrier;
(d) drawing the sterile pharmaceutical carrier of step (c) into a sterile second syringe fitted with a male luer cap comprising a second syringe barrel and a second syringe plunger;
(e) replacing the male luer cap in step (c) with a sterile female syringe connector;
(f) connecting the sterile first syringe containing the sterile microparticulate formulation of step (b) with the sterile second syringe containing the sterile pharmaceutically acceptable carrier of step (c) via the female syringe connector of step (d);
(g) pushing the sterile first syringe plunger so that the sterile microparticulate formulation and the sterile pharmaceutical carrier mix in the sterile second syringe barrel;
(h) pushing the sterile second syringe plunger so that the sterile microparticulate formulation and the sterile pharmaceutical carrier mix in the sterile first syringe barrel; and
(i) repeating steps (g) and (i) at least 5-50 times to yield the sterile flowable sustained release microparticulate composition suitable for delivery into a cerebral ventricle.

According to one embodiment, the method of preparing a flowable sustained release microparticulate composition, comprises:
(A) providing a sterile microparticulate formulation comprising at least one therapeutic agent, and a plurality of microparticles of uniform size distribution, wherein the therapeutic agent is dispersed through or on each microparticle, and wherein the microparticulate formulation is prepacked in a first syringe comprising a first syringe barrel, a first syringe plunger and a female luer cap;
(B) removing air trapped within the first syringe;
(C) providing a sterile pharmaceutically acceptable carrier, wherein the sterile pharmaceutically acceptable carrier is prepacked in a second syringe comprising a second syringe barrel, a second syringe plunger, and a male luer cap;
(D) replacing the male luer cap of the second syringe in step (C) with a female syringe connector;
(E) connecting the first syringe containing the sterile microparticulate formulation of step (B) with the second syringe containing the sterile pharmaceutically acceptable carrier of step (C) via the female syringe connector of step (D);
(F) pushing the first syringe plunger so that the sterile microparticulate formulation and the sterile pharmaceutically acceptable carrier mix in the second syringe barrel;
(G) pushing the second syringe plunger so that the sterile microparticulate formulation and the sterile pharmaceutically acceptable carrier mix in the first syringe barrel; and
(H) repeating steps (F) and (G) at least 5-50 times to yield the flowable sustained release microparticulate composition in ready to administer form.

According to one embodiment, the sterile microparticulate formulation can be stored in a frozen state, for e.g. at −20° C. or −80° C. According to another embodiment, the sterile microparticulate formulation can be stored in a refrigerated state, for e.g. at 4° C. According to another embodiment, the sterile microparticulate formulation can be stored at room temperature.

According to one embodiment, the sterile pharmaceutically acceptable carrier can be stored in a frozen state, for e.g. at −20° C. or −80° C. According to another embodiment, the sterile pharmaceutically acceptable carrier can be stored in a refrigerated state, for e.g. at 4° C. According to another embodiment, the sterile pharmaceutically acceptable carrier can be stored at room temperature.

According to one embodiment, the method of preparing a flowable sustained release microparticulate composition comprises (i) repeating steps (g) and (h) at least 5 times to yield the flowable sustained release microparticulate composition in ready to administer form. According to another embodiment, the method of preparing a flowable sustained release microparticulate composition comprises (i) repeating steps (g) and (h) at least 10 times to yield the flowable sustained release microparticulate composition in ready to administer form. According to another embodiment, the method of preparing a flowable sustained release microparticulate composition comprises (i) repeating steps (g) and (h) at least 15 times to yield the flowable sustained release microparticulate composition in ready to administer form. According to another embodiment, the method of preparing a flowable sustained release microparticulate composition comprises (i) repeating steps (g) and (h) at least 20 times to yield the flowable sustained release microparticulate composition in ready to administer form. According to another embodiment, the method of preparing a flowable sustained release microparticulate composition comprises (i) repeating steps (g) and (h) at least 25 times to yield the flowable sustained release microparticulate composition in ready to administer form. According to another embodiment, the method of preparing a flowable sustained release microparticulate composition comprises (i) repeating steps (g) and (h) at least 30 times to yield the flowable sustained release microparticulate composition in ready to administer form. According to another embodiment, the method of preparing a flowable sustained release microparticulate composition comprises (i) repeating steps (g) and (h) at least 35 times to yield the flowable sustained release microparticulate composition in ready to administer form. According to another embodiment, the method of preparing a flowable sustained release microparticulate composition comprises (i) repeating steps (g) and (h) at least 40 times to yield the flowable sustained release microparticulate composition in ready to administer form. According to another embodiment, the method of preparing a flowable sustained release microparticulate composition comprises (i) repeating steps (g) and (h) at least 45 times to yield the flowable sustained release microparticulate composition in ready to administer form. According to another embodiment, the method of preparing a flowable sustained release microparticulate composition comprises (i) repeating steps (g) and (h) at least 50 times to yield the flowable sustained release microparticulate composition in ready to administer form.

According to one embodiment, the method of preparing a flowable sustained release microparticulate composition comprises (H) repeating steps (F) and (G) at least 5 times to yield the flowable sustained release microparticulate composition in ready to administer form. According to another embodiment, the method of preparing a flowable sustained release microparticulate composition comprises (H) repeating steps (F) and (G) at least 10 times to yield the flowable sustained release microparticulate composition in ready to administer form. According to another embodiment, the method of preparing a flowable sustained release microparticulate composition comprises (H) repeating steps (F) and (G) at least 15 times to yield the flowable sustained release microparticulate composition in ready to administer form. According to another embodiment, the method of preparing a flowable sustained release microparticulate composition comprises (H) repeating steps (F) and (G) at least 20 times to yield the flowable sustained release microparticulate composition in ready to administer form. According to another embodiment, the method of preparing a flowable sustained release microparticulate composition comprises (H) repeating steps (F) and (G) at least 25 times to yield the flowable sustained release microparticulate composition in ready to administer form. According to another embodiment, the method of preparing a flowable sustained release microparticulate composition comprises (H) repeating steps (F) and (G) at least 30 times to yield the flowable sustained release microparticulate composition in ready to administer form. According to another embodiment, the method of preparing a flowable sustained release microparticulate composition comprises (H) repeating steps (F) and (G) at least 35 times to yield the flowable sustained release microparticulate composition in ready to administer form. According to another embodiment, the method of preparing a flowable sustained release microparticulate composition comprises (H) repeating steps (F) and (G) at least 40 times to yield the flowable sustained release microparticulate composition in ready to administer form. According to another embodiment, the method of preparing a flowable sustained release microparticulate composition comprises (H) repeating steps (F) and (G) at least 45 times to yield the flowable sustained release microparticulate composition in ready to administer form. According to another embodiment, the method of preparing a flowable sustained release microparticulate composition comprises (H) repeating steps (F) and (G) at least 50 times to yield the flowable sustained release microparticulate composition in ready to administer form.

Therapeutic Agent

According to some embodiments, the at least one therapeutic agent is a calcium channel antagonist, an endothelin antagonist, a transient receptor potential (TRP) protein antagonist, or a combination thereof.

According to one embodiment, the at least one therapeutic agent is a calcium channel antagonist. According to some embodiments, the calcium channel antagonist is selected from the group consisting of an L-type voltage dependent calcium channel inhibitor, an R-type voltage dependent calcium channel inhibitor, an N-type voltage dependent calcium channel inhibitor, a P/Q-type voltage dependent calcium channel inhibitor, a T-type voltage dependent calcium channel inhibitor, or a combination thereof. According to one embodiment, the calcium channel antagonist is an L-type voltage dependent calcium channel inhibitor. According to another embodiment, the calcium channel antagonist is an R-type voltage dependent calcium channel inhibitor. According to another embodiment, the calcium channel antagonist is an N-type voltage dependent calcium channel inhibitor. According to another embodiment, the calcium channel antagonist is a P/Q-type voltage dependent calcium channel inhibitor. According to another embodiment, the calcium channel antagonist is a T-type voltage dependent calcium channel inhibitor.

For example, L-type voltage dependent calcium channel inhibitor include, but are not limited to: dihydropyridine L-type antagonists such as nisoldipine, nicardipine and nifedipine, AHF (such as 4aR,9aS)-(+)-4a-Amino-1,2,3,4,4a,9a-hexahydro-4aH-fluorene, HCl), isradipine (such as 4-(4-Benzofurazanyl)-1,-4-dihydro-2,6-dimethyl-3,5-pyridinedicarboxylic acid methyl 1-methhylethyl ester), calciseptine (such as isolated from (Dendroaspis polylepis ploylepis), H-Arg-Ile-Cys-Tyr-Ile-His-Lys-Ala-Ser-Leu-Pro-Arg-Ala-Thr-Lys-Thr-Cys-Val-Glu-Asn-Thr-Cys-Tyr-Lys-Met-Phe-Ile-Arg-Thr-Gln-Arg-Glu-Tyr-Ile-Ser-Glu-Arg-Gly-Cys-Gly-Cys-Pro-Thr-Ala- Met-Trp-Pro-Tyr-Gln-Thr-Glu-Cys-Cys-Lys-Gly-Asp-Arg-Cys-Asn-Lys-OH, Calcicludine (such as isolated from Dendroaspis angusticeps (eastern green mamba)), (H-Trp-Gln-Pro-Pro-Trp-Tyr-Cys-Lys-Glu-Pro-Val-Arg-Ile-Gly-Ser-Cys-Lys-Lys-Gln-Phe-Ser-Ser-Phe-Tyr-Phe-Lys-Trp-Thr-Ala-Lys-Lys-Cys-Leu-Pro-Phe-Leu-Phe-Ser-Gly-Cys-Gly-Gly-Asn-Ala- Asn-Arg-Phe-Gln-Thr-Ile-Gly-Glu-Cys-Arg-Lys-Lys-Cys-Leu-Gly-Lys-OH, Cilnidipine (such as also FRP-8653, a dihydropyridine-type inhibitor), Dilantizem (such as (2S, 3S)-(+)-cis-3-Acetoxy-5-(2-dimethylaminoethyl)-2,3-dihydro-2-(4-methoxyphenyl)-1,5-benzothiazepin-4(5H)-one hydrochloride), diltiazem (such as benzothiazepin-4(5H)-one, 3-(acetyloxy)-5-[2-(dimethylamino)ethyl]-2,3-dihydro-2-(4-methoxyphenyl)-,(+)-cis-,monohydrochloride), Felodipine (such as 4-(2,3-Dichlorophenyl)-1,4-dihydro-2,6-dimethyl-3,5-pyridinecarboxylic acid ethyl methyl ester), FS-2 (such as an isolate from Dendroaspis polylepis polylepis venom), FTX-3.3 (such as an isolate from Agelenopsis aperta), Neomycin sulfate (such as $C_{23}H_{46}N_6O_{13}.3H_2SO_4$), Nicardipine (such as 1,4-Dihydro-2,6-dimethyl-4-(3-nitrophenyl)methyl-2-[methyl(phenylmethypa-mino]-3,5-pyridinedicarboxylic acid ethyl ester hydrochloride, also YC-93, Nifedipine (such as 1,4-Dihydro-2,6-dimethyl-4-(2-nitrophenyl)-3,5-pyridinedicarboxylic acid dimethyl ester), Nimodipine (such as 4-Dihydro-2,6-dimethyl-4-(3-nitrophenyl)-3,5-pyridinedicarboxylic acid 2-methoxyethyl 1-methylethyl ester) or (Isopropyl 2-methoxyethyl 1,4-dihydro-2,6-dimethyl-4-(m-nitrophenyl)-3,5-pyridinedicarboxylate), Nitrendipine (such as 1,4-Dihydro-2,6-dimethyl-4-(3-nitrophenyl)-3,5-pyridinedicarboxylic acid ethyl methyl ester), S-Petasin (such as (3S,4aR,5R,6R)-[2,3,4,4a,5,6,7,8-Octahydro-3-(2-propenyl)-4a,5-dimethyl-2-O-xo-6-naphthyl] Z-3'-methylthio-1'-propenoate), Phloretin (such as 2',4',6'-Trihydroxy-3-(4-hydroxyphenyl)propiophenone, also 3-(4-Hydroxyphenyl)-1-(2,4,6-trihydroxyphenyl)-1-propanone, also b-(4-Hydroxyphenyl)-2,4,6-trihydroxypropiophenone), Protopine (such as $C_{20}H_{19}NO_5Cl$), SKF-96365 (such as 1-[b-[3-(4-Methoxyphenyl)propoxy]-4-methoxyphenethyl]-1H-imidazole, HCl), Tetrandine (such as 6,6',7,12-Tetramethoxy-2,2'-dimethylberbaman), (.+-.)-Methoxyverapamil or (+)-Verapamil (such as 54N-(3,4-Dimethoxyphenylethyl)methylamino]-2-(3,4- dimethoxyphenyl)-2-iso-propylvaleronitrile hydrochloride), and (R)-(+)-Bay K8644 (such as R-(+)-1,4-Dihydro-2,6-dimethyl-5-nitro-442-(trifluoromethyl)phenyl]-3-pyridinecarboxylic acid methyl ester). The foregoing examples may be specific to L-type voltage-gated calcium channels or may inhibit a broader range of voltage-gated calcium channels, e.g. N, P/Q, R, and T-type.

According to some embodiments, the L-type voltage dependent calcium channel inhibitor is a dihydropyridine. Exemplary dihydropyridines include, but are not limited to, amlodipine, aranidipine, azelnidipine, bamidipine, benidipine, cinaldipine, efonidipine, felodipine, isradipine, lacidipine, lemildipine, lercanidipine, nicardipine, nifedipine, nilvadipine, nimodipine, nisoldipine, nitrendipine, manidipine, pranidipine, etc. According to one embodiment, the dihydropyridine is nimodipine. According to one embodiment, the nimodipine has a half life of 7-10 days when formulated as described herein, and appropriate lipid solubility.

According to some embodiments, the L-type voltage dependent calcium channel inhibitor is a phenylalkylamine. Exemplary phenylalkylamines include, but are not limited to, gallopamil, verapamil, etc. According to some embodiments, the L-type voltage dependent calcium channel inhibitor is a 1-4 benzothiazepine. According to one embodiment, the 1-4 benzothiazepine is diltiazem. According to one embodiment, the L-type voltage dependent calcium channel inhibitor is bepridil.

According to another embodiment, the at least one therapeutic agent is an endothelin antagonist. Exemplary endothelin antagonists include, but are not limited to, A-127722, ABT-627, BMS 182874, BQ-123, BQ-153, BQ-162, BQ-485, BQ-518, BQ-610, EMD-122946, FR 139317, IPI-725, L-744453, LU 127043, LU 135252, PABSA, PD 147953, PD 151242, PD 155080, PD 156707, RO 611790, SB-247083, clazosentan, atrasentan, sitaxsentan sodium, TA-0201, TBC 11251, TTA-386, WS-7338B, ZD-1611, aspirin, A-182086, CGS 27830, CP 170687, J-104132, L-751281, L-754142, LU 224332, LU 302872, PD 142893, PD 145065, PD 160672, RO-470203, bosentan, RO 462005, RO 470203, SB 209670, SB 217242, TAK-044, A-192621, A-308165, BQ-788, BQ-017, IRL 1038, IRL 2500, PD-161721, RES 701-1, RO 468443, etc.

According to another embodiment, the at least one therapeutic agent is a transient receptor potential (TRP) protein antagonist. Exemplary transient receptor potential (TRP) protein antagonists include, but are not limited to, gadolinium chloride, lanthanum chloride, SKF 96365 (1-(beta-[3-(4-methoxy-phenyl)propoxy]-4-methoxyphenethyl)-1H-imidazole hydrochloride), and LOE 908 ((RS)-(3,4-dihydro-6,7-dimethoxyisoquinoline-1-gamma 1)-2-phenyl-N,N-di-[2-(2,3,4-trimethoxyphenyl)ethyl]acetamide).

According to some embodiments, the at least one therapeutic agent is an isolated molecule. According to some embodiments, the at least one therapeutic agent is substantially pure.

Microparticulate Formulation

According to one embodiment, the flowable sustained release microparticulate composition comprises a plurality of microparticles comprising at least one therapeutic agent.

According to some embodiments, the at least one therapeutic agent is provided in the form of a microparticle. According to another embodiment, the least one therapeutic agent is disposed on or in the microparticle. According to one embodiment, the at least one therapeutic agent is dispersed throughout each microparticle. According to some embodiments, the at least one therapeutic agent is impregnated on the surface of each microparticle. According to another embodiment, the at least one therapeutic agent is contained within the core of the microparticle surrounded by a coating. According to another embodiment, the least one therapeutic agent is adsorbed into each microparticle.

According to some such embodiments, the microparticles are of uniform size distribution. According to some embodiments, the uniform distribution of microparticle size is achieved by a homogenization process to form a uniform emulsion comprising microparticles. According to some such embodiments, each microparticle comprises a matrix. According to some embodiments, the matrix comprises the least one therapeutic agent.

According to some embodiments, the microparticle can be of any order release kinetics, including a zero order release, first order release, second order release, delayed release, sustained release, immediate release, and a combination thereof. The microparticle can include, in addition to therapeutic agent(s), any of those materials routinely used in the art of pharmacy and medicine, including, but not limited to, erodible, nonerodible, biodegradable, or nonbiodegradable material or combinations thereof According to some embodiments, the microparticle is a microcapsule that contains the least one therapeutic agent in a solution or in a semi-solid state. According to some embodiments, the microparticle contains the least one therapeutic agent, in whole or in part. According to some embodiments, the microparticle is a nanoparticle that contains the least one therapeutic agent, in whole or in part. According to some embodiments, the microparticles can be of virtually any shape.

According to some embodiments, each microparticle is loaded with at least 40% by weight to at least 80% by weight of the at least one therapeutic agent. According to one embodiment, each microparticle is loaded with at least 40% by weight of the at least one therapeutic agent. According to another embodiment, each microparticle is loaded with at least 45% by weight of the at least one therapeutic agent. According to another embodiment, each microparticle is loaded with at least 50% by weight of the at least one therapeutic agent. According to another embodiment, each microparticle is loaded with at least 55% by weight of the at least one therapeutic agent. According to another embodiment, each microparticle is loaded with at least 60% by weight of the at least one therapeutic agent. According to another embodiment, each microparticle is loaded with at least 63% by weight of the at least one therapeutic agent. According to another embodiment, each microparticle is loaded with at least 65% by weight of the at least one therapeutic agent. According to another embodiment, each microparticle is loaded with at least 70% by weight of the at least one therapeutic agent. According to another embodiment, each microparticle is loaded with at least 75% by weight of the at least one therapeutic agent. According to another embodiment, each microparticle is loaded with at least 80% by weight of the at least one therapeutic agent.

According to some embodiments, the particle size is between about 25 μm to about 100 μm. According to some embodiments, the particle size is between about 30 μm to about 80 μm. According to one embodiment, the particle size is at least about 25 μm. According to another embodiment, the particle size is at least about 30 μm. According to another embodiment, the particle size is at least about 35 μm. According to another embodiment, the particle size is at least about 40 μm. According to another embodiment, the particle size is at least about 45 μm. According to another embodiment, the particle size is at least about 50 μm. According to another embodiment, the particle size is at least about 55 μm. According to another embodiment, the particle size is at least about 60 μm. According to another embodiment, the particle size is at least about 65 μm. According to another embodiment, the particle size is at least about 70 μm. According to another embodiment, the particle size is at least about 75 μm. According to another embodiment, the particle size is at least about 80 μm. According to another embodiment, the particle size is at least about 85 μm. According to another embodiment, the particle size is at least about 90 μm. According to another embodiment, the particle size is at least about 95 μm. According to another embodiment, the particle size is at least about 100 μm.

According to another embodiment, the at least one therapeutic agent can be provided in strings. The strings can contain the at least one therapeutic agent in a core surrounded by a coating, or the at least one therapeutic agent can be dispersed throughout the string, or the at least one therapeutic agent can be absorbed into the string. The string can be of any order release kinetics, including zero order release, first order release, second order release, delayed release, sustained release, immediate release, etc., and any combination thereof. The string can include, in addition to therapeutic agent(s), any of those materials routinely used in the art of pharmacy and medicine, including, but not limited to, erodible, nonerodible, biodegradable, or nonbiodegradable material or combinations thereof.

According to another embodiment, the at least one therapeutic agent can be provided in at least one sheet. The sheet can contain the at least one therapeutic agent and at least one additional therapeutic agent in a core surrounded by a coating, or the at least one therapeutic agent and at least one additional therapeutic agent can be dispersed throughout the sheet, or the at least one therapeutic agent can be absorbed into the sheet. The sheet can be of any order release kinetics, including zero order release, first order release, second order release, delayed release, sustained release, immediate release, etc., and any combination thereof. The sheet can include, in addition to the at least one therapeutic agent and at least one additional therapeutic agent, any of those materials routinely used in the art of pharmacy and medicine, including, but not limited to, erodible, nonerodible, biodegradable, or nonbiodegradable material or combinations thereof.

According to some embodiments, the microparticulate formulation comprises a suspension of microparticles. According to one embodiment, the microparticulate formulation comprises a powder suspension of microparticles. According to some embodiments, the microparticulate formulation further comprises at least one of a suspending agent, a stabilizing agent and a dispersing agent. According to some such embodiments, the microparticulate formulation is presented as a suspension. According to some such embodiments, the microparticulate formulation is presented as a solution. According to some such embodiments, the microparticulate formulation is presented as an emulsion.

According to some embodiments, the microparticulate formulation comprises an aqueous solution of the at least one therapeutic agent in water-soluble form. According to some embodiments, the microparticulate formulation comprises an oily suspension of the at least one therapeutic agent. Oily suspension of the at least one therapeutic agent can be prepared using suitable lipophilic solvents. Exemplary lipophilic solvents or vehicles include, but are not limited to, fatty oils such as sesame oil, or synthetic fatty acid esters, such as ethyl oleate or triglycerides. According to some embodiments, the microparticulate formulation comprises an aqueous suspension of the at least one therapeutic agent. Aqueous injection suspensions can contain substances which increase the viscosity of the suspension, such as sodium carboxymethyl cellulose, sorbitol, hyaluronic acid, or dextran. Optionally, the suspension can also contain suitable stabilizers or agents which increase the solubility of the compounds to allow for the preparation of highly concentrated solutions. Alternatively, the at least one therapeutic agent can be in powder form for constitution with a suitable vehicle, e.g., sterile pyrogen-free water, before use. The microparticulate formulation is dispersed in a vehicle to form a dispersion, with the microparticles as the dispersed phase, and the vehicle as the dispersion medium.

The microparticulate formulation can include, for example, microencapsulated dosage forms, and if appropriate, with one or more excipients, encochleated, coated onto microscopic gold particles, contained in liposomes, pellets for implantation into the tissue, or dried onto an object to be rubbed into the tissue. As used herein, the term "microencapsulation" refers to a process in which very tiny droplets or particles are surrounded or coated with a continuous film of biocompatible, biodegradable, polymeric or non-polymeric material to produce solid structures including, but not limited to, nonpareils, pellets, crystals, agglomerates, microspheres, or nanoparticles. The microparticulate formulation can be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The microparticulate formulations are suitable for use in a variety of drug delivery systems. For a brief review of methods for drug delivery, see Langer (1990) Science 249, 1527-1533, which is incorporated herein by reference.

Microencapsulation Process

Examples of microencapsulation processes and products; methods for the production of emulsion-based microparticles; emulsion-based microparticles and methods for the production thereof; solvent extraction microencapsulation with tunable extraction rates; a microencapsulation process with solvent and salt; a continuous double emulsion process for making microparticles; drying methods for tuning microparticle properties, controlled release systems from polymer blends; polymer mixtures comprising polymers having different non-repeating units and methods for making and using the same; and an emulsion based process for preparing microparticles and workhead assembly for use with same, are disclosed and described in U.S. Pat. No. 5,407,609 (entitled Microencapsulation Process and Products Thereof), U.S. application Ser. No. 10/553,003 (entitled Method for the production of emulsion-based microparticles), U.S. application Ser. No. 11/799,700 (entitled Emulsion-based microparticles and methods for the production thereof), U.S. application Ser. No. 12/557,946 (entitled Solvent Extraction Microencapsulation With Tunable Extraction Rates), U.S. application Ser. No. 12/779,138 (entitled Hyaluronic Acid (HA) Injection Vehicle), U.S. application Ser. No. 12/562,455 entitled Microencapsulation Process With Solvent And Salt), U.S. application Ser. No. 12/338,488 (entitled Process For Preparing Microparticles Having A Low Residual Solvent Volume); U.S. application Ser. No. 12/692,027 (entitled Controlled Release Systems From Polymer Blends); U.S. application Ser. No. 12/692,020 (entitled Polymer Mixtures Comprising Polymers Having Different Non-Repeating Units And Methods For Making And Using Same); U.S. application Ser. No. 10/565,401 (entitled "Controlled release compositions"); U.S. application Ser. No. 12/692,029 (entitled "Drying Methods for Tuning Microparticle Properties); U.S. application Ser. No. 12/968,708 (entitled "Emulsion Based Process for Preparing Microparticles and Workhead for Use with Same); and U.S. application Ser. No. 13/074,542 (entitled Composition and Methods for Improved Retention of a Pharmaceutical Composition at a Local Administration Site") The content of each of these are incorporated herein by reference in its entirety.

According to some embodiments, delivery of the at least one therapeutic agent using microparticle technology involves bioresorbable, polymeric particles that encapsulate the at least one therapeutic agent and at least one additional therapeutic agent.

Microparticle Polymer Matrix

According to one embodiment, the microparticles comprise a matrix. According to some embodiments, the at least one therapeutic agent is impregnated in or on a naturally occurring biopolymer matrix, a synthetic polymer matrix, or a combination thereof. According to one embodiment, the microparticulate formulation comprises a polymer matrix, wherein the at least one therapeutic agent is impregnated in the polymer matrix. According to one embodiment, the polymer is a slow release compound. According to one embodiment, the polymer is a biodegradable polymer. According to one embodiment, the polymer is poly (D, L-Lactide-co-glycolide). According to another embodiment, the polymer is poly(orthoester). According to another embodiment, the polymer is poly(anhydride). According to another embodiment, the polymer is polylactide-polyglycolide.

Both non-biodegradable and biodegradable polymeric materials can be used in the manufacture of particles for delivering the therapeutic agents. Such polymers can be natural or synthetic polymers. The polymer is selected based on the period of time over which release is desired. Bioadhesive polymers of particular interest include, but are not limited to, bioerodible hydrogels as described by Sawhney et al in Macromolecules (1993) 26, 581-587, the teachings of which are incorporated herein. Exemplary bioerodible hydrogels include, but are not limited to, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate). According to one embodiment, the bioadhesive polymer is hyaluronic acid. In some such embodiments, the bioadhesive polymer include less than about 2.3% of hyaluronic acid.

According to another embodiment, the polymer enhances aqueous solubility of the microparticulate formulation. Examples of suitable polymers include but are not limited to polyethylene glycol, poly-(d-glutamic acid), poly-(1-glutamic acid), poly-(1-glutamic acid), poly-(d-aspartic acid), poly-(1-aspartic acid), poly-(1-aspartic acid) and copolymers thereof. Polyglutamic acids having molecular weights between about 5,000 to about 100,000, with molecular weights between about 20,000 and about 80,000 may be used and with molecular weights between about 30,000 and about 60,000 may also be used. The polymer is conjugated via an ester linkage to one or more hydroxyls of an inventive epothilone using a protocol as essentially described by U.S. Pat. No. 5,977,163 which is incorporated herein by reference. Particular conjugation sites include the hydroxyl off carbon-21 in the case of 21-hydroxy-derivatives of the present invention. Other conjugation sites include, but are not limited to, the hydroxyl off carbon 3 and/or the hydroxyl off carbon 7.

According to some embodiments, the at least one therapeutic agent is impregnated in or on a polyglycolide (PGA) matrix. PGA is a linear aliphatic polyester developed for use in sutures. Studies have reported PGA copolymers formed with trimethylene carbonate, polylactic acid (PLA), and polycaprolactone. Some of these copolymers may be formulated as microparticles for sustained drug release.

According to some embodiments, the at least one therapeutic agent is impregnated in or on a polyester-polyethylene glycol matrix. Polyester-polyethylene glycol compounds can be synthesized; these are soft and may be used for drug delivery.

According to some embodiments, the at least one therapeutic agent is impregnated in or on a poly (amino)-derived biopolymer matrix. Poly (amino)-derived biopolymers can include, but are not limited to, those containing lactic acid and lysine as the aliphatic diamine (see, for example, U.S. Pat. No. 5,399,665), and tyrosine-derived polycarbonates and polyacrylates. Modifications of polycarbonates may alter the length of the alkyl chain of the ester (ethyl to octyl), while modifications of polyarylates may further include altering the length of the alkyl chain of the diacid (for example, succinic to sebasic), which allows for a large permutation of polymers and great flexibility in polymer properties.

According to some embodiments, the at least one therapeutic agent is impregnated in or on a polyanhydride matrix. Polyanhydrides are prepared by the dehydration of two diacid molecules by melt polymerization (see, for example, U.S. Pat. No. 4,757,128). These polymers degrade by surface erosion (as compared to polyesters that degrade by bulk erosion). The release of the drug can be controlled by the hydrophilicity of the monomers chosen.

According to some embodiments, the at least one therapeutic agent is impregnated in or on a photopolymerizable biopolymer matrix. Photopolymerizable biopolymers include, but are not limited to, lactic acid/polyethylene glycol/acrylate copolymers.

According to some embodiments, the at least one therapeutic agent is impregnated in or on a hydrogel matrix. The term "hydrogel" refers to a substance resulting in a solid, semisolid, pseudoplastic or plastic structure containing a necessary aqueous component to produce a gelatinous or jelly-like mass. Hydrogels generally comprise a variety of polymers, including hydrophilic polymers, acrylic acid, acrylamide and 2-hydroxyethylmethacrylate (HEMA).

According to some embodiments, the at least one therapeutic agent is impregnated in or on a naturally-occurring biopolymer matrix. Naturally-occurring biopolymers include, but are not limited to, protein polymers, collagen, polysaccharides, and photopolymerizable compounds.

According to some embodiments, the at least one therapeutic agent is impregnated in or on a protein polymer matrix. Protein polymers have been synthesized from self-assembling protein polymers such as, for example, silk fibroin, elastin, collagen, and combinations thereof.

According to some embodiments, the at least one therapeutic agent is impregnated in or on a naturally-occurring polysaccharide matrix. Naturally-occurring polysaccharides include, but are not limited to, chitin and its derivatives, hyaluronic acid, dextran and cellulosics (which generally are not biodegradable without modification), and sucrose acetate isobutyrate (SAIB).

According to some embodiments, the at least one therapeutic agent is impregnated in or on a chitin matrix. Chitin is composed predominantly of 2-acetamido-2-deoxy-D-glucose groups and is found in yeasts, fungi and marine invertebrates (shrimp, crustaceous) where it is a principal component of the exoskeleton. Chitin is not water soluble and the deacetylated chitin, chitosan, only is soluble in acidic solutions (such as, for example, acetic acid). Studies have reported chitin derivatives that are water soluble, very high molecular weight (greater than 2 million daltons), viscoelastic, non-toxic, biocompatible and capable of crosslinking with peroxides, gluteraldehyde, glyoxal and other aldehydes and carbodiamides, to form gels.

According to some embodiments, the at least one therapeutic agent is impregnated in or on a hyaluronic acid (HA) matrix. Hyaluronic acid (HA), which is composed of alternating glucuronidic and glucosaminidic bonds and is found in mammalian vitreous humor, extracellular matrix of the brain, synovial fluid, umbilical cords and rooster combs from which it is isolated and purified, also can be produced by fermentation processes.

Pharmaceutically Acceptable Carrier

According to some embodiments, the flowable sustained release microparticulate composition comprises (ii) a pharmaceutically acceptable carrier.

According to one embodiment, the pharmaceutically acceptable carrier is a solid carrier or excipient. According to another embodiment, the pharmaceutically acceptable carrier is a gel-phase carrier or excipient. Examples of carriers or excipients include, but are not limited to, calcium carbonate, calcium phosphate, various monomeric and polymeric sugars (including without limitation hyaluronic acid), starches, cellulose derivatives, gelatin, and polymers. An exemplary carrier can also include saline vehicle, e.g. hydroxylpropyl methyl cellulose (HPMC) in phosphate buffered saline (PBS). According to another embodiment, the pharmaceutically acceptable carrier is a buffer solution. Exemplary buffer solutions can include without limitation a phosphate buffered saline (PBS) solution.

According to some embodiments, the pharmaceutically acceptable carrier imparts stickiness to the composition. According to one embodiment, the pharmaceutically acceptable carrier comprises hyaluronic acid. According to some embodiments, the pharmaceutically acceptable carrier comprises 0% to 5% hyaluronic acid. According to one embodiment, the pharmaceutically acceptable carrier comprises less than 0.05% hyaluronic acid. According to another embodiment, the pharmaceutically acceptable carrier comprises less than 0.1% hyaluronic acid. According to another embodiment, the pharmaceutically acceptable carrier comprises less than 0.2% hyaluronic acid. According to another embodiment, the pharmaceutically acceptable carrier comprises less than 0.3% hyaluronic acid. According to another embodiment, the pharmaceutically acceptable carrier comprises less than 0.4% hyaluronic acid. According to another embodiment, the pharmaceutically acceptable carrier comprises less than 0.5% hyaluronic acid. According to another embodiment, the pharmaceutically acceptable carrier comprises less than 0.6% hyaluronic acid. According to another embodiment, the pharmaceutically acceptable carrier comprises less than 0.7% hyaluronic acid. According to another embodiment, the pharmaceutically acceptable carrier comprises less than 0.8% hyaluronic acid. According to another embodiment, the pharmaceutically acceptable carrier comprises less than 0.9% hyaluronic acid. According to another embodiment, the pharmaceutically acceptable carrier comprises less than 1.0% hyaluronic acid. According to another embodiment, the pharmaceutically acceptable carrier comprises less than 1.1% hyaluronic acid. According to another embodiment, the pharmaceutically acceptable carrier comprises less than 1.2% hyaluronic acid. According to another embodiment, the pharmaceutically acceptable carrier comprises less than 1.3% hyaluronic acid. According to another embodiment, the pharmaceutically acceptable carrier comprises less than 1.4% hyaluronic acid. According to another embodiment, the pharmaceutically acceptable carrier comprises less than 1.5% hyaluronic acid. According to another embodiment, the pharmaceutically acceptable carrier comprises less than 1.6% hyaluronic acid. According to another embodiment, the pharmaceutically acceptable carrier comprises less than 1.7% hyaluronic acid. According to another embodiment, the pharmaceutically acceptable carrier comprises less than 1.8% hyaluronic acid. According to another embodiment, the pharmaceutically acceptable carrier comprises less than 1.9% hyaluronic acid. According to another embodiment, the pharmaceutically acceptable carrier comprises less than 2.0% hyaluronic acid. According to another embodiment, the pharmaceutically acceptable carrier comprises less than 2.1% hyaluronic acid. According to another embodiment, the pharmaceutically acceptable carrier comprises less than 2.2% hyaluronic acid. According to another embodiment, the pharmaceutically acceptable carrier comprises less than 2.3% hyaluronic acid. According to another embodiment, the pharmaceutically acceptable carrier comprises less than 2.4% hyaluronic acid. According to another embodiment, the pharmaceutically acceptable carrier comprises less than 2.5% hyaluronic acid. According to another embodiment, the pharmaceutically acceptable carrier comprises less than 2.6% hyaluronic acid. According to another embodiment, the pharmaceutically acceptable carrier comprises less than 2.7% hyaluronic acid. According to another embodiment, the pharmaceutically acceptable carrier comprises less than 2.8% hyaluronic acid. According to another embodiment, the pharmaceutically acceptable carrier comprises less than 2.9% hyaluronic acid. According to another embodiment, the pharmaceutically acceptable carrier comprises less than 3.0% hyaluronic acid. According to another embodiment, the pharmaceutically acceptable carrier comprises less than 3.5% hyaluronic acid. According to another embodiment, the pharmaceutically acceptable carrier comprises less than 4.0% hyaluronic acid. According to another embodiment, the pharmaceutically acceptable carrier comprises less than 4.5% hyaluronic acid. According to another embodiment, the pharmaceutically acceptable carrier comprises less than 5.0% hyaluronic acid.

In some embodiments, the pharmaceutically acceptable carrier includes, but is not limited to, a gel, slow-release solid or semisolid compound, optionally as a sustained release gel. In some such embodiments, the at least one therapeutic agent is embedded into the pharmaceutically acceptable carrier. In some embodiments, the at least one therapeutic agent is coated on the pharmaceutically acceptable carrier. The coating can be of any desired material, preferably a polymer or mixture of different polymers. Optionally, the polymer can be utilized during the granulation stage to form a matrix with the active ingredient so as to obtain a desired release pattern of the active ingredient. The gel, slow-release solid or semisolid compound is capable of releasing the active agent over a desired period of time. The gel, slow-release solid or semisolid compound can be implanted in a tissue within the parenchyma of human brain, including, but not limited to, in proximity to a blood vessel, such as a cerebral artery.

According to another embodiment, the pharmaceutically acceptable carrier comprises a slow-release solid compound. According to one such embodiment, the at least one therapeutic agent is embedded in the slow-release solid compound or coated on the slow-release solid compound. According to yet another embodiment, the pharmaceutically acceptable carrier comprises a slow-release microparticle containing the at least one therapeutic agent.

According to another embodiment, the pharmaceutically acceptable carrier is a gel compound, such as a biodegradable hydrogel.

Additional Components

According to some embodiments, the flowable sustained release microparticulate composition further comprises a preservative agent. According to some such embodiments, the flowable sustained release microparticulate very composition is presented in a unit dosage form. Exemplary unit dosage forms include, but are not limited to, ampoules or multi-dose containers.

The flowable sustained release microparticulate compositions for parenteral (including but not limited to, subcutaneous, intradermal, intramuscular, intravenous, intraarterial, intrathecal, intraventricular and intraarticular) administration include aqueous and non-aqueous sterile injection solutions that can contain anti-oxidants, buffers, bacteriostats and solutes, which render the formulation isotonic with the blood or CSF of the intended recipient; and aqueous and non-aqueous sterile suspensions, which can include suspending agents and thickening agents.

According to some embodiments, the flowable sustained release microparticulate composition is formulated for parenteral injection, surgical implantation, or a combination thereof. According to some such embodiments, the flowable sustained release microparticulate composition is in the form of a pharmaceutically acceptable sterile aqueous or nonaqueous solution, dispersion, suspension or emulsion or a sterile powder for reconstitution into a sterile injectable solution or dispersion. Examples of suitable aqueous and nonaqueous carriers, diluents, solvents or vehicles include, but are not limited to, water, ethanol, dichloromethane, acetonitrile, ethyl acetate, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Suspensions can further contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

According to some embodiments, the flowable sustained release microparticulate composition is formulated in an injectable depot form. Injectable depot forms are made by forming microencapsulated matrices of the therapeutic agent in a biodegradable polymer. Depending upon the ratio of drug to polymer and the nature of the particular polymer employed, the rate of drug release may be controlled. Such long acting formulations can be formulated with suitable polymeric or hydrophobic materials (for example as an emulsion in an acceptable oil) or ion exchange resins, or as sparingly soluble derivatives, for example, as a sparingly soluble salt. Examples of biodegradable polymers include, but are not limited to, polylactide-polyglycolide, poly(orthoesters) and poly(anhydrides). Depot injectable formulations are also prepared by entrapping the drug in liposomes or microemulsions which are compatible with body tissues.

According to some embodiments, the flowable sustained release microparticulate composition further comprises an adjuvant. Exemplary adjuvants include, but are not limited to, preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. Isotonic agents, for example, sugars, sodium chloride and the like, can also be included. Prolonged absorption of the injectable pharmaceutical form can be brought about by the use of agents delaying absorption, for example, aluminum monostearate and gelatin.

The flowable sustained release microparticulate compositions can be sterilized, for example, by terminal gamma irradiation, filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol, dichloromethane, ethyl acetate, acetonitrile, etc. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono- or diglycerides. In addition, fatty acids such as oleic acid are used in the preparation of injectables.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

IV. Kit for Preparing a Flowable Sustained Release Microparticulate Composition

In another aspect, the described invention provides a sterile kit for treating at least one cerebral artery in a subarachnoid space at risk of interruption due to a brain injury comprising:
(i) a sterile surgical injection apparatus;
(ii) a sterile first syringe comprising a barrel, and a plunger;
(iii) a sterile second syringe comprising a barrel and a plunger;
(iv) a sterile female luer cap;
(v) a sterile male luer cap;
(vi) a sterile female syringe connector;
(vii) a sterile microparticulate formulation suitable for administration into a cerebral ventricle comprising a therapeutic amount of at least one therapeutic agent, wherein the therapeutic amount is effective to reduce a delayed complication of an interruption of a cerebral artery in a subarachnoid space,
wherein the microparticulate formulation comprises a plurality of microparticles of uniform size distribution, and wherein the at least one therapeutic agent is dispersed throughout each microparticle, and
(vii) a sterile pharmaceutically acceptable carrier.

According to some embodiments, the surgical injection apparatus is a needle, a cannula, a catheter, or a combination thereof. According to one embodiment, the surgical injection apparatus is a needle. According to another embodiment, the surgical injection apparatus is a cannula. According to another embodiment, the surgical injection apparatus is a catheter. According to some embodiments, the surgical injection apparatus can range from 18 gauge to 10 gauge. According to one embodiment, the surgical injection apparatus is an 18 gauge surgical injection apparatus. According to another embodiment, the surgical injection apparatus is a 17 gauge surgical injection apparatus. According to another embodiment, the surgical injection apparatus is a 16 gauge surgical injection apparatus. According to another embodiment, the surgical injection apparatus is a 15 gauge surgical injection apparatus. According to another embodiment, the surgical injection apparatus is a 14 gauge surgical injection apparatus. According to another embodiment, the surgical injection apparatus is a 13 gauge surgical injection apparatus. According to another embodiment, the surgical injection apparatus is a 12 gauge surgical injection apparatus. According to another embodiment, the surgical injection apparatus is a 11 gauge surgical injection apparatus. According to another embodiment, the surgical injection apparatus is a 10 gauge surgical injection apparatus.

According to some embodiments, each syringe is of between 1 ml to 10 ml volume. According to one embodiment, each syringe is a 1 ml syringe. According to another embodiment, each syringe is a 2 ml syringe. According to another embodiment, each syringe is a 3 ml syringe. According to another embodiment, each syringe is a 4 ml syringe. According to another embodiment, each syringe is a 5 ml syringe. According to another embodiment, each syringe is a 6 ml syringe. According to another embodiment, each syringe is a 7 ml syringe. According to another embodiment, each syringe is a 8 ml syringe. According to another embodiment, each syringe is a 9 ml syringe. According to another embodiment, each syringe is a 10 ml syringe.

According to one embodiment, the kit further comprises at least two sterile biocompatible containers, wherein the microparticulate formulation is stored in the first container and the pharmaceutically acceptable carrier is stored in the second container. According to some embodiments, the container can be a vial, a bottle, a tube, a bag, a packet, a pillow, an ampoule, etc.

According to another embodiment, the sterile microparticulate formulation is prepacked within the sterile first syringe. According to another embodiment, the sterile pharmaceutically acceptable carrier is prepacked within the sterile second syringe.

According to one embodiment, the sterile microparticulate formulation can be stored in a frozen state, for e.g. at −20° C. or −80° C. According to another embodiment, the sterile microparticulate formulation can be stored in a refrigerated state, for e.g. at 4° C. According to another embodiment, the sterile microparticulate formulation can be stored at room temperature.

According to one embodiment, the sterile pharmaceutically acceptable carrier can be stored in a frozen state, for e.g. at −20° C. or −80° C. According to another embodiment, the sterile pharmaceutically acceptable carrier can be stored in a refrigerated state, for e.g. at 4° C. According to another embodiment, the sterile pharmaceutically acceptable carrier can be stored at room temperature.

Therapeutic Agent

According to some embodiments, the at least one therapeutic agent is a calcium channel antagonist, an endothelin antagonist, a transient receptor potential (TRP) protein antagonist, or a combination thereof.

According to one embodiment, the at least one therapeutic agent is a calcium channel antagonist. According to some embodiments, the calcium channel antagonist is selected from the group consisting of an L-type voltage dependent calcium channel inhibitor, an R-type voltage dependent calcium channel inhibitor, an N-type voltage dependent calcium channel inhibitor, a P/Q-type voltage dependent calcium channel inhibitor, a T-type voltage dependent calcium channel inhibitor, or a combination thereof. According to one embodiment, the calcium channel antagonist is an L-type voltage dependent calcium channel inhibitor. According to another embodiment, the calcium channel antagonist is an R-type voltage dependent calcium channel inhibitor. According to another embodiment, the calcium channel antagonist is an N-type voltage dependent calcium channel inhibitor. According to another embodiment, the calcium channel antagonist is a P/Q-type voltage dependent calcium channel inhibitor. According to another embodiment, the calcium channel antagonist is a T-type voltage dependent calcium channel inhibitor.

For example, L-type voltage dependent calcium channel inhibitor include, but are not limited to: dihydropyridine L-type antagonists such as nisoldipine, nicardipine and nifedipine, AHF (such as 4aR,9aS)-(+)-4a-Amino-1,2,3,4,4a,9a-hexahydro-4aH-fluorene, HCl), isradipine (such as 4-(4-Benzofurazanyl)-1,-4-dihydro-2,6-dimethyl-3,5-pyridinedicarboxylic acid methyl 1-methhylethyl ester), calciseptine (such as isolated from (*Dendroaspis polylepis* ploylepis), H-Arg-Ile-Cys-Tyr-Ile-His-Lys-Ala-Ser-Leu-Pro-Arg-Ala-Thr-Lys-Thr-Cys-Val-Glu-Asn-Thr-Cys-Tyr-Lys-Met-Phe-Ile-Arg-Thr-Gln-Arg-Glu-Tyr-Ile-Ser-Glu-Arg-Gly-Cys-Gly-Cys-Pro-Thr-Ala- Met-Trp-Pro-Tyr-Gln-Thr-Glu-Cys-Cys-Lys-Gly-Asp-Arg-Cys-Asn-Lys-OH, Calcicludine (such as isolated from *Dendroaspis angusticeps* (eastern green mamba)), (H-Trp-Gln-Pro-Pro-Trp-Tyr-Cys-Lys-Glu-Pro-Val-Arg-Ile-Gly-Ser-Cys-Lys-Lys-Gln-Phe-Ser-Ser-Phe-Tyr-Phe-Lys-Trp-Thr-Ala-Lys-Lys-Cys-Leu-Pro-Phe-Leu-Phe-Ser-Gly-Cys-Gly-Gly-Asn-Ala- Asn-Arg-Phe-Gln-Thr-Ile-Gly-Glu-Cys-Arg-Lys-Lys-Cys-Leu-Gly-Lys-OH, Cilnidipine (such as also FRP-8653, a dihydropyridine-type inhibitor), Dilantizem (such as (2S, 3S)-(+)-cis-3-Acetoxy-5-(2-dimethylaminoethyl)-2,3-dihydro-2-(4-methoxyphenyl)-1,5-benzothiazepin-4(5H)-one hydrochloride), diltiazem (such as benzothiazepin-4(5H)-one, 3-(acetyloxy)-5-[2-(dimethylamino)ethyl]-2,3-dihydro-2-(4-methoxyphenyl)-,(+)-cis-,monohydrochloride), Felodipine (such as 4-(2,3-Dichlorophenyl)-1,4-dihydro-2,6-dimethyl-3,5-pyridinecarboxylic acid ethyl methyl ester), FS-2 (such as an isolate from *Dendroaspis polylepis* polylepis venom), FTX-3.3 (such as an isolate from *Agelenopsis aperta*), Neomycin sulfate (such as $C_{23}H_{46}N_6O_{13} \cdot 3H_2SO_4$), Nicardipine (such as 1,4-Dihydro-2,6-dimethyl-4-(3-nitrophenyl)methyl-2-[methyl(phenylmethypa-mino]-3,5-pyridinedicarboxylic acid ethyl ester hydrochloride, also YC-93, Nifedipine (such as 1,4-Dihydro-2,6-dimethyl-4-(2-nitrophenyl)-3,5-pyridinedicarboxylic acid dimethyl ester), Nimodipine (such as 4-Dihydro-2,6-dimethyl-4-(3-nitrophenyl)-3,5-pyridinedicarboxylic acid 2-methoxyethyl 1-methylethyl ester) or (Isopropyl 2-methoxyethyl 1,4-dihydro-2,6-dimethyl-4-(m-nitrophenyl)-3,5-pyridinedicarboxylate), Nitrendipine (such as 1,4-Dihydro-2,6-dimethyl-4-(3-nitrophenyl)-3,5-pyridinedicarboxylic acid ethyl methyl ester), S-Petasin (such as (3S,4aR,5R,6R)-[2,3,4,4a,5,6,7,8-Octahydro-3-(2-propenyl)-4a,5-dimethyl-2-O-xo-6-naphthyl] Z-3'-methylthio-1'-propenoate), Phloretin (such as 2',4',6'-Trihydroxy-3-(4-hydroxyphenyl)propiophenone, also 3-(4-Hydroxyphenyl)-1-(2,4,6-trihydroxyphenyl)-1-propanone, also b-(4-Hydroxyphenyl)-2,4,6-trihydroxypropiophenone), Protopine (such as $C_{20}H_{19}NO_5Cl$), SKF-96365 (such as 1-[b-[3-(4-Methoxyphenyl)propoxy]-4-methoxyphenethyl]-1H-imidazole, HCl), Tetrandine (such as 6,6',7,12-Tetramethoxy-2,2'-dimethylberbaman), (.+−.)-Methoxyverapamil or (+)-Verapamil (such as 54N-(3,4-Dimethoxyphenylethyl)methylamino]-2-(3,4-dimethoxyphenyl)-2-iso-propylvaleronitrile hydrochloride), and (R)-(+)-Bay K8644 (such as R-(+)-1,4-Dihydro-2,6-dimethyl-5-nitro-442-(trifluoromethyl)phenyl]-3-pyridinecarboxylic acid methyl ester). The foregoing examples may be specific to L-type voltage-gated calcium channels or may inhibit a broader range of voltage-gated calcium channels, e.g. N, P/Q, R, and T-type.

According to some embodiments, the L-type voltage dependent calcium channel inhibitor is a dihydropyridine. Exemplary dihydropyridines include, but are not limited to, amlodipine, aranidipine, azelnidipine, bamidipine, benidipine, cinaldipine, efonidipine, felodipine, isradipine, lacidipine, lemildipine, lercanidipine, nicardipine, nifedipine, nilvadipine, nimodipine, nisoldipine, nitrendipine, manidipine, pranidipine, etc. According to one embodiment, the dihydropyridine is nimodipine. According to one embodiment, the nimodipine has a half life of 7-10 days when formulated as described herein, and appropriate lipid solubility.

According to some embodiments, the L-type voltage dependent calcium channel inhibitor is a phenylalkylamine. Exemplary phenylalkylamines include, but are not limited to, gallopamil, verapamil, etc. According to some embodiments, the L-type voltage dependent calcium channel inhibitor is a 1-4 benzothiazepine. According to one embodiment, the 1-4 benzothiazepine is diltiazem. According to one embodiment, the L-type voltage dependent calcium channel inhibitor is bepridil.

According to another embodiment, the at least one therapeutic agent is an endothelin antagonist. Exemplary endothelin antagonists include, but are not limited to, A-127722, ABT-627, BMS 182874, BQ-123, BQ-153, BQ-162, BQ-485, BQ-518, BQ-610, EMD-122946, FR 139317, IPI-725, L-744453, LU 127043, LU 135252, PABSA, PD 147953, PD 151242, PD 155080, PD 156707, RO 611790, SB-247083, clazosentan, atrasentan, sitaxsentan sodium, TA-0201, TBC 11251, TTA-386, WS-7338B, ZD-1611, aspirin, A-182086, CGS 27830, CP 170687, J-104132, L-751281, L-754142, LU 224332, LU 302872, PD 142893, PD 145065, PD 160672, RO-470203, bosentan, RO 462005, RO 470203, SB 209670, SB 217242, TAK-044, A-192621, A-308165, BQ-788, BQ-017, IRL 1038, IRL 2500, PD-161721, RES 701-1, RO 468443, etc.

According to another embodiment, the at least one therapeutic agent is a transient receptor potential (TRP) protein antagonist. Exemplary transient receptor potential (TRP) protein antagonists include, but are not limited to, gadolinium chloride, lanthanum chloride, SKF 96365 (1-(beta-[3-(4-methoxy-phenyl)propoxy]-4-methoxyphenethyl)-1H-imidazole hydrochloride), and LOE 908 ((RS)-(3,4-dihydro-6,7-dimethoxyisoquinoline-1-gamma 1)-2-phenyl-N,N-di-[2-(2,3,4-trimethoxyphenyl)ethyl]acetamide).

According to some embodiments, the at least one therapeutic agent is an isolated molecule. According to some embodiments, the at least one therapeutic agent is substantially pure.

Microparticulate Formulation

According to one embodiment, the flowable sustained release microparticulate composition comprises a plurality of microparticles comprising at least one therapeutic agent.

According to some embodiments, the at least one therapeutic agent is provided in the form of a microparticle. According to another embodiment, the least one therapeutic agent is disposed on or in the microparticle. According to one embodiment, the at least one therapeutic agent is dispersed throughout each microparticle. According to some embodiments, the at least one therapeutic agent is impregnated on the surface of each microparticle. According to another embodiment, the at least one therapeutic agent is contained within the core of the microparticle surrounded by a coating. According to another embodiment, the least one therapeutic agent is adsorbed into each microparticle.

According to some such embodiments, the microparticles are of uniform size distribution. According to some embodiments, the uniform distribution of microparticle size is achieved by a homogenization process to form a uniform emulsion comprising microparticles. According to some such embodiments, each microparticle comprises a matrix. According to some embodiments, the matrix comprises the least one therapeutic agent.

According to some embodiments, the microparticle can be of any order release kinetics, including a zero order release, first order release, second order release, delayed release, sustained release, immediate release, and a combination thereof. The microparticle can include, in addition to therapeutic agent(s), any of those materials routinely used in the art of pharmacy and medicine, including, but not limited to, erodible, nonerodible, biodegradable, or nonbiodegradable material or combinations thereof According to some embodiments, the microparticle is a microcapsule that contains the least one therapeutic agent in a solution or in a semi-solid state. According to some embodiments, the microparticle contains the least one therapeutic agent, in whole or in part. According to some embodiments, the microparticle is a nanoparticle that contains the least one therapeutic agent, in whole or in part. According to some embodiments, the microparticles can be of virtually any shape.

According to some embodiments, each microparticle is loaded with at least 40% by weight to at least 80% by weight of the at least one therapeutic agent. According to one embodiment, each microparticle is loaded with at least 40% by weight of the at least one therapeutic agent. According to another embodiment, each microparticle is loaded with at least 45% by weight of the at least one therapeutic agent. According to another embodiment, each microparticle is loaded with at least 50% by weight of the at least one therapeutic agent. According to another embodiment, each microparticle is loaded with at least 55% by weight of the at least one therapeutic agent. According to another embodiment, each microparticle is loaded with at least 60% by weight of the at least one therapeutic agent. According to another embodiment, each microparticle is loaded with at least 63% by weight of the at least one therapeutic agent. According to another embodiment, each microparticle is loaded with at least 65% by weight of the at least one therapeutic agent. According to another embodiment, each microparticle is loaded with at least 70% by weight of the at least one therapeutic agent. According to another embodiment, each microparticle is loaded with at least 75% by weight of the at least one therapeutic agent. According to another embodiment, each microparticle is loaded with at least 80% by weight of the at least one therapeutic agent.

According to some embodiments, the particle size is between about 25 µm to about 100 µm. According to some embodiments, the particle size is between about 30 µm to about 80 µm. According to one embodiment, the particle size is at least about 25 µm. According to another embodiment, the particle size is at least about 30 µm. According to another embodiment, the particle size is at least about 35 µm. According to another embodiment, the particle size is at least about 40 µm. According to another embodiment, the particle size is at least about 45 µm. According to another embodiment, the particle size is at least about 50 µm. According to another embodiment, the particle size is at least about 55 µm. According to another embodiment, the particle size is at least about 60 µm. According to another embodiment, the particle size is at least about 65 µm. According to another embodiment, the particle size is at least about 70 µm. According to another embodiment, the particle size is at least about 75 µm. According to another embodiment, the particle size is at least about 80 µm. According to another embodiment, the particle size is at least about 85 µm. According to another embodiment, the particle size is at least about 90 µm. According to another embodiment, the particle size is at least about 95 µm. According to another embodiment, the particle size is at least about 100 µm.

According to another embodiment, the at least one therapeutic agent can be provided in strings. The strings can contain the at least one therapeutic agent in a core surrounded by a coating, or the at least one therapeutic agent can be dispersed throughout the string, or the at least one therapeutic agent can be absorbed into the string. The string can be of any order release kinetics, including zero order release, first order release, second order release, delayed release, sustained release, immediate release, etc., and any combination thereof. The string can include, in addition to therapeutic agent(s), any of those materials routinely used in the art of pharmacy and medicine, including, but not limited to, erodible, nonerodible, biodegradable, or nonbiodegradable material or combinations thereof.

According to another embodiment, the at least one therapeutic agent can be provided in at least one sheet. The sheet can contain the at least one therapeutic agent and at least one additional therapeutic agent in a core surrounded by a coating, or the at least one therapeutic agent and at least one additional therapeutic agent can be dispersed throughout the sheet, or the at least one therapeutic agent can be absorbed into the sheet. The sheet can be of any order release kinetics, including zero order release, first order release, second order release, delayed release, sustained release, immediate release, etc., and any combination thereof. The sheet can include, in addition to the at least one therapeutic agent and at least one additional therapeutic agent, any of those materials routinely used in the art of pharmacy and medicine, including, but not limited to, erodible, nonerodible, biodegradable, or nonbiodegradable material or combinations thereof.

According to some embodiments, the microparticulate formulation comprises a suspension of microparticles. According to one embodiment, the microparticulate formulation comprises a powder suspension of microparticles. According to some embodiments, the microparticulate formulation further comprises at least one of a suspending agent, a stabilizing agent and a dispersing agent. According to some such embodiments, the microparticulate formulation is presented as a suspension. According to some such embodiments, the microparticulate formulation is presented as a solution. According to some such embodiments, the microparticulate formulation is presented as an emulsion.

According to some embodiments, the microparticulate formulation comprises an aqueous solution of the at least one therapeutic agent in water-soluble form. According to some embodiments, the microparticulate formulation comprises an oily suspension of the at least one therapeutic agent. Oily suspension of the at least one therapeutic agent can be prepared using suitable lipophilic solvents. Exemplary lipophilic solvents or vehicles include, but are not limited to, fatty oils such as sesame oil, or synthetic fatty acid esters, such as ethyl oleate or triglycerides. According to some embodiments, the microparticulate formulation comprises an aqueous suspension of the at least one therapeutic agent. Aqueous injection suspensions can contain substances which increase the viscosity of the suspension, such as sodium carboxymethyl cellulose, sorbitol, hyaluronic acid, or dextran. Optionally, the suspension can also contain suitable stabilizers or agents which increase the solubility of the compounds to allow for the preparation of highly concentrated solutions. Alternatively, the at least one therapeutic agent can be in powder form for constitution with a suitable vehicle, e.g., sterile pyrogen-free water, before use. The microparticulate formulation is dispersed in a vehicle to form a dispersion, with the microparticles as the dispersed phase, and the vehicle as the dispersion medium.

The microparticulate formulation can include, for example, microencapsulated dosage forms, and if appropriate, with one or more excipients, encochleated, coated onto microscopic gold particles, contained in liposomes, pellets for implantation into the tissue, or dried onto an object to be rubbed into the tissue. As used herein, the term "microencapsulation" refers to a process in which very tiny droplets or particles are surrounded or coated with a continuous film of biocompatible, biodegradable, polymeric or non-polymeric material to produce solid structures including, but not limited to, nonpareils, pellets, crystals, agglomerates, microspheres, or nanoparticles. The microparticulate formulation can be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The microparticulate formulations are suitable for use in a variety of drug delivery systems. For a brief review of methods for drug delivery, see Langer (1990) Science 249, 1527-1533, which is incorporated herein by reference.

Microencapsulation Process

Examples of microencapsulation processes and products; methods for the production of emulsion-based microparticles; emulsion-based microparticles and methods for the production thereof; solvent extraction microencapsulation with tunable extraction rates; a microencapsulation process with solvent and salt; a continuous double emulsion process for making microparticles; drying methods for tuning microparticle properties, controlled release systems from polymer blends; polymer mixtures comprising polymers having different non-repeating units and methods for making and using the same; and an emulsion based process for preparing microparticles and workhead assembly for use with same, are disclosed and described in U.S. Pat. No. 5,407,609 (entitled Microencapsulation Process and Products Thereof), U.S. application Ser. No. 10/553,003 (entitled Method for the production of emulsion-based microparticles), U.S. application Ser. No. 11/799,700 (entitled Emulsion-based microparticles and methods for the production thereof), U.S. application Ser. No. 12/557,946 (entitled Solvent Extraction Microencapsulation With Tunable Extraction Rates), U.S. application Ser. No. 12/779,138 (entitled Hyaluronic Acid (HA) Injection Vehicle), U.S. application Ser. No. 12/562,455 entitled Microencapsulation Process With Solvent And Salt), U.S. application Ser. No. 12/338,488 (entitled Process For Preparing Microparticles Having A Low Residual Solvent Volume); U.S. application Ser. No. 12/692,027 (entitled Controlled Release Systems From Polymer Blends); U.S. application Ser. No. 12/692,020 (entitled Polymer Mixtures Comprising Polymers Having Different Non-Repeating Units And Methods For Making And Using Same); U.S. application Ser. No. 10/565,401 (entitled "Controlled release compositions"); U.S. application Ser. No. 12/692,029 (entitled "Drying Methods for Tuning Microparticle Properties); U.S. application Ser. No. 12/968,708 (entitled "Emulsion Based Process for Preparing Microparticles and Workhead for Use with Same); and U.S. application Ser. No. 13/074,542 (entitled Composition and Methods for Improved Retention of a Pharmaceutical Composition at a Local Administration Site") The content of each of these are incorporated herein by reference in its entirety.

According to some embodiments, delivery of the at least one therapeutic agent using microparticle technology involves bioresorbable, polymeric particles that encapsulate the at least one therapeutic agent and at least one additional therapeutic agent.

Microparticle Polymer Matrix

According to one embodiment, the microparticles comprise a matrix. According to some embodiments, the at least one therapeutic agent is impregnated in or on a naturally occurring biopolymer matrix, a synthetic polymer matrix, or a combination thereof. According to one embodiment, the microparticulate formulation comprises a polymer matrix, wherein the at least one therapeutic agent is impregnated in the polymer matrix. According to one embodiment, the polymer is a slow release compound. According to one embodiment, the polymer is a biodegradable polymer. According to one embodiment, the polymer is poly (D, L-Lactide-co-glycolide). According to another embodiment, the polymer is poly(orthoester). According to another embodiment, the polymer is poly(anhydride). According to another embodiment, the polymer is polylactide-polyglycolide.

Both non-biodegradable and biodegradable polymeric materials can be used in the manufacture of particles for delivering the therapeutic agents. Such polymers can be natural or synthetic polymers. The polymer is selected based on the period of time over which release is desired. Bioadhesive polymers of particular interest include, but are not limited to, bioerodible hydrogels as described by Sawhney et al in Macromolecules (1993) 26, 581-587, the teachings of which are incorporated herein. Exemplary bioerodible hydrogels include, but are not limited to, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly (lauryl methacrylate), poly(phenyl methacrylate), poly(methyl acrylate), poly(isopropyl acrylate), poly(isobutyl acrylate), and poly(octadecyl acrylate). According to one embodiment, the bioadhesive polymer is hyaluronic acid. In some such embodiments, the bioadhesive polymer include less than about 2.3% of hyaluronic acid.

According to another embodiment, the polymer enhances aqueous solubility of the microparticulate formulation. Examples of suitable polymers include but are not limited to polyethylene glycol, poly-(d-glutamic acid), poly-(1-glutamic acid), poly-(1-glutamic acid), poly-(d-aspartic acid), poly-(1-aspartic acid), poly-(1-aspartic acid) and copolymers thereof. Polyglutamic acids having molecular weights between about 5,000 to about 100,000, with molecular weights between about 20,000 and about 80,000 may be used and with molecular weights between about 30,000 and about 60,000 may also be used. The polymer is conjugated via an ester linkage to one or more hydroxyls of an inventive epothilone using a protocol as essentially described by U.S. Pat. No. 5,977,163 which is incorporated herein by reference. Particular conjugation sites include the hydroxyl off carbon-21 in the case of 21-hydroxy-derivatives of the present invention. Other conjugation sites include, but are not limited, to the hydroxyl off carbon 3 and/or the hydroxyl off carbon 7.

According to some embodiments, the at least one therapeutic agent is impregnated in or on a polyglycolide (PGA) matrix. PGA is a linear aliphatic polyester developed for use in sutures. Studies have reported PGA copolymers formed with trimethylene carbonate, polylactic acid (PLA), and polycaprolactone. Some of these copolymers may be formulated as microparticles for sustained drug release.

According to some embodiments, the at least one therapeutic agent is impregnated in or on a polyester-polyethylene glycol matrix. Polyester-polyethylene glycol compounds can be synthesized; these are soft and may be used for drug delivery.

According to some embodiments, the at least one therapeutic agent is impregnated in or on a poly (amino)-derived biopolymer matrix. Poly (amino)-derived biopolymers can include, but are not limited to, those containing lactic acid and lysine as the aliphatic diamine (see, for example, U.S. Pat. No. 5,399,665), and tyrosine-derived polycarbonates and polyacrylates. Modifications of polycarbonates may alter the length of the alkyl chain of the ester (ethyl to octyl), while modifications of polyarylates may further include altering the length of the alkyl chain of the diacid (for example, succinic to sebasic), which allows for a large permutation of polymers and great flexibility in polymer properties.

According to some embodiments, the at least one therapeutic agent is impregnated in or on a polyanhydride matrix. Polyanhydrides are prepared by the dehydration of two diacid molecules by melt polymerization (see, for example, U.S. Pat. No. 4,757,128). These polymers degrade by surface erosion (as compared to polyesters that degrade by bulk erosion). The release of the drug can be controlled by the hydrophilicity of the monomers chosen.

According to some embodiments, the at least one therapeutic agent is impregnated in or on a photopolymerizable biopolymer matrix. Photopolymerizable biopolymers include, but are not limited to, lactic acid/polyethylene glycol/acrylate copolymers.

According to some embodiments, the at least one therapeutic agent is impregnated in or on a hydrogel matrix. The term "hydrogel" refers to a substance resulting in a solid, semisolid, pseudoplastic or plastic structure containing a necessary aqueous component to produce a gelatinous or jelly-like mass. Hydrogels generally comprise a variety of polymers, including hydrophilic polymers, acrylic acid, acrylamide and 2-hydroxyethylmethacrylate (HEMA).

According to some embodiments, the at least one therapeutic agent is impregnated in or on a naturally-occurring biopolymer matrix. Naturally-occurring biopolymers include, but are not limited to, protein polymers, collagen, polysaccharides, and photopolymerizable compounds.

According to some embodiments, the at least one therapeutic agent is impregnated in or on a protein polymer matrix. Protein polymers have been synthesized from self-assembling protein polymers such as, for example, silk fibroin, elastin, collagen, and combinations thereof.

According to some embodiments, the at least one therapeutic agent is impregnated in or on a naturally-occurring polysaccharide matrix. Naturally-occurring polysaccharides include, but are not limited to, chitin and its derivatives, hyaluronic acid, dextran and cellulosics (which generally are not biodegradable without modification), and sucrose acetate isobutyrate (SAIB).

According to some embodiments, the at least one therapeutic agent is impregnated in or on a chitin matrix. Chitin is composed predominantly of 2-acetamido-2-deoxy-D-glucose groups and is found in yeasts, fungi and marine invertebrates (shrimp, crustaceous) where it is a principal component of the exoskeleton. Chitin is not water soluble and the deacetylated chitin, chitosan, only is soluble in acidic solutions (such as, for example, acetic acid). Studies have reported chitin derivatives that are water soluble, very high molecular weight (greater than 2 million daltons), viscoelastic, non-toxic, biocompatible and capable of crosslinking with peroxides, gluteraldehyde, glyoxal and other aldehydes and carbodiamides, to form gels.

According to some embodiments, the at least one therapeutic agent is impregnated in or on a hyaluronic acid (HA) matrix. Hyaluronic acid (HA), which is composed of alternating glucuronidic and glucosaminidic bonds and is found in mammalian vitreous humor, extracellular matrix of the brain, synovial fluid, umbilical cords and rooster combs from which it is isolated and purified, also can be produced by fermentation processes.

Pharmaceutically Acceptable Carrier

According to some embodiments, the flowable sustained release microparticulate composition comprises (ii) a pharmaceutically acceptable carrier.

According to one embodiment, the pharmaceutically acceptable carrier is a solid carrier or excipient. According to another embodiment, the pharmaceutically acceptable carrier is a gel-phase carrier or excipient. Examples of carriers or excipients include, but are not limited to, calcium carbonate, calcium phosphate, various monomeric and polymeric sugars (including without limitation hyaluronic acid), starches, cellulose derivatives, gelatin, and polymers. An exemplary carrier can also include saline vehicle, e.g. hydroxylpropyl methyl cellulose (HPMC) in phosphate buffered saline (PBS). According to another embodiment, the pharmaceutically acceptable carrier is a buffer solution. Exemplary buffer solutions can include without limitation a phosphate buffered saline (PBS) solution.

According to some embodiments, the pharmaceutically acceptable carrier imparts stickiness to the composition. According to one embodiment, the pharmaceutically acceptable carrier comprises hyaluronic acid. According to some embodiments, the pharmaceutically acceptable carrier comprises 0% to 5% hyaluronic acid. According to one embodiment, the pharmaceutically acceptable carrier comprises less than 0.05% hyaluronic acid. According to another embodiment, the pharmaceutically acceptable carrier comprises less than 0.1% hyaluronic acid. According to another embodiment, the pharmaceutically acceptable carrier comprises less than 0.2% hyaluronic acid. According to another embodiment, the pharmaceutically acceptable carrier comprises less than 0.3% hyaluronic acid. According to another embodiment, the pharmaceutically acceptable carrier comprises less than 0.4% hyaluronic acid. According to another embodiment, the pharmaceutically acceptable carrier comprises less than 0.5% hyaluronic acid. According to another embodiment, the pharmaceutically acceptable carrier comprises less than 0.6% hyaluronic acid. According to another embodiment, the pharmaceutically acceptable carrier comprises less than 0.7% hyaluronic acid. According to another embodiment, the pharmaceutically acceptable carrier comprises less than 0.8% hyaluronic acid. According to another embodiment, the pharmaceutically acceptable carrier comprises less than 0.9% hyaluronic acid. According to another embodiment, the pharmaceutically acceptable carrier comprises less than 1.0% hyaluronic acid. According to another embodiment, the pharmaceutically acceptable carrier comprises less than 1.1% hyaluronic acid. According to another embodiment, the pharmaceutically acceptable carrier comprises less than 1.2% hyaluronic acid. According to another embodiment, the pharmaceutically acceptable carrier comprises less than 1.3% hyaluronic acid. According to another embodiment, the pharmaceutically acceptable carrier comprises less than 1.4% hyaluronic acid. According to another embodiment, the pharmaceutically acceptable carrier comprises less than 1.5% hyaluronic acid. According to another embodiment, the pharmaceutically acceptable carrier comprises less than 1.6% hyaluronic acid. According to another embodiment, the pharmaceutically acceptable carrier comprises less than 1.7% hyaluronic acid. According to another embodiment, the pharmaceutically acceptable carrier comprises less than 1.8% hyaluronic acid. According to another embodiment, the pharmaceutically acceptable carrier comprises less than 1.9% hyaluronic acid. According to another embodiment, the pharmaceutically acceptable carrier comprises less than 2.0% hyaluronic acid. According to another embodiment, the pharmaceutically acceptable carrier comprises less than 2.1% hyaluronic acid. According to another embodiment, the pharmaceutically acceptable carrier comprises less than 2.2% hyaluronic acid. According to another embodiment, the pharmaceutically acceptable carrier comprises less than 2.3% hyaluronic acid. According to another embodiment, the pharmaceutically acceptable carrier comprises less than 2.4% hyaluronic acid. According to another embodiment, the pharmaceutically acceptable carrier comprises less than 2.5% hyaluronic acid. According to another embodiment, the pharmaceutically acceptable carrier comprises less than 2.6% hyaluronic acid. According to another embodiment, the pharmaceutically acceptable carrier comprises less than 2.7% hyaluronic acid. According to another embodiment, the pharmaceutically acceptable carrier comprises less than 2.8% hyaluronic acid. According to another embodiment, the pharmaceutically acceptable carrier comprises less than 2.9% hyaluronic acid. According to another embodiment, the pharmaceutically acceptable carrier comprises less than 3.0% hyaluronic acid. According to another embodiment, the pharmaceutically acceptable carrier comprises less than 3.5% hyaluronic acid. According to another embodiment, the pharmaceutically acceptable carrier comprises less than 4.0% hyaluronic acid. According to another embodiment, the pharmaceutically acceptable carrier comprises less than 4.5% hyaluronic acid. According to another embodiment, the pharmaceutically acceptable carrier comprises less than 5.0% hyaluronic acid.

In some embodiments, the pharmaceutically acceptable carrier includes, but is not limited to, a gel, slow-release solid or semisolid compound, optionally as a sustained release gel. In some such embodiments, the at least one therapeutic agent is embedded into the pharmaceutically acceptable carrier. In some embodiments, the at least one therapeutic agent is coated on the pharmaceutically acceptable carrier. The coating can be of any desired material, preferably a polymer or mixture of different polymers. Optionally, the polymer can be utilized during the granulation stage to form a matrix with the active ingredient so as to obtain a desired release pattern of the active ingredient. The gel, slow-release solid or semisolid compound is capable of releasing the active agent over a desired period of time. The gel, slow-release solid or semisolid compound can be implanted in a tissue within the parenchyma of human brain, including, but not limited to, in proximity to a blood vessel, such as a cerebral artery.

According to another embodiment, the pharmaceutically acceptable carrier comprises a slow-release solid compound. According to one such embodiment, the at least one therapeutic agent is embedded in the slow-release solid compound or coated on the slow-release solid compound. According to yet another embodiment, the pharmaceutically acceptable carrier comprises a slow-release microparticle containing the at least one therapeutic agent.

According to another embodiment, the pharmaceutically acceptable carrier is a gel compound, such as a biodegradable hydrogel.

Additional Components

According to some embodiments, the flowable sustained release microparticulate composition further comprises a preservative agent. According to some such embodiments, the flowable sustained release microparticulate very composition is presented in a unit dosage form. Exemplary unit dosage forms include, but are not limited to, ampoules or multi-dose containers.

The flowable sustained release microparticulate compositions for parenteral (including but not limited to, subcutaneous, intradermal, intramuscular, intravenous, intraarterial, intrathecal, intraventricular and intraarticular) administration include aqueous and non-aqueous sterile injection solutions that can contain anti-oxidants, buffers, bacteriostats and solutes, which render the formulation isotonic with the blood or CSF of the intended recipient; and aqueous and non-aqueous sterile suspensions, which can include suspending agents and thickening agents.

According to some embodiments, the flowable sustained release microparticulate composition is formulated for parenteral injection, surgical implantation, or a combination thereof. According to some such embodiments, the flowable sustained release microparticulate composition is in the form of a pharmaceutically acceptable sterile aqueous or nonaqueous solution, dispersion, suspension or emulsion or a sterile powder for reconstitution into a sterile injectable solution or dispersion. Examples of suitable aqueous and nonaqueous carriers, diluents, solvents or vehicles include, but are not limited to, water, ethanol, dichloromethane, acetonitrile, ethyl acetate, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants. Suspensions can further contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

According to some embodiments, the flowable sustained release microparticulate composition is formulated in an injectable depot form. Injectable depot forms are made by forming microencapsulated matrices of the therapeutic agent in a biodegradable polymer. Depending upon the ratio of drug to polymer and the nature of the particular polymer employed, the rate of drug release may be controlled. Such long acting formulations can be formulated with suitable polymeric or hydrophobic materials (for example as an emulsion in an acceptable oil) or ion exchange resins, or as sparingly soluble derivatives, for example, as a sparingly soluble salt. Examples of biodegradable polymers include, but are not limited to, polylactide-polyglycolide, poly(orthoesters) and poly(anhydrides). Depot injectable formulations are also prepared by entrapping the drug in liposomes or microemulsions which are compatible with body tissues.

According to some embodiments, the flowable sustained release microparticulate composition further comprises an adjuvant. Exemplary adjuvants include, but are not limited to, preservative agents, wetting agents, emulsifying agents, and dispersing agents. Prevention of the action of microorganisms can be ensured by various antibacterial and antifungal agents, for example, parabens, chlorobutanol, phenol, sorbic acid, and the like. Isotonic agents, for example, sugars, sodium chloride and the like, can also be included. Prolonged absorption of the injectable pharmaceutical form can be brought about by the use of agents delaying absorption, for example, aluminum monostearate and gelatin.

The flowable sustained release microparticulate compositions can be sterilized, for example, by terminal gamma irradiation, filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol, dichloromethane, ethyl acetate, acetonitrile, etc. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono- or diglycerides. In addition, fatty acids such as oleic acid are used in the preparation of injectables.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

As used herein, the singular forms "a", "an" and "the" include plural referents unless the context clearly dictates otherwise. For example, reference to a "polypeptide" means one or more polypeptides.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Effect of Nimodipine Formulations on Cerebral Angiographic Vasospasm in a Subarachnoid Hemorrhage (SAH) Dog Model Treatment Groups A total of 24 mongrel dogs were randomly assigned to one of three groups as presented in Table 1.

Table 1. Treatment Group Assignments

TABLE 1

| Group Assignments | | |
|---|---|---|
| Group Number | Treatment | Number of Animals |
| 1 | Microparticulate Placebo Formulation | 4 males + 4 females |
| 2 | Microparticulate Placebo Formulation followed by Oral Nimodipine (0.86 mg/kg dose) | 4 males + 4 females |
| 3 | Intraventricular administration of Microparticulate Nimodipine Test Formulation (100 mg dose) | 4 males + 4 females |

Formulations

The test formulation of a microparticulate nimodipine formulation containing a uniform size distribution of microparticles was prepared by combining a polymer solution (e.g., a 50-50 glycolide-lactide blend) with a solvent in the presence of nimodipine. The mixture was added to a surfactant containing aqueous solution to form an emulsion and the solvent extracted to produce the flowable microparticulate nimodipine formulation. The particle size distribution for 63% nimodipine (wt %) and 1.3% water was 66 µm (mean), 95 µm ($95^{th}$ percentile) and 39 µm ($10^{th}$ percentile). The initial drug load was 65% nimodipine (weight per volume). The placebo microparticulate formulation containing a uniform size distribution of microparticles was prepared by combining a polymer solution (e.g., a 50-50 glycolide-lactide blend) with a solvent in the absence of nimodipine.

Figure 12:
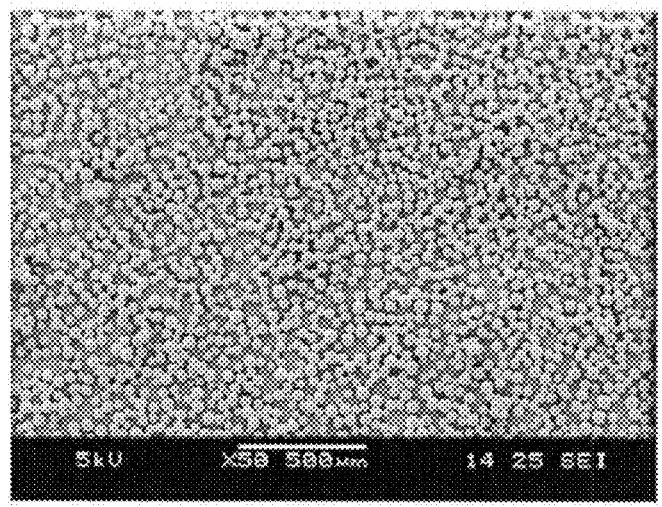
FIG. 12 shows a scanning electron micrograph (SEM) image of a microparticulate nimodipine formulation according to the present invention.
Figure 13:
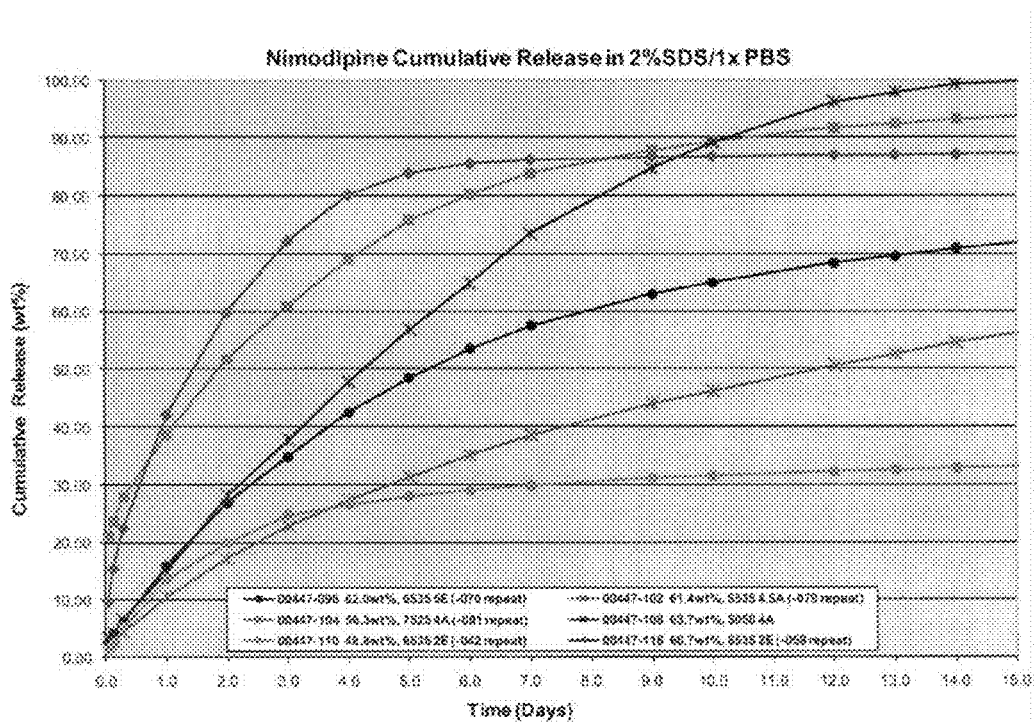
FIG. 13 shows the in vitro cumulative release of exemplary microparticulate nimodipine formulations expressed as weight % of the over time.

FIG. 12 shows a scanning electron micrograph (SEM) image of microparticulate nimodipine formulation according to the present invention. FIG. 13 shows the in vitro cumulative release of exemplary microparticulate nimodipine formulations expressed as weight % of the over time. For measuring in vitro release profiles, samples of microparticulate nimodipine formulations were analyzed for nimodipine content by high performance liquid chromatography (HPLC) at specific time points (1 hr, 2 hrs, 6 hrs, 24 hrs and then each day for 14 days). Exemplary microparticulate formulations are capable of releasing in vitro about 50% to 100% of nimodipine within a time frame of 6 to 14 days in vitro.

According to some embodiments, for intracisternal administration, the microparticulate formulation is admixed with a pharmaceutically acceptable carrier.

Administration

FIG. 14 shows an exemplary view of the application of a microparticulate composition of the described invention containing a calcium channel antagonist, an endothelin receptor antagonist, or a TRP protein antagonist, or a combination thereof, to the cerebral ventricles through an intraventricular catheter (Figure from Mccomb J G: Techniques of CSF diversion. In: Scott R M (ed). Hydrocephalus. Vol. 3. Williams & Wilkins: Baltimore. 1990. page 48, pp. 128). FIG. 15 is a schematic depicting a microparticulate composition of the described invention comprising a calcium channel antagonist, an endothelin receptor antagonist, or a TRP protein antagonist, or a combination thereof, in or on microparticles being carried by CSF flow from the ventricles to the arteries of the subarachnoid space (Pollay M: Cerebrospinal fluid. In: Tindall G T, Cooper P R, Barrow D L (eds). The Practice of Neurosurgery. Vol. 1. Williams & Wilkins: Baltimore. 1996. page 36, pp. 1381).

The microparticulate nimodipine formulation (100 mg Intraventricular) was administered to treatment group 3 by syringe through a catheter (14 gauge to 18 gauge) into a cerebral ventricle. The microparticulate placebo composition was administered to treatment group 1 (Placebo) and treatment group 2 (Oral Nimodipine) with a vehicle (e.g. hyaluronic acid) by surgical injection within the cisterna magna of the subarachnoid space. Following administration of microparticulate placebo composition on day 1, treatment group 2 (Oral Nimodipine) then received oral nimodipine capsules (0.86 mg/kg) six times per day till day 21. The syringes were loaded taking into account the overfill needed to fill the dead volume in the delivery system. The oral control and placebo groups received the control article in the same manner as the treated group. The dose of oral nimodipine is equivalent to 30 mg every 4 hours in humans when converting dose based on body surface area, or to 60 mg every 4 hours when converting dose based on body weight (Reagan-Shaw, S. et al., "Dose translation from animal to human studies revisited," FASEB J., 22: 659-661 (2008)). This dose was chosen since it is a dose that has been associated with decreased blood pressure in dogs (Zabramski, J. et al., "Chronic cerebral vasospasm: effect of calcium antagonists," Neurosurgery, 18: 129-135 (1986)).

For reconstitution/injection, a syringe comprising diluent was attached via a connector to a syringe comprising the microparticulate nimodipine formulation. In case of treatment groups 1, and 2, i.e., for intracisternal administration, a plunger is cycled to draw the vehicle into the microparticulate formulation. The resulting microparticulate composition is then pushed into the left syringe, which is disconnected from the connector. For delivery, the composition is injectable either through a surgical needle or the surgical needle can be fitted with and injected through a cannula or catheter of any appropriate size.

Surgical Procedures

On Day 1, all dogs underwent baseline assessment followed by angiography and injection of autologous blood, 0.5 ml/g, into the cisterna magna. Following blood injection, the microparticulate placebo composition was injected into the cisterna magna of treatment group 1 animals (Placebo) and treatment group 2 animals (Oral Nimodipine) and the microparticulate nimodipine formulation was injected into the right lateral ventricle of treatment group 3 animals (Intraventrentricular Nimodipine).

The animals were suspended prone and tilted 30° head down for 15 minutes following completion of injections. The animals were awakened and returned to their cages. On Day 3, the animals underwent repeat blood injection (05 ml/kg) into the cisterna magna.

Endpoints

On days 8 and 15, the animals were anesthetized, and angiography, removal of CSF from the cistern magna and collection of plasma, were repeated. Other endpoints included daily blood pressure measurements, behavior assessment, and brain and spinal cord pathology. After angiography on day 15, animals were not recovered from anesthesia. They were euthanized under anesthesia, perfused with phosphate-buffered saline and then neutral buffered formalin, and the brains subjected to histological analysis.

Angiographic Vasospasm

Angiographic vasospasm was assessed by comparing the diameters of the basilar arteries on days 1, 8, and 15. Angiography was measured by a blinded assessor and analyzed by analysis of variance (ANOVA) between groups at each time and within groups over time. If values were not normally distributed, the Kruskal-Wallis ANOVA on ranks with pairwise comparisons (Dunn's post-test method) if significant variance was found. For normally distributed data, pairwise comparisons were by the Holm-Sidak method for multiple comparisons. Individual percent vasospasm was determined for each animal for Days 8 and 15 using formula (1):

$$\frac{[\text{Follow}-\text{up}(\text{Day 8 or 15}) MeanLumenDiameter] - [\text{Baseline}(\text{Day 1}) MeanLumenDiameter]}{BaselineMeanLumenDiameter} \times 100 \qquad (1)$$

Figure 16:
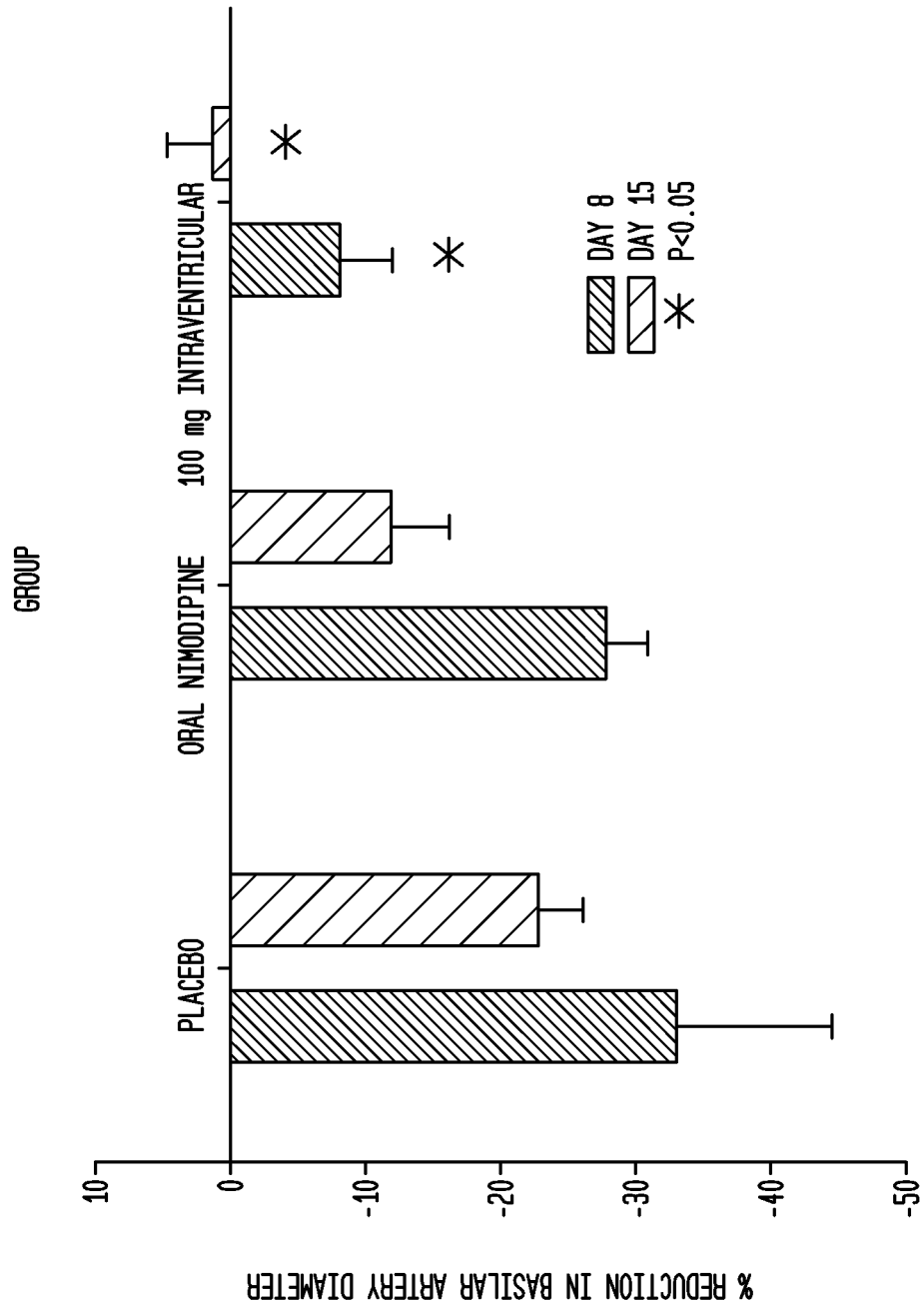
FIG. 16 is a bar graph showing percent change in angiographic diameter of the basilar artery 8 and 15 days after subarachnoid hemorrhage (SAH) in dogs treated with placebo microparticle composition (placebo, n=8), oral nimodipine plus placebo microparticle composition (oral nimodipine, n=8), or 100 mg intraventricular nimodipine microparticles (n=8). Analysis of variance showed significantly less angiographic vasospasm 8 and 15 days after SAH in dogs treated with intraventricular nimodipine microparticles ($P<0.05$, values are means±standard error of the mean).

Average percent vasospasm for Days 8 and 15 compared to diameter on day 1 was also determined for each group. FIG. 16 is a bar graph showing percent change in angiographic diameter of the basilar artery 8 and 15 days after subarachnoid hemorrhage (SAH) in dogs treated with placebo microparticle composition (placebo, n=8), oral nimodipine plus placebo microparticle composition (oral nimodipine, n=8), or 100 mg intraventricular nimodipine microparticles (n=8). Analysis of variance showed significantly less angiographic vasospasm 8 and 15 days after SAH in dogs treated with intraventricular nimodipine microparticles (P<0.05, values are means±standard error of the mean).

Comparison of the percent change in basilar artery diameter between groups on day 8 showed that there was significant variance (n=8 per group, P=0.006, FIG. 16). Pairwise comparison showed significantly less angiographic vasospasm in the group treated with 100 mg intraventricular nimodipine microparticles compared to those receiving oral nimodipine (P<0.05) or placebo microparticles only (P<0.05). On day 15, there also was significant variance between groups (P=0.001) with significantly less angiographic vasospasm in the group treated with 100 mg intraventricular nimodipine microparticles compared to the placebo group that did not receive any nimodipine (P<0.05) and to oral nimodipine (P=0.05). Comparing within each group over time, there was significant angiographic vasospasm on days 8 and 15 in the group that did not receive oral nimodipine (P=0.001) and in the group treated with oral nimodipine (P<0.001) whereas there was no significant variance in the group treated with intraventricular nimodipine microparticles. Thus, these data show that (1) intraventricular sustained-release nimodipine microparticles reduce angiographic vasospasm, and (2) that there is no toxicity associated with intraventricular nimodipine microparticles containing 100 mg nimodipine.

Behavioral Observations

Behavior was assessed on a 3-component scale that has been used to determine effects of SAH and drug treatment on SAH in dogs as described in Cahill, J. et al., "Vasospasm and p53-induced apoptosis in an experimental model of subarachnoid hemorrhage," Stroke, 37: 1868-1874 (2006). Observations for morbidity, mortality, injury, and the availability of food and water were conducted twice daily for all animals. Body weights were measured and recorded prior to randomization and weekly during the study. A complete physical examination was conducted on all animals each day.

Behavioral observations were conducted daily for each animal enrolled on study. Behavior of each animal was examined daily. Behavior pertaining to behavior categories of appetite, activity and neurological defect were given behavioral scores according to Tables 2-4.

Table 2 provides behavioral scores given for appetite.

TABLE 2

Behavioral Score for Appetite
Appetite

| Score | Observation |
|---|---|
| 2 | Finished meal |
| 1 | Left meal unfinished |
| 0 | Scarcely ate |

Table 3 provides behavioral scores for activity.

TABLE 3

Behavioral scores for Activity
Activity

| Score | Observation |
|---|---|
| 2 | Active, barking or standing |
| 1 | Lying down, will stand and walk with some stimulation |
| 0 | Almost always lying down |

Table 4 provides behavioral scores for neurological defects. Neurological defect scored was ability to walk because of ataxia or paresis.

TABLE 4

Behavioral scores for neurological defects
Neurological Defects

| Score | Observation |
|---|---|
| 2 | No deficit |
| 1 | Unable to walk because of ataxia or paresis |
| 0 | Impossible to walk or stand because of ataxia or paresis |

Figure 17:
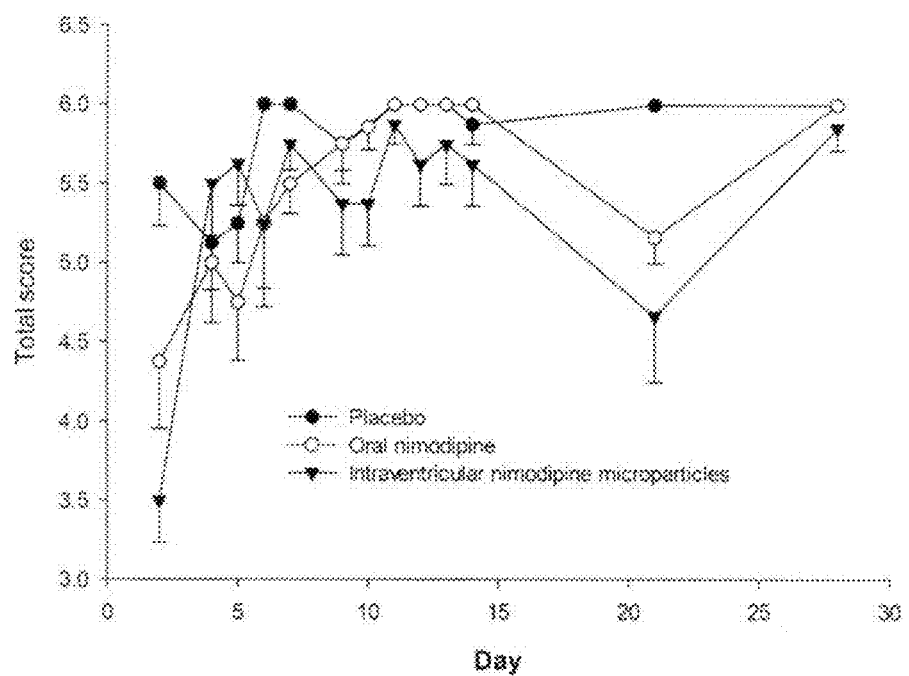
FIG. 17 shows a plot of averaged behavioral scores of dogs subjected to subarachnoid hemorrhage (SAH) in dogs treated with placebo microparticle composition (placebo, n=8), oral nimodipine plus placebo microparticle composition (oral nimodipine, n=8), or 100 mg intraventricular nimodipine microparticles (n=8). Values are means±standard error of the mean (n=8 per measurement).

FIG. 17 shows a plot of averaged behavioral scores of dogs subjected to subarachnoid hemorrhage (SAH) in dogs treated with placebo microparticle composition (placebo, n=8), oral nimodipine plus placebo microparticle composition (oral nimodipine, n=8), or 100 mg intraventricular nimodipine microparticles (n=8). Values are means±standard error of the mean (n=8 per measurement).

There were no significant differences in behavior between groups at any time after SAH (FIG. 17, ANOVA).

Plasma and Cerebrospinal Fluid (CSF) Analysis

Figure 18:
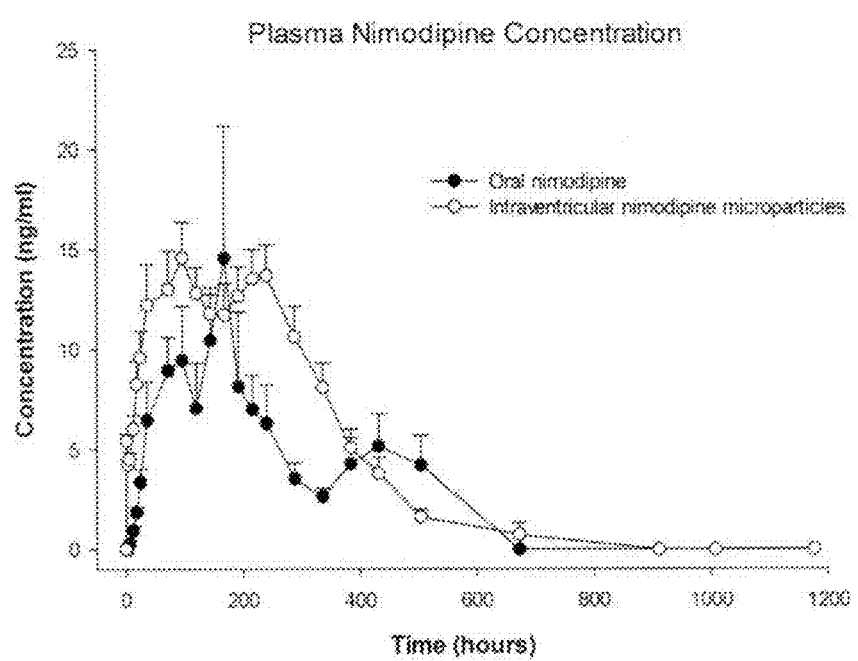
FIG. 18 shows a plot of the plasma concentration of nimodipine (ng/ml) in the 2 groups treated with oral nimodipine (administered for 21 days [504 hours]) or with intraventricular nimodipine microparticles. Both groups have similar plasma concentrations, showing systemic exposure to nimodipine after intraventricular microparticle injection (values are means±standard error of the mean [n=8 per measurement]).

FIG. 18 shows a plot of the plasma concentration of nimodipine (ng/ml) in the 2 groups treated with oral nimodipine (administered for 21 days [504 hours]) or with intraventricular nimodipine microparticles. Both groups have similar plasma concentrations, showing systemic exposure to nimodipine after intraventricular microparticle injection (values are means±standard error of the mean [n=8 per measurement]).

Figure 19:
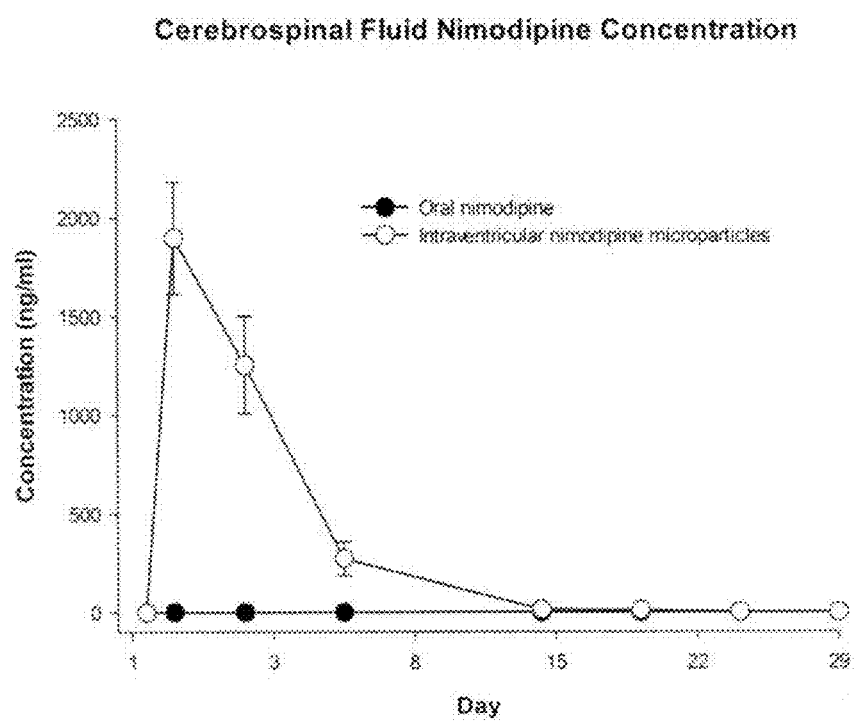
FIG. 19 shows a plot of the cerebrospinal fluid (CSF) concentration of nimodipine in CSF obtained from cisterna magna in the 2 groups treated with oral nimodipine or with intraventricular nimodipine microparticles. Values are means±standard error of the mean (n=8 per measurement).

FIG. 19 shows a plot of the cerebrospinal fluid (CSF) concentration of nimodipine in CSF obtained from cisterna magna in the 2 groups treated with oral nimodipine or with intraventricular nimodipine microparticles. Values are means±standard error of the mean (n=8 per measurement).

Plasma and CSF concentrations of nimodipine demonstrated sustained release of nimodipine with concentrations that were higher in CSF than in plasma for the group treated with intraventricular nimodipine microparticles. CSF nimodipine concentrations were high and remained in a therapeutic range for up to 15 days after SAH, whereas they were low or undetectable when oral nimodipine was administered (FIGS. 18 and 19).

Histological Observations

Figure 20:
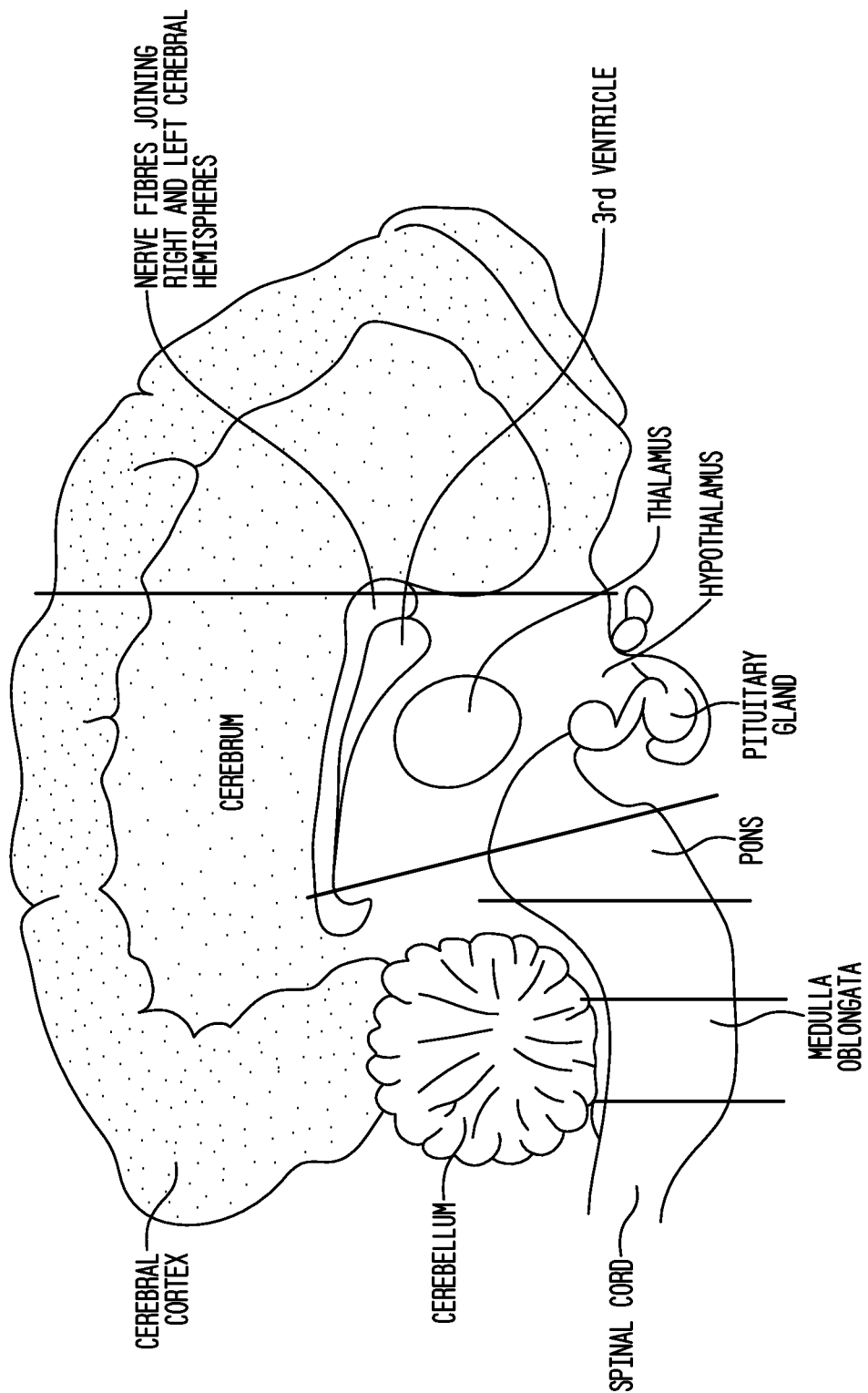
FIG. 20 shows sectional planes used in the canine model experiments.

FIG. 20 shows the sectional planes used in the canine model experiments. Table 5 provides a summary of macroscopic observations of the dogs subjected to subarachnoid hemorrhage (SAH) in dogs treated with placebo microparticles (placebo), oral nimodipine plus placebo microparticles (oral nimodipine), or 100 mg intraventricular nimodipine microparticles recovered at day 28 or day 49. The animals are grouped according to whether the animals died or were euthanized (DOS) or whether they underwent scheduled necropsy (SNC).

TABLE 5

Summary of Macroscopic Observations

| Tissue Observation | Recovery Day (day 28/day 49) | Severity | Placebo Male DOS | Placebo Male SNC | Placebo Female DOS | Placebo Female SNC | Oral Male DOS | Oral Male SNC | Oral Female DOS | Oral Female SNC | Intraventricular Nimodipine Male DOS | Intraventricular Nimodipine Male SNC | Intraventricular Nimodipine Female DOS | Intraventricular Nimodipine Female SNC |
|---|---|---|---|---|---|---|---|---|---|---|---|---|---|---|
| # of animals | | | 0 | 4 | 0 | 4 | 0 | 4 | 0 | 4 | 0 | 4 | 1 | 3 |
| All tissues Within normal limits | 28 d | | 0 | 2 | 0 | 3 | 0 | 2 | 0 | 2 | 0 | 2 | 0 | 1 |
| | 49 d | | 0 | 0 | 0 | 0 | 0 | 2 | 0 | 2 | 0 | 2 | 0 | 2 |
| Brain | | | | | | | | | | | | | | |
| discoloration, red | 28 d | mild | 0 | 2 | 0 | 0 | 0 | 0 | 0 | 0 | 0 | 0 | 2 | 0 |
| | 49 d | | 0 | 0 | 0 | 0 | 0 | 0 | 0 | 0 | 0 | 0 | 0 | 0 |
| focus/foci, red | 28 d | mild | 0 | 0 | 0 | 1 | 0 | 0 | 0 | 0 | 0 | 0 | 0 | 0 |
| | 49 d | | 0 | 0 | 0 | 0 | 0 | 0 | 0 | 0 | 0 | 0 | 0 | 0 |
| nodule | 28 d | present | 0 | 0 | 0 | 0 | 0 | 0 | 0 | 0 | 0 | 0 | 1 | 0 |
| | 49 d | | 0 | 0 | 0 | 0 | 0 | 0 | 0 | 0 | 0 | 0 | 0 | 0 |

Table 6 provides a summary of microscopic observations of the dogs subjected to subarachnoid hemorrhage (SAH) in dogs treated with placebo microparticles (placebo), oral nimodipine plus placebo microparticles (oral nimodipine), or 100 mg intraventricular nimodipine microparticles recovered at day 28 or day 49. The animals are grouped according to whether the animals died or were euthanized (DOS) or whether they underwent scheduled necropsy (SNC).

TABLE 6

Summary of Microscopic Observations

| Tissue Observation | Recovery Day (day 28/day 49) | Severity | Placebo Male DOS | Placebo Male SNC | Placebo Female DOS | Placebo Female SNC | Oral Male DOS | Oral Male SNC | Oral Female DOS | Oral Female SNC | Intraventricular Nimodipine Male DOS | Intraventricular Nimodipine Male SNC | Intraventricular Nimodipine Female DOS | Intraventricular Nimodipine Female SNC |
|---|---|---|---|---|---|---|---|---|---|---|---|---|---|---|
| # of animals | | | 0 | 4 | 0 | 4 | 0 | 4 | 0 | 3 | 0 | 4 | 1 | 3 |
| Brain | | | | | | | | | | | | | | |
| chromatolysis, central, neuronal | 28 d | minimal | 0 | 0 | 0 | 0 | 0 | 0 | 0 | 0 | 0 | 0 | 0 | 0 |
| | 49 d | | 0 | 0 | 0 | 0 | 0 | 0 | 0 | 0 | 0 | 0 | 0 | 0 |
| degeneration | 28 d | minimal | 0 | 0 | 0 | 0 | 0 | 0 | 0 | 0 | 0 | 0 | 0 | 0 |
| | 49 d | | 0 | 0 | 0 | 0 | 0 | 0 | 0 | 1 | 0 | 0 | 0 | 1 |
| | 28 d | mild | 0 | 0 | 0 | 0 | 0 | 0 | 0 | 0 | 0 | 0 | 1 | 0 |
| | 49 d | | 0 | 0 | 0 | 0 | 0 | 0 | 0 | 0 | 0 | 0 | 0 | 0 |
| degeneration, axonal/myelin | 28 d | minimal | 0 | 0 | 0 | 0 | 0 | 0 | 0 | 0 | 0 | 0 | 0 | 0 |
| | 49 d | | 0 | 0 | 0 | 0 | 0 | 0 | 0 | 0 | 0 | 0 | 0 | 0 |
| | 28 d | mild | 0 | 0 | 0 | 0 | 0 | 0 | 0 | 0 | 0 | 0 | 0 | 1 |
| | 49 d | | 0 | 0 | 0 | 0 | 0 | 0 | 0 | 0 | 0 | 0 | 0 | 0 |
| fibroplasia | 28 d | minimal | 0 | 0 | 0 | 0 | 0 | 1 | 0 | 0 | 0 | 2 | 0 | 0 |
| | 49 d | | 0 | 0 | 0 | 0 | 0 | 0 | 0 | 0 | 0 | 1 | 0 | 0 |
| | 28 d | mild | 0 | 0 | 0 | 0 | 0 | 1 | 0 | 0 | 0 | 0 | 0 | 0 |
| | 49 d | | 0 | 0 | 0 | 0 | 0 | 1 | 0 | 0 | 0 | 0 | 0 | 0 |
| granulation tissue | 28 d | minimal | 0 | 0 | 0 | 1 | 0 | 0 | 0 | 0 | 0 | 0 | 0 | 0 |
| | 49 d | | 0 | 0 | 0 | 0 | 0 | 0 | 0 | 0 | 0 | 1 | 0 | 1 |
| | 28 d | mild | 0 | 0 | 0 | 0 | 0 | 0 | 0 | 0 | 0 | 0 | 1 | 0 |
| | 49 d | | 0 | 0 | 0 | 0 | 0 | 0 | 0 | 0 | 0 | 0 | 0 | 0 |
| hemorrhage | 28 d | minimal | 0 | 0 | 0 | 1 | 0 | 0 | 0 | 0 | 0 | 0 | 0 | 0 |
| | 49 d | | 0 | 0 | 0 | 0 | 0 | 0 | 0 | 0 | 0 | 0 | 0 | 0 |
| | 28 d | mild | 0 | 0 | 0 | 1 | 0 | 0 | 0 | 1 | 0 | 0 | 0 | 0 |
| | 49 d | | 0 | 0 | 0 | 0 | 0 | 0 | 0 | 0 | 0 | 0 | 0 | 0 |
| | 28 d | moderate | 0 | 2 | 0 | 0 | 0 | 0 | 0 | 0 | 0 | 0 | 1 | 0 |
| | 49 d | | 0 | 0 | 0 | 0 | 0 | 0 | 0 | 0 | 0 | 0 | 0 | 0 |
| infiltration, lymphoid, perivascular | 28 d | minimal | 0 | 1 | 0 | 0 | 0 | 0 | 0 | 0 | 0 | 1 | 0 | 0 |
| | 49 d | | 0 | 0 | 0 | 0 | 0 | 0 | 0 | 0 | 0 | 0 | 0 | 0 |
| inflammation, granulomous | 28 d | minimal | 0 | 3 | 0 | 2 | 0 | 1 | 0 | 0 | 0 | 1 | 0 | 0 |
| | 49 d | | 0 | 0 | 0 | 0 | 0 | 1 | 0 | 0 | 0 | 0 | 0 | 0 |
| | 28 d | mild | 0 | 1 | 0 | 0 | 0 | 1 | 0 | 1 | 0 | 1 | 0 | 0 |
| | 49 d | | 0 | 0 | 0 | 0 | 0 | 0 | 0 | 0 | 0 | 0 | 0 | 0 |
| inflammation, meningeal | 28 d | minimal | 0 | 0 | 0 | 0 | 0 | 0 | 0 | 0 | 0 | 1 | 0 | 0 |
| | 49 d | | 0 | 0 | 0 | 0 | 0 | 0 | 0 | 0 | 0 | 0 | 0 | 0 |
| inflammation, subacute/chronic | 28 d | minimal | 0 | 1 | 0 | 1 | 0 | 0 | 0 | 2 | 0 | 1 | 0 | 1 |
| | 49 d | | 0 | 0 | 0 | 0 | 0 | 2 | 0 | 1 | 0 | 2 | 0 | 1 |
| | 28 d | mild | 0 | 1 | 0 | 0 | 0 | 0 | 0 | 0 | 0 | 0 | 0 | 0 |
| | 49 d | | 0 | 0 | 0 | 0 | 0 | 0 | 0 | 0 | 0 | 0 | 0 | 0 |

TABLE 6-continued

Summary of Microscopic Observations

| Tissue Observation | Recovery Day (day 28/day 49) | Severity | Placebo Male DOS | Placebo Male SNC | Placebo Female DOS | Placebo Female SNC | Oral Male DOS | Oral Male SNC | Oral Female DOS | Oral Female SNC | Intraventricular Nimodipine Male DOS | Intraventricular Nimodipine Male SNC | Intraventricular Nimodipine Female DOS | Intraventricular Nimodipine Female SNC |
|---|---|---|---|---|---|---|---|---|---|---|---|---|---|---|
| macrophages, pigmented | 28 d | minimal | 0 | 0 | 0 | 1 | 0 | 0 | 0 | 0 | 0 | 2 | 1 | 0 |
|  | 49 d |  | 0 | 0 | 0 | 0 | 0 | 0 | 0 | 0 | 0 | 0 | 0 | 1 |
|  | 28 d | mild | 0 | 1 | 0 | 0 | 0 | 2 | 0 | 0 | 0 | 0 | 0 | 0 |
|  | 49 d |  | 0 | 0 | 0 | 0 | 0 | 0 | 0 | 0 | 0 | 0 | 0 | 0 |
| mineralization, focal | 28 d | minimal | 0 | 0 | 0 | 0 | 0 | 0 | 0 | 0 | 0 | 0 | 0 | 0 |
|  | 49 d |  | 0 | 0 | 0 | 0 | 0 | 0 | 0 | 0 | 0 | 0 | 0 | 0 |
| neovascularization | 28 d | minimal | 0 | 0 | 0 | 0 | 0 | 0 | 0 | 0 | 0 | 1 | 0 | 0 |
|  | 49 d |  | 0 | 0 | 0 | 0 | 0 | 0 | 0 | 0 | 0 | 0 | 0 | 0 |
| within normal limits | 28 d |  | 0 | 0 | 0 | 1 | 0 | 0 | 0 | 0 | 0 | 0 | 0 | 0 |
|  | 49 d |  | 0 | 0 | 0 | 0 | 0 | 0 | 0 | 0 | 0 | 0 | 0 | 0 |
| Spinal Cord, Cervical |  |  |  |  |  |  |  |  |  |  |  |  |  |  |
| degeneration, axonal/myelin | 28 d | minimal | 0 | 0 | 0 | 0 | 0 | 0 | 0 | 0 | 0 | 0 | 0 | 1 |
|  | 49 d |  | 0 | 0 | 0 | 0 | 0 | 0 | 0 | 0 | 0 | 0 | 0 | 0 |
| fibroplasia | 28 d | minimal | 0 | 1 | 0 | 1 | 0 | 0 | 0 | 0 | 0 | 0 | 0 | 0 |
|  | 49 d |  | 0 | 0 | 0 | 0 | 0 | 0 | 0 | 0 | 0 | 0 | 0 | 0 |
|  | 28 d | mild | 0 | 3 | 0 | 1 | 0 | 1 | 0 | 2 | 0 | 2 | 1 | 1 |
|  | 49 d |  | 0 | 0 | 0 | 0 | 0 | 1 | 0 | 0 | 0 | 0 | 0 | 1 |
|  | 28 d | moderate | 0 | 0 | 0 | 1 | 0 | 1 | 0 | 0 | 0 | 0 | 0 | 0 |
|  | 49 d |  | 0 | 0 | 0 | 0 | 0 | 0 | 0 | 0 | 0 | 0 | 0 | 0 |
| hemorrhage | 28 d | minimal | 0 | 1 | 0 | 1 | 0 | 2 | 0 | 1 | 0 | 1 | 0 | 0 |
|  | 49 d |  | 0 | 0 | 0 | 0 | 0 | 0 | 0 | 0 | 0 | 0 | 0 | 0 |
| inflammation, granulomatous | 28 d | minimal | 0 | 1 | 0 | 2 | 0 | 1 | 0 | 0 | 0 | 0 | 0 | 0 |
|  | 49 d |  | 0 | 0 | 0 | 0 | 0 | 0 | 0 | 0 | 0 | 0 | 0 | 0 |
|  | 28 d | moderate | 0 | 0 | 0 | 0 | 0 | 0 | 0 | 1 | 0 | 0 | 0 | 0 |
|  | 49 d |  | 0 | 0 | 0 | 0 | 0 | 0 | 0 | 0 | 0 | 0 | 0 | 0 |
| inflammation, subacute/chronic | 28 d | minimal | 0 | 2 | 0 | 1 | 0 | 1 | 0 | 1 | 0 | 2 | 0 | 1 |
|  | 49 d |  | 0 | 0 | 0 | 0 | 0 | 1 | 0 | 1 | 0 | 2 | 0 | 0 |
|  | 28 d | mild | 0 | 2 | 0 | 1 | 0 | 1 | 0 | 0 | 0 | 0 | 0 | 0 |
|  | 49 d |  | 0 | 0 | 0 | 0 | 0 | 0 | 0 | 0 | 0 | 0 | 0 | 0 |
| macrophages, pigmented | 28 d | minimal | 0 | 0 | 0 | 0 | 0 | 2 | 0 | 0 | 0 | 0 | 0 | 0 |
|  | 49 d |  | 0 | 0 | 0 | 0 | 0 | 0 | 0 | 0 | 0 | 0 | 0 | 0 |
| within normal limits | 28 d |  | 0 | 0 | 0 | 0 | 0 | 0 | 0 | 0 | 0 | 0 | 0 | 0 |
|  | 49 d |  | 0 | 0 | 0 | 0 | 0 | 1 | 0 | 0 | 0 | 0 | 0 | 1 |
| Spinal Cord, Lumbar |  |  |  |  |  |  |  |  |  |  |  |  |  |  |
| fibroplasia | 28 d | minimal | 0 | 0 | 0 | 0 | 0 | 0 | 0 | 0 | 0 | 1 | 0 | 0 |
|  | 49 d |  | 0 | 0 | 0 | 0 | 0 | 0 | 0 | 0 | 0 | 0 | 0 | 0 |
| hemorrhage | 28 d | minimal | 0 | 1 | 0 | 0 | 0 | 0 | 0 | 0 | 0 | 0 | 0 | 0 |
|  | 49 d |  | 0 | 0 | 0 | 0 | 0 | 0 | 0 | 0 | 0 | 0 | 0 | 0 |
| mineralization | 28 d | minimal | 0 | 0 | 0 | 0 | 0 | 0 | 0 | 0 | 0 | 0 | 0 | 0 |
|  | 49 d |  | 0 | 0 | 0 | 0 | 0 | 0 | 0 | 0 | 0 | 0 | 0 | 0 |
| within normal limits | 28 d |  | 0 | 3 | 0 | 4 | 0 | 0 | 0 | 0 | 0 | 0 | 0 | 0 |
|  | 49 d |  | 0 | 0 | 0 | 0 | 0 | 0 | 0 | 0 | 0 | 1 | 0 | 2 |
| Spinal Cord, Thoracic |  |  |  |  |  |  |  |  |  |  |  |  |  |  |
| fibroplasia | 28 d | minimal | 0 | 0 | 0 | 0 | 0 | 0 | 0 | 0 | 0 | 1 | 0 | 0 |
|  | 49 d |  | 0 | 0 | 0 | 0 | 0 | 0 | 0 | 0 | 0 | 0 | 0 | 0 |
| hemorrhage | 28 d | minimal | 0 | 1 | 0 | 0 | 0 | 0 | 0 | 0 | 0 | 0 | 0 | 1 |
|  | 49 d |  | 0 | 0 | 0 | 0 | 0 | 0 | 0 | 0 | 0 | 1 | 0 | 0 |
| inflammation, granulomatous | 28 d | minimal | 0 | 0 | 0 | 2 | 0 | 0 | 0 | 0 | 0 | 0 | 0 | 0 |
|  | 49 d |  | 0 | 0 | 0 | 0 | 0 | 0 | 0 | 0 | 0 | 0 | 0 | 0 |
| inflammation, subacute/chronic | 28 d | minimal | 0 | 0 | 0 | 0 | 0 | 0 | 0 | 0 | 0 | 1 | 0 | 0 |
|  | 49 d |  | 0 | 0 | 0 | 0 | 0 | 0 | 0 | 0 | 0 | 0 | 0 | 0 |
| macrophages, pigmented | 28 d | minimal | 0 | 0 | 0 | 0 | 0 | 0 | 0 | 0 | 0 | 1 | 0 | 0 |
|  | 49 d |  | 0 | 0 | 0 | 0 | 0 | 0 | 0 | 0 | 0 | 0 | 0 | 0 |
| within normal limits | 28 d |  | 0 | 3 | 0 | 2 | 0 | 0 | 0 | 0 | 0 | 0 | 0 | 0 |
|  | 49 d |  | 0 | 0 | 0 | 0 | 0 | 0 | 0 | 0 | 0 | 0 | 0 | 1 |

EQUIVALENTS

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method of treating a delayed complication of a brain injury that deposits blood in a subarachnoid space of the brain, wherein the brain injury is mediated by decreased cerebral perfusion, comprising:
   a) providing a microparticulate composition comprising
      (i) a microparticulate suspension comprising a therapeutic amount of at least one therapeutic agent selected from the group consisting of a calcium channel antagonist, an endothelin (ET) receptor antagonist, and a transient receptor potential (TRP) channel antagonist, wherein the microparticulate formulation comprises a plurality of microparticles of a uniform distribution of microparticle size, and wherein each microparticle comprises a matrix,
      (ii) and a pharmaceutical carrier comprising an agent that affects viscosity of the suspension,
      the composition being characterized by
         1) dispersal of the at least one therapeutic amount of the therapeutic agent throughout each microparticle,
         2) the therapeutic amount is effective to improve cerebral perfusion and to treat the delayed complication comprising a delayed cerebral ischemia (DCI) comprising an angiographic vasospasm, formation of a plurality of microthromboemboli, a cortical spreading ischemia, or a combination thereof;
         3) gradual release of the therapeutic agent from the composition over an extended period of time, and
         4) its flowability around at least one cerebral artery in the subarachnoid space; and
   b) administering the composition locally into a cerebral ventricle so that the microparticulate suspension flows from the cerebrospinal fluid (CSF) in the cerebral ventricle into the cerebrospinal fluid (CSF) in the subarachnoid space before releasing the therapeutic agent in the subarachnoid space without entering systemic circulation in an amount to cause unwanted side effects.

2. The method according to claim 1, wherein the at least one therapeutic agent is a calcium channel antagonist selected from the group consisting of an L-type voltage dependent calcium channel inhibitor, an R-type voltage dependent calcium channel inhibitor, an N-type voltage dependent calcium channel inhibitor, a P/Q-type voltage dependent calcium channel inhibitor, a T-type voltage dependent calcium channel inhibitor, or a combination thereof.

3. The method according to claim 2, wherein the L-type voltage dependent calcium channel inhibitor is a dihydropyridine, selected from the group consisting of amlodipine, aranidipine, azelnidipine, bamidipine, benidipine, cinaldipine, efonidipine, felodipine, isradipine, lacidipine, lemildipine, lercanidipine, nicardipine, nifedipine, nilvadipine, nimodipine, nisoldipine, nitrendipine, manidipine, pranidipine, or a combination thereof.

4. The method according to claim 3, wherein the dihydropyridine is nimodipine.

5. The method according to claim 1, wherein the microparticulate suspension comprises a powder suspension of microparticles.

6. The method according to claim 1, wherein the microparticulate suspension further comprises a slow-release compound.

7. The method according to claim 6, wherein the slow release compound is a biodegradable polymer.

8. The method according to claim 7, wherein the biodegradable polymer is selected from the group consisting of polylactide-polyglycolide, poly(orthoester), and poly(anhydride).

9. The method according to claim 1, wherein administering occurs via an injection apparatus.

10. The method according to claim 9, wherein the injection apparatus is a needle, a cannula, a catheter, or a combination thereof.

11. The method according to claim 1, wherein one-half of the therapeutic amount of the therapeutic agent is released within 1 day to 30 days from delivery of the composition to the cerebral ventricle.

12. The method according to claim 1, wherein the cerebral ventricle is at least 0.001 mm from the cerebral artery in the subarachnoid space.

13. The method according to claim 12, wherein the cerebral ventricle is a lateral ventricle, a third ventricle, a fourth ventricle, or a combination thereof.

14. The method according to claim 1, wherein the flowable sustained release microparticulate composition produces a predominantly localized effect around a cerebral artery in the subarachnoid space.

15. The method according to claim 1, wherein the therapeutic amount of the therapeutic agent is effective to increase the internal diameter of a cerebral artery in the subarachnoid space.

16. The method according to claim 1, wherein the pharmaceutical carrier comprises a buffer solution.

17. The method according to claim 1, wherein the brain injury comprises a subarachnoid hemorrhage.

18. The method according to claim 1, wherein the agent that affects viscosity of the suspension is hyaluronic acid.

19. The method according to claim 1, wherein the microparticles have a diameter ranging from about 25 µm to about 100 µm.

* * * * *